United States Patent
Goren et al.

(10) Patent No.: US 12,234,472 B2
(45) Date of Patent: Feb. 25, 2025

(54) EUKARYOTIC CELLS COMPRISING ADENOVIRUS-ASSOCIATED VIRUS POLYNUCLEOTIDES

(71) Applicant: Regeneron Pharmaceuticals, Inc., Tarrytown, NY (US)

(72) Inventors: Michael Goren, Tarrytown, NY (US); Yu Zhao, Willison Park, NY (US); Alexandros Strikoudis, New York, NY (US); Darya Burakov, Tarrytown, NY (US); Gang Chen, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/047,341

(22) Filed: Oct. 18, 2022

(65) Prior Publication Data

US 2023/0193312 A1    Jun. 22, 2023

Related U.S. Application Data

(60) Provisional application No. 63/256,730, filed on Oct. 18, 2021.

(51) Int. Cl.
  *C12N 15/85*    (2006.01)
  *C07K 14/005*    (2006.01)
  *C12N 15/67*    (2006.01)

(52) U.S. Cl.
  CPC ............ *C12N 15/85* (2013.01); *C07K 14/005* (2013.01); *C12N 15/67* (2013.01); *C12N 2830/42* (2013.01); *C12N 2830/50* (2013.01); *C12N 2840/203* (2013.01)

(58) Field of Classification Search
  CPC .... C12N 15/85; C12N 15/67; C12N 2830/42; C12N 2830/50; C12N 2840/203; C07K 14/005
  See application file for complete search history.

(56) References Cited

U.S. PATENT DOCUMENTS

| | | |
|---|---|---|
| 5,464,758 A | 11/1995 | Gossen et al. |
| 5,658,785 A | 8/1997 | Johnson |
| 5,981,225 A | 11/1999 | Kochanek et al. |
| 5,985,846 A | 11/1999 | Kochanek et al. |
| 5,989,910 A | 11/1999 | Mermod et al. |
| 6,423,544 B1 | 7/2002 | Hardy |
| 6,558,948 B1 | 5/2003 | Kochanek et al. |
| 7,232,899 B2 | 6/2007 | Von Seggern et al. |
| 7,771,997 B2 | 8/2010 | Chen et al. |
| 8,734,809 B2 * | 5/2014 | Gao ........................ C12N 15/86 435/320.1 |
| 8,852,926 B2 | 10/2014 | Mo et al. |
| 9,315,773 B2 | 4/2016 | Schiedner et al. |
| 9,371,512 B2 | 6/2016 | Schiedner et al. |
| 9,469,856 B2 | 10/2016 | Dou et al. |
| 9,534,233 B2 | 1/2017 | Kochanek et al. |
| 9,777,291 B2 | 10/2017 | Chatterjee |
| 9,783,825 B2 | 10/2017 | Chatterjee |
| 9,803,218 B2 | 10/2017 | Chatterjee |
| 9,816,110 B2 | 11/2017 | Shen et al. |
| 9,834,789 B2 | 12/2017 | Chatterjee et al. |
| 10,081,798 B2 | 9/2018 | Wissing et al. |
| 10,544,429 B2 | 1/2020 | Farley et al. |
| 10,647,999 B2 | 5/2020 | Cawood et al. |
| 10,711,274 B2 | 7/2020 | Mueller et al. |
| 10,815,497 B2 | 10/2020 | Kyostio-Moore et al. |
| 10,858,631 B2 | 12/2020 | Vink |
| 11,643,666 B2 | 5/2023 | Colloca et al. |
| 11,697,824 B2 | 7/2023 | Cawood et al. |
| 2003/0192066 A1 | 10/2003 | Zhang et al. |
| 2009/0191597 A1 * | 7/2009 | Samulski ................. C12N 7/00 435/325 |
| 2013/0023033 A1 | 1/2013 | Wilson et al. |
| 2016/0177300 A1 | 6/2016 | Feary et al. |

(Continued)

FOREIGN PATENT DOCUMENTS

| | | |
|---|---|---|
| EP | 1230354 A2 | 8/2002 |
| EP | 1362096 A2 | 11/2003 |

(Continued)

OTHER PUBLICATIONS

Haifeng Chen, "Intron Splicing-mediated Expression of AAV Rep and Cap Genes and Production of AAV Vectors in Insect Cells",(The American Society of Gene Therapy), Published Mar. 18, 2008, vol. 6 (Year: 2008).*
Renaud-Gabardos et al., "Internal Ribosome entry site-based vectors for combined gene therapy", (World Journal of Experimental Medicine), Published Feb. 20, 2015, vol. 5 (Year: 2015).*
Chengwen et al, Engineering Adeno-associated Virus Vectors for Gene Therapy, (Nature Reviews Genetics), Published Feb. 10, 2020, vol. 21 (Year: 2020).*
Brown et al., Synthetic promoters for CHO cell engineering. Biotechnol Bioeng. Aug. 2014;111(8):1638-47.

(Continued)

*Primary Examiner* — Brian Whiteman
*Assistant Examiner* — Stephanie L Sullivan
(74) *Attorney, Agent, or Firm* — McCarter & English, LLP; John P. Isacson

(57) ABSTRACT

The present inventions provide eukaryotic cells, such as mammalian cells, that comprise adeno-associated virus (AAV) polynucleotides, including AAV capsid proteins (Cap), and are capable of expressing the polypeptides encoded by the AAV polynucleotides, and thereby are capable of producing AAV, including recombinant AAV. The eukaryotic cells also may comprise adenovirus (Ad) polynucleotides. The present inventions also provide methods of expressing AAV polynucleotides, as well as Ad polynucleotides, in eukaryotic cells, such as CHO cells, HEK 293 and BHK cells. The present inventions further provides other products and methods described herein.

15 Claims, 8 Drawing Sheets

Specification includes a Sequence Listing.

(56) References Cited

U.S. PATENT DOCUMENTS

| | | |
|---|---|---|
| 2018/0030480 A1 | 2/2018 | Shen et al. |
| 2018/0216118 A1 | 8/2018 | Chen et al. |
| 2018/0267516 A1 | 9/2018 | Fister et al. |
| 2019/0078099 A1 | 3/2019 | Zhou et al. |
| 2019/0171188 A1 | 6/2019 | Fister |
| 2019/0175716 A1 | 6/2019 | Gilbert et al. |
| 2019/0233544 A1 | 8/2019 | Babb et al. |
| 2020/0032221 A1 | 1/2020 | Tiernan et al. |
| 2020/0066369 A1 | 2/2020 | Downey et al. |
| 2020/0102578 A1 | 4/2020 | Farley et al. |
| 2020/0157567 A1 | 5/2020 | Cawood et al. |
| 2020/0199627 A1* | 6/2020 | Gu ............... C12N 15/8645 |
| 2020/0208121 A1 | 7/2020 | Hewitt et al. |
| 2020/0239909 A1 | 7/2020 | Cawood et al. |
| 2020/0277626 A1 | 9/2020 | Roska et al. |
| 2020/0277628 A1 | 9/2020 | Hein et al. |
| 2020/0325455 A1 | 10/2020 | Tiernan et al. |
| 2021/0163991 A1* | 6/2021 | Gillmeister ......... C12N 15/86 |
| 2022/0154215 A1 | 5/2022 | Greene |
| 2022/0162636 A1 | 5/2022 | Cawood et al. |
| 2022/0177854 A1 | 6/2022 | Chanas et al. |
| 2022/0259572 A1 | 8/2022 | Gu et al. |
| 2022/0307052 A1 | 9/2022 | Pechan et al. |
| 2022/0364103 A1 | 11/2022 | Xue et al. |
| 2023/0048994 A1 | 2/2023 | Smith et al. |
| 2023/0076955 A1 | 3/2023 | Cawood et al. |
| 2023/0257770 A1 | 8/2023 | Cawood et al. |
| 2023/0257831 A1 | 8/2023 | Cawood et al. |
| 2023/0279427 A1 | 9/2023 | Hu et al. |
| 2023/0287460 A1 | 9/2023 | Goren et al. |
| 2023/0304062 A1 | 9/2023 | Zhao et al. |
| 2023/0313228 A1 | 10/2023 | Cawood |
| 2023/0357794 A1 | 11/2023 | Cawood et al. |

FOREIGN PATENT DOCUMENTS

| | | |
|---|---|---|
| EP | 1743041 A1 | 1/2007 |
| EP | 2606128 A1 | 6/2013 |
| EP | 3456822 A1 | 3/2019 |
| EP | 3649239 A1 | 5/2020 |
| WO | 1999/53085 A2 | 10/1999 |
| WO | 2001/034940 A2 | 5/2001 |
| WO | 2002/066620 A2 | 8/2002 |
| WO | 2003/101189 A1 | 12/2003 |
| WO | 2005/106046 A1 | 11/2005 |
| WO | 2007/133797 A2 | 11/2007 |
| WO | 2012/041311 A1 | 4/2012 |
| WO | 2013/190032 A1 | 12/2013 |
| WO | 2015/092440 A1 | 6/2015 |
| WO | 2017/140406 A1 | 8/2017 |
| WO | 2017/221031 A1 | 12/2017 |
| WO | 2018/150269 A1 | 8/2018 |
| WO | 2018/150271 A1 | 8/2018 |
| WO | 2018/177758 A1 | 10/2018 |
| WO | 2018/189535 A1 | 10/2018 |
| WO | 2019/020992 A1 | 1/2019 |
| WO | 2019/030069 A2 | 2/2019 |
| WO | 2019/057691 A1 | 3/2019 |
| WO | 2019/073059 A1 | 4/2019 |
| WO | 2019/126634 A2 | 6/2019 |
| WO | 2019/141993 A1 | 7/2019 |
| WO | 2019/155016 A1 | 8/2019 |
| WO | 2019/157239 A1 | 8/2019 |
| WO | 2019/175600 A1 | 9/2019 |
| WO | 2020/16148 A1 | 1/2020 |
| WO | 2020/043869 A2 | 3/2020 |
| WO | 2020/072480 A1 | 4/2020 |
| WO | 2020/077411 A1 | 4/2020 |
| WO | 2020/084034 A1 | 4/2020 |
| WO | 2020/132165 A1 | 6/2020 |
| WO | 2020/165603 A1 | 8/2020 |
| WO | 2020/183133 A1 | 9/2020 |
| WO | 2020/232366 A2 | 11/2020 |
| WO | 2021/127432 A1 | 6/2021 |
| WO | 2021/188892 A1 | 9/2021 |
| WO | 2022/020712 A1 | 1/2022 |
| WO | 2022/038369 A1 | 2/2022 |
| WO | 2022/112218 A1 | 6/2022 |
| WO | 2022/223954 A1 | 10/2022 |
| WO | 2023/173105 A2 | 9/2023 |

OTHER PUBLICATIONS

Ede et al., Quantitative Analyses of Core Promoters Enable Precise Engineering of Regulated Gene Expression in Mammalian Cells. ACS Synth Biol. May 20, 2016;5(5):395-404.

Lagrange et al., New core promoter element in RNA polymerase II-dependent transcription: sequence-specific DNA binding by transcription factor IIB. Genes Dev. Jan. 1, 1998;12(1):34-44.

Liu et al., Rapid establishment of a HEK 293 cell line expressing FVIII-BDD using AAV site-specific integration plasmids. BMC Res Notes. Sep. 10, 2014;7:626, 6 pages.

Morita et al., Attenuated protein expression vectors for use in siRNA rescue experiments. Biotechniques. Aug. 2012;0(0):1-5.

Ramos et al., The TetR family of transcriptional repressors. Microbiol Mol Biol Rev. Jun. 2005;69(2):326-56.

Russell et al., Phage Bxb1 integrase mediates highly efficient site-specific recombination in mammalian cells. Biotechniques. Apr. 2006;40(4):462-464.

Saxena et al., Design of Synthetic Promoters for Gene Circuits in Mammalian Cells. Methods Mol Biol. 2017;1651:263-273.

Wissmann et al., Tn10 tet operator mutations affecting Tet repressor recognition. Nucleic Acids Res. May 27, 1986;14(10):4253-66.

Luo et al., AAVS1-Targeted Plasmid Integration in AAV Producer Cell Lines. Hum Gene Ther Methods. Jun. 2017;28(3):124-138.

White et al., Use of a negative selectable marker for rapid selection of recombinant vaccinia virus. Biotechniques. May 2011;50(5):303-9.

Wang et al., Adeno-associated virus vector as a platform for gene therapy delivery. Nat Rev Drug Discov. May 2019;18(5):358-378.

Wentz et al., Influence of lactate, ammonia, and osmotic stress on adherent and suspension BHK cells. Enzyme Microb Technol. Jan. 1992;14(1):68-75.

Worner et al., Adeno-associated virus capsid assembly is divergent and stochastic. Nat Commun. Mar. 12, 2021;12(1):1642, 9 pages.

Weitzman et al., Adeno-associated virus biology. Methods Mol Biol. 2011;807:1-23.

Gaidukov et al., A multi-landing pad DNA integration platform for mammalian cell engineering. Nucleic Acids Res. May 4, 2018;46(8):4072-4086.

Hamaker et al., Site-specific Integration Ushers in a New Era of Precise CHO Cell Line Engineering. Curr Opin Chem Eng. Dec. 2018;22:152-160.

Hein et al., Establishment of a Scalable Production Process using Stable Helper-Virus Free AAV Producer Cell Lines based on CEVEC's CAP Suspension Cell line. CEVEC Pharmaceuticals GmbH. Poster presentation, 1 page, (2020).

Hilliard et al., Systematic identification of safe harbor regions in the CHO genome through a comprehensive epigenome analysis. Biotechnol Bioeng. Feb. 2021;118(2):659-675.

Kolling et al., State-change decisions and dorsomedial prefrontal cortex: the importance of time. Curr Opin Behav Sci. Aug. 2018;22:152-160.

Lee et al., Construction of an rAAV Producer Cell Line through Synthetic Biology. ACS Synth Biol. Oct. 21, 2022;11(10):3285-3295. Pre-publication edition.

Lee et al., Site-specific integration in CHO cells mediated by CRISPR/Cas9 and homology-directed DNA repair pathway. Sci Rep. Feb. 25, 2015;5:8572, 11 pages.

Papapetrou et al., Gene Insertion Into Genomic Safe Harbors for Human Gene Therapy. Mol Ther. Apr. 2016;24(4):678-84.

Pellenz et al., New Human Chromosomal Sites with "Safe Harbor" Potential for Targeted Transgene Insertion. Hum Gene Ther. Jul. 2019;30(7):814-828.

Ramachandra et al., Efficient recombinase-mediated cassette exchange at the AAVS1 locus in human embryonic stem cells using baculoviral vectors. Nucleic Acids Res. Sep. 1, 2011;39(16):e107, 13 pages.

(56) References Cited

OTHER PUBLICATIONS

Sajgo et al., Dre—Cre sequential recombination provides new tools for retinal ganglion cell labeling and manipulation in mice. PLoS One. Mar. 7, 2014;9(3):e91435, 15 pages.

Suzuki et al., VCre/VloxP and SCre/SloxP: new site-specific recombination systems for genome engineering. Nucleic Acids Res. Apr. 2011;39(8):e49, 11 pages.

Tripp et al., Vector engineering of pRep-Cap and pHelper enhanced AAV productivity by triple transfection in suspension HEK293 cells. Lonza, ASGC Virtual. 17 pages, May 11-14, 2021.

Wissing, Elevecta®—Helper virus-free AAV production with stable CAP® and HEK293 producer cells. Digital Week, Cell & Gene Therapy Manufacturing & Commercialization. 34 pages, Feb. 19, 2021.

Ayuso et al., Production, purification and characterization of adeno-associated vectors. Curr Gene Ther. Dec. 2010;10(6):423-36.

Brent et al., A eukaryotic transcriptional activator bearing the DNA specificity of a prokaryotic repressor. Cell. Dec. 1985;43(3 Pt 2):729-36.

Douin et al., Use and comparison of different internal ribosomal entry sites (IRES) in tricistronic retroviral vectors. BMC Biotechnol. Jul. 27, 2004;4:16, 12 pages.

Gossen et al., Tight control of gene expression in mammalian cells by tetracycline-responsive promoters. Proc Natl Acad Sci U S A. Jun. 15, 1992;89(12):5547-51.

Gossen et al., Transcriptional activation by tetracyclines in mammalian cells. Science. Jun. 23, 1995;268(5218):1766-9.

Iida et al., Inducible gene expression by retrovirus-mediated transfer of a modified tetracycline-regulated system. J Virol. Sep. 1996;70(9):6054-9.

Jaubert et al., Tetracycline-regulated transactivators driven by the involucrin promoter to achieve epidermal conditional gene expression. J Invest Dermatol. Aug. 2004;123(2):313-8.

Labow et al., Conversion of the lac repressor into an allosterically regulated transcriptional activator for mammalian cells. Mol Cell Biol. Jul. 1990;10(7):3343-56.

Louvion et al., Fusion of GAL4-VP16 to a steroid-binding domain provides a tool for gratuitous induction of galactose-responsive genes in yeast. Gene. Sep. 6, 1993;131(1):129-34.

Mattioni et al., Regulation of protein activities by fusion to steroid binding domains. Methods Cell Biol. 1994;43 Pt A:335-52.

Murphy et al., Estrogen regulation of protein expression and signaling pathways in the heart. Biol Sex Differ. Mar. 10, 2014;5(1):6, 7 pages.

No et al., Ecdysone-inducible gene expression in mammalian cells and transgenic mice. Proc Natl Acad Sci U S A. Apr. 16, 1996;93(8):3346-51.

Ortiz et al., Tetracycline-inducible gene expression in Trichomonas vaginalis. Molecular and Biochemical Parasitology. Apr. 25, 2003;128(1):43-49.

Pedone et al., A tunable dual-input system for on-demand dynamic gene expression regulation. Nat Commun. Oct. 2, 2019;10(1):4481, 13 pages.

Pinto et al., Precise integration of inducible transcriptional elements (PrIITE) enables absolute control of gene expression. Nucleic Acids Res. Jul. 27, 2017;45(13):15 pages.

Sadowski et al., GAL4-VP16 is an unusually potent transcriptional activator. Nature. Oct. 6, 1988;335(6190):563-4.

Sato et al., Generation of mouse iPS cells using an inducible expression of transgenes via the cumate gene-switch. Anal Biochem. Jun. 15, 2020;599:113748, 7 pages.

Schmidt et al., Adeno-associated virus type 2 Rep78 induces apoptosis through caspase activation independently of p53. J Virol. Oct. 2000;74(20):9441-50.

Sergeeva et al., Multicopy Targeted Integration for Accelerated Development of High-Producing Chinese Hamster Ovary Cells. ACS Synth Biol. Sep. 18, 2020;9(9):2546-2561.

Shin et al., Streamlined Human Cell-Based Recombinase-Mediated Cassette Exchange Platform Enables Multigene Expression for the Production of Therapeutic Proteins. ACS Synth Biol. Jul. 16, 2021;10(7):1715-1727.

Sisson et al., Expression of the reverse tetracycline-transactivator gene causes emphysema-like changes in mice. Am J Respir Cell Mol Biol. May 2006;34(5):552-60.

Song et al., Investigation of arc repressor DNA-binding specificity by comparative molecular dynamics simulations. J Biomol Struct Dyn. 2015;33(10):2083-93.

International Search Report and Written Opinion for Application No. PCT/US2022/078266, dated Feb. 17, 2023, 24 pages.

International Search Report and Written Opinion for Application No. PCT/US2022/078271, dated Feb. 6, 2023, 22 pages.

Invitation to Pay Additional Fees for Application No. PCT/US2022/078275, dated Feb. 17, 2023, 14 pages.

Bae et al., Design and Testing of Vector-Producing HEK293T Cells Bearing a Genomic Deletion of the SV40 T Antigen Coding Region. Mol Ther Methods Clin Dev. Jul. 9, 2020;18:631-638.

Su et al., Self-attenuating adenovirus enables production of recombinant adeno-associated virus for high manufacturing yield without contamination. Nat Commun. Mar. 7, 2022;13(1):1182, with supplementary information, 32 pages.

Sun et al. Expression of heme oxygenase-1 and GFP gene mediated by recombinant adeno-associated-virus in transplanted liver in rats.

* cited by examiner

EUKARYOTIC CELLS COMPRISING ADENOVIRUS-ASSOCIATED VIRUS POLYNUCLEOTIDES

This application claims priority to U.S. Application Ser. No. 63/256,730, filed Oct. 18, 2021, which is hereby incorporated by reference in its entirety.

FIELD OF THE INVENTIONS

The present inventions provide eukaryotic cells that comprise adeno-associated virus (AAV) polynucleotides, including AAV capsid proteins (Cap). The cells are capable of expressing the polypeptides encoded by the AAV polynucleotides, and thereby are capable of producing AAV, including recombinant AAV. The eukaryotic cells also may comprise adenovirus (Ad) polynucleotides. The present inventions also provide methods of expressing AAV polynucleotides, as well as Ad polynucleotides, in eukaryotic cells. The present inventions also provide methods for producing recombinant adeno-associated virus utilizing eukaryotic cells that express AAV and Ad polypeptides encoded by polynucleotides, as well as recombinant AAV produced by these inventive methods. The present inventions further provide other products and methods described herein.

REFERENCE TO ELECTRONIC SEQUENCE LISTING

The application contains a Sequence Listing, which has been submitted electronically in .XML format and is hereby incorporated by reference in its entirety. Said .XML copy, created on Oct. 5, 2022, is named "135975-61702.xml" and is 229,879 bytes in size. The sequence listing contained in this .XML file is part of the specification and is hereby incorporated by reference herein in its entirety.

BACKGROUND OF THE INVENTIONS

Adeno-associated virus (AAV) is a non-enveloped, single-stranded DNA virus and is used as a gene delivery vector for both research and therapeutics. Weitzman and Linden, Adeno-Associated Virus Biology (chapter 1), Meth. Molec. Biol. 807:1-23 (2011). Gene transfer vectors based on AAV have demonstrated promise for human gene therapy based on their safety profile and potential to achieve long-term efficacy in animal models. Wang et al., Nature, 18:358-78 (2019). A major challenge for advancing AAV-based therapies into clinical development is the difficulty and cost of producing sufficient quantities of AAV through transient methodologies.

AAV has been produced in HEK 293, BHK, human amniotic (for example, epithelial cells such as HAEpiC) and SF9 lines. However, expression is transient due to the use of plasmid vectors containing the necessary AAV and helper virus genes. For example, recombinant AAV production in HEK 293 cells using adenovirus helper gene products utilizes adenovirus E2A, E4, VA RNA and AAV Rep and Cap, along with AAV inverted terminal repeats (ITR) flanking the polynucleotide of interest. The reliance on non-integrated plasmid vectors means that the requisite gene products will be lost over time and need to be continually re-established.

The AAV genome includes a capsid gene referred to as "Cap" or "CAP". Cap in nature is translated to produce, via alternative start codons and transcript splicing, three size-variant structural proteins referred to as VP1 (about 90 kDa), VP2 (about 72 kDa) and VP3 (about 60 kDa). An AAV capsid contains 60 subunits total of the VP proteins. A ratio of 1:1:10 is considered the most typical ratio for VP1: VP2: VP3, which is a stoichiometry of 5 VP1 subunits: 5 VP2 subunits: 50 VP3 subunits. However, there can be variation. Wörner et al., Nature Communications 12:1642 (2021). AAV polynucleotides and proteins, including CAP, can be selected from any serotype.

Thus, there exists the need to develop improved cells and production methods that avoid the transient nature of non-integrated plasmid vectors.

SUMMARY OF THE INVENTIONS

The present inventions provide stable eukaryotic cells, such as mammalian cells (for example, primate, rodent and canine cells), comprising integrated AAV polynucleotides and Ad polynucleotides. The protein and VA RNA products of the Ad polynucleotides act in a helper capacity. All AAV and Ad types are amenable for use according to the present inventions. The present inventions advantageously can employ site-specific integration into the cell genome, which refers to pre-selected genomic sites for exogenous DNA to be inserted into a cellular genome. Random insertion can be employed as well.

Herein described are polynucleotides, where each can comprise (i) a promoter, (ii) an intron, (iii) an internal ribosome entry site, (iv) a polynucleotide encoding Adeno-associated virus (AAV) Cap protein, and (v) a polyadenylation site. For example, the polynucleotide can be in a CHO cell and have the (i) promoter, (ii) intron, (iii) internal ribosome entry site and (iv) polynucleotide encoding AAV Cap protein can be operably linked. The polynucleotide can be integrated into a CHO cell genome, such as a CHO chromosome. Alternatively, the polynucleotide can be in a HEK 293 cell and have the (i) promoter, (ii) intron, (iii) internal ribosome entry site and (iv) polynucleotide encoding AAV Cap protein operably linked. The polynucleotide can be integrated into a HEK 293 cell genome, such as a HEK 293 cell chromosome. Another alternative is the polynucleotide can be in a BHK cell and have the (i) promoter, (ii) intron, (iii) internal ribosome entry site and (iv) polynucleotide encoding AAV Cap protein operably linked. The polynucleotide can be integrated into a BHK cell genome, such as a BHK cell chromosome. In yet another alternative is the polynucleotide can be in a human amniotic cell and have the (i) promoter, (ii) intron, (iii) internal ribosome entry site and (iv) polynucleotide encoding AAV Cap protein operably linked. The polynucleotide can be integrated into a human amniotic cell genome, such as a human amniotic cell chromosome. Additionally, the polynucleotide can be integrated into non-chromosomal locations as known by the person skilled in the art, such as episomes.

The polynucleotide can further comprise an operator. The promoter can be a CMV promoter and the operator can be a Tet operator. AAV proteins and polynucleotides, including CAP, can be selected from any serotype. When Cap is from serotype 5 ("Cap5") and expressed in a CHO cell, the polynucleotide allows for production of AAV Cap5 VP2 and VP3 protein, wherein the amount of VP3 produced is greater than the amount of VP2 produced. Production of VP1 can be less than 1% the level of VP2 production. Production ratios can vary based upon experimental conditions and analytical techniques.

Additionally, polynucleotides are described, wherein each can comprise (i) a promoter, (ii) an intron, (iii) a first internal ribosome entry site, (iv) a first polynucleotide encoding AAV Cap protein, (v) a second internal ribosome entry site, (vi) a second polynucleotide encoding AAV Cap protein, and (vii) a polyadenylation site. For example, the polynucleotide can be in a CHO cell and the (i) promoter, (ii) intron, (iii) first internal ribosome entry site, (iv) first polynucleotide encoding AAV Cap protein, (v) a second internal ribosome entry site, and (vi) second polynucleotide encoding AAV Cap protein can be operably linked. The polynucleotide can be integrated into a CHO cell genome. Alternatively, the polynucleotide can be in a HEK 293 cell and the (i) promoter, (ii) intron, (iii) first internal ribosome entry site, (iv) first polynucleotide encoding AAV Cap protein, (v) a second internal ribosome entry site, and (vi) second polynucleotide encoding AAV Cap protein are operably linked. The polynucleotide can be integrated into a HEK 293 cell genome. In another alternative, the polynucleotide can be in a BHK cell and the (i) promoter, (ii) intron, (iii) first internal ribosome entry site, (iv) first polynucleotide encoding AAV Cap protein, (v) a second internal ribosome entry site, and (vi) second polynucleotide encoding AAV Cap protein are operably linked. The polynucleotide can be integrated into a BHK cell genome. In another alternative, the polynucleotide can be in a human amniotic cell and the (i) promoter, (ii) intron, (iii) first internal ribosome entry site, (iv) first polynucleotide encoding AAV Cap protein, (v) a second internal ribosome entry site, and (vi) second polynucleotide encoding AAV Cap protein are operably linked. The polynucleotide can be integrated into a human amniotic cell genome. The polynucleotide can further comprise an operator. The promoter can be a CMV promoter and the operator can be a Tet operator. AAV proteins and polynucleotides, including CAP, can be selected from any serotype. When Cap is from serotype 5 ("Cap5") and expressed in a CHO cell, the polynucleotide allows for production of AAV Cap5 proteins VP1, VP2 and VP3. The amount of VP3 production can be greater than the amount of VP1 production and the amount of VP2 production. The amount of VP2 production can be greater than the amount of VP1 production. Production ratios can vary based upon experimental conditions and analytical techniques.

Moreover, there are described polynucleotides, wherein each polynucleotide can comprise (i) a promoter, (ii) an intron, (iii) a polynucleotide encoding AAV Cap protein, and (iv) a polyadenylation site, wherein the polynucleotide allows for production of AAV Cap VP1 protein when expressed. For example, the polynucleotide can be in a CHO cell and the (i) promoter, (ii) intron, and (iii) polynucleotide encoding AAV Cap protein can be operably linked. The polynucleotide can be integrated into a CHO cell genome. Alternatively, the polynucleotide can be in a HEK 293 cell and the (i) promoter, (ii) intron, and (iii) polynucleotide encoding AAV Cap protein can be operably linked. The polynucleotide can be integrated into a HEK 293 cell genome. In another alternative, the polynucleotide can be in a BHK cell and the (i) promoter, (ii) intron, and (iii) polynucleotide encoding AAV Cap protein can be operably linked. The polynucleotide can be integrated into a BHK cell genome. In still another alternative, the polynucleotide can be in a human amniotic cell and the (i) promoter, (ii) intron, and (iii) polynucleotide encoding AAV Cap protein can be operably linked. The polynucleotide can be integrated into a human amniotic cell genome. The polynucleotide can further comprise an operator. The promoter can be a CMV promoter and the operator can be a Tet operator.

Furthermore, there are described polynucleotides, wherein each can comprise (i) a promoter, (ii) an internal ribosome binding site, (iii) a polynucleotide encoding AAV Cap protein, and (iv) a polyadenylation site, wherein the polynucleotide allows for production of AAV VP1 Cap protein when expressed. The polynucleotide can be in a CHO cell and the (i) promoter, (ii) internal ribosome binding site, and (iii) polynucleotide encoding AAV Cap protein can be operably linked. The polynucleotide can be integrated into a CHO genome. Alternatively, the polynucleotide can be in a HEK 293 cell and the (i) promoter, (ii) internal ribosome binding site, and (iii) polynucleotide encoding AAV Cap protein can be operably linked. The polynucleotide can be integrated into a HEK 293 cell genome. In another alternative, the polynucleotide can be in a BHK cell and the (i) promoter, (ii) internal ribosome binding site, and (iii) polynucleotide encoding AAV Cap protein can be operably linked. The polynucleotide can be integrated into a BHK cell genome. In yet another alternative, the polynucleotide can be in a human amniotic cell and the (i) promoter, (ii) internal ribosome binding site, and (iii) polynucleotide encoding AAV Cap protein can be operably linked. The polynucleotide can be integrated into a human amniotic cell genome. The polynucleotide can comprise an operator. The promoter can be a CMV promoter and the operator can be a Tet operator.

Additionally, there are described eukaryotic cells, where each cell can comprise a polynucleotide comprising (i) a promoter, (ii) an intron, (iii) a first internal ribosome entry site, (iv) a first polynucleotide encoding AAV Cap protein, (v) a second internal ribosome entry site, (vi) a second polynucleotide encoding AAV Cap protein, and (vii) a polyadenylation site. The (i) promoter, (ii) intron, (iii) first internal ribosome entry site, (iv) first polynucleotide encoding AAV Cap protein, (v) a second internal ribosome entry site, and (vi) second polynucleotide encoding AAV Cap protein can be operably linked. The polynucleotide can be integrated into a cell genome. The cell can be a CHO cell, a HEK 293 cell, a BHK cell, a Human Amniotic Cell or other eukaryotic cell. The cell can further comprise an operator. The promoter can be a CMV promoter and the operator can be a Tet operator. The cell can further comprise: a polynucleotide encoding AAV Rep, a polynucleotide encoding Ad E1A, a polynucleotide encoding Ad E1B, a polynucleotide encoding Ad E2A or E2A orf, a polynucleotide encoding Ad E4 or E4 orf 6, a polynucleotide encoding VA RNA, and a polynucleotide encoding AAV ITRs and a protein of interest.

There are also described eukaryotic cells, where each cell can comprise (A) a first polynucleotide comprising (i) a promoter, (ii) an intron, (iii) an internal ribosome entry site, (iv) a polynucleotide encoding AAV Cap protein, and (v) a polyadenylation site; and (B) a second polynucleotide comprising (i) a promoter, (ii) an intron, (iii) a polynucleotide encoding AAV Cap protein, and (iv) a polyadenylation site. The (i) promoter, (ii) intron, (iii) internal ribosome entry site and (iv) polynucleotide encoding AAV Cap protein of (A) first polynucleotide can be operably linked, and wherein the (i) promoter, (ii) intron, and (iii) polynucleotide encoding AAV Cap protein of (B) second polynucleotide can be operably linked. The cell can have at least one polynucleotide integrated into a cell genome. The cell can be a CHO cell, a HEK 293 cell, a BHK cell, a human amniotic cell or other eukaryotic cell. The cell can further comprise an operator. The promoter can be a CMV promoter and the operator can be a Tet operator. The cell can further comprise a polynucleotide encoding AAV Rep, a polynucleotide encoding Ad E1A, a polynucleotide encoding Ad E1B, a polynucleotide encoding Ad E2A or E2A orf, a polynucleotide encoding E4 or E4 orf 6, a polynucleotide encoding VA RNA, and a polynucleotide encoding AAV ITRs and a protein of interest.

Additionally, there are described eukaryotic cells, where each cell can comprise: (A) a first polynucleotide comprising (i) a promoter, (ii) an intron, (iii) an internal ribosome entry site, (iv) a polynucleotide encoding AAV Cap protein, and (v) a polyadenylation site; and (B) a second polynucleotide comprising (i) a promoter, (ii) an internal ribosome entry site, (iii) a polynucleotide encoding AAV Cap protein, and (iv) a polyadenylation site. The cells can have the (i) promoter, (ii) intron, (iii) internal ribosome entry site and (iv) polynucleotide encoding AAV Cap protein of (A) first polynucleotide operably linked, and the (i) promoter, (ii) internal ribosome entry site, and (iii) polynucleotide encoding AAV Cap protein of (B) second polynucleotide operably linked. At least one polynucleotide can be integrated into a cell genome. The cell can be a CHO cell, a HEK 293 cell, a BHK cell, a human amniotic cell or other eukaryotic cell. The cell can further comprise an operator. The promoter can be a CMV promoter and the operator can be a Tet operator. The cell can further comprise: a polynucleotide encoding AAV Rep, a polynucleotide encoding Ad E1A, a polynucleotide encoding Ad E1B, a polynucleotide encoding Ad E2A or E2A orf, a polynucleotide encoding Ad E4 or E4 orf 6, a polynucleotide encoding VA RNA, and a polynucleotide encoding AAV ITRs and a protein of interest.

There also are described cell cultures comprising any of the above cells in any type of media, including growth media and maintenance media. Additionally, there are described methods of producing AAV proteins, including Cap proteins, and methods that can result in the production of recombinant AAV.

There are described methods of producing adeno-associated virus (AAV) Cap protein in cell culture, wherein a method comprises the steps of: providing eukaryotic cells, wherein a cell comprises a polynucleotide comprising (i) a promoter, (ii) an intron, (iii) a first internal ribosome entry site, (iv) a first polynucleotide encoding AAV Cap protein, (v) a second internal ribosome entry site, (vi) a second polynucleotide encoding AAV Cap protein, and (vii) a polyadenylation site; and culturing the cells in a culture medium to allow the cells to produce AAV Cap protein, wherein the polynucleotide allows for production of AAV Cap proteins VP1, VP2 and VP3. The (i) promoter, (ii) intron, (iii) first internal ribosome entry site, (iv) first polynucleotide encoding AAV Cap protein, (v) a second internal ribosome entry site, and (vi) second polynucleotide encoding AAV Cap protein can be operably linked. The polynucleotide can be integrated into a cell genome. The cell can be a CHO cell, a HEK 293 cell, a BHK cell, a human amniotic cell or other eukaryotic cell. The cell can further comprise an operator. The cell can further comprise: a polynucleotide encoding AAV Rep, a polynucleotide encoding Ad E1A, a polynucleotide encoding Ad E1B, a polynucleotide encoding Ad E2A or E2A orf, a polynucleotide encoding Ad E4 or E4 orf 6, a polynucleotide encoding VA RNA, and a polynucleotide encoding AAV ITRs and a protein of interest, wherein the cell can produce recombinant AAV.

Also described are methods of producing adeno-associated virus (AAV) Cap protein in cell culture, wherein a method comprises the steps of providing eukaryotic cells, where a cell comprises (a) a first polynucleotide comprising (i) a promoter, (ii) an intron, (iii) an internal ribosome entry site, (iv) a polynucleotide encoding AAV Cap protein, and (v) a polyadenylation site; and (b) a second polynucleotide comprising (i) a promoter, (ii) an intron, (iii) a polynucleotide encoding AAV Cap protein, and (iv) a polyadenylation site; and culturing the cells in a culture medium to allow the cells to produce AAV Cap protein, wherein the polynucleotide allows for production of AAV Cap proteins VP1, VP2 and VP3. The (i) promoter, (ii) intron, (iii) internal ribosome entry site and (iv) polynucleotide encoding AAV Cap protein of (a) first polynucleotide can be operably linked, and the (i) promoter, (ii) intron, and (iii) polynucleotide encoding AAV Cap protein of (b) second polynucleotide can be operably linked. The polynucleotide can be integrated into a cell genome. The cell can be a CHO cell, a HEK 293 cell, a BHK cell, a human amniotic cell or other eukaryotic cell. The cell can further comprise an operator. The promoter can be a CMV promoter and the operator can be a Tet operator. The cell can further comprise: a polynucleotide encoding AAV Rep, a polynucleotide encoding Ad E1A, a polynucleotide encoding Ad E1B, a polynucleotide encoding Ad E2A or E2A orf, a polynucleotide encoding Ad E4 or E4 orf 6, a polynucleotide encoding VA RNA, and a polynucleotide encoding AAV ITRs and a protein of interest, wherein the cell can produce recombinant AAV.

There are also described methods of producing adeno-associated virus (AAV) Cap protein in cell culture, wherein a method comprises the steps of: providing eukaryotic cells, where a cell comprises (a) a first polynucleotide comprising (i) a promoter, (ii) an intron, (iii) an internal ribosome entry site, (iv) a polynucleotide encoding AAV Cap protein, and (v) a polyadenylation site; and (b) a second polynucleotide comprising (i) a promoter, (ii) an internal ribosome entry site, (iii) a polynucleotide encoding AAV Cap protein, and (iv) a polyadenylation site; and culturing the cells in a culture medium to allow the cells to produce AAV Cap protein, wherein the polynucleotide allows for production of AAV Cap proteins VP1, VP2 and VP3. The (i) promoter, (ii) intron, (iii) internal ribosome entry site and (iv) polynucleotide encoding AAV Cap protein of (a) first polynucleotide can be operably linked, and the (i) promoter, (ii) internal ribosome entry site, and (iii) polynucleotide encoding AAV Cap protein of (b) second polynucleotide can be operably linked. The polynucleotide can be integrated into a cell genome. The cell can be a CHO cell, a HEK 293 cell, a BHK cell, a human amniotic cell or other eukaryotic cell. The cell can further comprise an operator. The promoter can be a CMV promoter and the operator can be a Tet operator. The cell can further comprise: a polynucleotide encoding AAV Rep, a polynucleotide encoding Ad E1A, a polynucleotide encoding Ad E1B, a polynucleotide encoding Ad E2A or E2A orf, a polynucleotide encoding Ad E4 or E4 orf 6, a polynucleotide encoding VA RNA, and a polynucleotide encoding AAV ITRs and a protein of interest, wherein the cell can produce recombinant AAV.

DETAILED DESCRIPTION OF THE INVENTIONS

Figure 1:
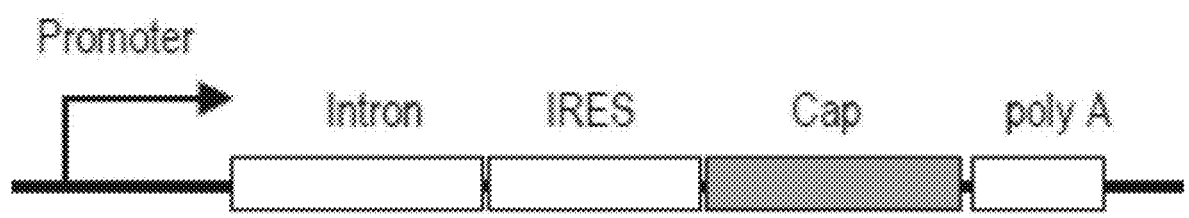
FIG. 1 is a schematic diagram of a polynucleotide comprising a promoter, an intron, an internal ribosome entry site (IRES), a polynucleotide encoding AAV Cap protein and a polyadenylation site (poly A).

Unless defined otherwise, all technical and scientific terms used herein have the same meaning as commonly understood by one of ordinary skill in the art to which these inventions belong.

Definitions

The term "about" in the context of numerical values and ranges refers to values or ranges that approximate or are close to the recited values or ranges such that the inventions can perform, such as having a sought rate, amount, degree, increase, decrease, or extent of expression, concentration, or time, as is apparent from the teachings contained herein. Thus, this term encompasses values beyond those simply resulting from systematic error. For example, "about" can signify values either above or below the stated value in a range of approx. +/−10% or more or less depending on the ability to perform.

"Intron" is a section of DNA located between exons. An intron is removed to form a mature messenger RNA. Preferred introns are those that can affect the starting point of translation, and exemplars are the hCMV-IE intron (Human cytomegalovirus immediate early protein) and FMDV intron (Foot and Mouth Disease Virus). The globin gene intron also has been reportedly used for expression.

A "nucleic acid moiety" includes any arrangement of single stranded or double stranded nucleotide sequences. Nucleic acid moieties can include, but are not limited to, polynucleotides, promoters, enhancers, operators, repressors, transcription termination signals, ribosomal entry sites and polyadenylation signals.

A "DNA cassette" or "cassette" is a type of nucleic acid moiety that comprises at least a promoter, at least one open reading frame and optionally a polyadenylation signal, for example an SV40 polyadenylation signal. Other nucleic acid moieties, such as operators, also are optional. A DNA cassette thus is a polynucleotide that comprises two or more shorter polynucleotides.

"Operably linked" refers to one or more nucleotide sequences in functional relationships with one or more other nucleotide sequences. Such functional relationships can directly or indirectly control, cause, regulate, enhance, facilitate, permit, attenuate, repress or block an action or activity in accordance with the selected design. Exemplars include single-stranded or double-stranded nucleic acid moieties, and can comprise two or more nucleotide sequences arranged within a given moiety in such a way that sequence(s) can exert at least one functional effect on other(s). For example, a promoter operably linked to the coding region of a DNA polynucleotide sequence can facilitate transcription of the coding region. Other elements, such as enhancers, operators, repressors, transcription termination signals, ribosomal entry sites and polyadenylation signals also can be operably linked with a polynucleotide of interest to control its expression. Arrangements and spacing to achieve operable linkages can be ascertained by approaches available to the person skilled in the art, such as screening using western blots and RT-PCR.

"Operator" indicates a DNA sequence that is introduced in or near a polynucleotide sequence in such a way that the polynucleotide sequence may be regulated by the interaction of a molecule capable of binding to the operator and, as a result, prevent or allow transcription of the polynucleotide sequence, as the case may be. One skilled in the art will recognize that the operator must be located sufficiently in proximity to the promoter such that it is capable of controlling or influencing transcription by the promoter, which can be considered a type of operable linkage. The operator may be placed either downstream or upstream of the promoter. These include, but are not limited to, the operator region of the Lex A gene of *E. coli*, which binds the Lex A peptide and the lactose and 45 tryptophan operators, which bind the repressor proteins encoded by the Lad and trpR genes of *E. coli*. The bacteriophage operators from the lambda Pi and the phage P22 Mnt and Arc. Preferred operators are the Tet (tetracycline) operator and the Arc operator. Operators can have a native sequence or a mutant sequence. For example, mutant sequences of the Tet operator are disclosed in Wissmann et al., *Nucleic Acids Res.* 14:4253-66 (1986).

The phrases "percent identity" or "% identical," in their various grammatical forms, when describing a sequence is meant to include homologous sequences that display the recited identity along regions of contiguous homology, but the presence of gaps, deletions, or insertions that have no homolog in the compared sequence are not taken into account in calculating percent identity. As used herein, a "percent identity" or "% identical" determination between homologs would not include a comparison of sequences where the homolog has no homologous sequence to compare in an alignment. Thus, "percent identity" and "% identical" do not include penalties for gaps, deletions, and insertions.

A "homologous sequence" in the context of nucleic acid sequences refers to a sequence that is substantially homologous to a reference nucleic acid sequence. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding nucleotides are identical over a relevant stretch of residues. In some embodiments, the relevant stretch is a complete (i.e., full) sequence.

"Polynucleotide" includes a sequence of nucleotides covalently joined, and includes RNA and DNA. Oligonucleotides are considered shorter polynucleotides. Genes are DNA polynucleotides (polydeoxyribonucleic acid) that ultimately encode polypeptides, which are translated from RNA (polyribonucleic acid) that was typically transcribed from DNA. DNA polynucleotides also can encode RNA polynucleotides that is not translated, but rather function as RNA "products". The type of polynucleotide (that is, DNA or RNA) is apparent from the context of the usage of the term.

A polynucleotide referred to or identified by the polypeptide it encodes sets forth and covers all suitable sequences in accordance with codon degeneracy. Polynucleotides, including those disclosed herein, include percent identity sequences and homologous sequences when indicated.

"Polypeptide" or "peptide" refers to sequence(s) of amino acids covalently joined. Polypeptides include natural, semi-synthetic and synthetic proteins and protein fragments. "Polypeptide" and "protein" can be used interchangeably. Oligopeptides are considered shorter polypeptides.

"Protein of interest" or "polypeptide of interest" can have any amino acid sequence, and includes any protein, polypeptide, or peptide, and derivatives, components, domains, chains and fragments thereof. Included are, but not limited to, viral proteins, bacterial proteins, fungal proteins, plant proteins and animal (including human) proteins. Protein types can include, but are not limited to, antibodies, bi-specific antibodies, multi-specific antibodies, antibody chains (including heavy and light), antibody fragments, Fv fragments, Fc fragments, Fc-containing proteins, Fc-fusion proteins, receptor Fc-fusion proteins, receptors, receptor domains, trap and mini-trap proteins, enzymes, factors, repressors, activators, ligands, reporter proteins, selection proteins, protein hormones, protein toxins, structural proteins, storage proteins, transport proteins, neurotransmitters and contractile proteins. Derivatives, components, chains and fragments of the above also are included. The sequences can be natural, semi-synthetic or synthetic. Proteins of interest and polypeptides of interest are encoded by "genes of interest," which also can be referred to as "polynucleotides of interest." Where multiple genes (same or different) are integrated, they can be referred to as "first," "second", "third," "fourth," "fifth," "sixth," "seventh," "eighth," "ninth," "tenth," etc. as is apparent from the context of use.

"Promoter" indicates a DNA sequence that cause transcription of a DNA sequence to which it is operably linked, i.e., linked in such a way as to permit transcription of the nucleotide sequence of interest when the appropriate signals are present and repressors are absent. The expression of a polynucleotide of interest may be placed under control of any promoter or enhancer element known in the art. A eukaryotic promoter can be operably linked to a TATA Box. The TATA Box is typically located upstream of the transcription start site.

Useful promoters that may be used include, but are not limited to, the SV40 early promoter region, SV40 E/L (early late) promoter, the promoter contained in the 3' long terminal repeat of Rous sarcoma virus, the regulatory sequences of the metallothionein gene, mouse or human cytomegalovirus major immediate early (CMV-MIE) promoter and other CMV promoters, including CMVmin promoters. Plant expression vectors comprising the nopaline synthetase promoter region, the cauliflower mosaic virus 35S RNA promoter, and the promoter of the photosynthetic enzyme ribulose biphosphate carboxylase; promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I; insulin; immunoglobulin; mouse mammary tumor virus; albumin; C.-feto protein; C.1-antitrypsin; 3-globin, and myosin light chain-2. Various forms of the CMV promoter can be used according to the inventions.

Minimal promoters, such as CMVmin promoters, can be truncated promoters or core promoters and are preferred for use in controlled expression systems. Minimal promoters and development approaches are widely known and disclosed in, for example, Saxena et al., *Methods Molec. Biol.* 1651:263-73 (2017); Ede et al., *ACS Synth Biol.* 5:395-404 (2016); Brown et al., *Biotech Bioeng.* 111:1638-47 (2014); Morita et al., *Biotechniques* 0:1-5 (2012); Lagrange et al., *Genes Dev.* 12:34-44 (1998). There are many CMVmin promoters described in the field.

"Reporter proteins" as used herein, refers to any protein capable of generating a detectable signal. Reporter proteins typically fluoresce, or catalyze a colorimetric or fluorescent reaction, and often are referred to as "fluorescent proteins" or "color proteins." However, a reporter protein also can be non-enzymatic and non-fluorescent as long as it can be detected by another protein or moiety, such as a cell surface protein detected with a fluorescent ligand. A reporter protein also can be an inactive protein that is made functional through interaction with another protein that is fluorescent or catalyzes a reaction. Accordingly, any suitable reporter protein, as understood by one of skill in the art, could be used. In some aspects, the reporter protein may be selected from fluorescent protein, luciferase, alkaline phosphatase, β-galactosidase, β-lactamase, dihydrofolate reductase, ubiquitin, and variants thereof. Fluorescent proteins are useful for the recognition of gene cassettes that have or have not been successfully inserted and/or replaced, as the case may be. Fluid cytometry and fluorescence-activated cell sorting are suitable for detection. Examples of fluorescent proteins are well-known in the art, including, but not limited to Discosoma coral (DsRed), green fluorescent protein (GFP), enhanced green fluorescent protein (eGFP), cyano fluorescent protein (CFP), enhanced cyano fluorescent protein (eCFP), yellow fluorescent protein (YFP), enhanced yellow fluorescent protein (eYFP) and far-red fluorescent protein (e.g. mKate, mKate2, mPlum, mRaspberry or E2-crimson. See, for example, U.S. Pat. Nos. 9,816,110. Reporter proteins are encoded by polynucleotides, and are referred to herein as "reporter genes" or "reporter protein genes." Reporters can be considered a type of marker. "Color" or "fluorescent," in their various grammatical forms, also can be used the more specifically refer to a reporter protein or gene . . .

A "repressor protein", also referred to as a "repressor," is a protein that can bind to DNA in order to repressor transcription. Repressors are of eukaryotic and prokaryotic origin. Prokaryotic repressors are preferred. Examples of repressor families include: TetR, LysR, Lacl, ArsR, IclR, MerR, AsnC, MarR, DeoR, GntR and Crp families. Repressor proteins in the TetR family include: ArcR, Actll, AmeR, AmrR, ArpR, BpeR, EnvR, EthR, HemR, HydR, IfeR, LanK, LfrR, LmrA, MtrR, Pip, PqrA, QacR, RifQ, RmrR, SimReg2, SmeT, SrpR, TcmR, TetR, TtgR, TrgW, UrdK, VarR YdeS, ArpA., BarA, Aur1B, CalR1, CprB, FarA, JadR*, JadR2, MphB, NonG, PhlF, TylQ, VanT, TarA, TyIP, BM1P1, Bm3R1, ButR, CampR, CamR, DhaR, KstR, LexA-like, AcnR, PaaRR, Psbl, Th1R, UidR, YDH1, Betl, McbR, MphR, PhaD, Q9ZF45, TtK, Yhgd, YixD, CasR, IcaR, LitR, LuxR, LuxT, OpaR, Orf2, SmcR, HapR, Ef0113, HlyIIR, BarB, ScbR, MmfR, AmtR, PsrA andYjdC proteins See Ramos et al., *Microbiol. Mol. Biol. Rev.,* 69:326-56 (2005). Still other repressors include PurR, LacR, MetJ and PadR, Repressor proteins are encoded by genes referred to as "repressor genes" or "repressor protein genes."

"Selectable" or "selection" marker proteins include proteins conferring certain traits, including but not limited to drug resistance or other selective advantages. Selection markers can give the cell receiving the selectable marker gene resistance towards a certain toxin, drug, antibiotic or other compound and permit the cell to produce protein and propagate in the presence of the toxin, drug, antibiotic or other compound, and are often referred to as "positive selectable markers." Suitable examples of antibiotic resistance markers include, but are not limited to, proteins that impart resistance to various antibiotics, such as kanamycin, spectinomycin, neomycin, gentamycin (G418), ampicillin, tetracycline, chloramphenicol, puromycin, hygromycin, zeocin, and/or blasticidin. There are other selectable markers, often referred to as "negative selectable markers," which cause a cell to stop propagating, stop protein production and/or are lethal to the cell in the presence of the negative selectable marker proteins. Thymidine kinase and certain fusion proteins can serve as negative selectable markers, including but not limited to GyrB-PKR. See White et al., *Biotechniques,* 50:303-309 (May 2011). Selectable marker proteins and corresponding genes can be referred to generically as first (1), second (2), third (3), fourth (4), fifth (5), sixth (6), seventh (7), eighth (8), ninth (9), tenth (10), etc., as is apparent from the context of usage . . .

All numerical limits and ranges set forth herein include all numbers or values thereabout or there between of the numbers of the range or limit. The ranges and limits described herein expressly denominate and set forth all integers, decimals and fractional values defined and encompassed by the range or limit.

DESCRIPTION

The inventions provide cells comprising AAV and optionally Ad polynucleotide sequences to allow production of recombinant AAV comprising a polynucleotide of interest, such as a gene or other sequence encoding a polypeptide of interest. The AAV and Ad polynucleotides provide the requisite structural and helper products required for AAV production.

AAV polynucleotides, and optionally Ad polynucleotides, can be integrated using a recombinase-mediated cassette exchange (RMCE), for example. "Stable" in the context of cell integration refers to a polynucleotide of interest, such as a gene, introduced into the genome of a cell and can be passed to subsequent generations of cells, and thereby can provide cell lines that are genetically homogeneous for a period of time.

Cells that are suitable for use with the inventions can be readily selected by those of skill in the art. In some embodiments the cell line is a eukaryotic cell line such as a yeast cell line, insect cell line (for example, Sf9 and Sf21 cells) or a mammalian cell line. Preferred mammalian cells include primate cells (including human), canine cells and rodent cells. Cells can be primary cells or immortalized cells. Suitable cells can be selected from Vero cells, COS cells, HEK 293 cells, HeLa cells, CHO cells, BHK cells, MDCK cells, amniotic cells (human), embryonic cells, cell lines transfected with viral genes, for example, AD5 E1, including but not limited to an immortalized human retinal cell transfected with an adenovirus gene, for example, a PER.C6 cell, or an NSO cell. In some embodiments, the cell is a Chinese hamster ovary (CHO) cell line. Some examples of CHO cells include, but are not limited to, CHO-ori, CHO-K1, CHO-s, CHO-DHB11, CHO-DXB11, CHO-K1SV, and mutants and variants thereof. In other embodiments, the cell is a HEK293 cell. Some examples of HEK293 cells include, but are not limited, to HEK293, HEK293A, HEK293E, HEK293F, HEK293FT, HEK293FTM, HEK293H, HEK293MSR, HEK293S, HEK293SG, HEK293SGGD, HEK293T and mutants and variants thereof.

For hamster cells such as CHO and BHK, integration can be accomplished by inventions disclosed in U.S. Pat. No. 7,771,997 ("Stable Site 1") and 9,816,110 ("Stable Site 2"), which are hereby incorporated by reference, including sequence information. Regeneron provides a suite of goods and services referred to as EESYR®. CHO cells with integrated sequences in Stable Site 1 and Stable Site 2 are disclosed in US 2019/0233544 A1, which is hereby incorporated by reference, including sequence information. Sequences set forth in these patents and Examples 14 and 15 can be used according to the inventions described and depicted herein. Additionally, an AAVS1-like region and the COSMC locus in hamster cells can be used according to the inventions.

Where human cells are employed, integration into adeno-associated virus integration site 1 (AAVS1) can be undertaken. See Lou et al., *Human Gene Therapy Methods,* 28:124-38 (2017); Liu et al., *BMC Research Note,* 7:626 (2014). AAVS1 is reported to be located on chromosome 19. Other integration sites in human cells can be used as well, such as CCR5 and hROSA26.

Modification of cellular genomes can be undertaken with known approaches, such as Cre/Lox, Flp/Frt, transcription activator-like effector nuclease (TALEN), a TAL effector domain fusion protein, zinc finger nuclease (ZFN), a ZFN dimer, or a RNA-guided DNA endonuclease system, such as CRISPR/Cas9. See U.S. Pat. No. 9,816,110 at cols. 17-18. Integration using Bxb1 integrase in human, mouse and rat cells also can be undertaken. Russell et al., *Biotechniques* 40:460-64 (2006).

To maximize stability and efficiency and facilitate integration and control of the inventions, Stable Integration Sites (SIS) can be created using Genomic Safe Harbors and the like in a wide variety of cell types and lines according to the teachings of U.S. Ser. No. 63/256,675. The descriptions (including examples) and figures providing methods and cells resulting from the methods of U.S. Ser. No. 63/256,675 are hereby incorporated by reference.

For production of recombinant AAV, the inventions provide for integration of AAV Cap to produce size variants VP1 (about 90 kDa), VP2 (about 72 kDa) and VP3 (about 60 kDa). The variants differ at their N-terminus.

Usually, recombinant AAV will contain a gene-of-interest (GOI) flanked by AAV ITRs (inverted terminal repeats), For production of recombinant AAV, seven additional polynucleotides, namely adenovirus E1A, E1B, E4, E2A, VA RNA and AAV Rep and Cap, are typically employed for production.

FIGS. 1-4 depict constructs that permit constitutive expression of Cap protein. FIGS. 5-8 depict constructs that permit controlled expression of Cap protein by inclusion of an operator downstream of the promoter. A preferred operator is the tetracycline operator (TetO), which binds the tetracycline repressor (TetR). Tetracycline, doxycycline and derivatives thereof can bind TetR so that TetR no longer binds TetO, and thus is permissive for transcription. An example of a CMV promoter and TetO is set forth in Example 13.

The inventions is further described by the following examples, which are illustrative of the many aspects of the invention, but do not limit the inventions in any manner.

Example 1—CHO Cells

One or more Cap-containing polynucleotides according to FIGS. 1-8 are stably inserted into the CHO genome. A preferred promoter is the hCMV-IE promoter, and optionally a tet operator can be operably linked to the promoter for expression control. Optionally, an intron can be located 3' of the promoter. A preferred intron is an hCMV-IE intron. AAV Cap, Rep and ITRs can be obtained from any AAV serotype. Preferred AAV serotypes are AAV2 and AAV5. AAV polynucleotide sequences are set forth in Example 11. Promoter, operator, IRES and intron sequences are set forth in Example 13.

AAV ITRs flanking a gene of interest, AAV Rep and Ad E1A, E1B, E2A (or E2A partial sequence (E2A orf)), E4 (or E4 partial sequence (E4 orf 6)) and VA RNA can be randomly integrated, site-specifically integrated or remain on a plasmid. Adenovirus polynucleotide sequences are available and are exemplified in Example 12. Adenovirus (Ad) proteins and polynucleotides can be selected from any serotype.

Example 2—HEK 293 Cells

One or more Cap-containing polynucleotides according to FIGS. 1-8 are stably inserted into the HEK 293 genome. A preferred promoter is the hCMV-IE promoter, and optionally a tet operator can be operably linked to the promoter for expression control. Optionally, an intron can be located 3' of the promoter. A preferred intron is an hCMV-IE intron. AAV Cap, Rep and ITRs can be obtained from any AAV serotype. Preferred AAV serotypes of AAV2 and AAV5. AAV polynucleotide sequences are set forth in Example 11.

AAV ITRs and Rep and Ad E1A, E1B, E2A (or E2A partial sequence (E2A orf)), E4 (or E4 partial sequence (E4 orf 6)) and VA RNA can be randomly integrated, site-specifically integrated or remain on a plasmid. Adenovirus polynucleotide sequences are available and are exemplified in Example 12.

Example 3—BHK Cells

BHK cells are fibroblast cells from baby hamster kidneys. There are adherent BHK lines and BHK lines that can propagate in suspension. Wentz and Schügerl, *Enzyme Microbial Tech.* 14:68-75 (1992).

One or more Cap-containing polynucleotides according to FIGS. 1-8 are stably inserted into the BHK genome. A preferred promoter is the hCMV-IE promoter, and optionally a tet operator can be operably linked to the promoter for expression control. Optionally, an intron can be located 3' of the promoter. A preferred intron is an hCMV-IE intron. AAV Cap, Rep and ITRs can be obtained from any AAV serotype. Preferred AAV serotypes of AAV2 and AAV5. AAV polynucleotide sequences are set forth in Example 11.

AAV ITRs and Rep and Ad E1A, E1B, E2A (or E2A partial sequence (E2A orf)), E4 (or E4 partial sequence (E4 orf 6)) and VA RNA can be randomly integrated, site-specifically integrated or remain on a plasmid. Adenovirus polynucleotide sequences are available and are exemplified in Example 12.

Example 4—Intron IRES CAP

Embodiments of this construct are depicted in FIG. 1 (constitutive) and 5 (controllable). In a cell, both embodiments can primarily produce VP2 and VP3, with more VP3 being produced than VP2. In an experiment in CHO cells using Cap5, an average ratio of about 1:5.7 of VP2 to VP3 was observed by conducting densitometry analyses on western blots. Some VP1 also can be produced, but the level observed was typically less than 1% the level of VP2 that is produced. Accordingly, this construct can be used with a construct that will produce primarily VP1. See Examples 6 and 7. Production ratios can vary based upon experimental conditions and analytical techniques. A preferred IRES is the encephalomyocarditis virus (referred to as "EMCV" or "ECMV") IRES.

Example 5—Intron IRES CAP IRES CAP

Figure 2:
FIG. 2 is a schematic diagram of a polynucleotide comprising a promoter, an intron, two internal ribosome entry sites, two polynucleotides encoding AAV Cap protein and a polyadenylation site.

Embodiments of this construct are depicted in FIG. 2 (constitutive) and 6 (controllable). This construct contains two IRES polynucleotides and two Cap polynucleotides. In a cell, both embodiments can produce a VP1, VP2 and VP3. The amount of VP3 production can be greater than the amount of VP1 production and the amount of VP2 production. The amount of VP2 production can be greater than the amount of VP1 production. In an experiment using CHO cells containing Cap5, an average ratio of about 1:2:9.3 of VP1 to VP2 to VP3 was observed by conducting densitometry analyses on western blots. Production ratios can vary based upon experimental conditions and analytical techniques. A preferred IRES is the encephalomyocarditis virus (referred to as "EMCV" or "ECMV") IRES.

Example 6—Intron CAP

Figure 3:
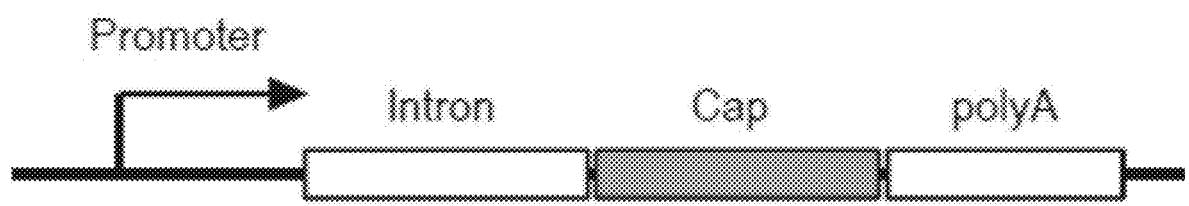
FIG. 3 is a schematic diagram of a polynucleotide comprising a promoter, an intron, a polynucleotide encoding AAV Cap protein and a polyadenylation site.

Embodiments of this construct are depicted in FIG. 3 (constitutive) and 7 (controllable). This construct contains an Intron and Cap polynucleotide, and produces predominantly VP1, and can be used with the constructs of Example 4 to produce VP1, VP2 and VP3.

Example 7—IRES CAP

Figure 4:
FIG. 4 is a schematic diagram of a polynucleotide comprising a promoter, an internal ribosome entry site, a polynucleotide encoding AAV Cap protein and a polyadenylation site.
Figure 5:
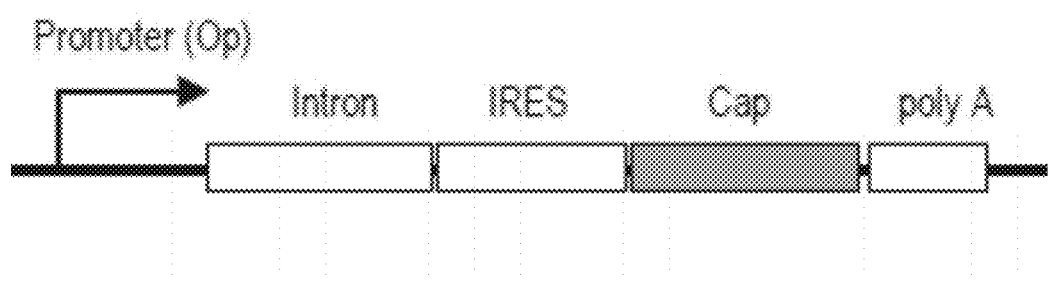
FIG. 5 is a schematic diagram of a polynucleotide comprising a promoter with operator (Op), an intron, an internal ribosome entry site, a polynucleotide encoding AAV Cap protein and a polyadenylation site.

Embodiments of this construct are depicted in FIG. 4 (constitutive) and 8 (controllable). This construct contains an Intron and Cap polynucleotide, and produces predominantly VP1, and can be used with the constructs of Example 4 to produce VP1, VP2 and VP3. A preferred IRES is the encephalomyocarditis virus (referred to as "EMCV" or "ECMV") IRES.

Example 8—CHO Cells Comprising Cap Constructs

Figure 6:
FIG. 6 is a schematic diagram of a polynucleotide comprising a promoter with operator (Op), an intron, two internal ribosome entry sites, two polynucleotides encoding AAV Cap protein and a polyadenylation site.
Figure 7:
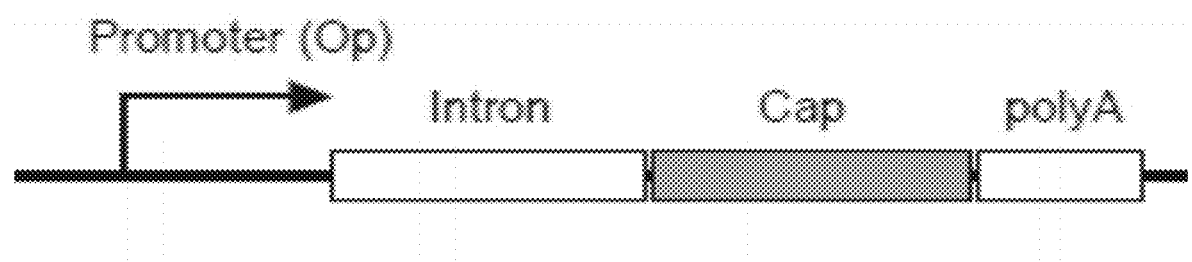
FIG. 7 is a schematic diagram of a polynucleotide comprising a promoter with operator (Op), an intron, a polynucleotide encoding AAV Cap protein and a polyadenylation site.

CHO cells of Example 1 can comprise an Intron IRES CAP IRES CAP polynucleotide of Example 5 (FIG. 2 or 6). In an experiment, CHO cells containing Cap5 expressed VP1: VP2: VP3 in an observed ratio of about 1:2:9.3 by conducting densitometry analyses on western blots.

Figure 8:
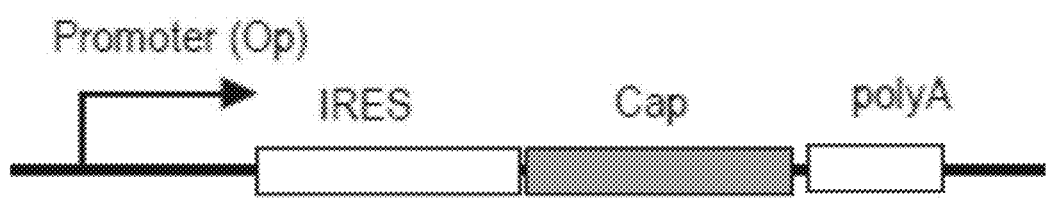
FIG. 8 is a schematic diagram of a polynucleotide comprising a promoter with operator (Op), an internal ribosome entry site, a polynucleotide encoding AAV Cap protein and a polyadenylation site.

As an alternative, CHO cells of Example 1 can comprise CAP polynucleotides of Example 4 (FIG. 1 or 5) and Examples 6 (FIG. 3 or 7) or 6 (FIGS. 4 and 8). Such cells would express VP1, VP2 and VP3, although possibly at different ratios than according to Example 5.

Example 9—HEK 293 Cells Comprising Cap Constructs

HEK 293 cells of Example 2 can comprise an Intron IRES CAP IRES CAP polynucleotide of Example 5 (FIG. 2 or 6).

As an alternative, HEK 293 cells of Example 2 can comprise CAP polynucleotides of Example 4 (FIG. 1 or 5) and Examples 6 (FIG. 3 or 7) or 7 (FIGS. 4 and 8). Such cells would express VP1, VP2 and VP3, although possibly at different ratios than according to Example 5.

Example 10—BHK Cells Comprising Cap Constructs

BHK cells of Example 3 can comprise an Intron IRES CAP IRES CAP polynucleotide of Example 5 (FIG. 2 or 6).

As an alternative, BHK cells of Example 3 can comprise CAP polynucleotides of Example 4 (FIG. 1 or 5) and Examples 6 (FIG. 3 or 7) or 7 (FIGS. 4 and 8). Such cells would express VP1, VP2 and VP3, although possibly at different ratios than according to Example 5.

Example 11-AAV Polynucleotide Sequences

AAV Rep, Cap and ITR sequences are known in the art. The present inventions are amenable to all AAV serotypes. AAV sequences from various AAV serotypes are set forth below. Many of these sequences are available from the National Center for Biotechnology Information (NCBI).

AAV-1

Full Genome: NC_002077

```
CapVP1:
                                                            (SEQ ID NO: 1)
ATGGCTGCCGATGGTTATCTTCCAGATTGGCTCGAGGACAACCTCTCTGAGGGCATTCGCGAGTGGTGGGACTTG

AAACCTGGAGCCCCGAAGCCCAAAGCCAACCAGCAAAAGCAGGACGACGGCCGGGGTCTGGTGCTTCCTGGCTAC

AAGTACCTCGGACCCTTCAACGGACTCGACAAGGGGGAGCCCGTCAACGCGGCGGACGCAGCGGCCCTCGAGCAC

GACAAGGCCTACGACCAGCAGCTCAAAGCGGGTGACAATCCGTACCTGCGGTATAACCACGCCGACGCCGAGTTT

CAGGAGCGTCTGCAAGAAGATACGTCTTTTGGGGGCAACCTCGGGCGAGCAGTCTTCCAGGCCAAGAAGCGGGTT

CTCGAACCTCTCGGTCTGGTTGAGGAAGGCGCTAAGACGGCTCCTGGAAAGAAACGTCCGGTAGAGCAGTCGCCA

CAAGAGCCAGACTCCTCCTCGGGCATCGGCAAGACAGGCCAGCAGCCCGCTAAAAAGAGACTCAATTTTGGTCAG

ACTGGCGACTCAGAGTCAGTCCCCGATCCACAACCTCTCGGAGAACCTCCAGCAACCCCCGCTGCTGTGGGACCT

ACTACAATGGCTTCAGGCGGTGGCGCACCAATGGCAGACAATAACGAAGGCGCCGACGGAGTGGGTAATGCCTCA

GGAAATTGGCATTGCGATTCCACATGGCTGGGCGACAGAGTCATCACCACCAGCACCCGCACCTGGGCCTTGCCC

ACCTACAATAACCACCTCTACAAGCAAATCTCCAGTGCTTCAACGGGGGCCAGCAACGACAACCACTACTTCGGC

TACAGCACCCCCTGGGGGTATTTTGATTTCAACAGATTCCACTGCCACTTTTCACCACGTGACTGGCAGCGACTC

ATCAACAACAATTGGGGATTCCGGCCCAAGAGACTCAACTTCAAACTCTTCAACATCCAAGTCAAGGAGGTCACG

ACGAATGATGGCGTCACAACCATCGCTAATAACCTTACCAGCACGGTTCAAGTCTTCTCGGACTCGGAGTACCAG

CTTCCGTACGTCCTCGGCTCTGCGCACCAGGGCTGCCTCCCTCCGTTCCCGGCGGACGTGTTCATGATTCCGCAA

TACGGCTACCTGACGCTCAACAATGGCAGCCAAGCCGTGGGACGTTCATCCTTTTACTGCCTGGAATATTTCCCT

TCTCAGATGCTGAGAACGGGCAACAACTTTACCTTCAGCTACACCTTTGAGGAAGTGCCTTTCCACAGCAGCTAC

GCGCACAGCCAGAGCCTGGACCGGCTGATGAATCCTCTCATCGACCAATACCTGTATTACCTGAACAGAACTCAA

AATCAGTCCGGAAGTGCCCAAAACAAGGACTTGCTGTTTAGCCGTGGGTCTCCAGCTGGCATGTCTGTTCAGCCC

AAAAACTGGCTACCTGGACCCTGTTATCGGCAGCAGCGCGTTTCTAAAACAAAAACAGACAACAACAACAGCAAT

TTTACCTGGACTGGTGCTTCAAAATATAACCTCAATGGGCGTGAATCCATCATCAACCCTGGCACTGCTATGGCC

TCACACAAAGACGACGAAGACAAGTTCTTTCCCATGAGCGGTGTCATGATTTTTGGAAAAGAGAGCGCCGGAGCT

TCAAACACTGCATTGGACAATGTCATGATTACAGACGAAGAGGAAATTAAAGCCACTAACCCTGTGGCCACCGAA

AGATTTGGGACCGTGGCAGTCAATTTCCAGAGCAGCAGCACAGACCCTGCGACCGGAGATGTGCATGCTATGGGA

GCATTACCTGGCATGGTGTGGCAAGATAGAGACGTGTACCTGCAGGGTCCCATTTGGGCCAAAATTCCTCACACA

GATGGACACTTTCACCCGTCTCCTCTTATGGGCGGCTTTGGACTCAAGAACCCGCCTCCTCAGATCCTCATCAAA

AACACGCCTGTTCCTGCGAATCCTCCGGCGGAGTTTTCAGCTACAAAGTTTGCTTCATTCATCACCCAATACTCC

ACAGGACAAGTGAGTGTGGAAATTGAATGGGAGCTGCAGAAAGAAAACAGCAAGCGCTGGAATCCCGAAGTGCAG

TACACATCCAATTATGCAAAATCTGCCAACGTTGATTTTACTGTGGACAACAATGGACTTTATACTGAGCCTCGC

CCCATTGGCACCCGTTACCTTACCCGTCCCCTGTAA

Rep78:
                                                            (SEQ ID NO: 2)
ATGCCGGGCTTCTACGAGATCGTGATCAAGGTGCCGAGCGACCTGGACGAGCACCTGCCGGGCATTTCTGACTCG

TTTGTGAGCTGGGTGGCCGAGAAGGAATGGGAGCTGCCCCCGGATTCTGACATGGATCTGAATCTGATTGAGCAG
```

-continued

```
GCACCCCTGACCGTGGCCGAGAAGCTGCAGCGCGACTTCCTGGTCCAATGGCGCCGCGTGAGTAAGGCCCCGGAG

GCCCTCTTCTTTGTTCAGTTCGAGAAGGGCGAGTCCTACTTCCACCTCCATATTCTGGTGGAGACCACGGGGGTC

AAATCCATGGTGCTGGGCCGCTTCCTGAGTCAGATTAGGGACAAGCTGGTGCAGACCATCTACCGCGGGATCGAG

CCGACCCTGCCCAACTGGTTCGCGGTGACCAAGACGCGTAATGGCGCCGGAGGGGGGAACAAGGTGGTGGACGAG

TGCTACATCCCCAACTACCTCCTGCCCAAGACTCAGCCCGAGCTGCAGTGGGCGTGGACTAACATGGAGGAGTAT

ATAAGCGCCTGTTTGAACCTGGCCGAGCGCAAACGGCTCGTGGCGCAGCACCTGACCCACGTCAGCCAGACCCAG

GAGCAGAACAAGGAGAATCTGAACCCCAATTCTGACGCGCCTGTCATCCGGTCAAAAACCTCCGCGCGCTACATG

GAGCTGGTCGGGTGGCTGGTGGACCGGGGCATCACCTCCGAGAAGCAGTGGATCCAGGAGGACCAGGCCTCGTAC

ATCTCCTTCAACGCCGCTTCCAACTCGCGGTCCCAGATCAAGGCCGCTCTGGACAATGCCGGCAAGATCATGGCG

CTGACCAAATCCGCGCCCGACTACCTGGTAGGCCCCGCTCCGCCCGCGGACATTAAAACCAACCGCATCTACCGC

ATCCTGGAGCTGAACGGCTACGAACCTGCCTACGCCGGCTCCGTCTTTCTCGGCTGGGCCCAGAAAAGGTTCGGG

AAGCGCAACACCATCTGGCTGTTTGGGCCGGCCACCACGGGCAAGACCAACATCGCGGAAGCCATCGCCCACGCC

GTGCCCTTCTACGGCTGCGTCAACTGGACCAATGAGAACTTTCCCTTCAATGATTGCGTCGACAAGATGGTGATC

TGGTGGGAGGAGGGCAAGATGACGGCCAAGGTCGTGGAGTCCGCCAAGGCCATTCTCGGCGGCAGCAAGGTGCGC

GTGGACCAAAAGTGCAAGTCGTCCGCCCAGATCGACCCCACCCCCGTGATCGTCACCTCCAACACCAACATGTGC

GCCGTGATTGACGGGAACAGCACCACCTTCGAGCACCAGCAGCCGTTGCAGGACCGGATGTTCAAATTTGAACTC

ACCCGCCGTCTGGAGCATGACTTTGGCAAGGTGACAAAGCAGGAAGTCAAAGAGTTCTTCCGCTGGGCGCAGGAT

CACGTGACCGAGGTGGCGCATGAGTTCTACGTCAGAAAGGGTGGAGCCAACAAAAGACCCGCCCCCGATGACGCG

GATAAAAGCGAGCCCAAGCGGGCCTGCCCCTCAGTCGCGGATCCATCGACGTCAGACGCGGAAGGAGCTCCGGTG

GACTTTGCCGACAGGTACCAAAACAAATGTTCTCGTCACGCGGGCATGCTTCAGATGCTGTTTCCCTGCAAGACA

TGCGAGAGAATGAATCAGAATTTCAACATTTGCTTCACGCACGGGACGAGAGACTGTTCAGAGTGCTTCCCCGGC

GTGTCAGAATCTCAACCGGTCGTCAGAAAGAGGACGTATCGGAAACTCTGTGCCATTCATCATCTGCTGGGCGG

GCTCCCGAGATTGCTTGCTCGGCCTGCGATCTGGTCAACGTGGACCTGGATGACTGTGTTTCTGAGCAATAA
```

AAV-2
Full Genome: NC_001401

Rep78:
(SEQ ID NO: 3)
```
ATGCCGGGGTTTTACGAGATTGTGATTAAGGTCCCCAGCGACCTTGACGAGCATCTGCCCGGCATTTCTGACAGC

TTTGTGAACTGGGTGGCCGAGAAGGAATGGGAGTTGCCGCCAGATTCTGACATGGATCTGAATCTGATTGAGCAG

GCACCCCTGACCGTGGCCGAGAAGCTGCAGCGCGACTTTCTGACGGAATGGCGCCGTGTGAGTAAGGCCCCGGAG

GCCCTTTTCTTTGTGCAATTTGAGAAGGGAGAGAGCTACTTCCACATGCACGTGCTCGTGGAAACCACCGGGGTG

AAATCCATGGTTTTGGGACGTTTCCTGAGTCAGATTCGCGAAAAACTGATTCAGAGAATTTACCGCGGGATCGAG

CCGACTTTGCCAAACTGGTTCGCGGTCACAAAGACCAGAAATGGCGCCGGAGGCGGGAACAAGGTGGTGGATGAG

TGCTACATCCCCAATTACTTGCTCCCCAAAACCCAGCCTGAGCTCCAGTGGGCGTGGACTAATATGGAACAGTAT

TTAAGCGCCTGTTTGAATCTCACGGAGCGTAAACGGTTGGTGGCGCAGCATCTGACGCACGTGTCGCAGACGCAG

GAGCAGAACAAAGAGAATCAGAATCCCAATTCTGATGCGCCGGTGATCAGATCAAAAACTTCAGCCAGGTACATG

GAGCTGGTCGGGTGGCTCGTGGACAAGGGGATTACCTCGGAGAAGCAGTGGATCCAGGAGGACCAGGCCTCATAC

ATCTCCTTCAATGCGGCCTCCAACTCGCGGTCCCAAATCAAGGCTGCCTTGGACAATGCGGGAAAGATTATGAGC

CTGACTAAAACCGCCCCCGACTACCTGGTGGGCCAGCAGCCCGTGGAGGACATTTCCAGCAATCGGATTTATAAA

ATTTTGGAACTAAACGGGTACGATCCCCAATATGCGGCTTCCGTCTTTCTGGGATGGGCCACGAAAAAGTTCGGC

AAGAGGAACACCATCTGGCTGTTTGGGCCTGCAACTACCGGGAAGACCAACATCGCGGAGGCCATAGCCCACACT
```

-continued

```
GTGCCCTTCTACGGGTGCGTAAACTGGACCAATGAGAACTTTCCCTTCAACGACTGTGTCGACAAGATGGTGATC

TGGTGGGAGGAGGGGAAGATGACCGCCAAGGTCGTGGAGTCGGCCAAAGCCATTCTCGGAGGAAGCAAGGTGCGC

GTGGACCAGAAATGCAAGTCCTCGGCCCAGATAGACCCGACTCCCGTGATCGTCACCTCCAACACCAACATGTGC

GCCGTGATTGACGGGAACTCAACGACCTTCGAACACCAGCAGCCGTTGCAAGACCGGATGTTCAAATTTGAACTC

ACCCGCCGTCTGGATCATGACTTTGGGAAGGTCACCAAGCAGGAAGTCAAAGACTTTTTCCGGTGGGCAAAGGAT

CACGTGGTTGAGGTGGAGCATGAATTCTACGTCAAAAAGGGTGGAGCCAAGAAAAGACCCGCCCCCAGTGACGCA

GATATAAGTGAGCCCAAACGGGTGCGCGAGTCAGTTGCGCAGCCATCGACGTCAGACGCGGAAGCTTCGATCAAC

TACGCAGACAGGTACCAAAACAAATGTTCTCGTCACGTGGGCATGAATCTGATGCTGTTTCCCTGCAGACAATGC

GAGAGAATGAATCAGAATTCAAATATCTGCTTCACTCACGGACAGAAAGACTGTTTAGAGTGCTTTCCCGTGTCA

GAATCTCAACCCGTTTCTGTCGTCAAAAAGGCGTATCAGAAACTGTGCTACATTCATCATATCATGGGAAAGGTG

CCAGACGCTTGCACTGCCTGCGATCTGGTCAATGTGGATTTGGATGACTGCATCTTTGAACAATAA
```

Rep52:
                                                                (SEQ ID NO: 4)
```
ATGGAGCTGGTCGGGTGGCTCGTGGACAAGGGGATTACCTCGGAGAAGCAGTGGATCCAGGAGGACCAGGCCTCA

TACATCTCCTTCAATGCGGCCTCCAACTCGCGGTCCCAAATCAAGGCTGCCTTGGACAATGCGGGAAAGATTATG

AGCCTGACTAAAACCGCCCCCGACTACCTGGTGGGCCAGCAGCCCGTGGAGGACATTTCCAGCAATCGGATTTAT

AAAATTTTGGAACTAAACGGGTACGATCCCCAATATGCGGCTTCCGTCTTTCTGGGATGGGCCACGAAAAAGTTC

GGCAAGAGGAACACCATCTGGCTGTTTGGGCCTGCAACTACCGGGAAGACCAACATCGCGGAGGCCATAGCCCAC

ACTGTGCCCTTCTACGGGTGCGTAAACTGGACCAATGAGAACTTTCCCTTCAACGACTGTGTCGACAAGATGGTG

ATCTGGTGGGAGGAGGGGAAGATGACCGCCAAGGTCGTGGAGTCGGCCAAAGCCATTCTCGGAGGAAGCAAGGTG

CGCGTGGACCAGAAATGCAAGTCCTCGGCCCAGATAGACCCGACTCCCGTGATCGTCACCTCCAACACCAACATG

TGCGCCGTGATTGACGGGAACTCAACGACCTTCGAACACCAGCAGCCGTTGCAAGACCGGATGTTCAAATTTGAA

CTCACCCGCCGTCTGGATCATGACTTTGGGAAGGTCACCAAGCAGGAAGTCAAAGACTTTTTCCGGTGGGCAAAG

GATCACGTGGTTGAGGTGGAGCATGAATTCTACGTCAAAAAGGGTGGAGCCAAGAAAAGACCCGCCCCCAGTGAC

GCAGATATAAGTGAGCCCAAACGGGTGCGCGAGTCAGTTGCGCAGCCATCGACGTCAGACGCGGAAGCTTCGATC

AACTACGCAGACAGGTACCAAAACAAATGTTCTCGTCACGTGGGCATGAATCTGATGCTGTTTCCCTGCAGACAA

TGCGAGAGAATGAATCAGAATTCAAATATCTGCTTCACTCACGGACAGAAAGACTGTTTAGAGTGCTTTCCCGTG

TCAGAATCTCAACCCGTTTCTGTCGTCAAAAAGGCGTATCAGAAACTGTGCTACATTCATCATATCATGGGAAAG

GTGCCAGACGCTTGCACTGCCTGCGATCTGGTCAATGTGGATTTGGATGACTGCATCTTTGAACAATAA
```

CapVP1:
                                                                (SEQ ID NO: 5)
```
ATGGCTGCCGATGGTTATCTTCCAGATTGGCTCGAGGACACTCTCTCTGAAGGAATAAGACAGTGGTGGAAGCTC

AAACCTGGCCCACCACCACCAAAGCCCGCAGAGCGGCATAAGGACGACAGCAGGGGTCTTGTGCTTCCTGGGTAC

AAGTACCTCGGACCCTTCAACGGACTCGACAAGGGAGAGCCGGTCAACGAGGCAGACGCCGCGGCCCTCGAGCAC

GACAAAGCCTACGACCGGCAGCTCGACAGCGGAGACAACCCGTACCTCAAGTACAACCACGCCGACGCGGAGTTT

CAGGAGCGCCTTAAAGAAGATACGTCTTTTGGGGGCAACCTCGGACGAGCAGTCTTCCAGGCGAAAAAGAGGGTT

CTTGAACCTCTGGGCCTGGTTGAGGAACCTGTTAAGACGGCTCCGGGAAAAAAGAGGCCGGTAGAGCACTCTCCT

GTGGAGCCAGACTCCTCCTCGGGAACCGGAAAGGCGGGCCAGCAGCCTGCAAGAAAAAGATTGAATTTTGGTCAG

ACTGGAGACGCAGACTCAGTACCTGACCCCCAGCCTCTCGGACAGCCACCAGCAGCCCCTCTGGTCTGGGAACT

AATACGATGGCTACAGGCAGTGGCGCACCAATGGCAGACAATAACGAGGGCGCCGACGGAGTGGGTAATTCCTCG

GGAAATTGGCATTGCGATTCCACATGGATGGGCGACAGAGTCATCACCACCAGCACCCGAACCTGGGCCCTGCCC

ACCTACAACAACCACCTCTACAAACAAATTTCCAGCCAATCAGGAGCCTCGAACGACAATCACTACTTTGGCTAC
```

-continued

AGCACCCCTTGGGGGTATTTTGACTTCAACAGATTCCACTGCCACTTTTCACCACGTGACTGGCAAAGACTCATC

AACAACAACTGGGGATTCCGACCCAAGAGACTCAACTTCAAGCTCTTTAACATTCAAGTCAAAGAGGTCACGCAG

AATGACGGTACGACGACGATTGCCAATAACCTTACCAGCACGGTTCAGGTGTTTACTGACTCGGAGTACCAGCTC

CCGTACGTCCTCGGCTCGGCGCATCAAGGATGCCTCCCGCCGTTCCCAGCAGACGTCTTCATGGTGCCACAGTAT

GGATACCTCACCCTGAACAACGGGAGTCAGGCAGTAGGACGCTCTTCATTTTACTGCCTGGAGTACTTTCCTTCT

CAGATGCTGCGTACCGGAAACAACTTTACCTTCAGCTACACTTTTGAGGACGTTCCTTTCCACAGCAGCTACGCT

CACAGCCAGAGTCTGGACCGTCTCATGAATCCTCTCATCGACCAGTACCTGTATTACTTGAGCAGAACAAACACT

CCAAGTGGAACCACCACGCAGTCAAGGCTTCAGTTTTCTCAGGCCGGAGCGAGTGACATTCGGGACCAGTCTAGG

AACTGGCTTCCTGGACCCTGTTACCGCCAGCAGCGAGTATCAAAGACATCTGCGGATAACAACAACAGTGAATAC

TCGTGGACTGGAGCTACCAAGTACCACCTCAATGGCAGAGACTCTCTGGTGAATCCGGGCCCGGCCATGGCAAGC

CACAAGGACGATGAAGAAAAGTTTTTTCCTCAGAGCGGGGTTCTCATCTTTGGGAAGCAAGGCTCAGAGAAAACA

AATGTGGACATTGAAAAGGTCATGATTACAGACGAAGAGGAAATCAGGACAACCAATCCCGTGGCTACGGAGCAG

TATGGTTCTGTATCTACCAACCTCCAGAGAGGCAACAGACAAGCAGCTACCGCAGATGTCAACACACAAGGCGTT

CTTCCAGGCATGGTCTGGCAGGACAGAGATGTGTACCTTCAGGGGCCCATCTGGGCAAAGATTCCACACACGGAC

GGACATTTTCACCCCTCTCCCCTCATGGGTGGATTCGGACTTAAACACCCTCCTCCACAGATTCTCATCAAGAAC

ACCCCGGTACCTGCGAATCCTTCGACCACCTTCAGTGCGGCAAAGTTTGCTTCCTTCATCACACAGTACTCCACG

GGACAGGTCAGCGTGGAGATCGAGTGGGAGCTGCAGAAGGAAAACAGCAAACGCTGGAATCCCGAAATTCAGTAC

ACTTCCAACTACAACAAGTCTGTTAATGTGGACTTTACTGTGGACACTAATGGCGTGTATTCAGAGCCTCGCCCC

ATTGGCACCAGATACCTGACTCGTAATCTGTAA

CapVP2: (SEQ ID NO: 6)

ACGGCTCCGGGAAAAAAGAGGCCGGTAGAGCACTCTCCTGTGGAGCCAGACTCCTCCTCGGGAACCGGAAAGGCG

GGCCAGCAGCCTGCAAGAAAAAGATTGAATTTTGGTCAGACTGGAGACGCAGACTCAGTACCTGACCCCCAGCCT

CTCGGACAGCCACCAGCAGCCCCCTCTGGTCTGGGAACTAATACGATGGCTACAGGCAGTGGCGCACCAATGGCA

GACAATAACGAGGGCGCCGACGGAGTGGGTAATTCCTCGGGAAATTGGCATTGCGATTCCACATGGATGGGCGAC

AGAGTCATCACCACCAGCACCCGAACCTGGGCCCTGCCCACCTACAACAACCACCTCTACAAACAAATTTCCAGC

CAATCAGGAGCCTCGAACGACAATCACTACTTTGGCTACAGCACCCCTTGGGGGTATTTTGACTTCAACAGATTC

CACTGCCACTTTTCACCACGTGACTGGCAAAGACTCATCAACAACAACTGGGGATTCCGACCCAAGAGACTCAAC

TTCAAGCTCTTTAACATTCAAGTCAAAGAGGTCACGCAGAATGACGGTACGACGACGATTGCCAATAACCTTACC

AGCACGGTTCAGGTGTTTACTGACTCGGAGTACCAGCTCCCGTACGTCCTCGGCTCGGCGCATCAAGGATGCCTC

CCGCCGTTCCCAGCAGACGTCTTCATGGTGCCACAGTATGGATACCTCACCCTGAACAACGGGAGTCAGGCAGTA

GGACGCTCTTCATTTTACTGCCTGGAGTACTTTCCTTCTCAGATGCTGCGTACCGGAAACAACTTTACCTTCAGC

TACACTTTTGAGGACGTTCCTTTCCACAGCAGCTACGCTCACAGCCAGAGTCTGGACCGTCTCATGAATCCTCTC

ATCGACCAGTACCTGTATTACTTGAGCAGAACAAACACTCCAAGTGGAACCACCACGCAGTCAAGGCTTCAGTTT

TCTCAGGCCGGAGCGAGTGACATTCGGGACCAGTCTAGGAACTGGCTTCCTGGACCCTGTTACCGCCAGCAGCGA

GTATCAAAGACATCTGCGGATAACAACAACAGTGAATACTCGTGGACTGGAGCTACCAAGTACCACCTCAATGGC

AGAGACTCTCTGGTGAATCCGGGCCCGGCCATGGCAAGCCACAAGGACGATGAAGAAAAGTTTTTTCCTCAGAGC

GGGGTTCTCATCTTTGGGAAGCAAGGCTCAGAGAAAACAAATGTGGACATTGAAAAGGTCATGATTACAGACGAA

GAGGAAATCAGGACAACCAATCCCGTGGCTACGGAGCAGTATGGTTCTGTATCTACCAACCTCCAGAGAGGCAAC

AGACAAGCAGCTACCGCAGATGTCAACACACAAGGCGTTCTTCCAGGCATGGTCTGGCAGGACAGAGATGTGTAC

CTTCAGGGGCCCATCTGGGCAAAGATTCCACACACGGACGGACATTTTCACCCCTCTCCCCTCATGGGTGGATTC

GGACTTAAACACCCTCCTCCACAGATTCTCATCAAGAACACCCCGGTACCTGCGAATCCTTCGACCACCTTCAGT

-continued

```
GCGGCAAAGTTTGCTTCCTTCATCACACAGTACTCCACGGGACAGGTCAGCGTGGAGATCGAGTGGGAGCTGCAG

AAGGAAAACAGCAAACGCTGGAATCCCGAAATTCAGTACACTTCCAACTACAACAAGTCTGTTAATGTGGACTTT

ACTGTGGACACTAATGGCGTGTATTCAGAGCCTCGCCCCATTGGCACCAGATACCTGACTCGTAATCTGTAA
```

CapVP3:

(SEQ ID NO: 7)
```
ATGGCTACAGGCAGTGGCGCACCAATGGCAGACAATAACGAGGGCGCCGACGGAGTGGGTAATTCCTCGGGAAAT

TGGCATTGCGATTCCACATGGATGGGCGACAGAGTCATCACCACCAGCACCCGAACCTGGGCCCTGCCCACCTAC

AACAACCACCTCTACAAACAAATTTCCAGCCAATCAGGAGCCTCGAACGACAATCACTACTTTGGCTACAGCACC

CCTTGGGGGTATTTTGACTTCAACAGATTCCACTGCCACTTTTCACCACGTGACTGGCAAAGACTCATCAACAAC

AACTGGGGATTCCGACCCAAGAGACTCAACTTCAAGCTCTTTAACATTCAAGTCAAAGAGGTCACGCAGAATGAC

GGTACGACGACGATTGCCAATAACCTTACCAGCACGGTTCAGGTGTTTACTGACTCGGAGTACCAGCTCCCGTAC

GTCCTCGGCTCGGCGCATCAAGGATGCCTCCCGCCGTTCCCAGCAGACGTCTTCATGGTGCCACAGTATGGATAC

CTCACCCTGAACAACGGGAGTCAGGCAGTAGGACGCTCTTCATTTTACTGCCTGGAGTACTTTCCTTCTCAGATG

CTGCGTACCGGAAACAACTTTACCTTCAGCTACACTTTTGAGGACGTTCCTTTCCACAGCAGCTACGCTCACAGC

CAGAGTCTGGACCGTCTCATGAATCCTCTCATCGACCAGTACCTGTATTACTTGAGCAGAACAAACACTCCAAGT

GGAACCACCACGCAGTCAAGGCTTCAGTTTTCTCAGGCCGGAGCGAGTGACATTCGGGACCAGTCTAGGAACTGG

CTTCCTGGACCCTGTTACCGCCAGCAGCGAGTATCAAAGACATCTGCGGATAACAACAACAGTGAATACTCGTGG

ACTGGAGCTACCAAGTACCACCTCAATGGCAGAGACTCTCTGGTGAATCCGGGCCCGGCCATGGCAAGCCACAAG

GACGATGAAGAAAAGTTTTTTCCTCAGAGCGGGGTTCTCATCTTTGGGAAGCAAGGCTCAGAGAAAACAAATGTG

GACATTGAAAAGGTCATGATTACAGACGAAGAGGAAATCAGGACAACCAATCCCGTGGCTACGGAGCAGTATGGT

TCTGTATCTACCAACCTCCAGAGAGGCAACAGACAAGCAGCTACCGCAGATGTCAACACACAAGGCGTTCTTCCA

GGCATGGTCTGGCAGGACAGAGATGTGTACCTTCAGGGGCCCATCTGGGCAAAGATTCCACACACGGACGGACAT

TTTCACCCCTCTCCCCTCATGGGTGGATTCGGACTTAAACACCCTCCTCCACAGATTCTCATCAAGAACACCCCG

GTACCTGCGAATCCTTCGACCACCTTCAGTGCGGCAAAGTTTGCTTCCTTCATCACACAGTACTCCACGGGACAG

GTCAGCGTGGAGATCGAGTGGGAGCTGCAGAAGGAAAACAGCAAACGCTGGAATCCCGAAATTCAGTACACTTCC

AACTACAACAAGTCTGTTAATGTGGACTTTACTGTGGACACTAATGGCGTGTATTCAGAGCCTCGCCCCATTGGC

ACCAGATACCTGACTCGTAATCTGTAA
```

CapAAP:

(SEQ ID NO: 8)
```
CTGGAGACGCAGACTCAGTACCTGACCCCCAGCCTCTCGGACAGCCACCAGCAGCCCCCTCTGGTCTGGGAACTA

ATACGATGGCTACAGGCAGTGGCGCACCAATGGCAGACAATAACGAGGGCGCCGACGGAGTGGGTAATTCCTCGG

GAAATTGGCATTGCGATTCCACATGGATGGGCGACAGAGTCATCACCACCAGCACCCGAACCTGGGCCCTGCCCA

CCTACAACAACCACCTCTACAAACAAATTTCCAGCCAATCAGGAGCCTCGAACGACAATCACTACTTTGGCTACA

GCACCCCTTGGGGGTATTTTGACTTCAACAGATTCCACTGCCACTTTTCACCACGTGACTGGCAAAGACTCATCA

ACAACAACTGGGGATTCCGACCCAAGAGACTCAACTTCAAGCTCTTTAACATTCAAGTCAAAGAGGTCACGCAGA

ATGACGGTACGACGACGATTGCCAATAACCTTACCAGCACGGTTCAGGTGTTTACTGACTCGGAGTACCAGCTCC

CGTACGTCCTCGGCTCGGCGCATCAAGGATGCCTCCCGCCGTTCCCAGCAGACGTCTTCATGGTGCCACAGTATG

GATACCTCACCCTGA
```

AAV-3
Full Genome: NC_001729

Rep78:

(SEQ ID NO: 9)
```
ATGCCGGGGTTCTACGAGATTGTCCTGAAGGTCCCGAGTGACCTGGACGAGCGCCTGCCGGGCATTTCTAACTCG
```

-continued

```
TTTGTTAACTGGGTGGCCGAGAAGGAATGGGACGTGCCGCCGGATTCTGACATGGATCCGAATCTGATTGAGCAG

GCACCCCTGACCGTGGCCGAAAAGCTTCAGCGCGAGTTCCTGGTGGAGTGGCGCCGCGTGAGTAAGGCCCCGGAG

GCCCTCTTTTTTGTCCAGTTCGAAAAGGGGGAGACCTACTTCCACCTGCACGTGCTGATTGAGACCATCGGGGTC

AAATCCATGGTGGTCGGCCGCTACGTGAGCCAGATTAAAGAGAAGCTGGTGACCCGCATCTACCGCGGGGTCGAG

CCGCAGCTTCCGAACTGGTTCGCGGTGACCAAAACGCGAAATGGCGCCGGGGGCGGGAACAAGGTGGTGGACGAC

TGCTACATCCCCAACTACCTGCTCCCCAAGACCCAGCCCGAGCTCCAGTGGGCGTGGACTAACATGGACCAGTAT

TTAAGCGCCTGTTTGAATCTCGCGGAGCGTAAACGGCTGGTGGCGCAGCATCTGACGCACGTGTCGCAGACGCAG

GAGCAGAACAAAGAGAATCAGAACCCCAATTCTGACGCGCCGGTCATCAGGTCAAAAACCTCAGCCAGGTACATG

GAGCTGGTCGGGTGGCTGGTGGACCGCGGGATCACGTCAGAAAAGCAATGGATTCAGGAGGACCAGGCCTCGTAC

ATCTCCTTCAACGCCGCCTCCAACTCGCGGTCCCAGATCAAGGCCGCGCTGGACAATGCCTCCAAGATCATGAGC

CTGACAAAGACGGCTCCGGACTACCTGGTGGGCAGCAACCCGCCGGAGGACATTACCAAAAATCGGATCTACCAA

ATCCTGGAGCTGAACGGGTACGATCCGCAGTACGCGGCCTCCGTCTTCCTGGGCTGGGCGCAAAAGAAGTTCGGG

AAGAGGAACACCATCTGGCTCTTTGGGCCGGCCACGACGGGTAAAACCAACATCGCGGAAGCCATCGCCCACGCC

GTGCCCTTCTACGGCTGCGTAAACTGGACCAATGAGAACTTTCCCTTCAACGATTGCGTCGACAAGATGGTGATC

TGGTGGGAGGAGGGCAAGATGACGGCCAAGGTCGTGGAGAGCGCCAAGGCCATTCTGGGCGGAAGCAAGGTGCGC

GTGGACCAAAAGTGCAAGTCATCGGCCCAGATCGAACCCACTCCCGTGATCGTCACCTCCAACACCAACATGTGC

GCCGTGATTGACGGGAACAGCACCACCTTCGAGCATCAGCAGCCGCTGCAGGACCGGATGTTTGAATTTGAACTT

ACCCGCCGTTTGGACCATGACTTTGGGAAGGTCACCAAACAGGAAGTAAAGGACTTTTTCCGGTGGGCTTCCGAT

CACGTGACTGACGTGGCTCATGAGTTCTACGTCAGAAAGGGTGGAGCTAAGAAACGCCCCGCCTCCAATGACGCG

GATGTAAGCGAGCCAAAACGGGAGTGCACGTCACTTGCGCAGCCGACAACGTCAGACGCGGAAGCACCGGCGGAC

TACGCGGACAGGTACCAAAACAAATGTTCTCGTCACGTGGGCATGAATCTGATGCTTTTTCCCTGTAAAACATGC

GAGAGAATGAATCAAATTTCCAATGTCTGTTTTACGCATGGTCAAAGAGACTGTGGGGAATGCTTCCCTGGAATG

TCAGAATCTCAACCCGTTTCTGTCGTCAAAAAGAAGACTTATCAGAAACTGTGTCCAATTCATCATATCCTGGGA

AGGGCACCCGAGATTGCCTGTTCGGCCTGCGATTTGGCCAATGTGGACTTGGATGACTGTGTTTCTGAGCAATAA
```

CapVP1:

(SEQ ID NO: 10)
```
ATGGCTGCTGACGGTTATCTTCCAGATTGGCTCGAGGACAACCTTTCTGAAGGCATTCGTGAGTGGTGGGCTCTG

AAACCTGGAGTCCCTCAACCCAAAGCGAACCAACAACACCAGGACAACCGTCGGGGTCTTGTGCTTCCGGGTTAC

AAATACCTCGGACCCGGTAACGGACTCGACAAAGGAGAGCCGGTCAACGAGGCGGACGCGGCAGCCCTCGAACAC

GACAAAGCTTACGACCAGCAGCTCAAGGCCGGTGACAACCCGTACCTCAAGTACAACCACGCCGACGCCGAGTTT

CAGGAGCGTCTTCAAGAAGATACGTCTTTTGGGGGCAACCTTGGCAGAGCAGTCTTCCAGGCCAAAAAGAGGATC

CTTGAGCCTCTTGGTCTGGTTGAGGAAGCAGCTAAAACGGCTCCTGGAAAGAAGGGGGCTGTAGATCAGTCTCCT

CAGGAACCGGACTCATCATCTGGTGTTGGCAAATCGGGCAAACAGCCTGCCAGAAAAAGACTAAATTTCGGTCAG

ACTGGAGACTCAGAGTCAGTCCCAGACCCTCAACCTCTCGGAGAACCACCAGCAGCCCCCACAAGTTTGGGATCT

AATACAATGGCTTCAGGCGGTGGCGCACCAATGGCAGACAATAACGAGGGTGCCGATGGAGTGGGTAATTCCTCA

GGAAATTGGCATTGCGATTCCCAATGGCTGGGCGACAGAGTCATCACCACCAGCACCAGAACCTGGGCCCTGCCC

ACTTACAACAACCATCTCTACAAGCAAATCTCCAGCCAATCAGGAGCTTCAAACGACAACCACTACTTTGGCTAC

AGCACCCCTTGGGGGTATTTTGACTTTAACAGATTCCACTGCCACTTCTCACCACGTGACTGGCAGCGACTCATT

AACAACAACTGGGGATTCCGGCCCAAGAAACTCAGCTTCAAGCTCTTCAACATCCAAGTTAGAGGGGTCACGCAG

AACGATGGCACGACGACTATTGCCAATAACCTTACCAGCACGGTTCAAGTGTTTACGGACTCGGAGTATCAGCTC

CCGTACGTGCTCGGTCGGCGCACCAAGGCTGTCTCCCGCCGTTTCCAGCGGACGTCTTCATGGTCCCTCAGTAT

GGATACCTCACCCTGAACAACGGAAGTCAAGCGGTGGGACGCTCATCCTTTTACTGCCTGGAGTACTTCCCTTCG
```

-continued

```
CAGATGCTAAGGACTGGAAATAACTTCCAATTCAGCTATACCTTCGAGGATGTACCTTTTCACAGCAGCTACGCT

CACAGCCAGAGTTTGGATCGCTTGATGAATCCTCTTATTGATCAGTATCTGTACTACCTGAACAGAACGCAAGGA

ACAACCTCTGGAACAACCAACCAATCACGGCTGCTTTTTAGCCAGGCTGGGCCTCAGTCTATGTCTTTGCAGGCC

AGAAATTGGCTACCTGGGCCCTGCTACCGGCAACAGAGACTTTCAAAGACTGCTAACGACAACAACAACAGTAAC

TTTCCTTGGACAGCGGCCAGCAAATATCATCTCAATGGCCGCGACTCGCTGGTGAATCCAGGACCAGCTATGGCC

AGTCACAAGGACGATGAAGAAAAATTTTTCCCTATGCACGGCAATCTAATATTTGGCAAAGAAGGGACAACGGCA

AGTAACGCAGAATTAGATAATGTAATGATTACGGATGAAGAAGAGATTCGTACCACCAATCCTGTGGCAACAGAG

CAGTATGGAACTGTGGCAAATAACTTGCAGAGCTCAAATACAGCTCCCACGACTGGAACTGTCAATCATCAGGGG

GCCTTACCTGGCATGGTGTGGCAAGATCGTGACGTGTACCTTCAAGGACCTATCTGGGCAAAGATTCCTCACACG

GATGGACACTTTCATCCTTCTCCTCTGATGGGAGGCTTTGGACTGAAACATCCGCCTCCTCAAATCATGATCAAA

AATACTCCGGTACCGGCAAATCCTCCGACGACTTTCAGCCCGGCCAAGTTTGCTTCATTTATCACTCAGTACTCC

ACTGGACAGGTCAGCGTGGAAATTGAGTGGGAGCTACAGAAAGAAAACAGCAAACGTTGGAATCCAGAGATTCAG

TACACTTCCAACTACAACAAGTCTGTTAATGTGGACTTTACTGTAGACACTAATGGTGTTTATAGTGAACCTCGC

CCTATTGGAACCCGGTATCTCACACGAAACTTGTGA
```

AAV-4
Full Genome: NC_001829

Rep78:
                                                                    (SEQ ID NO: 11)
```
ATGCCGGGGTTCTACGAGATCGTGCTGAAGGTGCCCAGCGACCTGGACGAGCACCTGCCCGGCATTTCTGACTCT

TTTGTGAGCTGGGTGGCCGAGAAGGAATGGGAGCTGCCGCCGGATTCTGACATGGACTTGAATCTGATTGAGCAG

GCACCCCTGACCGTGGCCGAAAAGCTGCAACGCGAGTTCCTGGTCGAGTGGCGCCGCGTGAGTAAGGCCCCGGAG

GCCCTCTTCTTTGTCCAGTTCGAGAAGGGGGACAGCTACTTCCACCTGCACATCCTGGTGGAGACCGTGGGCGTC

AAATCCATGGTGGTGGGCCGCTACGTGAGCCAGATTAAAGAGAAGCTGGTGACCCGCATCTACCGCGGGGTCGAG

CCGCAGCTTCCGAACTGGTTCGCGGTGACCAAGACGCGTAATGGCGCCGGAGGCGGGAACAAGGTGGTGGACGAC

TGCTACATCCCCAACTACCTGCTCCCCAAGACCCAGCCCGAGCTCCAGTGGGCGTGGACTAACATGGACCAGTAT

ATAAGCGCCTGTTTGAATCTCGCGGAGCGTAAACGGCTGGTGGCGCAGCATCTGACGCACGTGTCGCAGACGCAG

GAGCAGAACAAGGAAAACCAGAACCCCAATTCTGACGCGCCGGTCATCAGGTCAAAAACCTCCGCCAGGTACATG

GAGCTGGTCGGGTGGCTGGTGGACCGCGGGATCACGTCAGAAAAGCAATGGATCCAGGAGGACCAGGCGTCCTAC

ATCTCCTTCAACGCCGCCTCCAACTCGCGGTCACAAATCAAGGCCGCGCTGGACAATGCCTCCAAAATCATGAGC

CTGACAAAGACGGCTCCGGACTACCTGGTGGGCCAGAACCCGCCGGAGGACATTTCCAGCAACCGCATCTACCGA

ATCCTCGAGATGAACGGGTACGATCCGCAGTACGCGGCCTCCGTCTTCCTGGGCTGGGCGCAAAAGAAGTTCGGG

AAGAGGAACACCATCTGGCTCTTTGGGCCGGCCACGACGGGTAAAACCAACATCGCGGAAGCCATCGCCCACGCC

GTGCCCTTCTACGGCTGCGTGAACTGGACCAATGAGAACTTTCCGTTCAACGATTGCGTCGACAAGATGGTGATC

TGGTGGGAGGAGGGCAAGATGACGGCCAAGGTCGTAGAGAGCGCCAAGGCCATCCTGGGCGGAAGCAAGGTGCGC

GTGGACCAAAAGTGCAAGTCATCGGCCCAGATCGACCCAACTCCCGTGATCGTCACCTCCAACACCAACATGTGC

GCGGTCATCGACGGAAACTCGACCACCTTCGAGCACCAACAACCACTCCAGGACCGGATGTTCAAGTTCGAGCTC

ACCAAGCGCCTGGAGCACGACTTTGGCAAGGTCACCAAGCAGGAAGTCAAAGACTTTTTCCGGTGGGCGTCAGAT

CACGTGACCGAGGTGACTCACGAGTTTTACGTCAGAAAGGGTGGAGCTAGAAAGAGGCCCGCCCCCAATGACGCA

GATATAAGTGAGCCCAAGCGGGCCTGTCCGTCAGTTGCGCAGCCATCGACGTCAGACGCGGAAGCTCCGGTGGAC

TACGCGGACAGGTACCAAAACAAATGTTCTCGTCACGTGGGTATGAATCTGATGCTTTTTCCCTGCCGGCAATGC

GAGAGAATGAATCAGAATGTGGACATTTGCTTCACGCACGGGGTCATGGACTGTGCCGAGTGCTTCCCCGTGTCA
```

-continued

GAATCTCAACCCGTGTCTGTCGTCAGAAAGCGGACGTATCAGAAACTGTGTCCGATTCATCACATCATGGGAGG

GCGCCCGAGGTGGCCTGCTCGGCCTGCGAACTGGCCAATGTGGACTTGGATGACTGTGACATGGAACAATAA

CapVP1:

(SEQ ID NO: 12)

ATGACTGACGGTTACCTTCCAGATTGGCTAGAGGACAACCTCTCTGAAGGCGTTCGAGAGTGGTGGGCGCTGCAA

CCTGGAGCCCCTAAACCCAAGGCAAATCAACAACATCAGGACAACGCTCGGGGTCTTGTGCTTCCGGGTTACAAA

TACCTCGGACCCGGCAACGGACTCGACAAGGGGGAACCCGTCAACGCAGCGGACGCGGCAGCCCTCGAGCACGAC

AAGGCCTACGACCAGCAGCTCAAGGCCGGTGACAACCCCTACCTCAAGTACAACCACGCCGACGCGGAGTTCCAG

CAGCGGCTTCAGGGCGACACATCGTTTGGGGGCAACCTCGGCAGAGCAGTCTTCCAGGCCAAAAAGAGGGTTCTT

GAACCTCTTGGTCTGGTTGAGCAAGCGGGTGAGACGGCTCCTGGAAAGAAGAGACCGTTGATTGAATCCCCCCAG

CAGCCCGACTCCTCCACGGGTATCGGCAAAAAAGGCAAGCAGCCGGCTAAAAAGAAGCTCGTTTTCGAAGACGAA

ACTGGAGCAGGCGACGGACCCCCTGAGGGATCAACTTCCGGAGCCATGTCTGATGACAGTGAGATGCGTGCAGCA

GCTGGCGGAGCTGCAGTCGAGGGCGGACAAGGTGCCGATGGAGTGGGTAATGCCTCGGGTGATTGGCATTGCGAT

TCCACCTGGTCTGAGGGCCACGTCACGACCACCAGCACCAGAACCTGGGTCTTGCCCACCTACAACAACCACCTC

TACAAGCGACTCGGAGAGAGCCTGCAGTCCAACACCTACAACGGATTCTCCACCCCCTGGGGATACTTTGACTTC

AACCGCTTCCACTGCCACTTCTCACCACGTGACTGGCAGCGACTCATCAACAACAACTGGGGCATGCGACCCAAA

GCCATGCGGGTCAAAATCTTCAACATCCAGGTCAAGGAGGTCACGACGTCGAACGGCGAGACAACGGTGGCTAAT

AACCTTACCAGCACGGTTCAGATCTTTGCGGACTCGTCGTACGAACTGCCGTACGTGATGGATGCGGGTCAAGAG

GGCAGCCTGCCTCCTTTTCCCAACGACGTCTTTATGGTGCCCCAGTACGGCTACTGTGGACTGGTGACCGGCAAC

ACTTCGCAGCAACAGACTGACAGAAATGCCTTCTACTGCCTGGAGTACTTTCCTTCGCAGATGCTGCGGACTGGC

AACAACTTTGAAATTACGTACAGTTTTGAGAAGGTGCCTTTCCACTCGATGTACGCGCACAGCCAGAGCCTGGAC

CGGCTGATGAACCCTCTCATCGACCAGTACCTGTGGGGACTGCAATCGACCACCACCGGAACCACCCTGAATGCC

GGGACTGCCACCACCAACTTTACCAAGCTGCGGCCTACCAACTTTTCCAACTTTAAAAAGAACTGGCTGCCCGGG

CCTTCAATCAAGCAGCAGGGCTTCTCAAAGACTGCCAATCAAAACTACAAGATCCCTGCCACCGGGTCAGACAGT

CTCATCAAATACGAGACGCACAGCACTCTGGACGGAAGATGGAGTGCCCTGACCCCCGGACCTCCAATGGCCACG

GCTGGACCTGCGGACAGCAAGTTCAGCAACAGCCAGCTCATCTTTGCGGGGCCTAAACAGAACGGCAACACGGCC

ACCGTACCCGGGACTCTGATCTTCACCTCTGAGGAGGAGCTGGCAGCCACCAACGCCACCGATACGGACATGTGG

GGCAACCTACCTGGCGGTGACCAGAGCAACAGCAACCTGCCGACCGTGGACAGACTGACAGCCTTGGGAGCCGTG

CCTGGAATGGTCTGGCAAAACAGAGACATTTACTACCAGGGTCCCATTTGGGCCAAGATTCCTCATACCGATGGA

CACTTTCACCCCTCACCGCTGATTGGTGGGTTTGGGCTGAAACACCCGCCTCCTCAAATTTTTATCAAGAACACC

CCGGTACCTGCGAATCCTGCAACGACCTTCAGCTCTACTCCGGTAAACTCCTTCATTACTCAGTACAGCACTGGC

CAGGTGTCGGTGCAGATTGACTGGGAGATCCAGAAGGAGCGGTCCAAACGCTGGAACCCCGAGGTCCAGTTTACC

TCCAACTACGGACAGCAAAACTCTCTGTTGTGGGCTCCCGATGCGGCTGGGAAATACACTGAGCCTAGGGCTATC

GGTACCCGCTACCTCACCCACCACCTGTAA

AAV-5
Full Genome: NC_006152

Rep78:

(SEQ ID NO: 13)

ATGGCTACCTTCTATGAAGTCATTGTTCGCGTCCCATTTGACGTGGAGGAACATCTGCCTGGAATTTCTGACAGC

TTTGTGGACTGGGTAACTGGTCAAATTTGGGAGCTGCCTCCAGAGTCAGATTTAAATTTGACTCTGGTTGAACAG

CCTCAGTTGACGGTGGCTGATAGAATTCGCCGCGTGTTCCTGTACGAGTGGAACAAATTTTCCAAGCAGGAGTCC

AAATTCTTTGTGCAGTTTGAAAAGGGATCTGAATATTTTCATCTGCACACGCTTGTGGAGACCTCCGGCATCTCT

-continued

```
TCCATGGTCCTCGGCCGCTACGTGAGTCAGATTCGCGCCCAGCTGGTGAAAGTGGTCTTCCAGGGAATTGAACCC

CAGATCAACGACTGGGTCGCCATCACCAAGGTAAAGAAGGGCGGAGCCAATAAGGTGGTGGATTCTGGGTATATT

CCCGCCTACCTGCTGCCGAAGGTCCAACCGGAGCTTCAGTGGGCGTGGACAAACCTGGACGAGTATAAATTGGCC

GCCCTGAATCTGGAGGAGCGCAAACGGCTCGTCGCGCAGTTTCTGGCAGAATCCTCGCAGCGCTCGCAGGAGGCG

GCTTCGCAGCGTGAGTTCTCGGCTGACCCGGTCATCAAAAGCAAGACTTCCCAGAAATACATGGCGCTCGTCAAC

TGGCTCGTGGAGCACGGCATCACTTCCGAGAAGCAGTGGATCCAGGAAAATCAGGAGAGCTACCTCTCCTTCAAC

TCCACCGGCAACTCTCGGAGCCAGATCAAGGCCGCGCTCGACAACGCGACCAAAATTATGAGTCTGACAAAAAGC

GCGGTGGACTACCTCGTGGGGAGCTCCGTTCCCGAGGACATTTCAAAAAACAGAATCTGGCAAATTTTTGAGATG

AATGGCTACGACCCGGCCTACGCGGGATCCATCCTCTACGGCTGGTGTCAGCGCTCCTTCAACAAGAGGAACACC

GTCTGGCTCTACGGACCCGCCACGACCGGCAAGACCAACATCGCGGAGGCCATCGCCCACACTGTGCCCTTTTAC

GGCTGCGTGAACTGGACCAATGAAAACTTTCCCTTTAATGACTGTGTGGACAAAATGCTCATTTGGTGGGAGGAG

GGAAAGATGACCAACAAGGTGGTTGAATCCGCCAAGGCCATCCTGGGGGGCTCAAAGGTGCGGGTCGATCAGAAA

TGTAAATCCTCTGTTCAAATTGATTCTACCCCTGTCATTGTAACTTCCAATACAAACATGTGTGGTGGTGGAT

GGGAATTCCACGACCTTTGAACACCAGCAGCCGCTGGAGGACCGCATGTTCAAATTTGAACTGACTAAGCGGCTC

CCGCCAGATTTTGGCAAGATTACTAAGCAGGAAGTCAAGGACTTTTTTGCTTGGGCAAAGGTCAATCAGGTGCCG

GTGACTCACGAGTTTAAAGTTCCCAGGGAATTGGCGGGAACTAAAGGGGCGGAGAAATCTCTAAAACGCCCACTG

GGTGACGTCACCAATACTAGCTATAAAAGTCTGGAGAAGCGGGCCAGGCTCTCATTTGTTCCCGAGACGCCTCGC

AGTTCAGACGTGACTGTTGATCCCGCTCCTCTGCGACCGCTCAATTGGAATTCAAGGTATGATTGCAAATGTGAC

TATCATGCTCAATTTGACAACATTTCTAACAAATGTGATGAATGTGAATATTTGAATCGGGGCAAAAATGGATGT

ATCTGTCACAATGTAACTCACTGTCAAATTTGTCATGGGATTCCCCCCTGGGAAAAGGAAAACTTGTCAGATTTT

GGGGATTTTGACGATGCCAATAAAGAACAGTAA
```

CapVP1:

(SEQ ID NO: 14)

```
ATGTCTTTTGTTGATCACCCTCCAGATTGGTTGGAAGAAGTTGGTGAAGGTCTTCGCGAGTTTTTGGGCCTTGAA

GCGGGCCCACCGAAACCAAAACCCAATCAGCAGCATCAAGATCAAGCCCGTGGTCTTGTGCTGCCTGGTTATAAC

TATCTCGGACCCGGAAACGGTCTCGATCGAGGAGAGCCTGTCAACAGGGCAGACGAGGTCGCGCGAGAGCACGAC

ATCTCGTACAACGAGCAGCTTGAGGCGGGAGACAACCCCTACCTCAAGTACAACCACGCGGACGCCGAGTTTCAG

GAGAAGCTCGCCGACGACACATCCTTCGGGGGAAACCTCGGAAAGGCAGTCTTTCAGGCCAAGAAAAGGGTTCTC

GAACCTTTTGGCCTGGTTGAAGAGGGTGCTAAGACGGCCCCTACCGGAAAGCGGATAGACGACCACTTTCCAAAA

AGAAAGAAGGCTCGGACCGAAGAGGACTCCAAGCCTTCCACCTCGTCAGACGCCGAAGCTGGACCCAGCGGATCC

CAGCAGCTGCAAATCCCAGCCCAACCAGCCTCAAGTTTGGGAGCTGATACAATGTCTGCGGGAGGTGGCGGCCCA

TTGGGCGACAATAACCAAGGTGCCGATGGAGTGGGCAATGCCTCGGGAGATTGGCATTGCGATTCCACGTGGATG

GGGGACAGAGTCGTCACCAAGTCCACCCGAACCTGGGTGCTGCCCAGCTACAACAACCACCAGTACCGAGAGATC

AAAAGCGGCTCCGTCGACGGAAGCAACGCCAACGCCTACTTTGGATACAGCACCCCCTGGGGGTACTTTGACTTT

AACCGCTTCCACAGCCACTGGAGCCCCCGAGACTGGCAAAGACTCATCAACAACTACTGGGGCTTCAGACCCCGG

TCCCTCAGAGTCAAAATCTTCAACATTCAAGTCAAAGAGGTCACGGTGCAGGACTCCACCACCACCATCGCCAAC

AACCTCACCTCCACCGTCCAAGTGTTTACGGACGACGACTACCAGCTGCCCTACGTCGTCGGCAACGGGACCGAG

GGATGCCTGCCGGCCTTCCCTCCGCAGGTCTTTACGCTGCCGCAGTACGGTTACGCGACGCTGAACCGCGACAAC

ACAGAAAATCCCACCGAGAGGAGCAGCTTCTTCTGCCTAGAGTACTTTCCCAGCAAGATGCTGAGAACGGGCAAC

AACTTTGAGTTTACCTACAACTTTGAGGAGGTGCCCTTCCACTCCAGCTTCGCTCCCAGTCAGAACCTGTTCAAG

CTGGCCAACCCGCTGGTGGACCAGTACTTGTACCGCTTCGTGAGCACAAATAACACTGGCGGAGTCCAGTTCAAC
```

-continued

```
AAGAACCTGGCCGGGAGATACGCCAACACCTACAAAAACTGGTTCCCGGGGCCCATGGGCCGAACCCAGGGCTGG

AACCTGGGCTCCGGGGTCAACCGCGCCAGTGTCAGCGCCTTCGCCACGACCAATAGGATGGAGCTCGAGGGCGCG

AGTTACCAGGTGCCCCCGCAGCCGAACGGCATGACCAACAACCTCCAGGGCAGCAACACCTATGCCCTGGAGAAC

ACTATGATCTTCAACAGCCAGCCGGCGAACCCGGGCACCACCGCCACGTACCTCGAGGGCAACATGCTCATCACC

AGCGAGAGCGAGACGCAGCCGGTGAACCGCGTGGCGTACAACGTCGGCGGGCAGATGGCCACCAACAACCAGAGC

TCCACCACTGCCCCCGCGACCGGCACGTACAACCTCCAGGAAATCGTGCCCGGCAGCGTGTGGATGGAGAGGGAC

GTGTACCTCCAAGGACCCATCTGGGCCAAGATCCCAGAGACGGGGGCGCACTTTCACCCCTCTCCGGCCATGGGC

GGATTCGGACTCAAACACCCACCGCCCATGATGCTCATCAAGAACACGCCTGTGCCCGGAAATATCACCAGCTTC

TCGGACGTGCCCGTCAGCAGCTTCATCACCCAGTACAGCACCGGGCAGGTCACCGTGGAGATGGAGTGGGAGCTC

AAGAAGGAAAACTCCAAGAGGTGGAACCCAGAGATCCAGTACACAAACAACTACAACGACCCCCAGTTTGTGGAC

TTTGCCCCGGACAGCACCGGGGAATACAGAACCACCAGACCTATCGGAACCCGATACCTTACCCGACCCCTTTAA
```

AAV-6
Full Genome: AF028704

Rep78:
(SEQ ID NO: 15)
```
ATGCCGGGGTTTTACGAGATTGTGATTAAGGTCCCCAGCGACCTTGACGAGCATCTGCCCGGCATTTCTGACAGC

TTTGTGAACTGGGTGGCCGAGAAGGAATGGGAGTTGCCGCCAGATTCTGACATGGATCTGAATCTGATTGAGCAG

GCACCCCTGACCGTGGCCGAGAAGCTGCAGCGCGACTTCCTGGTCCAGTGGCGCCGCGTGAGTAAGGCCCCGGAG

GCCCTCTTCTTTGTTCAGTTCGAGAAGGGCGAGTCCTACTTCCACCTCCATATTCTGGTGGAGACCACGGGGGTC

AAATCCATGGTGCTGGGCCGCTTCCTGAGTCAGATTAGGGACAAGCTGGTGCAGACCATCTACCGCGGGATCGAG

CCGACCCTGCCCAACTGGTTCGCGGTGACCAAGACGCGTAATGGCGCCGGAGGGGGGAACAAGGTGGTGGACGAG

TGCTACATCCCCAACTACCTCCTGCCCAAGACTCAGCCCGAGCTGCAGTGGGCGTGGACTAACATGGAGGAGTAT

ATAAGCGCGTGTTTAAACCTGGCCGAGCGCAAACGGCTCGTGGCGCACGACCTGACCCACGTCAGCCAGACCCAG

GAGCAGAACAAGGAGAATCTGAACCCCAATTCTGACGCGCCTGTCATCCGGTCAAAAACCTCCGCACGCTACATG

GAGCTGGTCGGGTGGCTGGTGGACCGGGGCATCACCTCCGAGAAGCAGTGGATCCAGGAGGACCAGGCCTCGTAC

ATCTCCTTCAACGCCGCCTCCAACTCGCGGTCCCAGATCAAGGCCGCTCTGGACAATGCCGGCAAGATCATGGCG

CTGACCAAATCCGCGCCCGACTACCTGGTAGGCCCCGCTCCGCCCGCCGACATTAAAACCAACCGCATTTACCGC

ATCCTGGAGCTGAACGGCTACGACCCTGCCTACGCCGGCTCCGTCTTTCTCGGCTGGGCCCAGAAAAGGTTCGGA

AAACGCAACACCATCTGGCTGTTTGGGCCGGCCACCACGGGCAAGACCAACATCGCGGAAGCCATCGCCCACGCC

GTGCCCTTCTACGGCTGCGTCAACTGGACCAATGAGAACTTTCCCTTCAACGATTGCGTCGACAAGATGGTGATC

TGGTGGGAGGAGGGCAAGATGACGGCCAAGGTCGTGGAGTCCGCCAAGGCCATTCTCGGCGGCAGCAAGGTGCGC

GTGGACCAAAAGTGCAAGTCGTCCGCCCAGATCGATCCCACCCCCGTGATCGTCACCTCCAACACCAACATGTGC

GCCGTGATTGACGGGAACAGCACCACCTTCGAGCACCAGCAGCCGTTGCAGGACCGGATGTTCAAATTTGAACTC

ACCCGCCGTCTGGAGCATGACTTTGGCAAGGTGACAAAGCAGGAAGTCAAAGAGTTCTTCCGCTGGGCGCAGGAT

CACGTGACCGAGGTGGCGCATGAGTTCTACGTCAGAAAGGGTGGAGCCAACAAGAGACCCGCCCCCGATGACGCG

GATAAAAGCGAGCCCAAGCGGGCCTGCCCCTCAGTCGCGGATCCATCGACGTCAGACGCGGAAGGAGCTCCGGTG

GACTTTGCCGACAGGTACCAAAACAAATGTTCTCGTCACGCGGGCATGCTTCAGATGCTGTTTCCCTGCAAACA

TGCGAGAGAATGAATCAGAATTTCAACATTTGCTTCACGCACGGGACCAGAGACTGTTCAGAATGTTTCCCCGGC

GTGTCAGAATCTCAACCGGTCGTCAGAAAGAGGACGTATCGGAAACTCTGTGCCATTCATCATCTGCTGGGGCGG

GCTCCCGAGATTGCTTGCTCGGCCTGCGATCTGGTCAACGTGGATCTGGATGACTGTGTTTCTGAGCAATAA
```

CapVP1:

(SEQ ID NO: 16)
ATGGCTGCCGATGGTTATCTTCCAGATTGGCTCGAGGACAACCTCTCTGAGGGCATTCGCGAGTGGTGGGACTTG

AAACCTGGAGCCCCGAAACCCAAAGCCAACCAGCAAAAGCAGGACGACGGCCGGGGTCTGGTGCTTCCTGGCTAC

AAGTACCTCGGACCCTTCAACGGACTCGACAAGGGGGAGCCCGTCAACGCGGCGGATGCAGCGGCCCTCGAGCAC

GACAAGGCCTACGACCAGCAGCTCAAAGCGGGTGACAATCCGTACCTGCGGTATAACCACGCCGACGCCGAGTTT

CAGGAGCGTCTGCAAGAAGATACGTCTTTTGGGGGCAACCTCGGGCGAGCAGTCTTCCAGGCCAAGAAGAGGGTT

CTCGAACCTTTTGGTCTGGTTGAGGAAGGTGCTAAGACGGCTCCTGGAAAGAAACGTCCGGTAGAGCAGTCGCCA

CAAGAGCCAGATCCTCCTCGGGCATTGGCAAGACAGGCCAGCAGCCCGCTAAAAAGAGACTCAATTTTGGTCAG

ACTGGCGACTCAGAGTCAGTCCCCGACCCACAACCTCTCGGAGAACCTCCAGCAACCCCCGCTGCTGTGGGACCT

ACTACAATGGCTTCAGGCGGTGGCGCACCAATGGCAGACAATAACGAAGGCGCCGACGGAGTGGGTAATGCCTCA

GGAAATTGGCATTGCGATTCCACATGGCTGGGCGACAGAGTCATCACCACCAGCACCCGAACATGGGCCTTGCCC

ACCTATAACAACCACCTCTACAAGCAAATCTCCAGTGCTTCAACGGGGGCCAGCAACGACAACCACTACTTCGGC

TACAGCACCCCCTGGGGGTATTTTGATTTCAACAGATTCCACTGCCATTTCTCACCACGTGACTGGCAGCGACTC

ATCAACAACAATTGGGGATTCCGGCCCAAGAGACTCAACTTCAAGCTCTTCAACATCCAAGTCAAGGAGGTCACG

ACGAATGATGGCGTCACGACCATCGCTAATAACCTTACCAGCACGGTTCAAGTCTTCTCGGACTCGGAGTACCAG

TTGCCGTACGTCCTCGGCTCTGCGCACCAGGGCTGCCTCCCTCCGTTCCCGGCGACGTGTTCATGATTCCGCAG

TACGGCTACCTAACGCTCAACAATGGCAGCCAGGCAGTGGGACGGTCATCCTTTTACTGCCTGGAATATTTCCCA

TCGCAGATGCTGAGAACGGGCAATAACTTTACCTTCAGCTACACCTTCGAGGACGTGCCTTTCCACAGCAGCTAC

GCGCACAGCCAGAGCCTGGACCGGCTGATGAATCCTCTCATCGACCAGTACCTGTATTACCTGAACAGAACTCAG

AATCAGTCCGGAAGTGCCCAAAACAAGGACTTGCTGTTTAGCCGGGGGTCTCCAGCTGGCATGTCTGTTCAGCCC

AAAAACTGGCTACCTGGACCCTGTTACCGGCAGCAGCGCGTTTCTAAAACAAAAACAGACAACAACAACAGCAAC

TTTACCTGGACTGGTGCTTCAAAATATAACCTTAATGGGCGTGAATCTATAATCAACCCTGGCACTGCTATGGCC

TCACACAAAGACGACAAAGACAAGTTCTTTCCCATGAGCGGTGTCATGATTTTTGGAAAGGAGAGCGCCGGAGCT

TCAAACACTGCATTGGACAATGTCATGATCACAGACGAAGAGGAAATCAAAGCCACTAACCCCGTGGCCACCGAA

AGATTTGGGACTGTGGCAGTCAATCTCCAGAGCAGCAGCACAGACCCTGCGACCGGAGATGTGCATGTTATGGGA

GCCTTACCTGGAATGGTGTGGCAAGACAGAGACGTATACCTGCAGGGTCCTATTTGGGCCAAAATTCCTCACACG

GATGGACACTTTCACCCGTCTCCTCTCATGGGCGGCTTTGGACTTAAGCACCCGCCTCCTCAGATCCTCATCAAA

AACACGCCTGTTCCTGCGAATCCTCCGGCAGAGTTTTCGGCTACAAAGTTTGCTTCATTCATCACCCAGTATTCC

ACAGGACAAGTGAGCGTGGAGATTGAATGGGAGCTGCAGAAAGAAAACAGCAAAGCTGGAATCCCGAAGTGCAG

TATACATCTAACTATGCAAAATCTGCCAACGTTGATTTCACTGTGGACAACAATGGACTTTATACTGAGCCTCGC

CCCATTGGCACCCGTTACCTCACCCGTCCCCTGTAA

AAV-7
Full Genome: NC_006260

Rep78:

(SEQ ID NO: 17)
ATGCCGGGTTTCTACGAGATCGTGATCAAGGTGCCGAGCGACCTGGACGAGCACCTGCCGGGCATTTCTGACTCG

TTTGTGAACTGGGTGGCCGAGAAGGAATGGGAGCTGCCCCCGGATTCTGACATGGATCTGAATCTGATCGAGCAG

GCACCCCTGACCGTGGCCGAGAAGCTGCAGCGCGACTTCCTGGTCCAATGGCGCCGCGTGAGTAAGGCCCCGGAG

GCCCTGTTCTTTGTTCAGTTCGAGAAGGGCGAGAGCTACTTCCACCTTCACGTTCTGGTGGAGACCACGGGGGTC

AAGTCCATGGTGCTAGGCCGCTTCCTGAGTCAGATTCGGGAGAAGCTGGTCCAGACCATCTACCGCGGGGTCGAG

CCCACGCTGCCCAACTGGTTCGCGGTGACCAAGACGCGTAATGGCGCCGGCGGGGGGAACAAGGTGGTGGACGAG

-continued

```
TGCTACATCCCCAACTACCTCCTGCCCAAGACCCAGCCCGAGCTGCAGTGGGCGTGGACTAACATGGAGGAGTAT
ATAAGCGCGTGTTTGAACCTGGCCGAACGCAAACGGCTCGTGGCGCAGCACCTGACCCACGTCAGCCAGACGCAG
GAGCAGAACAAGGAGAATCTGAACCCCAATTCTGACGCGCCCGTGATCAGGTCAAAAACCTCCGCGCGCTACATG
GAGCTGGTCGGGTGGCTGGTGGACGGGGCATCACCTCCGAGAAGCAGTGGATCCAGGAGGACCAGGCCTCGTAC
ATCTCCTTCAACGCCGCCTCCAACTCGCGGTCCCAGATCAAGGCCGCGCTGGACAATGCCGGCAAGATCATGGCG
CTGACCAAATCCGCGCCCGACTACCTGGTGGGGCCCTCGCTGCCCGCGGACATTAAAACCAACCGCATCTACCGC
ATCCTGGAGCTGAACGGGTACGATCCTGCCTACGCCGGCTCCGTCTTTCTCGGCTGGGCCCAGAAAAAGTTCGGG
AAGCGCAACACCATCTGGCTGTTTGGGCCCGCCACCACCGGCAAGACCAACATTGCGGAAGCCATCGCCCACGCC
GTGCCCTTCTACGGCTGCGTCAACTGGACCAATGAGAACTTTCCCTTCAACGATTGCGTCGACAAGATGGTGATC
TGGTGGGAGGAGGGCAAGATGACGGCCAAGGTCGTGGAGTCCGCCAAGGCCATTCTCGGCGGCAGCAAGGTGCGC
GTGGACCAAAAGTGCAAGTCGTCCGCCCAGATCGACCCCACCCCCGTGATCGTCACCTCCAACACCAACATGTGC
GCCGTGATTGACGGGAACAGCACCACCTTCGAGCACCAGCAGCCGTTGCAGGACCGGATGTTCAAATTTGAACTC
ACCCGCCGTCTGGAGCACGACTTTGGCAAGGTGACGAAGCAGGAAGTCAAAGAGTTCTTCCGCTGGGCCAGTGAT
CACGTGACCGAGGTGGCGCATGAGTTCTACGTCAGAAAGGGCGGAGCCAGCAAAAGACCCGCCCCCGATGACGCG
GATATAAGCGAGCCCAAGCGGGCCTGCCCCTCAGTCGCGGATCCATCGACGTCAGACGCGGAAGGAGCTCCGGTG
GACTTTGCCGACAGGTACCAAAACAAATGTTCTCGTCACGCGGGCATGATTCAGATGCTGTTTCCCTGCAAAACG
TGCGAGAGAATGAATCAGAATTTCAACATTTGCTTCACACACGGGGTCAGAGACTGTTTAGAGTGTTTCCCCGGC
GTGTCAGAATCTCAACCGGTCGTCAGAAAAAAGACGTATCGGAAACTCTGCGCGATTCATCATCTGCTGGGGCGG
GCGCCCGAGATTGCTTGCTCGGCCTGCGACCTGGTCAACGTGGACCTGGACGACTGCGTTTCTGAGCAATAA
```

CapVP1:

(SEQ ID NO: 18)

ATGGCTGCCGATGGTTATCTTCCAGATTGGCTCGAGGACAACCTCTCTGAGGGCATTCGCGAGTGGTGGGACCTG

AAACCTGGAGCCCCGAAACCCAAAGCCAACCAGCAAAAGCAGGACAACGGCCGGGGTCTGGTGCTTCCTGGCTAC

AAGTACCTCGGACCCTTCAACGGACTCGACAAGGGGGAGCCCGTCAACGCGGCGGACGCAGCGGCCCTCGAGCAC

GACAAGGCCTACGACCAGCAGCTCAAAGCGGGTGACAATCCGTACCTGCGGTATAACCACGCCGACGCCGAGTTT

CAGGAGCGTCTGCAAGAAGATACGTCATTTGGGGGCAACCTCGGGCGAGCAGTCTTCCAGGCCAAGAAGCGGGTT

CTCGAACCTCTCGGTCTGGTTGAGGAAGGCGCTAAGACGGCTCCTGCAAAGAAGAGACCGGTAGAGCCGTCACCT

CAGCGTTCCCCCGACTCCTCCACGGGCATCGGCAAGAAAGGCCAGCAGCCCGCCAGAAAGAGACTCAATTTCGGT

CAGACTGGCGACTCAGAGTCAGTCCCCGACCCTCAACCTCTCGGAGAACCTCCAGCAGCGCCCTCTAGTGTGGGA

TCTGGTACAGTGGCTGCAGGCGGTGGCGCACCAATGGCAGACAATAACGAAGGTGCCGACGGAGTGGGTAATGCC

TCAGGAAATTGGCATTGCGATTCCACATGGCTGGGCGACAGAGTCATTACCACCAGCACCCGAACCTGGGCCCTG

CCCACCTACAACAACCACCTCTACAAGCAAATCTCCAGTGAAACTGCAGGTAGTACCAACGACAACACCTACTTC

GGCTACAGCACCCCCTGGGGGTATTTTGACTTTAACAGATTCCACTGCCACTTCTCACCACGTGACTGGCAGCGA

CTCATCAACAACAACTGGGGATTCCGGCCCAAGAAGCTGCGGTTCAAGCTCTTCAACATCCAGGTCAAGGAGGTC

ACGACGAATGACGGCGTTACGACCATCGCTAATAACCTTACCAGCACGATTCAGGTATTCTCGGACTCGGAATAC

CAGCTGCCGTACGTCCTCGGCTCTGCGCACCAGGGCTGCCTGCCTCCGTTCCCGGCGGACGTCTTCATGATTCCT

CAGTACGGCTACCTGACTCTCAACAATGGCAGTCAGTCTGTGGGACGTTCCTCCTTCTACTGCCTGGAGTACTTC

CCCTCTCAGATGCTGAGAACGGGCAACAACTTTGAGTTCAGCTACAGCTTCGAGGACGTGCCTTTCCACAGCAGC

TACGCACACAGCCAGAGCCTGGACCGGCTGATGAATCCCCTCATCGACCAGTACTTGTACTACCTGGCCAGAACA

CAGAGTAACCCAGGAGGCACAGCTGGCAATCGGGAACTGCAGTTTTACCAGGGCGGGCCTTCAACTATGGCCGAA

CAAGCCAAGAATTGGTTACCTGGACCTTGCTTCCGGCAACAAAGAGTCTCCAAAACGCTGGATCAAAACAACAAC

AGCAACTTTGCTTGGACTGGTGCCACCAAATATCACCTGAACGGCAGAAACTCGTTGGTTAATCCCGGCGTCGCC

-continued

ATGGCAACTCACAAGGACGACGAGGACCGCTTTTTCCCATCCAGCGGAGTCCTGATTTTTGGAAAAACTGGAGCA

ACTAACAAAACTACATTGGAAAATGTGTTAATGACAAATGAAGAAGAAATTCGTCCTACTAATCCTGTAGCCACG

GAAGAATACGGGATAGTCAGCAGCAACTTACAAGCGGCTAATACTGCAGCCCAGACACAAGTTGTCAACAACCAG

GGAGCCTTACCTGGCATGGTCTGGCAGAACCGGGACGTGTACCTGCAGGGTCCCATCTGGGCCAAGATTCCTCAC

ACGGATGGCAACTTTCACCCGTCTCCTTTGATGGGCGGCTTTGGACTTAAACATCCGCCTCCTCAGATCCTGATC

AAGAACACTCCCGTTCCCGCTAATCCTCCGGAGGTGTTTACTCCTGCCAAGTTTGCTTCGTTCATCACACAGTAC

AGCACCGGACAAGTCAGCGTGGAAATCGAGTGGGAGCTGCAGAAGGAAAACAGCAAGCGCTGGAACCCGGAGATT

CAGTACACCTCCAACTTTGAAAAGCAGACTGGTGTGGACTTTGCCGTTGACAGCCAGGGTGTTTACTCTGAGCCT

CGCCCTATTGGCACTCGTTACCTCACCCGTAATCTGTAA

AAV-8
Full Genome: NC_006261

Rep78:
(SEQ ID NO: 19)
ATGCCGGGCTTCTACGAGATCGTGATCAAGGTGCCGAGCGACCTGGACGAGCACCTGCCGGGCATTTCTGACTCG

TTTGTGAACTGGGTGGCCGAGAAGGAATGGGAGCTGCCCCCGGATTCTGACATGGATCGGAATCTGATCGAGCAG

GCACCCCTGACCGTGGCCGAGAAGCTGCAGCGCGACTTCCTGGTCCAATGGCGCCGCGTGAGTAAGGCCCCGGAG

GCCCTCTTCTTTGTTCAGTTCGAGAAGGGCGAGAGCTACTTTCACCTGCACGTTCTGGTCGAGACCACGGGGGTC

AAGTCCATGGTGCTAGGCCGCTTCCTGAGTCAGATTCGGGAAAAGCTTGGTCCAGACCATCTACCCGCGGGGTCG

AGCCCCACCTTGCCCAACTGGTTCGCGGTGACCAAAGACGCGGTAATGGCGCCGGCGGGGGGGAACAAGGTGGTG

GACGAGTGCTACATCCCCAACTACCTCCTGCCCAAGACTCAGCCCGAGCTGCAGTGGGCGTGGACTAACATGGAG

GAGTATATAAGCGCGTGCTTGAACCTGGCCGAGCGCAAACGGCTCGTGGCGCAGCACCTGACCCACGTCAGCCAG

ACGCAGGAGCAGAACAAGGAGAATCTGAACCCCAATTCTGACGCGCCCGTGATCAGGTCAAAAACCTCCGCGCGC

TATATGGAGCTGGTCGGGTGGCTGGTGGACCGGGGCATCACCTCCGAGAAGCAGTGGATCCAGGAGGACCAGGCC

TCGTACATCTCCTTCAACGCCGCCTCCAACTCGCGGTCCCAGATCAAGGCCGCGCTGGACAATGCCGGCAAGATC

ATGGCGCTGACCAAATCCGCGCCCGACTACCTGGTGGGCCCTCGCTGCCCGCGGACATTACCCAGAACCGCATC

TACCGCATCCTCGCTCTCAACGGCTACGACCCTGCCTACGCCGGCTCCGTCTTTCTCGGCTGGGCTCAGAAAAAG

TTCGGGAAACGCAACACCATCTGGCTGTTTGGACCCGCCACCACCGGCAAGACCAACATTGCGGAAGCCATCGCC

CACGCCGTGCCCTTCTACGGCTGCGTCAACTGGACCAATGAGAACTTTCCCTTCAATGATTGCGTCGACAAGATG

GTGATCTGGTGGGAGGAGGGCAAGATGACGGCCAAGGTCGTGGAGTCCGCCAAGGCCATTCTCGGCGGCAGCAAG

GTGCGCGTGGACCAAAAGTGCAAGTCGTCCGCCCAGATCGACCCCACCCCCGTGATCGTCACCTCCAACACCAAC

ATGTGCGCCGTGATTGACGGGAACAGCACCACCTTCGAGCACCAGCAGCCTCTCCAGGACCGGATGTTTAAGTTC

GAACTCACCCGCCGTCTGGAGCACGACTTTGGCAAGGTGACAAAGCAGGAAGTCAAAGAGTTCTTCCGCTGGGCC

AGTGATCACGTGACCGAGGTGGCGCATGAGTTTTACGTCAGAAAGGGCGGAGCCAGCAAAAGACCCGCCCCCGAT

GACGCGGATAAAAGCGAGCCCAAGCGGGCCTGCCCCTCAGTCGCGGATCCATCGACGTCAGACGCGGAAGGAGCT

CCGGTGGACTTTGCCGACAGGTACCAAAACAAATGTTCTCGTCACGCGGGCATGCTTCAGATGCTGTTTCCCTGC

AAAACGTGCGAGAGAATGAATCAGAATTTCAACATTTGCTTCACACACGGGGTCAGAGACTGCTCAGAGTGTTTC

CCCGGCGTGTCAGAATCTCAACCGGTCGTCAGAAAGAGGACGTATCGGAAACTCTGTGCGATTCATCATCTGCTG

GGGCGGGCTCCCGAGATTGCTTGCTCGGCCTGCGATCTGGTCAACGTGGACCTGGATGACTGTGTTTCTGAGCAA

TAA

CapVP1:
(SEQ ID NO: 20)
ATGGCTGCCGATGGTTATCTTCCAGATTGGCTCGAGGACAACCTCTCTGAGGGCATTCGCGAGTGGTGGGCGCTG

-continued

```
AAACCTGGAGCCCCGAAGCCCAAAGCCAACCAGCAAAAGCAGGACGACGGCCGGGGTCTGGTGCTTCCTGGCTAC

AAGTACCTCGGACCCTTCAACGGACTCGACAAGGGGGAGCCCGTCAACGCGGCGGACGCAGCGGCCCTCGAGCAC

GACAAGGCCTACGACCAGCAGCTGCAGGCGGGTGACAATCCGTACCTGCGGTATAACCACGCCGACGCCGAGTTT

CAGGAGCGTCTGCAAGAAGATACGTCTTTTGGGGGCAACCTCGGGCGAGCAGTCTTCCAGGCCAAGAAGCGGGTT

CTCGAACCTCTCGGTCTGGTTGAGGAAGGCGCTAAGACGGCTCCTGGAAAGAAGAGACCGGTAGAGCCATCACCC

CAGCGTTCTCCAGACTCCTCTACGGGCATCGGCAAGAAAGGCCAACAGCCCGCCAGAAAAAGACTCAATTTTGGT

CAGACTGGCGACTCAGAGTCAGTTCCAGACCCTCAACCTCTCGGAGAACCTCCAGCAGCGCCCTCTGGTGTGGGA

CCTAATACAATGGCTGCAGGCGGTGGCGCACCAATGGCAGACAATAACGAAGGCGCCGACGGAGTGGGTAGTTCC

TCGGGAAATTGGCATTGCGATTCCACATGGCTGGGCGACAGAGTCATCACCACCAGCACCCGAACCTGGGCCCTG

CCCACCTACAACAACCACCTCTACAAGCAAATCTCCAACGGGACATCGGAGGAGCCACCAACGACAACACCTAC

TTCGGCTACAGCACCCCCTGGGGGTATTTTGACTTTAACAGATTCCACTGCCACTTTTCACCACGTGACTGGCAG

CGACTCATCAACAACAACTGGGGATTCCGGCCCAAGAGACTCAGCTTCAAGCTCTTCAACATCCAGGTCAAGGAG

GTCACGCAGAATGAAGGCACCAAGACCATCGCCAATAACCTCACCAGCACCATCCAGGTGTTTACGGACTCGGAG

TACCAGCTGCCGTACGTTCTCGGCTCTGCCCACCAGGGCTGCCTGCCTCCGTTCCCGGCGGACGTGTTCATGATT

CCCCAGTACGGCTACCTAACACTCAACAACGGTAGTCAGGCCGTGGGACGCTCCTCCTTCTACTGCCTGGAATAC

TTTCCTTCGCAGATGCTGAGAACCGGCAACAACTTCCAGTTTACTTACACCTTCGAGGACGTGCCTTTCCACAGC

AGCTACGCCCACAGCCAGAGCTTGGACCGGCTGATGAATCCTCTGATTGACCAGTACCTGTACTACTTGTCTCGG

ACTCAAACAACAGGAGGCACGGCAAATACGCAGACTCTGGGCTTCAGCCAAGGTGGGCCTAATACAATGGCCAAT

CAGGCAAAGAACTGGCTGCCAGGACCCTGTTACCGCCAACAACGCGTCTCAACGACAACGGGCAAAACAACAAT

AGCAACTTTGCCTGGACTGCTGGGACCAAATACCATCTGAATGGAAGAAATTCATTGGCTAATCCTGGCATCGCT

ATGGCAACACACAAAGACGACGAGGAGCGTTTTTTTCCCAGTAACGGGATCCTGATTTTTGGCAAACAAATGCT

GCCAGAGACAATGCGGATTACAGCGATGTCATGCTCACCAGCGAGGAAGAAATCAAAACCACTAACCCTGTGGCT

ACAGAGGAATACGGTATCGTGGCAGATAACTTGCAGCAGCAAAACACGGCTCCTCAAATTGGAACTGTCAACAGC

CAGGGGGCCTTACCCGGTATGGTCTGGCAGAACCGGGACGTGTACCTGCAGGGTCCCATCTGGGCCAAGATTCCT

CACACGGACGGCAACTTCCACCCGTCTCCGCTGATGGGCGGCTTTGGCCTGAAACATCCTCCGCCTCAGATCCTG

ATCAAGAACACGCCTGTACCTGCGGATCCTCCGACCACCTTCAACCAGTCAAAGCTGAACTCTTTCATCACGCAA

TACAGCACCGGACAGGTCAGCGTGGAAATTGAATGGGAGCTGCAGAAGGAAAACAGCAAGCGCTGGAACCCCGAG

ATCCAGTACACCTCCAACTACTACAAATCTACAAGTGTGGACTTTGCTGTTAATACAGAAGGCGTGTACTCTGAA

CCCCGCCCCATTGGCACCCGTTACCTCACCCGTAATCTGTAA
```

AAV-9
Cap only: AY530579

CapVP1:
(SEQ ID NO: 21)

```
ATGGCTGCCGATGGTTATCTTCCAGATTGGCTCGAGGACAACCTTAGTGAAGGAATTCGCGAGTGGTGGGCTTTG

AAACCTGGAGCCCCTCAACCCAAGGCAAATCAACAACATCAAGACAACGCTCGAGGTCTTGTGCTTCCGGGTTAC

AAATACCTTGGACCCGGCAACGGACTCGACAAGGGGGAGCCGGTCAACGCAGCAGACGCGGCGGCCCTCGAGCAC

GACAAGGCCTACGACCAGCAGCTCAAGGCCGGAGACAACCCGTACCTCAAGTACAACCACGCCGACGCCGAGTTC

CAGGAGCGGCTCAAAGAAGATACGTCTTTTGGGGGCAACCTCGGGCGAGCAGTCTTCCAGGCCAAAAAGAGGCTT

CTTGAACCTCTTGGTCTGGTTGAGGAAGCGGCTAAGACGGCTCCTGGAAAGAAGAGGCCTGTAGAGCAGTCTCCT

CAGGAACCGGACTCCTCCGCGGGTATTGGCAAATCGGGTGCACAGCCCGCTAAAAAGAGACTCAATTTCGGTCAG

ACTGGCGACACAGAGTCAGTCCCAGACCCTCAACCAATCGGAGAACCTCCCGCAGCCCCCTCAGGTGTGGGATCT
```

-continued

```
CTTACAATGGCTTCAGGTGGTGGCGCACCAGTGGCAGACAATAACGAAGGTGCCGATGGAGTGGGTAGTTCCTCG

GGAAATTGGCATTGCGATTCCCAATGGCTGGGGGACAGAGTCATCACCACCAGCACCCGAACCTGGGCCCTGCCC

ACCTACAACAATCACCTCTACAAGCAAATCTCCAACAGCACATCTGGAGGATCTTCAAATGACAACGCCTACTTC

GGCTACAGCACCCCCTGGGGGTATTTTGACTTCAACAGATTCCACTGCCACTTCTCACCACGTGACTGGCAGCGA

CTCATCAACAACAACTGGGGATTCCGGCCTAAGCGACTCAACTTCAAGCTCTTCAACATTCAGGTCAAAGAGGTT

ACGGACAACAATGGAGTCAAGACCATCGCCAATAACCTTACCAGCACGGTCCAGGTCTTCACGGACTCAGACTAT

CAGCTCCCGTACGTGCTCGGGTCGGCTCACGAGGGCTGCCTCCCGCCGTTCCCAGCGGACGTTTTCATGATTCCT

CAGTACGGGTATCTGACGCTTAATGATGGAAGCCAGGCCGTGGGTCGTTCGTCCTTTTACTGCCTGGAATATTTC

CCGTCGCAAATGCTAAGAACGGGTAACAACTTCCAGTTCAGCTACGAGTTTGAGAACGTACCTTTCCATAGCAGC

TACGCTCACAGCCAAAGCCTGGACCGACTAATGAATCCACTCATCGACCAATACTTGTACTATCTCTCAAAGACT

ATTAACGGTTCTGGACAGAATCAACAAACGCTAAAATTCAGTGTGGCCGGACCCAGCAACATGGCTGTCCAGGGA

AGAAACTACATACCTGGACCCAGCTACCGACAACAACGTGTCTCAACCACTGTGACTCAAAACAACAACAGCGAA

TTTGCTTGGCCTGGAGCTTCTTCTTGGGCTCTCAATGGACGTAATAGCTTGATGAATCCTGGACCTGCTATGGCC

AGCCACAAAGAAGGAGAGGACCGTTTCTTTCCTTTGTCTGGATCTTTAATTTTTGGCAAACAAGGAACTGGAAGA

GACAACGTGGATGCGGACAAAGTCATGATAACCAACGAAGAAGAAATTAAAACTACTAACCCGGTAGCAACGGAG

TCCTATGGACAAGTGGCCACAAACCACCAGAGTGCCCAAGCACAGGCGCAGACCGGCTGGGTTCAAAACCAAGGA

ATACTTCCGGGTATGGTTTGGCAGGACAGAGATGTGTACCTGCAAGGACCCATTTGGGCCAAAATTCCTCACACG

GACGGCAACTTTCACCCTTCTCCGCTGATGGGAGGGTTTGGAATGAAGCACCCGCCTCCTCAGATCCTCATCAAA

AACACACCTGTACCTGCGGATCCTCCAACGGCCTTCAACAAGGACAAGCTGAACTCTTTCATCACCCAGTATTCT

ACTGGCCAAGTCAGCGTGGAGATCGAGTGGGAGCTGCAGAAGGAAAACAGCAAGCGCTGGAACCCGGAGATCCAG

TACACTTCCAACTATTACAAGTCTAATAATGTTGAATTTGCTGTTAATACTGAAGGTGTATATAGTGAACCCCGC

CCCATTGGCACCAGATACCTGACTCGTAATCTGTAA
```

AAV-10
Partial Genome: AY631965

Rep78:
(SEQ ID NO: 22)
```
ATGCCGGGCTTCTACGAGATCGTGATCAAGGTGCCGAGCGACCTGGACGAGCACCTGCCGGGCATTTCTGACTCG

TTTGTGAACTGGGTGGCCGAGAAGGAATGGGAGCTGCCCCCGGATTCTGACATGGATCGGAATCTGATCGAGCAG

GCACCCCTGACCGTGGCCGAGAAGCTGCAGCGCGACTTCCTGGTCCACTGGCGCCGCGTGAGTAAGGCCCCGGAG

GCCCTCTTCTTTGTTCAGTTCGAGAAGGGCGAGTCCTACTTTCACCTGCACGTTCTGGTCGAGACCACGGGGGTC

AAGTCCATGGTCCTGGGCCGCTTCCTGAGTCAGATCAGAGACAGGCTGGTGCAGACCATCTACCGCGGGGTAGAG

CCCACGCTGCCCAACTGGTTCGCGGTGACCAAGACGCGAAATGGCGCCGGCGGGGGGAACAAGGTGGTGGACGAG

TGCTACATCCCCAACTACCTCCTGCCCAAGACGCAGCCCGAGCTGCAGTGGGCGTGGACTAACATGGAGGAGTAT

ATAAGCGCGTGTCTGAACCTCGCGGAGCGTAAACGGCTCGTGGCGCAGCACCTGACCCACGTCAGCCAGACGCAG

GAGCAGAACAAGGAGAATCTGAACCCGAATTCTGACGCGCCCGTGATCAGGTCAAAAACCTCCGCGCGCTACATG

GAGCTGGTCGGGTGGCTGGTGGACCGGGGCATCACCTCCGAGAAGCAGTGGATCCAGGAGGACCAGGCCTCGTAC

ATCTCCTTCAACGCCGCCTCCAACTCGCGGTCCCAGATCAAGGCCGCGCTGGACAATGCCGGAAAGATCATGGCG

CTGACCAAATCCGCGCCCGACTACCTGGTAGGCCCGTCCTTACCCGCGGACATTAAGGCCAACCGCATCTACCGC

ATCCTGGAGCTCAACGGCTACGACCCCGCCTACGCCGGCTCCGTCTTCCTGGGCTGGGCGCAGAAAAAGTTCGGT

AAAAGGAATACAATTTGGCTGTTCGGGCCCGCCACCACCGGCAAGACCAACATCGCGGAAGCCATCGCCCACGCC

GTGCCCTTCTACGGCTGCGTCAACTGGACCAATGAGAACTTTCCCTTCAACGATTGCGTCGACAAGATGGTGATC
```

-continued

TGGTGGGAGGAGGGCAAGATGACCGCCAAGGTCGTGGAGTCCGCCAAGGCCATTCTGGGCGGAAGCAAGGTGCGC

GTCGACCAAAAGTGCAAGTCCTCGGCCCAGATCGACCCCACGCCCGTGATCGTCACCTCCAACACCAACATGTGC

GCCGTGATCGACGGGAACAGCACCACCTTCGAGCACCAGCAGCCCCTGCAGGACCGCATGTTCAAGTTCGAGCTC

ACCCGCCGTCTGGAGCACGACTTTGGCAAGGTGACCAAGCAGGAAGTCAAAGAGTTCTTCCGCTGGGCTCAGGAT

CACGTGACTGAGGTGACGCATGAGTTCTACGTCAGAAAGGGCGGAGCCACCAAAAGACCCGCCCCCAGTGACGCG

GATATAAGCGAGCCCAAGCGGGCCTGCCCCTCAGTTGCGGAGCCATCGACGTCAGACGCGGAAGCACCGGTGGAC

TTTGCGGACAGGTACCAAAACAAATGTTCTCGTCACGCGGGCATGCTTCAGATGCTGTTTCCCTGCAAGACATGC

GAGAGAATGAATCAGAATTTCAACGTCTGCTTCACGCACGGGGTCAGAGACTGCTCAGAGTGCTTCCCCGGCGCG

TCAGAATCTCAACCTGTCGTCAGAAAAAAGACGTATCAGAAACTGTGCGCGATTCATCATCTGCTGGGGGGGCA

CCCGAGATTGCGTGTTCGGCCTGCGATCTCGTCAACGTGGACTTGGATGACTGTGTTTCTGAGCAATAA

CapVP1:

(SEQ ID NO: 23)
ATGGCTGCTGACGGTTATCTTCCAGATTGGCTCGAGGACAACCTCTCTGAGGGCATTCGCGAGTGGTGGGACCTG

AAACCTGGAGCCCCCAAGCCCAAGGCCAACCAGCAGAAGCAGGACGACGGCCGGGGTCTGGTGCTTCCTGGCTAC

AAGTACCTCGGACCCTTCAACGGACTCGACAAGGGGGAGCCCGTCAACGCGGCGGACGCAGCGGCCCTCGAGCAC

GACAAGGCCTACGACCAGCAGCTCAAAGCGGGTGACAATCCGTACCTGCGGTATAACCACGCCGACGCCGAGTTT

CAGGAGCGTCTGCAAGAAGATACGTCTTTTGGGGGCAACCTCGGGCGAGCAGTCTTCCAGGCCAAGAAGCGGGTT

CTCGAACCTCTCGGTCTGGTTGAGGAAGCTGCTAAGACGGCTCCTGGAAAGAAGAGACCGGTAGAACCGTCACCT

CAGCGTTCCCCCGACTCCTCCACGGGCATCGGCAAGAAAGGCCAGCAGCCCGCTAAAAAGAGACTGAACTTTGGG

CAGACTGGCGAGTCAGAGTCAGTCCCCGACCCTCAACCAATCGGAGAACCACCAGCAGGCCCCTCTGGTCTGGGA

TCTGGTACAATGGCTGCAGGCGGTGGCGCTCCAATGGCAGACAATAACGAAGGCGCCGACGGAGTGGGTAGTTCC

TCAGGAAATTGGCATTGCGATTCCACATGGCTGGGCGACAGAGTCATCACCACCAGCACCCGAACCTGGGCCCTG

CCCACCTACAACAACCACCTCTACAAGCAAATCTCCAACGGGACATCGGGAGGAAGCACCAACGACAACACCTAC

TTCGGCTACAGCACCCCTGGGGGTATTTTGACTTCAACAGATTCCACTGCCACTTCTCACCACGTGACTGGCAG

CGACTCATCAACAACAACTGGGGATTCCGGCCAAAAAGACTCAGCTTCAAGCTCTTCAACATCCAGGTCAAGGAG

GTCACGCAGAATGAAGGCACCAAGACCATCGCCAATAACCTTACCAGCACGATTCAGGTATTTACGGACTCGGAA

TACCAGCTGCCGTACGTCCTCGGCTCCGCGCACCAGGGCTGCCTGCCTCCGTTCCCGGCGGATGTCTTCATGATT

CCCCAGTACGGCTACCTGACACTGAACAATGGAAGTCAAGCCGTAGGCCGTTCCTCCTTCTACTGCCTGGAATAT

TTTCCATCTCAAATGCTGCGAACTGGAAACAATTTTGAATTCAGCTACACCTTCGAGGACGTGCCTTTCCACAGC

AGCTACGCACACAGCCAGAGCTTGGACCGACTGATGAATCCTCTCATTGACCAGTACCTGTACTACTTATCCAGA

ACTCAGTCCACAGGAGGAACTCAAGGTACCCAGCAATTGTTATTTTCTCAAGCTGGGCCTGCAAACATGTCGGCT

CAGGCCAAGAACTGGCTGCCTGGACCTTGCTACCGGCAGCAGCGAGTCTCCACGACACTGTCGCAAAACAACAAC

AGCAACTTTGCTTGGACTGGTGCCACCAAATATCACCTGAACGGAAGAGACTCTCTGGTGAATCCCGGTGTCGCC

ATGGCAACCCACAAGGACGACGAGGAACGCTTCTTCCCGTCGAGCGGAGTCCTGATGTTTGGAAAACAGGGTGCT

GGAAGAGACAATGTGGACTACAGCAGCGTTATGCTAACAAGCGAAGAAGAAATTAAAACCACTAACCCTGTAGCC

ACAGAACAATACGGCGTGGCTGACAACTTGCAGCAAGCCAATACAGGGCCTATTGTGGGAAATGTCAACAGC

CAAGGAGCCTTACCTGGCATGGTCTGGCAGAACCGAGACGTGTACCTGCAGGGTCCCATCTGGGCCAAGATTCCT

CACACGGACGGCAACTTTCACCCGTCTCCTCTGATGGGCGGCTTTGGACTTAAACACCCGCCTCCACAGATCCTG

ATCAAGAACACGCCGGTACCTGCGGATCCTCCAACAACGTTCAGCCAGGCGAAATTGGCTTCCTTCATCACGCAG

TACAGCACCGGACAGGTCAGCGTGGAAATCGAGTGGGAGCTGCAGAAGGAGAACAGCAAACGCTGGAACCCAGAG

ATTCAGTACACTTCAAACTACTACAAATCTACAAATGTGGACTTTGCTGTCAATACAGAGGGAACTTATTCTGAG

CCTCGCCCCATTGGTACTCGTTATCTGACACGTAATCTGTAA

AAV-11
Partial Genome: AY631966

Rep78:
(SEQ ID NO: 24)
ATGCCGGGCTTCTACGAGATCGTGATCAAGGTGCCGAGCGACCTGGACGAGCACCTGCCGGGCATTTCTGACTCG

TTTGTGAACTGGGTGGCCGAGAAGGAATGGGAGCTGCCCCCGGATTCTGACATGGATCGGAATCTGATCGAGCAG

GCACCCCTGACCGTGGCCGAGAAGCTGCAGCGCGACTTCCTGGTCCACTGGCGCCGCGTGAGTAAGGCCCCGGAG

GCCCTCTTCTTTGTTCAGTTCGAGAAGGGCGAGTCCTACTTCCACCTCCACGTTCTCGTCGAGACCACGGGGGTC

AAGTCCATGGTCCTGGGCCGCTTCCTGAGTCAGATCAGAGACAGGCTGGTGCAGACCATCTACCGCGGGGTCGAG

CCCACGCTGCCCAACTGGTTCGCGGTGACCAAGACGCGAAATGGCGCCGGCGGGGGGAACAAGGTGGTGGACGAG

TGCTACATCCCCAACTACCTCCTGCCCAAGACCCAGCCCGAGCTGCAGTGGGCGTGGACTAACATGGAGGAGTAT

ATAAGCGCGTGTCTAAACCTCGCGGAGCGTAAACGGCTCGTGGCGCAGCACCTGACCCACGTCAGCCAGACGCAG

GAGCAGAACAAGGAGAATCTGAACCCGAATTCTGACGCGCCCGTGATCAGGTCAAAAACCTCCGCGCGCTACATG

GAGCTGGTCGGGTGGCTGGTGGACCGGGGCATCACCTCCGAGAAGCAGTGGATCCAGGAGGACCAGGCCTCGTAC

ATCTCCTTCAACGCCGCCTCCAACTCGCGGTCCCAGATCAAGGCCGCGCTGGACAATGCCGGAAAGATCATGGCG

CTGACCAAATCCGCGCCCGACTACCTGGTAGGCCCGTCCTTACCCGGGACATTAAGGCCAACCGCATCTACCGC

ATCCTGGAGCTCAACGGCTACGACCCCGCCTACGCCGGCTCCGTCTTCCTGGGCTGGGCGCAGAAAAAGTTCGGT

AAACGCAACACCATCTGGCTGTTTGGGCCCGCCACCACCGGCAAGACCAACATCGCGGAAGCCATAGCCCACGCC

GTGCCCTTCTACGGCTGCGTGAACTGGACCAATGAGAACTTTCCCTTCAACGATTGCGTCGACAAGATGGTGATC

TGGTGGAGGAGGGCAAGATGACCGCCAAGGTCGTGGAGTCCGCCAAGGCCATTCTGGGCGGAAGCAAGGTGCGC

GTGGACCAAAAGTGCAAGTCCTCGGCCCAGATCGACCCCACGCCCGTGATCGTCACCTCCAACACCAACATGTGC

GCCGTGATCGACGGGAACAGCACCACCTTCGAGCACCAGCAGCCGCTGCAGGACCGCATGTTCAAGTTCGAGCTC

ACCCGCCGTCTGGAGCACGACTTTGGCAAGGTGACCAAGCAGGAAGTCAAAGAGTTCTTCCGCTGGGCTCAGGAT

CACGTGACTGAGGTGGCGCATGAGTTCTACGTCAGAAAGGGCGGAGCCACCAAAAGACCCGCCCCCAGTGACGCG

GATATAAGCGAGCCCAAGCGGGCCTGCCCCTCAGTTCCGGAGCCATCGACGTCAGACGCGGAAGCACCGGTGGAC

TTTGCGGACAGGTACCAAAACAAATGTTCTCGTCACGCGGGCATGCTTCAGATGCTGTTTCCCTGCAAGACATGC

GAGAGAATGAATCAGAATTTCAACGTCTGCTTCACGCACGGGGTCAGAGACTGCTCAGAGTGCTTCCCCGGCGCG

TCAGAATCTCAACCCGTCGTCAGAAAAAAGACGTATCAGAAACTGTGCGCGATTCATCATCTGCTGGGGGGGCA

CCCGAGATTGCGTGTTCGGCCTGCGATCTCGTCAACGTGGACTTGGATGACTGTGTTTCTGAGCAATAA

CapVP1:
(SEQ ID NO: 25)
ATGGCTGCTGACGGTTATCTTCCAGATTGGCTCGAGGACAACCTCTCTGAGGGCATTCGCGAGTGGTGGGACCTG

AAACCTGGAGCCCCGAAGCCCAAGGCCAACCAGCAGAAGCAGGACGACGGCCGGGGTCTGGTGCTTCCTGGCTAC

AAGTACCTCGGACCCTTCAACGGACTCGACAAGGGGGAGCCCGTCAACGCGGCGACGCAGCGGCCCTCGAGCAC

GACAAGGCCTACGACCAGCAGCTCAAAGCGGGTGACAATCCGTACCTGCGGTATAACCACGCCGACGCCGAGTTT

CAGGAGCGTCTGCAAGAAGATACGTCTTTTGGGGGCAACCTCGGCGAGCAGTCTTCCAGGCCAAGAAGAGGGTA

CTCGAACCTCTGGGCCTGGTTGAAGAAGGTGCTAAAACGGCTCCTGGAAAGAAGAGACCGTTAGAGTCACCACAA

GAGCCCGACTCCTCCTCGGGCATCGGCAAAAAAGGCAAACAACCAGCCAGAAAGAGGCTCAACTTTGAAGAGGAC

ACTGGAGCCGGAGACGGACCCCCTGAAGGATCAGATACCAGCGCCATGTCTTCAGACATTGAAATGCGTGCAGCA

CCGGGCGGAAATGCTGTCGATGCGGGACAAGGTTCCGATGGAGTGGGTAATGCCTCGGGTGATTGGCATTGCGAT

TCCACCTGGTCTGAGGGCAAGGTCACAACAACCTCGACCAGAACCTGGGTCTTGCCCACCTACAACAACCACTTG

TACCTGCGTCTCGGAACAACATCAAGCAGCAACACCTACAACGGATTCTCCACCCCCTGGGGATATTTTGACTTC

AACAGATTCCACTGTCACTTCTCACCACGTGACTGGCAAAGACTCATCAACAACAACTGGGGACTACGACCAAAA

-continued

```
GCCATGCGCGTTAAAATCTTCAATATCCAAGTTAAGGAGGTCACAACGTCGAACGGCGAGACTACGGTCGCTAAT

AACCTTACCAGCACGGTTCAGATATTTGCGGACTCGTCGTATGAGCTCCCGTACGTGATGGACGCTGGACAAGAG

GGGAGCCTGCCTCCTTTCCCCAATGACGTGTTCATGGTGCCTCAATATGGCTACTGTGGCATCGTGACTGGCGAG

AATCAGAACCAAACGGACAGAAACGCTTTCTACTGCCTGGAGTATTTTCCTTCGCAAATGTTGAGAACTGGCAAC

AACTTTGAAATGGCTTACAACTTTGAGAAGGTGCCGTTCCACTCAATGTATGCTCACAGCCAGAGCCTGGACAGA

CTGATGAATCCCTCCTGGACCAGTACCTGTGGCACTTACAGTCGACTACCTCTGGAGAGACTCTGAATCAAGGC

AATGCAGCAACCACATTTGGAAAAATCAGGAGTGGAGACTTTGCCTTTTACAGAAAGAACTGGCTGCCTGGGCCT

TGTGTTAAACAGCAGAGATTCTCAAAAACTGCCAGTCAAAATTACAAGATTCCTGCCAGCGGGGGCAACGCTCTG

TTAAAGTATGACACCCACTATACCTTAAACAACCGCTGGAGCAACATCGCGCCCGGACCTCCAATGGCCACAGCC

GGACCTTCGGATGGGGACTTCAGTAACGCCCAGCTTATATTCCCTGGACCATCTGTTACCGGAAATACAACAACT

TCAGCCAACAATCTGTTGTTTACATCAGAAGAAGAAATTGCTGCCACCAACCCAAGAGACACGGACATGTTTGGC

CAGATTGCTGACAATAATCAGAATGCTACAACTGCTCCCATAACCGGCAACGTGACTGCTATGGGAGTGCTGCCT

GGCATGGTGTGGCAAAACAGAGACATTTACTACCAAGGGCCAATTTGGGCCAAGATCCCACACGCGGACGGACAT

TTTCATCCTTCACCGCTGATTGGTGGGTTTGGACTGAAACACCCGCCTCCCCAGATATTCATCAAGAACACTCCC

GTACCTGCCAATCCTGCGACAACCTTCACTGCAGCCAGAGTGGACTCTTTCATCACACAATACAGCACCGGCCAG

GTCGCTGTTCAGATTGAATGGGAAATTGAAAAGGAACGCTCCAAACGCTGGAATCCTGAAGTGCAGTTTACTTCA

AACTATGGGAACCAGTCTTCTATGTTGTGGGCTCCTGATACAACTGGGAAGTATACAGAGCCGCGGGTTATTGGC

TCTCGTTATTTGACTAATCATTTGTAA
```

AAV-12
Partial Genome: DQ813647

Rep78:
(SEQ ID NO: 26)
```
ATGCCGGGGTTCTACGAGGTGGTGATCAAGGTGCCCAGCGACCTGGACGAGCACCTGCCCGGCATTTCTGACTCC

TTTGTGAACTGGGTGGCCGAGAAGGAATGGGAGTTGCCCCCGGATTCTGACATGGATCAGAATCTGATTGAGCAG

GCACCCCTGACCGTGGCCGAGAAGCTGCAGCGCGAGTTCCTGGTGGAATGGCGCCGAGTGAGTAAATTTCTGGAG

GCCAAGTTTTTTGTGCAGTTTGAAAAGGGGGACTCGTACTTTCATTTGCATATTCTGATTGAAATTACCGGCGTG

AAATCCATGGTGGTGGGCCGCTACGTGAGTCAGATTAGGGATAAACTGATCCAGCGCATCTACCGCGGGGTCGAG

CCCCAGCTGCCCAACTGGTTCGCGGTCACAAAGACCCGAAATGGCGCCGGAGGCGGGAACAAGGTGGTGGACGAG

TGCTACATCCCCAACTACCTGCTCCCCAAGGTCCAGCCCGAGCTTCAGTGGGCGTGGACTAACATGGAGGAGTAT

ATAAGCGCCTGTTTGAACCTCGCGGAGCGTAAACGGCTCGTGGCGCAGCACCTGACGCACGTCTCCCAGACCCAG

GAGGGCGACAAGGAGAATCTGAACCCGAATTCTGACGCGCCGGTGATCCGGTCAAAAACCTCCGCCAGGTACATG

GAGCTGGTCGGGTGGCTGGTGGACAAGGGCATCACGTCCGAGAAGCAGTGGATCCAGGAGGACCAGGCCTCGTAC

ATCTCCTTCAACGCGGCCTCCAACTCCCGGTCGCAGATCAAGGCGGCCCTGGACAATGCCTCCAAAATCATGAGC

CTCACCAAAACGGCTCCGGACTATCTCATCGGGCAGCAGCCCGTGGGGACATTACCACCAACCGGATCTACAAA

ATCCTGGAACTGAACGGGTACGACCCCCAGTACGCCGCCTCCGTCTTTCTCGGCTGGGCCCAGAAAAAGTTTGGA

AAGCGCAACACCATCTGGCTGTTTGGGCCCGCCACCACCGGCAAGACCAACATCGCGGAAGCCATCGCCCACGCG

GTCCCCTTCTACGGCTGCGTCAACTGGACCAATGAGAACTTTCCCTTCAACGACTGCGTCGACAAAATGGTGATT

TGGTGGGAGGAGGGCAAGATGACCGCCAAGGTCGTAGAGTCCGCCAAGGCCATTCTGGGCGGCAGCAAGGTGCGC

GTGGACCAAAAATGCAAGGCCTCTGCGCAGATCGACCCCACCCCCGTGATCGTCACCTCCAACACCAACATGTGC

GCCGTGATTGACGGGAACAGCACCACCTTCGAGCACCAGCAGCCCCTGCAGGACCGGATGTTCAAGTTTGAACTC

ACCCGCCGCCTCGACCACGACTTTGGCAAGGTCACCAAGCAGGAAGTCAAGGACTTTTTCCGGTGGGCGGCTGAT
```

-continued

CACGTGACTGACGTGGCTCATGAGTTTTACGTCACAAAGGGTGGAGCTAAGAAAAGGCCCGCCCCCTCTGACGAG

GATATAAGCGAGCCCAAGCGGCCGCGCGTGTCATTTGCGCAGCCGGAGACGTCAGACGCGGAAGCTCCCGGAGAC

TTCGCCGACAGGTACCAAAACAAATGTTCTCGTCACGCGGGTATGCTGCAGATGCTCTTTCCCTGCAAGACGTGC

GAGAGAATGAATCAGAATTCCAACGTCTGCTTCACGCACGGTCAGAAAGATTGCGGGGAGTGCTTTCCCGGGTCA

GAATCTCAACCGGTTTCTGTCGTCAGAAAAACGTATCAGAAACTGTGCATCCTTCATCAGCTCCGGGGGCACCC

GAGATCGCCTGCTCTGCTTGCGACCAACTCAACCCCGATTTGGACGATTGCCAATTTGAGCAATAA

CapVP1:

(SEQ ID NO: 27)
ATGGCTGCTGACGGTTATCTTCCAGATTGGCTCGAGGACAACCTCTCTGAAGGCATTCGCGAGTGGTGGCGCTG

AAACCTGGAGCTCCACAACCCAAGGCCAACCAACAGCATCAGGACAACGGCAGGGGTCTTGTGCTTCCTGGGTAC

AAGTACCTCGGACCCTTCAACGGACTCGACAAGGGAGAGCCGGTCAACGAGGCAGACGCCGCGGCCCTCGAGCAC

GACAAGGCCTACGACAAGCAGCTCGAGCAGGGGACAACCCGTATCTCAAGTACAACCACGCCGACGCCGAGTTC

CAGCAGCGCTTGGCGACCGACACCTCTTTTGGGGGCAACCTCGGGCGAGCAGTCTTCCAGGCCAAAAAGAGGATT

CTCGAGCCTCTGGGTCTGGTTGAAGAGGGCGTTAAAACGGCTCCTGGAAAGAAACGCCCATTAGAAAAGACTCCA

AATCGGCCGACCAACCCGGACTCTGGGAAGGCCCCGGCCAAGAAAAAGCAAAAAGACGGCGAACCAGCCGACTCT

GCTAGAAGGACACTCGACTTTGAAGACTCTGGAGCAGGAGACGGACCCCCTGAGGGATCATCTTCCGGAGAAATG

TCTCATGATGCTGAGATGCGTGCGGCGCCAGGCGGAAATGCTGTCGAGGCGGGACAAGGTGCCGATGGAGTGGGT

AATGCCTCCGGTGATTGGCATTGCGATTCCACCTGGTCAGAGGGCCGAGTCACCACCACCAGCACCCGAACCTGG

GTCCTACCCACGTACAACAACCACCTGTACCTGCGAATCGGAACAACGGCCAACAGCAACACCTACAACGGATTC

TCCACCCCCTGGGGATACTTTGACTTTAACCGCTTCCACTGCCACTTTTCCCCACGCGACTGGCAGCGACTCATC

AACAACAACTGGGGACTCAGGCCGAAATCGATGCGTGTTAAAATCTTCAACATACAGGTCAAGGAGGTCACGACG

TCAAACGGCGAGACTACGGTCGCTAATAACCTTACCAGCACGGTTCAGATCTTTGCGGATTCGACGTATGAACTC

CCATACGTGATGGACGCCGGTCAGGAGGGGAGCTTTCCTCCGTTTCCCAACGACGTCTTTATGGTTCCCCAATAC

GGATACTGCGGAGTTGTCACTGGAAAAAACCAGAACCAGACAGACAGAAATGCCTTTTACTGCCTGGAATACTTT

CCATCCCAAATGCTAAGAACTGGCAACAATTTTGAAGTCAGTTACCAATTTGAAAAAGTTCCTTTCCATTCAATG

TACGCGCACAGCCAGAGCCTGGACAGAATGATGAATCCTTTACTGGATCAGTACCTGTGGCATCTGCAATCGACC

ACTACCGGAAATTCCCTTAATCAAGGAACAGCTACCACCACGTACGGGAAAATTACCACTGGAGACTTTGCCTAC

TACAGGAAAAACTGGTTGCCTGGAGCCTGCATTAAACAACAAAAATTTTCAAAGAATGCCAATCAAAACTACAAG

ATTCCCGCCAGCGGGGAGACGCCCTTTAAAGTATGACACGCATACCACTCTAAATGGGCGATGGAGTAACATG

GCTCCTGGACCTCCAATGGCAACCGCAGGTGCCGGGGACTCGGATTTTAGCAACAGCCAGCTGATCTTTGCCGGA

CCCAATCCGAGCGGTAACACGACCACATCTTCAAACAATTTGTTGTTTACCTCAGAAGAGGAGATTGCCACAACA

AACCCACGAGACACGGACATGTTTGGACAGATTGCAGATAATAATCAAAATGCCACCACCGCCCCTCACATCGCT

AACCTGGACGCTATGGGAATTGTTCCCGGAATGGTCTGGCAAAACAGAGACATCTACTACCAGGGCCCTATTTGG

GCCAAGGTCCCTCACACGGACGGACACTTTCACCCTTCGCCGCTGATGGGAGGATTTGGACTGAAACACCCGCCT

CCACAGATTTTCATCAAAAACACCCCCGTACCCGCCAATCCCAATACTACCTTTAGCGCTGCAAGGATTAATTCT

TTTCTGACGCAGTACAGCACCGGACAAGTTGCCGTTCAGATCGACTGGGAAATTCAGAAGGAGCATTCCAAACGC

TGGAATCCCGAAGTTCAATTTACTTCAAACTACGGCACTCAAAATTCTATGCTGTGGGCTCCCGACAATGCTGGC

AACTACCACGAACTCCGGGCTATTGGGTCCCGTTTCCTCACCCACCACTTGTAA

AAV-13
Partial Genome: EU285562

Rep78:
(SEQ ID NO: 28)
ATGCCGGGATTCTACGAGATTGTCCTGAAGGTGCCCAGCGACCTGGACGAGCACCTGCCTGGCATTTCTGACTCT
TTTGTAAACTGGGTGGCGGAGAAGGAATGGGAGCTGCCGCCGGATTCTGACATGGATCTGAATCTGATTGAGCAG
GCACCCCTAACCGTGGCCGAAAAGCTGCAACGCGAATTCCTGGTCGAGTGGCGCCGCGTGAGTAAGGCCCCGGAG
GCCCTCTTCTTTGTTCAGTTCGAGAAGGGGGACAGCTACTTCCACCTACACATTCTGGTGGAGACCGTGGGCGTG
AAATCCATGGTGGTGGGCCGCTACGTGAGCCAGATTAAAGAGAAGCTGGTGACCCGCATCTACCGCGGGGTCGAG
CCGCAGCTTCCGAACTGGTTCGCGGTGACCAAGACGCGTAATGGCGCCGGAGGCGGGAACAAGGTGGTGGACGAC
TGCTACATCCCCAACTACCTGCTCCCCAAGACCCAGCCCGAGCTCCAGTGGGCGTGGACTAATATGGACCAGTAT
TTAAGCGCCTGTTTGAATCTCGCGGAGCGTAAACGGCTGGTGGCGCAGCATCTGACGCACGTGTCGCAGACGCAG
GAGCAGAACAAAGAGAACCAGAATCCCAATTCTGACGCGCCGGTGATCAGATCAAAAACCTCCGCGAGGTACATG
GAGCTGGTCGGGTGGCTGGTGGACCGCGGGATCACGTCAGAAAAGCAATGGATCCAGGAGGACCAGGCCTCTTAC
ATCTCCTTCAACGCCGCCTCCAACTCGCGGTCACAAATCAAGGCCGCACTGGACAATGCCTCCAAATTTATGAGC
CTGACAAAAACGGCTCCGGACTACCTGGTGGGAAACAACCCGCCGGAGGACATTACCAGCAACCGGATCTACAAA
ATCCTCGAGATGAACGGGTACGATCCGCAGTACGCGGCCTCCGTCTTCCTGGGCTGGGCGCAAAAGAAGTTCGGG
AAGAGGAACACCATCTGGCTCTTTGGGCCGGCCACGACGGGTAAAACCAACATCGCTGAAGCTATCGCCCACGCC
GTGCCCTTTTACGGCTGCGTGAACTGGACCAATGAGAACTTTCCGTTCAACGATTGCGTCGACAAGATGGTGATC
TGGTGGGAGGAGGGCAAGATGACGGCCAAGGTCGTGGAGTCCGCCAAGGCCATTCTGGGCGGAAGCAAGGTGCGC
GTGGACCAAAAGTGCAAGTCATCGGCCCAGATCGACCCAACTCCCGTCATCGTCACCTCCAACACCAACATGTGC
GCGGTCATCGACGGAAATTCCACCACCTTCGAGCACCAACAACCACTCCAAGACCGGATGTTCAAGTTCGAGCTC
ACCAAGCGCCTGGAGCACGACTTTGGCAAGGTCACCAAGCAGGAAGTCAAGGACTTTTTCCGGTGGGCGTCAGAT
CACGTGACTGAGGTGTCTCACGAGTTTTACGTCAGAAAGGGTGGAGCTAGAAAGAGGCCCGCCCCCAATGACGCA
GATATAAGTGAGCCCAAGCGGGCCTGTCCGTCAGTTGCGCAGCCATCGACGTCAGACGCGGAAGCTCCGGTGGAC
TACGCGGACAGGTACCAAAACAAATGTTCTCGTCACGTGGGCATGAATCTGATGCTTTTTCCCTGCCGGCAATGC
GAGAGAATGAATCAGAATGTGGACATTTGCTTCACGCACGGGGTCATGGACTGTGCCGAGTGCTTCCCCGTGTCA
GAATCTCAACCCGTGTCTGTCGTCAGAAAGCGGACATATCAGAAACTGTGTCCGATTCATCACATCATGGGGAGG
GCGCCCGAGGTGGCTTGTTCGGCCTGCGATCTGGCCAATGTGGACTTGGATGACTGTGACATGGAGCAATAA

CapVP1:
(SEQ ID NO: 29)
ATGACTGACGGTTACCTTCCAGATTGGCTAGAGGACAACCTCTCTGAAGGCGTTCGAGAGTGGTGGGCGCTGCAA
CCTGGAGCCCCTAAACCCAAGGCAAATCAACAACATCAGGACAACGCTCGGGGTCTTGTGCTTCCGGGTTACAAA
TACCTCGGACCCGGCAACGGACTTGACAAGGGGGAACCCGTCAACGCAGCGGACGCGGCAGCCCTCGAACACGAC
AAGGCCTACGACCAGCAGCTCAAGGCCGGTGACAACCCCTACCTCAAGTACAACCACGCCGACGCCGAGTTTCAG
GAGCGTCTTCAAGAAGATACGTCTTTTGGGGGCAACCTCGGACGAGCAGTCTTCCAGGCCAAAAAGAGGATCCTT
GAGCCTCTGGGTCTGGTTGAGGAAGCGGCTAAGACGGCTCCTGGAAAAAAGAGACCTGTAGAGCAATCTCCAGCA
GAACCGGACTCCTCTTCGGGCATCGGCAAATCAGGCCAGCAGCCCGCTAGAAAAAGACTGAATTTTGGTCAGACT
GGCGACACAGAGTCAGTCCCAGACCCTCAACCACTCGGACAACCTCCCGCAGCCCCTCTGGTGTGGGATCTACT
ACAATGGCTTCAGGCGGTGGCGCACCAATGGCAGACAATAACGAGGGTGCCGATGGAGTGGGTAATTCCTCAGGA
AATTGGCATTGCGATTCCCAATGGCTGGGCGACAGAGTCATCACCACCAGCACCCGCACCTGGGCCCTGCCCACC
TACAACAATCACCTCTACAAGCAAATCTCCAGCCAATCAGGAGCCACCAACGACAACCACTACTTTGGCTACAGC
ACCCCCTGGGGGTATTTTGACTTCAACAGATTCCACTGCCACTTTTCACCACGTGACTGGCAAAGACTCATCAAC

```
AACAACTGGGGATTCCGACCCAAGAGACTCAACTTCAAGCTCTTTAACATTCAAGTCAAAGAGGTCACGCAGAAT

GACGGTACGACGACGATTGCCAATAACCTTACCAGCACGGTTCAGGTGTTTACTGACTCCGAGTACCAGCTCCCG

TACGTCCTCGGCTCGGCGCATCAGGGATGCCTCCCGCCGTTCCCAGCAGACGTCTTCATGGTCCCACAGTATGGA

TACCTCACCCTGAACAACGGGAGTCAGGCGGTAGGACGCTCTTCCTTTTACTGCCTGGAGTACTTTCCTTCTCAG

ATGCTGCGTACTGGAAACAACTTTCAGTTTAGCTACACTTTTGAAGACGTGCCTTTCCACAGCAGCTACGCTCAC

AGCCAAAGTCTGGACCGTCTCATGAATCCTCTGATCGACCAGTACCTGTACTATCTGAACAGGACACAAACAGCC

AGTGGAACTCAGCAGTCTCGGCTACTGTTTAGCCAAGCTGGACCCACCAGTATGTCTCTTCAAGCTAAAAACTGG

CTGCCTGGACCTTGCTACAGACAGCAGCGTCTGTCAAAGCAGGCAAACGACAACAACAACAGCAACTTTCCCTGG

ACTGGTGCCACCAAATATCATCTGAATGGCCGGGACTCATTGGTGAACCCGGGCCCTGCTATGGCCAGTCACAAG

GATGACAAAGAAAAGTTTTTCCCCATGCATGGAACCCTGATATTTGGTAAAGAAGGAACAAATGCCAACAACGCG

GATTTGGAAAATGTCATGATTACAGATGAAGAAGAAATCCGCACCACCAATCCCGTGGCTACGGAGCAGTACGGG

ACTGTGTCAAATAATTTGCAAAACTCAAACGCTGGTCCAACTACTGGAACTGTCAATCACCAAGGAGCGTTACCT

GGTATGGTGTGGCAGGATCGAGACGTGTACCTGCAGGGACCCATTTGGGCCAAGATTCCTCACACCGATGGACAC

TTTCATCCTTCTCCACTGATGGGAGGTTTTGGGCTCAAACACCCGCCTCCTCAGATCATGATCAAAAACACTCCC

GTTCCAGCCAATCCTCCCACAAACTTTAGTGCGGCAAAGTTTGCTTCCTTCATCACACAGTACTCCACGGGGCAG

GTCAGCGTGGAGATCGAGTGGGAGCTGCAGAAGGAGAACAGCAAACGCTGGAATCCCGAAATTCAGTACACTTCC

AACTACAACAAATCTGTTAATGTGGACTTTACTGTGGACACTAATGGTGTGTATTCAGAGCCTCGCCCCATTGGC

ACCAGATACCTGACTCGTAATCTGTAA
```

ITR Sequence (SEQ ID NO: 30)
```
CCTGCAGGCAGCTGCGCGCTCGCTCGCTCACTGAGGCCGCCCGGGCAAA
GCCCGGGCGTCGGGCGACCTTTGGTCGCCCGGCCTCAGTGAGCGAGCGA
GCGCGCAGAGAGGGAGTGGCCAACTCCATCACTAGGGGTTCCT
```

Rep2 Sequence - Contains Rep78 and Rep52 (start codon underlined)

(SEQ ID NO: 31)
```
ATGCCGGGGTTTTACGAGATTGTGATTAAGGTCCCCAGCGACCTTGACGAGCATCTGCCCGGCATTTCTGACAGC

TTTGTGAACTGGGTGGCCGAGAAGGAATGGGAGTTGCCGCCAGATTCTGACATGGATCTGAATCTGATTGAGCAG

GCACCCCTGACCGTGGCCGAGAAGCTGCAGCGCGACTTTCTGACGGAATGGCGCCGTGTGAGTAAGGCCCCGGAG

GCCCTTTTCTTTGTGCAATTTGAGAAGGGAGAGAGCTACTTCCACATGCACGTGCTCGTGGAAACCACCGGGGTG

AAATCCATGGTTTTGGGACGTTTCCTGAGTCAGATTCGCGAAAAACTGATTCAGAGAATTTACCGCGGGATCGAG

CCGACTTTGCCAAACTGGTTCGCGGTCACAAAGACCAGAAATGGCGCCGGAGGCGGGAACAAGGTGGTGGATGAG

TGCTACATCCCCAATTACTTGCTCCCCAAAACCCAGCCTGAGCTCCAGTGGGCGTGGACTAATATGGAACAGTAT

TTAAGCGCCTGTTTGAATCTCACGGAGCGTAAACGGTTGGTGGCGCAGCATCTGACGCACGTGTCGCAGACGCAG

GAGCAGAACAAAGAGAATCAGAATCCCAATTCTGATGCGCCGGTGATCAGATCAAAAACTTCAGCCAGGTAATG

GAGCTGGTCGGGTGGCTCGTGGACAAGGGGATTACCTCGGAGAAGCAGTGGATCCAGGAGGACCAGGCCTCATAC

ATCTCCTTCAATGCGGCCTCCAACTCGCGGTCCCAAATCAAGGCTGCCTTGGACAATGCGGGAAAGATTATGAGC

CTGACTAAAACCGCCCCCGACTACCTGGTGGGCCAGCAGCCCGTGGAGGACATTTCCAGCAATCGGATTTATAAA

ATTTTGGAACTAAACGGGTACGATCCCCAATATGCGGCTTCCGTCTTTCTGGGATGGGCCACGAAAAAGTTCGGC

AAGAGGAACACCATCTGGCTGTTTGGGCCTGCAACTACCGGGAAGACCAACATCGCGGAGGCCATAGCCCACACT

GTGCCCTTCTACGGGTGCGTAAACTGGACCAATGAGAACTTTCCCTTCAACGACTGTGTCGACAAGATGGTGATC

TGGTGGGAGGAGGGGAAGATGACCGCCAAGGTCGTGGAGTCGGCCAAAGCCATTCTCGGAGGAAGCAAGGTGCGC

GTGGACCAGAAATGCAAGTCCTCGGCCCAGATAGACCCGACTCCCGTGATCGTCACCTCCAACACCAACATGTGC
```

-continued

GCCGTGATTGACGGGAACTCAACGACCTTCGAACACCAGCAGCCGTTGCAAGACCGGATGTTCAAATTTGAACTC

ACCCGCCGTCTGGATCATGACTTTGGGAAGGTCACCAAGCAGGAAGTCAAAGACTTTTTCCGGTGGGCAAAGGAT

CACGTGGTTGAGGTGGAGCATGAATTCTACGTCAAAAAGGGTGGAGCCAAGAAAAGACCCGCCCCCAGTGACGCA

GATATAAGTGAGCCCAAACGGGTGCGCGAGTCAGTTGCGCAGCCATCGACGTCAGACGCGGAAGCTTCGATCAAC

TACGCAGACAGGTACCAAAACAAATGTTCTCGTCACGTGGGCATGAATCTGATGCTGTTTCCCTGCAGACAATGC

GAGAGAATGAATCAGAATTCAAATATCTGCTTCACTCACGGACAGAAAGACTGTTTAGAGTGCTTTCCCGTGTCA

GAATCTCAACCCGTTTCTGTCGTCAAAAAGGCGTATCAGAAACTGTGCTACATTCATCATATCATGGGAAAGGTG

CCAGACGCTTGCACTGCCTGCGATCTGGTCAATGTGGATTTGGATGACTGCATCTTTGAACAATAA

Cap2 Sequence - contains sequentially VP1, VP2, AAP, VP3 (start codons underlined)

(SEQ ID NO: 32)

ATGGCTGCCGATGGTTATCTTCCAGATTGGCTCGAGGACACTCTCTCTGAAGGAATAAGACAGTGGTGGAAGCTC

AAACCTGGCCCACCACCACCAAAGCCCGCAGAGCGGCATAAGGACGACAGCAGGGGTCTTGTGCTTCCTGGGTAC

AAGTACCTCGGACCCTTCAACGGACTCGACAAGGGAGAGCCGGTCAACGAGGCAGACGCCGCGGCCCTCGAGCAC

GACAAAGCCTACGACCGGCAGCTCGACAGCGGAGACAACCCGTACCTCAAGTACAACCACGCCGACGCGGAGTTT

CAGGAGCGCCTTAAAGAAGATACGTCTTTTGGGGGCAACCTCGGACGAGCAGTCTTCCAGGCGAAAAAGAGGGTT

CTTGAACCTCTGGGCCTGGTTGAGGAACCTGTTAAG<u>AC</u>GGCTCCGGGAAAAAAGAGGCCGGTAGAGCACTCTCCT

GTGGAGCCAGACTCCTCCTCGGGAACCGGAAAGGCGGGCCAGCAGCCTGCAAGAAAAAGATTGAATTTTGGTCAG

AC<u>TG</u>GAGACGCAGACTCAGTACCTGACCCCCAGCCTCTCGGACAGCCACCAGCAGCCCCTCTGGTCTGGGAACT

AATAC<u>GAT</u>GGCTACAGGCAGTGGCGCACCAATGGCAGACAATAACGAGGGCGCCGACGGAGTGGGTAATTCCTCG

GGAAATTGGCATTGCGATTCCACATGGATGGGCGACAGAGTCATCACCACCAGCACCCGAACCTGGGCCCTGCCC

ACCTACAACAACCACCTCTACAAACAAATTTCCAGCCAATCAGGAGCCTCGAACGACAATCACTACTTTGGCTAC

AGCACCCCTTGGGGGTATTTTGACTTCAACAGATTCCACTGCCACTTTTCACCACGTGACTGGCAAAGACTCATC

AACAACAACTGGGGATTCCGACCCAAGAGACTCAACTTCAAGCTCTTTAACATTCAAGTCAAAGAGGTCACGCAG

AATGACGGTACGACGACGATTGCCAATAACCTTACCAGCACGGTTCAGGTGTTTACTGACTCGGAGTACCAGCTC

CCGTACGTCCTCGGCTCGGCGCATCAAGGATGCCTCCCGCCGTTCCCAGCAGACGTCTTCATGGTGCCACAGTAT

GGATACCTCACCCTGAACAACGGGAGTCAGGCAGTAGGACGCTCTTCATTTTACTGCCTGGAGTACTTTCCTTCT

CAGATGCTGCGTACCGGAAACAACTTTACCTTCAGCTACACTTTTGAGGACGTTCCTTTCCACAGCAGCTACGCT

CACAGCCAGAGTCTGGACCGTCTCATGAATCCTCTCATCGACCAGTACCTGTATTACTTGAGCAGAACAAACACT

CCAAGTGGAACCACCACGCAGTCAAGGCTTCAGTTTTCTCAGGCCGGAGCGAGTGACATTCGGGACCAGTCTAGG

AACTGGCTTCCTGGACCCTGTTACCGCCAGCAGCGAGTATCAAAGACATCTGCGGATAACAACAACAGTGAATAC

TCGTGGACTGGAGCTACCAAGTACCACCTCAATGGCAGAGACTCTCTGGTGAATCCGGGCCCGGCCATGGCAAGC

CACAAGGACGATGAAGAAAGTTTTTTCCTCAGAGCGGGTTCTCATCTTTGGGAAGCAAGGCTCAGAGAAAACA

AATGTGGACATTGAAAAGGTCATGATTACAGACGAAGAGGAAATCAGGACAACCAATCCCGTGGCTACGGAGCAG

TATGGTTCTGTATCTACCAACCTCCAGAGAGGCAACAGACAAGCAGCTACCGCAGATGTCAACACACAAGGCGTT

CTTCCAGGCATGGTCTGGCAGGACAGAGATGTGTACCTTCAGGGGCCCATCTGGGCAAAGATTCCACACACGGAC

GGACATTTTCACCCCTCTCCCCTCATGGGTGGATTCGGACTTAAACACCCTCCTCCACAGATTCTCATCAAGAAC

ACCCCGGTACCTGCGAATCCTTCGACCACCTTCAGTGCGGCAAAGTTTGCTTCCTTCATCACACAGTACTCCACG

GGACAGGTCAGCGTGGAGATCGAGTGGGAGCTGCAGAAGGAAAACAGCAAACGCTGGAATCCCGAAATTCAGTAC

ACTTCCAACTACAACAAGTCTGTTAATGTGGACTTTACTGTGGACACTAATGGCGTGTATTCAGAGCCTCGCCCC

ATTGGCACCAGATACCTGACTCGTAATCTGTAA

Cap5 Sequence - contains sequentially VP1, VP2, AAP, VP3 (start codons underlined)

(SEQ ID NO: 33)

ATGGCTTTTGTTGATCACCCTCCAGATTGGTTGGAAGAAGTTGGTGAAGGTCTTCGCGAGTTTTTGGGCCTTGAA

GCGGGCCCACCGAAACCAAAACCCAATCAGCAGCATCAAGATCAAGCCCGTGGTCTTGTGCTGCCTGGTTATAAC

TATCTCGGACCCGGAAACGGTCTCGATCGAGGAGAGCCTGTCAACAGGGCAGACGAGGTCGCGCGAGAGCACGAC

ATCTCGTACAACGAGCAGCTTGAGGCGGGAGACAACCCCTACCTCAAGTACAACCACGCGGACGCCGAGTTTCAG

GAGAAGCTCGCCGACGACACATCCTTCGGGGGAAACCTCGGAAAGGCAGTCTTTCAGGCCAAGAAAAGGGTTCTC

GAACCTTTTGGCCTGGTTGAAGAGGGTGCTAAG<u>AC</u>GGCCCCTACCGGAAAGCGGATAGACGACCACTTTCCAAAA

AGAAAGAAGGCTCGGACCGAAGAGGACTCCAAGCCTTCCACCTCGTCAGACGCCGAAGC<u>TG</u>GACCCAGCGGATCC

CAGCAGCTGCAAATCCCAGCCCAACCAGCCTCAAGTTTGGGAGCTGATACA<u>ATG</u>TCTGCGGGAGGTGGCGGCCCA

TTGGGCGACAATAACCAAGGTGCCGATGGAGTGGGCAATGCCTCGGGAGATTGGCATTGCGATTCCACGTGGATG

GGGGACAGAGTCGTCACCAAGTCCACCCGAACCTGGGTGCTGCCCAGCTACAACAACCACCAGTACCGAGAGATC

AAAAGCGGCTCCGTCGACGGAAGCAACGCCAACGCCTACTTTGGATACAGCACCCCCTGGGGGTACTTTGACTTT

AACCGCTTCCACAGCCACTGGAGCCCCCGAGACTGGCAAAGACTCATCAACAACTACTGGGGCTTCAGACCCCGG

TCCCTCAGAGTCAAAATCTTCAACATTCAAGTCAAAGAGGTCACGGTGCAGGACTCCACCACCACCATCGCCAAC

AACCTCACCTCCACCGTCCAAGTGTTTACGGACGACGACTACCAGCTGCCCTACGTCGTCGGCAACGGGACCGAG

GGATGCCTGCCGGCCTTCCCTCCGCAGGTCTTTACGCTGCCGCAGTACGGTTACGCGACGCTGAACCGCGACAAC

ACAGAAAATCCCACCGAGAGGAGCAGCTTCTTCTGCCTAGAGTACTTTCCCAGCAAGATGCTGAGAACGGGCAAC

AACTTTGAGTTTACCTACAACTTTGAGGAGGTGCCCTTCCACTCCAGCTTCGCTCCCAGTCAGAACCTCTTCAAG

CTGGCCAACCCGCTGGTGGACCAGTACTTGTACCGCTTCGTGAGCACAAATAACACTGGCGGAGTCCAGTTCAAC

AAGAACCTGGCCGGGAGATACGCCAACACCTACAAAAACTGGTTCCCGGGGCCCATGGGCCGAACCCAGGGCTGG

AACCTGGGCTCCGGGGTCAACCGCGCCAGTGTCAGCGCCTTCGCCACGACCAATAGGATGGAGCTCGAGGGCGCG

AGTTACCAGGTGCCCCCGCAGCCGAACGGCATGACCAACAACCTCCAGGGCAGCAACACCTATGCCCTGGAGAAC

ACTATGATCTTCAACAGCCAGCCGGCGAACCCGGGCACCACCGCCACGTACCTCGAGGGCAACATGCTCATCACC

AGCGAGAGCGAGACGCAGCCGGTGAACCGCGTGGCGTACAACGTCGGCGGGCAGATGGCCACCAACAACCAGAGC

TCCACCACTGCCCCCGCGACCGGCACGTACAACCTCCAGGAAATCGTGCCCGGCAGCGTGTGGATGGAGAGGGAC

GTGTACCTCCAAGGACCCATCTGGGCCAAGATCCCAGAGACGGGGGCGCACTTTCACCCCTCTCCGGCCATGGGC

GGATTCGGACTCAAACACCCACCGCCCATGATGCTCATCAAGAACACGCCTGTGCCCGGAAATATCACCAGCTTC

TCGGACGTGCCCGTCAGCAGCTTCATCACCCAGTACAGCACCGGGCAGGTCACCGTGGAGATGGAGTGGGAGCTC

AAGAAGGAAAACTCCAAGAGGTGGAACCCAGAGATCCAGTACACAAACAACTACAACGACCCCCAGTTTGTGGAC

TTTGCCCCGGACAGCACCGGGGAATACAGAAGCACCAGACCTATCGGAACCCGATACCTTACCCGACCCCTTTAA

Example 12—Adenovirus Polynucleotide Sequences

Adenovirus (Ad) polynucleotides can be selected from any serotype, and representative polynucleotides are exemplified below.

E2A Full Sequence (SEQ ID NO: 34)

CGACCGCACCCTGTGACGAAAGCCGCCCGCAAGCTGCGCCCCTGAGTTAGTCATCTGAACTTCGGCCTGGGCGT

CTCTGGGAAGTACCACAGTGGTGGGAGCGGGACTTTCCTGGTACACCAGGGCAGCGGGCCAACTACGGGGATTAA

GGTTATTACGAGGTGTGGTGGTAATAGCCGCCTGTTCGAGGAGAATTCGGTTTCGGTGGGCGCGGATTCCGTTGA

CCCGGGATATCATGTGGGGTCCCGCGCTCATGTAGTTTATTCGGGTTGAGTAGTCTTGGGCAGCTCCAGCCGCAA

GTCCCATTTGTGGCTGGTAACTCCACATGTAGGGCGTGGGAATTTCCTTGCTCATAATGGCGCTGACGACAGGTG

CTGGCGCCGGGTGTGGCCGCTGGAGATGACGTAGTTTTCGCGCTTAAATTTGAGAAAGGGCGCGAAACTAGTCCT

TAAGAGTCAGCGCGCAGTATTTGCTGAAGAGAGCCTCCGCGTCTTCCAGCGTGCGCCGAAGCTGATCTTCGCTTT

TGTGATACAGGCAGCTGCGGGTGAGGGAGCGCAGAGACCTGTTTTTATTTTCAGCTCTTGTTCTTGGCCCCTGC

TTTGTTGAAATATAGCATACAGAGTGGGAAAAATCCTATTTCTAAGCTCGCGGGTCGATACGGGTTCGTTGGGCG

CCAGACGCAGCGCTCCTCCTCCTGCTGCTGCCGCCGCTGTGGATTTCTTGGGCTTTGTCAGAGTCTTGCTATCCG

GTCGCCTTTGCTTCTGTGTGACCGCTGCTGTTGCTGCCGCTGCCGCTGCCGCCGGTGCAGTAGGGGCTGTAGAGA

TGACGGTAGTAATGCAGGATGTTACGGGGGAAGGCCACGCCGTGATGGTAGAGAAGAAAGCGGCGGGCGAAGGAG

ATGTTGCCCCCACAGTCTTGCAAGCAAGCAACTATGGCGTTCTTGTGCCCGCGCCACGAGCGGTAGCCTTGGCGC

TGTTGTTGCTCTTGGGCTAACGGCGGCGGCTGCTTAGACTTACCGGCCCTGGTTCCAGTGGTGTCCCATCTACGG

TTGGGTCGGCGAACAGGCAGTGCCGGCGGCGCCTGAGGAGCGGAGGTTGTAGCGATGCTGGGAACGGTTGCCAAT

TTCTGGGGCGCCGGCGAGGGGAATGCGACCGAGGGTGACGGTGTTTCGTCTGACACCTCTTCGGCCTCGGAAGCT

TCGTCTAGGCTGTCCCAGTCTTCCATCATCTCCTCCTCCTCGTCCAAAACCTCCTCTGCCTGACTGTCCCAGTAT

TCCTCCTCGTCCGTGGGTGGCGGCGGCGGCAGCTGCAGCTTCTTTTTGGGTGCCATCCTGGGAAGCAAGGGCCCG

CGGCTGCTGATAGGGCTGCGGCGGCGGGGGGATTGGGTTGAGCTCCTCGCCGGACTGGGGGTCCAGGTAAACCCC

CCGTCCCTTTCGTAGCAGAAACTCTTGGCGGGCTTTGTTGATGGCTTGCAATTGGCCAAGGATGTGGCCCTGGGT

AATGACGCAGGCGGTAAGCTCCGCATTTGGCGGGCGGGATTGGTCTTCGTAGAACCTAATCTCGTGGGCGTGGTA

GTCCTCAGGTACAAATTTGCGAAGGTAAGCCGACGTCCACAGCCCCGGAGTGAGTTTCAACCCCGGAGCCGCGGA

CTTTTCGTCAGGCGAGGGACCCTGCAGCTCAAAGGTACCGATAATTTGACTTTCGCTAAGCAGTTGCGAATTGCA

GACCAGGGAGCGGTGCGGGGTGCATAGGTTGCAGCGACAGTGACACTCCAGTAGGCCGTCACCGCTCACGTCTTC

CATGATGTCGGAGTGGTAGGCAAGGTAGTTGGCTAGCTGCAGAAGGTAGCAGTGACCCCAAAGCGGCGGAGGGCA

TTCACGGTACTTAATGGGCACAAAGTCGCTAGGAAGCGCACAGCAGGTGGCGGGCAGAATTCCTGAACGCTCTAG

GATAAAGTTCCTAAAGTTTTGCAACATGCTTTGACTGGTGAAGTCTGGCAGACCCTGTTGCAGGGTTTTAAGCAG

GCGTTCGGGGAAGATAATGTCCGCCAGGTGCGCGGCCACGGAGCGCTCGTTGAAGGCCGTCCATAGGTCCTTCAA

GTTTTGCTTTAGCAGCTTCTGCAGCTCCTTTAGGTTGCGCTCCTCCAGGCATTGCTGCCACACGCCCATGGCCGT

TTGCCAGGTGTAGCACAGAAATAAGTAAACGCAGTCGCGGACGTAGTCGCGGCGCGCCTCGCCCTTGAGCGTGGA

ATGAAGCACGTTTTGCCCGAGGCGGTTTTCGTGCAAAATTCCAAGGTAGGAGACCAGGTTGCAGAGCTCCACGTT

GGAAATTTTGCAGGCCTGGCGCACGTAGCCCTGGCGAAAGGTGTAGTGCAACGTTTCCTCTAGCTTGCGCTGCAT

CTCCGGGTCAGCAAAGAACCGCTGCATGCACTCAAGCTCCACGGTAACAAGCACTGCGGCCATCATTAGCTTGCG

TCGCTCCTCCAAGTCGGCAGGCTCGCGCGTCTCAAGCCAGCGCGCCAGCTGCTCATCGCCAACTGCGGGTAGGCC

CTCCTCGGTTTGTTCTTGCAAGTTTGCATCCCTCTCCAGGGGTCGTGCACGGCGCACGATCAGCTCGCTCATGAC

TGTGCTCATAACCTTGGGGGGTAGGTTAAGTGCCGGGTAGGCAAAGTGGGTGACCTCGATGCTGCGTTTCAGCAC

-continued

```
GGCTAGGCGCGCGTTGTCACCCTCAAGTTCCACCAGCACTCCACAGTGACTTTCATTTTCGCTGTTTTCTTGTTG
CAGAGCGTTTGCCGCGCGTTTCTCGTCGCGTCCAAGACCCTCAAAGATTTTTGGCACTTCGTCGAGCGAGGCGAT
ATCAGGTATGACAGCGCCCTGCCGCAAGGCCAGCTGCTTGTCCGCTCGGCTGCGGTTGGCACGGCAGGATAGGGG
TATCTTGCAGTTTTGGAAAAAGATGTGATAGGTGGCAAGCACCTCTGGCACGGCAAATACGGGGTAGAAGTTGAG
GCGCGGGTTGGGCTCGCATGTGCCGTTTTCTTGGCGTTTGGGGGGTACGCGCGGTGAGAACAGGTGGCGTTCGTA
GGCAAGGCTGACATCCGCTATGGCGAGGGGCACATCGCTGCGCTCTTGCAACGCGTCGCAGATAATGGCGCACTG
GCGCTGCAGATGCTTCAACAGCACGTCGTCTCCCACATCTAGGTAGTCGCCATGCCTTTGGTCCCCCCGCCCGAC
TTGTTCCTCGTTTGCCTCTGCGTCGTCCTGGTCTTGCTTTTTATCCTCTGTTGGTACTGAGCGATCCTCGTCGTC
TTCGCTTACAAAACCTGGGTCCTGCTCGATAATCACTTCCTCCTCCTCAAGCGGGGTGCCTCGACGGGGAAGGT
GGTAGGCGCGTTGGCGGCATCGGTGGAGGCGGTGGTGGCGAACTCAAAGGGGGCGGTTAGGCTGTCCTCCTTCTC
GACTGACTCCATGATCTTTTTCTGCCTATAGGAGAAGGAAATGGCCAGTCGGGAAGAGGAGCAGCGCGAAACCAC
CCCCGAGCGCGGACGCGGTGCGGCGCGACGTCCACCAACCATGGAGGACGTGTCGTCCCCGTCGCCGTCGCCGCC
GCCTCCCCGCGCGCCCCCAAAAAAGCGGCTGAGGCGGCGTCTCGAGTCCGAGGACGAAGAAGACTCGTCACAAGA
TGCGCTGGTGCCGCGCACACCCAGCCCGCGGCCATCGACCTCGACGCGGATTTGGCCATTGCGTCCAAAAAGAA
AAAGAAGCGCCCCTCTCCCAAGCCCGAGCGCCCGCCATCCCCAGAGGTGATCGTGGACAGCGAGGAAGAAAGAGA
AGATGTGGCGCTACAAATGGTGGGTTTCAGCAACCCACCGGTGCTAATCAAGCACGGCAAGGGAGGTAAGCGCAC
GGTGCGGCGGCTGAATGAAGACGACCCAGTGGCGCGGGGTATGCGGACGCAAGAGGAAAAGGAAGAGTCCAGTGA
AGCGGAAAGTGAAAGCACGGTGATAAACCCGCTGAGCCTGCCGATCGTGTCTGCGTGGGAGAAGGGCATGGAGGC
TGCGCGCGCGTTGATGGACAAGTACCACGTGGATAACGATCTAAAGGCAAACTTCAAGCTACTGCCTGACCAAGT
GGAAGCTCTGGCGGCCGTATGCAAGACCTGGCTAAACGAGGAGCACCGCGGGTTGCAGCTGACCTTCACCAGCAA
CAAGACCTTTGTGACGATGATGGGGCGATTCCTGCAGGCGTACCTGCAGTCGTTTGCAGAGGTAACCTACAAGCA
CCACGAGCCCACGGGCTGCGCGTTGTGGCTGCACCGCTGCGCTGAGATCGAAGGCGAGCTTAAGTGTCTACACGG
GAGCATTATGATAAATAAGGAGCACGTGATTGAAATGGATGTGACGAGCGAAAACGGGCAGCGCGCGCTGAAGGA
GCAGTCTAGCAAGGCCAAGATCGTGAAGAACCGGTGGGGCCGAAATGTGGTGCAGATCTCCAACACCGACGCAAG
GTGCTGCGTGCATGACGCGGCCTGTCCGGCCAATCAGTTTTCCGGCAAGTCTTGCGGCATGTTCTTCTCTGAAGG
CGCAAAGGCTCAGGTGGCTTTTAAGCAGATCAAGGCTTTCATGCAGGCGCTGTATCCTAACGCCCAGACCGGGCA
CGGTCACCTTCTGATGCCACTACGGTGCGAGTGCAACTCAAAGCCTGGGCATGCACCCTTTTTGGGAAGGCAGCT
ACCAAAGTTGACTCCGTTCGCCCTGAGCAACGCGGAGGACCTGGACGCGGATCTGATCTCCGACAAGAGCGTGCT
GGCCAGCGTGCACCACCCGGCGCTGATAGTGTTCCAGTGCTGCAACCCTGTGTATCGCAACTCGCGCGCGCAGGG
CGGAGGCCCCAACTGCGACTTCAAGATATCGGCGCCCGACCTGCTAAACGCGTTGGTGATGGTGCGCAGCCTGTG
GAGTGAAAACTTCACCGAGCTGCCGCGGATGGTTGTGCCTGAGTTTAAGTGGAGCACTAAACACCAGTATCGCAA
CGTGTCCCTGCCAGTGGCGCATAGCGATGCGCGGCAGAACCCCTTTGATTTTTAAACGGCGCAGACGGCAAGGGT
GGGGGGTAAATAATCACCCGAGAGTGTACAAATAAAAACATTTGCCTTTATTGAAAGTGTCTCCTAGTACATTAT
TTTTACATGTTTTTCAAGTGACAAAAAGAAGTGGCGCTCCTAATCTGCGCACTGTGGCTGCGGAAGTAGGGCGAG
TGGCGCTCCAGGAAGCTGTAGAGCTGTTCCTGGTTGCGACGCAGGGTGGGCTGTACCTGGGGACTGTTAAGCATG
GAGTTGGGTACC
```

E2A ORF Sequence (SEQ ID NO: 35)

```
ATGGCCAGTCGGGAAGAGGAGCAGCGCGAAACCACCCCCGAGCGCGGACGCGGTGCGGCGCGACGTCCACCAACC
ATGGAGGACGTGTCGTCCCCGTCGCCGTCGCCGCCGCCTCCCCGCGCGCCCCCAAAAAAGCGGCTGAGGCGGCGT
CTCGAGTCCGAGGACGAAGAAGACTCGTCACAAGATGCGCTGGTGCCGCGCACACCCAGCCCGCGGCCATCGACC
```

```
TCGACGGCGGATTTGGCCATTGCGTCCAAAAAGAAAAAGAAGCGCCCCTCTCCCAAGCCCGAGCGCCCGCCATCC

CCAGAGGTGATCGTGGACAGCGAGGAAGAAAGAGAAGATGTGGCGCTACAAATGGTGGGTTTCAGCAACCCACCG

GTGCTAATCAAGCACGGCAAGGGAGGTAAGCGCACGGTGCGGCGGCTGAATGAAGACGACCCAGTGGCGCGGGT

ATGCGGACGCAAGAGGAAAAGGAAGAGTCCAGTGAAGCGGAAAGTGAAAGCACGGTGATAAACCCGCTGAGCCTG

CCGATCGTGTCTGCGTGGGAGAAGGGCATGGAGGCTGCGCGCGCGTTGATGGACAAGTACCACGTGGATAACGAT

CTAAAGGCAAACTTCAAGCTACTGCCTGACCAAGTGGAAGCTCTGGCGGCCGTATGCAAGACCTGGCTAAACGAG

GAGCACCGCGGGTTGCAGCTGACCTTCACCAGCAACAAGACCTTTGTGACGATGATGGGGCGATTCCTGCAGGCG

TACCTGCAGTCGTTTGCAGAGGTAACCTACAAGCACCACGAGCCCACGGGCTGCGCGTTGTGGCTGCACCGCTGC

GCTGAGATCGAAGGCGAGCTTAAGTGTCTACACGGGAGCATTATGATAAATAAGGAGCACGTGATTGAAATGGAT

GTGACGAGCGAAAACGGGCAGCGCGCGCTGAAGGAGCAGTCTAGCAAGGCCAAGATCGTGAAGAACCGGTGGGGC

CGAAATGTGGTGCAGATCTCCAACACCGACGCAAGGTGCTGCGTGCATGACGCGGCCTGTCCGGCCAATCAGTTT

TCCGGCAAGTCTTGCGGCATGTTCTTCTCTGAAGGCGCAAAGGCTCAGGTGGCTTTTAAGCAGATCAAGGCTTTC

ATGCAGGCGCTGTATCCTAACGCCCAGACCGGGCACGGTCACCTTCTGATGCCACTACGGTGCGAGTGCAACTCA

AAGCCTGGGCATGCACCCTTTTTGGGAAGGCAGCTACCAAAGTTGACTCCGTTCGCCCTGAGCAACGCGGAGGAC

CTGGACGCGGATCTGATCTCCGACAAGAGCGTGCTGGCCAGCGTGCACCACCCGGCGCTGATAGTGTTCCAGTGC

TGCAACCCTGTGTATCGCAACTCGCGCGCGCAGGGCGGAGGCCCCAACTGCGACTTCAAGATATCGGCGCCCGAC

CTGCTAAACGCGTTGGTGATGGTGCGCAGCCTGTGGAGTGAAAACTTCACCGAGCTGCCGCGGATGGTTGTGCCT

GAGTTTAAGTGGAGCACTAAACACCAGTATCGCAACGTGTCCCTGCCAGTGGCGCATAGCGATGCGCGGCAGAAC

CCCTTTGATTTTTAA
```
E4 Full Sequence
(SEQ ID NO: 36)
```
CCCGGGCGTTTTAGGGCGGAGTAACTTGCATGTATTGGGAATTGTAGTTTTTTTAAAATGGGAAGTGACGTATCG

TGGGAAAACGGAAGTGAAGATTTGAGGAAGTTGTGGGTTTTTTGGCTTTCGTTTCTGGGCGTAGGTTCGCGTGCG

GTTTTCTGGGTGTTTTTTGTGGACTTTAACCGTTACGTCATTTTTTAGTCCTATATATACTCGCTCTGTACTTGG

CCCTTTTTACACTGTGACTGATTGAGCTGGTGCCGTGTCGAGTGGTGTTTTTTAATAGGTTTTTTTACTGGTAAG

GCTGACTGTTATGGCTGCCGCTGTGGAAGCGCTGTATGTTGTTCGGAGCGGGAGGGTGCTATTTTGCCTAGGCA

GGAGGGTTTTTCAGGTGTTTATGTGTTTTTCTCTCCTATTAATTTTGTTATACCTCCTATGGGGGCTGTAATGTT

GTCTCTACGCCTGCGGGTATGTATTCCCCCGGGCTATTTCGGTCGCTTTTTAGCACTGACCGATGTTAACCAACC

TGATGTGTTTACCGAGTCTTACATTATGACTCCGGACATGACCGAGGAACTGTCGGTGGTGCTTTTTAATCACGG

TGACCAGTTTTTTTACGGTCACGCCGGCATGGCCGTAGTCCGTCTTATGCTTATAAGGGTTGTTTTTCCTGTTGT

AAGACAGGCTTCTAATGTTTAAATGTTTTTTTTTTGTTATTTTATTTTGTGTTTAATGCAGGAACCCGCAGACA

TGTTTGAGAGAAAAATGGTGTCTTTTTCTGTGGTGGTTCCGGAACTTACCTGCCTTTATCTGCATGAGCATGACT

ACGATGTGCTTGCTTTTTTGCGCGAGGCTTTGCCTGATTTTTTGAGCAGCACCTTGCATTTTATATCGCCGCCCA

TGCAACAAGCTTACATAGGGGCTACGCTGGTTAGCATAGCTCCGAGTATGCGTGTCATAATCAGTGTGGGTTCTT

TTGTCATGGTTCCTGGCGGGGAAGTGGCCGCGCTGGTCCGTGCAGACCTGCACGATTATGTTCAGCTGGCCCTGC

GAAGGGACCTACGGGATCGCGGTATTTTTGTTAATGTTCCGCTTTTGAATCTTATACAGGTCTGTGAGGAACCTG

AATTTTTGCAATCATGATTCGCTGCTTGAGGCTGAAGGTGGAGGGCGCTCTGGAGCAGATTTTTACAATGGCCGG

ACTTAATATTCGGGATTTGCTTAGAGACATATTGATAAGGTGGCGAGATGAAAATTATTGGGCATGGTTGAAGG

TGCTGGAATGTTTATAGAGGAGATTCACCCTGAAGGGTTTAGCCTTTACGTCCACTTGGACGTGAGGGCAGTTTG

CCTTTTGGAAGCCATTGTGCAACATCTTACAAATGCCATTATCTGTTCTTTGGCTGTAGAGTTTGACCACGCCAC

CGGAGGGGAGCGCGTTCACTTAATAGATCTTCATTTTGAGGTTTTGGATAATCTTTTGGAATAAAAAAAAAAAA

CATGGTTCTTCCAGCTCTTCCCGCTCCTCCCGTGTGTGACTCGCAGAACGAATGTGTAGGTTGGCTGGGTGTGGC
```

-continued

```
TTATTCTGCGGTGGTGGATGTTATCAGGGCAGCGGCGCATGAAGGAGTTTACATAGAACCCGAAGCCAGGGGGCG
CCTGGATGCTTTGAGAGAGTGGATATACTACAACTACTACACAGAGCGAGCTAAGCGACGAGACCGGAGACGCAG
ATCTGTTTGTCACGCCCGCACCTGGTTTTGCTTCAGGAAATATGACTACGTCCGGCGTTCCATTTGGCATGACAC
TACGACCAACACGATCTCGGTTGTCTCGGCGCACTCCGTACAGTAGGGATCGCCTACCTCCTTTTGAGACAGAGA
CCCGCGCTACCATACTGGAGGATCATCCGCTGCTGCCCGAATGTAACACTTTGACAATGCACAACGTGAGTTACG
TGCGAGGTCTTCCCTGCAGTGTGGGATTTACGCTGATTCAGGAATGGGTTGTTCCCTGGGATATGGTTCTGACGC
GGGAGGAGCTTGTAATCCTGAGGAAGTGTATGCACGTGTGCCTGTGTTGTGCCAACATTGATATCATGACGAGCA
TGATGATCCATGGTTACGAGTCCTGGGCTCTCCACTGTCATTGTTCCAGTCCCGGTTCCCTGCAGTGCATAGCCG
GCGGGCAGGTTTTGGCCAGCTGGTTTAGGATGGTGGTGGATGGCGCCATGTTTAATCAGAGGTTTATATGGTACC
GGGAGGTGGTGAATTACAACATGCCAAAAGAGGTAATGTTTATGTCCAGCGTGTTTATGAGGGGTCGCCACTTAA
TCTACCTGCGCTTGTGGTATGATGGCCACGTGGGTTCTGTGGTCCCCGCCATGAGCTTTGGATACAGCGCCTTGC
ACTGTGGGATTTTGAACAATATTGTGGTGCTGTGCTGCAGTTACTGTGCTGATTTAAGTGAGATCAGGGTGCGCT
GCTGTGCCCGGAGGACAAGGCGTCTCATGCTGCGGGCGGTGCGAATCATCGCTGAGGAGACCACTGCCATGTTGT
ATTCCTGCAGGACGGAGCGGCGGCGGCAGCAGTTTATTCGCGCGCTGCTGCAGCACCACCGCCCTATCCTGATGC
ACGATTATGACTCTACCCCCATGTAGGCGTGGACTTCCCCTTCGCCGCCCGTTGAGCAACCGCAAGTTGGACAGC
AGCCTGTGGCTCAGCAGCTGGACAGCGACATGAACTTAAGCGAGCTGCCCGGGGAGTTTATTAATATCACTGATG
AGCGTTTGGCTCGACAGGAAACCGTGTGGAATATAACACCTAAGAATATGTCTGTTACCCATGATATGATGCTTT
TTAAGGCCAGCCGGGGAGAAAGGACTGTGTACTCTGTGTGTTGGGAGGGAGGTGGCAGGTTGAATACTAGGGTTC
TGTGAGTTTGATTAAGGTACGGTGATCAATATAAGCTATGTGGTGGTGGGGCTATACTACTGAATGAAAAATGAC
TTGAAATTTTCTGCAATTGAAAAATAAACACGTTGAAACATAACATGCAACAGGTTCACGATTCTTTATTCCTGG
GCAATGTAGGAGAAGGTGTAAGAGTTGGTAGCAAAAGTTTCAGTGGTGTATTTTCCACTTTCCCAGGACCATGTA
AAAGACATAGAGTAAGTGCTTACCTCGCTAGTTTCTGTGGATTCACTAGAA
```

E4 Orf6 Sequence (SEQ ID NO: 37)
```
ATGACTACGTCCGGCGTTCCATTTGGCATGACACTACGACCAACACGATCTCGGTTGTCTCGGCGCACTCCGTAC
AGTAGGGATCGCCTACCTCCTTTTGAGACAGAGACCCGCGCTACCATACTGGAGGATCATCCGCTGCTGCCCGAA
TGTAACACTTTGACAATGCACAACGTGAGTTACGTGCGAGGTCTTCCCTGCAGTGTGGGATTTACGCTGATTCAG
GAATGGGTTGTTCCCTGGGATATGGTTCTGACGCGGGAGGAGCTTGTAATCCTGAGGAAGTGTATGCACGTGTGC
CTGTGTTGTGCCAACATTGATATCATGACGAGCATGATGATCCATGGTTACGAGTCCTGGGCTCTCCACTGTCAT
TGTTCCAGTCCCGGTTCCCTGCAGTGCATAGCCGGCGGGCAGGTTTTGGCCAGCTGGTTTAGGATGGTGGTGGAT
GGCGCCATGTTTAATCAGAGGTTTATATGGTACCGGGAGGTGGTGAATTACAACATGCCAAAAGAGGTAATGTTT
ATGTCCAGCGTGTTTATGAGGGGTCGCCACTTAATCTACCTGCGCTTGTGGTATGATGGCCACGTGGGTTCTGTG
GTCCCCGCCATGAGCTTTGGATACAGCGCCTTGCACTGTGGGATTTTGAACAATATTGTGGTGCTGTGCTGCAGT
TACTGTGCTGATTTAAGTGAGATCAGGGTGCGCTGCTGTGCCCGGAGGACAAGGCGTCTCATGCTGCGGGCGGTG
CGAATCATCGCTGAGGAGACCACTGCCATGTTGTATTCCTGCAGGACGGAGCGGCGGCGGCAGCAGTTTATTCGC
GCGCTGCTGCAGCACCACCGCCCTATCCTGATGCACGATTATGACTCTACCCCCATGTAG
```

VA Sequence (VA transcripts I and II are underlined)

(SEQ ID NO: 38)
```
CGTAATCCGTAGATGTACCTGGACATCCAGGTGATGCCGGCGGCGGTGGTGGAGGCGCGCGGAAAGTCGCGGAC
GCGGTTCCAGATGTTGCGCAGCGGCAAAAAGTGCTCCATGGTCGGGACGCTCTGGCCGGTGAGGCGTGCGCAGTC
GTTGACGCTCTAGACCGTGCAAAAGGAGAGCCTGTAAGCGGGCACTCTTCCGTGGTCTGGTGGATAAATTCGCAA
GGGTATCATGGCGGACGACCGGGGTTCGAACCCCGGATCCGGCCGTCCGCCGTGATCCATGCGGTTACCGCCCGC
```

-continued

```
GTGTCGAACCCAGGTGTGCGACGTCAGACAACGGGGGAGCGCTCCTTTTGGCTTCCTTCCAGGCGCGGCGGCTGC

TGCGCTAGCTTTTTTGGCCACTGGCCGCGCGGCGTAAGCGGTTAGGCTGGAAAGCGAAAGCATTAAGTGGCTC

GCTCCCTGTAGCCGGAGGGTTATTTTCCAAGGGTTGAGTCGCAGGACCCCCGGTTCGAGTCTCGGGCCGGCCGGA

CTGCGGCGAACGGGGGTTTGCCTCCCCGTCATGCAAGACCCCGCTTGCAAATTCCTCCGGAAACAGGGACGAGCC

CCTTTTTTGCTTTTCCCAGATGCATCCGGTGCTGCGGCAGATGCGCCCCCCTCCTCAGCAGCGGCAAGAGCAAGA

GCAGCGGCAGACATGCAGGGCACCCTCCCCTTCTCCTACCGCGTCAGGAGGGGCAACATCCTACATCGA
```

Sequences for E1A and E1B are Both Contained within Accession AY339865.1

Ad5 E1A

Two proteins can be transcribed, a 32 kDa protein (first accession number) and a 27 kDa protein (second accession number). These are both splice variants from the transcript:

Accession 1: AAQ19284.1
Accession 2: AAQ19285.1

(SEQ ID NO: 39)
```
ATGAGACATATTATCTGCCACGGAGGTGTTATTACCGAAGAAATGGCCGCCAGTCTTTTGGACCAGCTGATCGAA

GAGGTACTGGCTGATAATCTTCCACCTCCTAGCCATTTTGAACCACCTACCCTTCACGAACTGTATGATTTAGAC

GTGACGGCCCCCGAAGATCCCAACGAGGAGGCGGTTTCGCAGATTTTTCCCGACTCTGTAATGTTGGCGGTGCAG

GAAGGGATTGACTTACTCACTTTTCCGCCGGCGCCCGGTTCTCCGGAGCCGCCTCACCTTTCCCGGCAGCCCGAG

CAGCCGGAGCAGAGAGCCTTGGGTCCGGTTCTATGCCAAACCTTGTACCGGAGGTGATCGATCTTACCTGCCAC

GAGGCTGGCTTTCCACCCAGTGACGACGAGGATGAAGAGGGTGAGGAGTTTGTGTTAGATTATGTGGAGCACCCC

GGGCACGGTTGCAGGTCTTGTCATTATCACCGGAGGAATACGGGGGACCCAGATATTATGTGTTCGCTTTGCTAT

ATGAGGACCTGTGGCATGTTTGTCTACAGTCCTGTGTCTGAACCTGAGCCTGAGCCCGAGCCAGAACCGGAGCCT

GCAAGACCTACCCGCCGTCCTAAAATGGCGCCTGCTATCCTGAGACGCCCGACATCACCTGTGTCTAGAGAATGC

AATAGTAGTACGGATAGCTGTGACTCCGGTCCTTCTAACACACCTCCTGAGATACACCCGGTGGTCCCGCTGTGC

CCCATTAAACCAGTTGCCGTGAGAGTTGGTGGGCGTCGCCAGGCTGTGGAATGTATCGAGGACTTGCTTAACGAG

CCTGGGCAACCTTTGGACTTGAGCTGTAAACGCCCCAGGCCATAA
```

(SEQ ID NO: 40)
```
ATGAGACATATTATCTGCCACGGAGGTGTTATTACCGAAGAAATGGCCGCCAGTCTTTTGGACCAGCTGATCGAA

GAGGTACTGGCTGATAATCTTCCACCTCCTAGCCATTTTGAACCACCTACCCTTCACGAACTGTATGATTTAGAC

GTGACGGCCCCCGAAGATCCCAACGAGGAGGCGGTTTCGCAGATTTTTCCCGACTCTGTAATGTTGGCGGTGCAG

GAAGGGATTGACTTACTCACTTTTCCGCCGGCGCCCGGTTCTCCGGAGCCGCCTCACCTTTCCCGGCAGCCCGAG

CAGCCGGAGCAGAGAGCCTTGGGTCCGGTTCTATGCCAAACCTTGTACCGGAGGTGATCGATCTTACCTGCCAC

GAGGCTGGCTTTCCACCCAGTGACGACGAGGATGAAGAGGGTCCTGTGTCTGAACCTGAGCCTGAGCCCGAGCCA

GAACCGGAGCCTGCAAGACCTACCCGCCGTCCTAAAATGGCGCCTGCTATCCTGAGACGCCCGACATCACCTGTG

TCTAGAGAATGCAATAGTAGTACGGATAGCTGTGACTCCGGTCCTTCTAACACACCTCCTGAGATACACCCGGTG

GTCCCGCTGTGCCCCATTAAACCAGTTGCCGTGAGAGTTGGTGGGCGTCGCCAGGCTGTGGAATGTATCGAGGAC

TTGCTTAACGAGCCTGGGCAACCTTTGGACTTGAGCTGTAAACGCCCCAGGCCATAA
```

Ad5 E1B_19K

Accession: AAQ19286.1

(SEQ ID NO: 41)
```
ATGGAGGCTTGGGAGTGTTTGGAAGATTTTTCTGCTGTGCGTAACTTGCTGGAACAGAGCTCTAACAGTACCTCT

TGGTTTTGGAGGTTTCTGTGGGGCTCATCCCAGGCAAAGTTAGTCTGCAGAATTAAGGAGGATTACAAGTGGGAA
```

-continued

```
TTTGAAGAGCTTTTGAAATCCTGTGGTGAGCTGTTTGATTCTTTGAATCTGGGTCACCAGGCGCTTTTCCAAGAG

AAGGTCATCAAGACTTTGGATTTTTCCACACCGGGGCGCGCTGCGGCTGCTGTTGCTTTTTTGAGTTTTATAAAG

GATAAATGGAGCGAAGAAACCCATCTGAGCGGGGGGTACCTGCTGGATTTTCTGGCCATGCATCTGTGGAGAGCG

GTTGTGAGACACAAGAATCGCCTGCTACTGTTGTCTTCCGTCCGCCCGGCGATAATACCGACGGAGGAGCAGCAG

CAGCAGCAGGAGGAAGCCAGGCGGCGGCGGCAGGAGCAGAGCCCATGGAACCCGAGAGCCGGCCTGGACCCTCGG

GAATGA
```

Ad5 E1B_55K

```
Accession: AAQ19287.1
                                                                 (SEQ ID NO: 42)
ATGGAGCGAAGAAACCCATCTGAGCGGGGGGTACCTGCTGGATTTTCTGGCCATGCATCTGTGGAGAGCGGTTGT

GAGACACAAGAATCGCCTGCTACTGTTGTCTTCCGTCCGCCCGGCGATAATACCGACGGAGGAGCAGCAGCAGCA

GCAGGAGGAAGCCAGGCGGCGGCGGCAGGAGCAGAGCCCATGGAACCCGAGAGCCGGCCTGGACCCTCGGGAATG

AATGTTGTACAGGTGGCTGAACTGTATCCAGAACTGAGACGCATTTTGACAATTACAGAGGATGGGCAGGGGCTA

AAGGGGGTAAAGAGGGAGCGGGGGGCTTGTGAGGCTACAGAGGAGGCTAGGAATCTAGCTTTTAGCTTAATGACC

AGACACCGTCCTGAGTGTATTACTTTTCAACAGATCAAGGATAATTGCGCTAATGAGCTTGATCTGCTGGCGCAG

AAGTATTCCATAGAGCAGCTGACCACTTACTGGCTGCAGCCAGGGGATGATTTTGAGGAGGCTATTAGGGTATAT

GCAAAGGTGGCACTTAGGCCAGATTGCAAGTACAAGATCAGCAAACTTGTAAATATCAGGAATTGTTGCTACATT

TCTGGGAACGGGGCCGAGGTGGAGATAGATACGGAGGATAGGGTGGCCTTTAGATGTAGCATGATAAATATGTGG

CCGGGGGTGCTTGGCATGGACGGGGTGGTTATTATGAATGTAAGGTTTACTGGCCCCAATTTTAGCGGTACGGTT

TTCCTGGCCAATACCAACCTTATCCTACACGGTGTAAGCTTCTATGGGTTTAACAATACCTGTGTGGAAGCCTGG

ACCGATGTAAGGGTTCGGGGCTGTGCCTTTTACTGCTGCTGGAAGGGGGTGGTGTGTCGCCCCAAAAGCAGGGCT

TCAATTAAGAAATGCCTCTTTGAAAGGTGTACCTTGGGTATCCTGTCTGAGGGTAACTCCAGGGTGCGCCACAAT

GTGGCCTCCGACTGTGGTTGCTTCATGCTAGTGAAAAGCGTGGCTGTGATTAAGCATAACATGGTATGTGGCAAC

TGCGAGGACAGGGCCTCTCAGATGCTGACCTGCTCGGACGGCAACTGTCACCTGCTGAAGACCATTCACGTAGCC

AGCCACTCTCGCAAGGCCTGGCCAGTGTTTGAGCATAACATACTGACCCGCTGTTCCTTGCATTTGGGTAACAGG

AGGGGGGTGTTCCTACCTTACCAATGCAATTTGAGTCACACTAAGATATTGCTTGAGCCCGAGAGCATGTCCAAG

GTGAACCTGAACGGGGTGTTTGACATGACCATGAAGATCTGGAAGGTGCTGAGGTACGATGAGACCCGCACCAGG

TGCAGACCCTGCGAGTGTGGCGGTAAACATATTAGGAACCAGCCTGTGATGCTGGATGTGACCGAGGAGCTGAGG

CCCGATCACTTGGTGCTGGCCTGCACCCGCGCTGAGTTTGGCTCTAGCGATGAAGATACAGATTGA
```

Sequences for E2A and ELA are both contained within
Accession MN088492
Ad5 E2A orf:

```
Accession: QHX41645.1
                                                                 (SEQ ID NO: 43)
ATGGCCAGTCGGGAAGAGGAGCAGCGCGAAACCACCCCCGAGCGCGGACGCGGTGCGGCGCGACGTCCACCAACC

ATGGAGGACGTGTCGTCCCCGTCGCCGTCGCCGCCGCCTCCCCGCGCGCCCCCAAAAAAGCGGCTGAGGCGGCGT

CTCGAGTCCGAGGACGAAGAAGACTCGTCACAAGATGCGCTGGTGCCGCGCACACCCAGCCCGCGGCCATCGACC

TCGACGGCGGATTTGGCCATTGCGTCCAAAAAGAAAAAGAAGCGCCCCTCTCCCAAGCCCGAGCGCCCGCCATCC

CCAGAGGTGATCGTGGACAGCGAGGAAGAAAGAGAAGATGTGGCGCTACAAATGGTGGGTTTCAGCAACCCACCG

GTGCTAATCAAGCACGGCAAGGGAGGTAAGCGCACGGTGCGGCGGCTGAATGAAGACGACCCAGTGGCGCGGGGT

ATGCGGACGCAAGAGGAAAAGGAAGAGTCCAGTGAAGCGGAAAGTGAAAGCACGGTGATAAACCCGCTGAGCCTG
```

-continued

```
CCGATCGTGTCTGCGTGGGAGAAGGGCATGGAGGCTGCGCGCGCGTTGATGGACAAGTACCACGTGGATAACGAT
CTAAAGGCAAACTTCAAGCTACTGCCTGACCAAGTGGAAGCTCTGGCGGCCGTATGCAAGACCTGGCTAAACGAG
GAGCACCGCGGGTTGCAGCTGACCTTCACCAGCAACAAGACCTTTGTGACGATGATGGGCGATTCCTGCAGGCG
TACCTGCAGTCGTTTGCAGAGGTAACCTACAAGCACCACGAGCCCACGGGCTGCGCGTTGTGGCTGCACCGCTGC
GCTGAGATCGAAGGCGAGCTTAAGTGTCTACACGGGAGCATTATGATAAATAAGGAGCACGTGATTGAAATGGAT
GTGACGAGCGAAAACGGGCAGCGCGCGCTGAAGGAGCAGTCTAGCAAGGCCAAGATCGTGAAGAACCGGTGGGGC
CGAAATGTGGTGCAGATCTCCAACACCGACGCAAGGTGCTGCGTGCATGACGCGGCCTGTCCGGCCAATCAGTTT
TCCGGCAAGTCTTGCGGCATGTTCTTCTCTGAAGGCGCAAAGGCTCAGGTGGCTTTTAAGCAGATCAAGGCTTTC
ATGCAGGCGCTGTATCCTAACGCCCAGACCGGGCACGGTCACCTTCTGATGCCACTACGGTGCGAGTGCAACTCA
AAGCCTGGGCATGCACCCTTTTTGGGAAGGCAGCTACCAAAGTTGACTCCGTTCGCCCTGAGCAACGCGGAGGAC
CTGGACGCGGATCTGATCTCCGACAAGAGCGTGCTGGCCAGCGTGCACCACCCGGCGCTGATAGTGTTCCAGTGC
TGCAACCCTGTGTATCGCAACTCGCGCGCGCAGGGCGGAGGCCCCAACTGCGACTTCAAGATATCGGCGCCCGAC
CTGCTAAACGCGTTGGTGATGGTGCGCAGCCTGTGGAGTGAAAACTTCACCGAGCTGCCGCGGATGGTTGTGCCT
GAGTTTAAGTGGAGCACTAAACACCAGTATCGCAACGTGTCCCTGCCAGTGGCGCATAGCGATGCGCGGCAGAAC
CCCTTTGATTTTTAA
```

Ad5 E4A:
Two proteins are present in this ORF. The first is a splice variant contained within the ORF. The second is a non-spliced transcript present in the ORF. Accession 1: QHX41659.1
Accession 2: QHX41660.1

```
                                                              (SEQ ID NO: 44)
ATGACTACGTCCGGCGTTCCATTTGGCATGACACTACGACCAACACGATCTCGGTTGTCTCGGCGCACTCCGTAC
AGTAGGGATCGCCTACCTCCTTTTGAGACAGAGACCCGCGCTACCATACTGGAGGATCATCCGCTGCTGCCCGAA
TGTAACACTTTGACAATGCACAACGCGTGGACTTCCCCTTCGCCGCCCGTTGAGCAACCGCAAGTTGGACAGCAG
CCTGTGGCTCAGCAGCTGGACAGCGACATGAACTTAAGCGAGCTGCCCGGGGAGTTTATTAATATCACTGATGAG
CGTTTGGCTCGACAGGAAACCGTGTGGAATATAACACCTAAGAATATGTCTGTTACCCATGATATGATGCTTTTT
AAGGCCAGCCGGGGAGAAAGGACTGTGTACTCTGTGTGTTGGGAGGGAGGTGGCAGGTTGAATACTAGGGTTCTG
TGA
                                                              (SEQ ID NO: 45)
ATGACTACGTCCGGCGTTCCATTTGGCATGACACTACGACCAACACGATCTCGGTTGTCTCGGCGCACTCCGTAC
AGTAGGGATCGCCTACCTCCTTTTGAGACAGAGACCCGCGCTACCATACTGGAGGATCATCCGCTGCTGCCCGAA
TGTAACACTTTGACAATGCACAACGTGAGTTACGTGCGAGGTCTTCCCTGCAGTGTGGGATTTACGCTGATTCAG
GAATGGGTTGTTCCCTGGGATATGGTTCTGACGCGGGAGGAGCTTGTAATCCTGAGGAAGTGTATGCACGTGTGC
CTGTGTTGTGCCAACATTGATATCATGACGAGCATGATGATCCATGGTTACGAGTCCTGGGCTCTCCACTGTCAT
TGTTCCAGTCCCGGTTCCCTGCAGTGCATAGCCGGCGGGCAGGTTTTGGCCAGCTGGTTTAGGATGGTGGTGGAT
GGCGCCATGTTTAATCAGAGGTTTATATGGTACCGGGAGGTGGTGAATTACAACATGCCAAAAGAGGTAATGTTT
ATGTCCAGCGTGTTTATGAGGGGTCGCCACTTAATCTACCTGCGCTTGTGGTATGATGGCCACGTGGGTTCTGTG
GTCCCCGCCATGAGCTTTGGATACAGCGCCTTGCACTGTGGGATTTTGAACAATATTGTGGTGCTGTGCTGCAGT
TACTGTGCTGATTTAAGTGAGATCAGGGTGCGCTGCTGTGCCCGAGGACAAGGCGTCTCATGCTGCGGGCGGTG
CGAATCATCGCTGAGGAGACCACTGCCATGTTGTATTCCTGCAGGACGGAGCGGCGGCGGCAGCAGTTTATTCGC
GCGCTGCTGCAGCACCACCGCCCTATCCTGATGCACGATTATGACTCTACCCCCATGTAG
```

Ad5 VA:

Accession: AF369965.1
(SEQ ID NO: 46)
TCGATGTAGGATGTTGCCCCTCCTGACGCGGTAGGAGAAGGGGAGGGTGCCCTGCATGTCTGCCGCTGCTCTTGC

TCTTGCCGCTGCTGAGGAGGGGGGCGCATCTGCCGCAGCACCGGATGCATCTGGGAAAAGCAAAAAAGGGGCTCG

TCCCTGTTTCCGGAGGAATTTGCAAGCGGGGTCTTGCATGACGGGGAGGCAAACCCCCGTTCGCCGCAGTCCGGC

CGGCCCGAGACTCGAACCGGGGGTCCTGCGACTCAACCCTTGGAAAATAACCCTCCGGCTACAGGGAGCGAGCCA

CTTAATGCTTTCGCTTTCCAGCCTAACCGCTTACGCCGCGCGGCCAGTGGCCAAAAAAGCTAGCGCAGCAGCC

GCCGCGCCTGGAAGGAAGCCAAAAGGAGCGCTCCCCCGTTGTCTGACGTCGCACACCTGGGTTCGACACGCGGGC

GGTAACCGCATGGATCACGGCGGACGGCCGGATCCGGGGTTCGAACCCCGGTCGTCCGCCATGATACCCTTGCGA

ATTTATCCACCAGACCACGGAAGAGTGCCCGCTTACAGGCTCTCCTTTTGCACGGTCTAGAGCGTCAACGACTGC

GCACGCCTCACCGGCCAGAGCGTCCCGACCATGGAGCACTTTTTGCCGCTGCGCAACATCTGGAACCGCGTCCGC

GACTTTCCGCGCGCCTCCACCACCGCCGCCGGCATCACCTGGATGTCCAGGTACATCTACGGATTACG

Example 13—Promoter, Operator, IRES and Intron
Sequences

CMV Promoter
(SEQ ID NO: 47)
TAGTTATTAATAGTAATCAATTACGGGGTCATTAGTTCATAGCCCATATATGGAGTTCCGCGTTACATAACTTAC

GGTAAATGGCCCGCCTGGCTGACCGCCCAACGACCCCCGCCCATTGACGTCAATAATGACGTATGTTCCCATAGT

AACGCCAATAGGGACTTTCCATTGACGTCAATGGGTGGAGTATTTACGGTAAACTGCCCACTTGGCAGTACATCA

AGTGTATCATATGCCAAGTACGCCCCCTATTGACGTCAATGACGGTAAATGGCCCGCCTGGCATTATGCCCAGTA

CATGACCTTATGGGACTTTCCTACTTGGCAGTACATCTACGTATTAGTCATCGCTATTACCATGGTGATGCGGTT

TTGGCAGTACATCAATGGGCGTGGATAGCGGTTTGACTCACGGGGATTTCCAAGTCTCCACCCCATTGACGTCAA

TGGGAGTTTGTTTTGGCACCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCGTCGACGTTTAGTGAACCG

2xTet Operator Sequence
(SEQ ID NO: 48)
TCCCTATCAGTGATAGAGATCTCCCTATCAGTGATAGAGA hCMV Intron Sequence
(SEQ ID NO: 49)
GTAAGTACCGCCTATAGAGTCTATAGGCCCACCCCCTTGGCTTCTTATGCATGCTATACTGTTTTTGGCTTGGGG

TCTATACACCCCCGCTTCCTCATGTTATAGGTGATGGTATAGCTTAGCCTATAGGTGTGGGTTATTGACCATTAT

TGACCACTCCCCTATTGGTGACGATACTTTCCATTACTAATCCATAACATGGCTCTTTGCCACAACTCTCTTTAT

TGGCTATATGCCAATACACTGTCCTTCAGAGACTGACACGGACTCTGTATTTTTACAGGATGGGGTCTCATTTAT

TATTTACAAATTCACATATACAACACCACCGTCCCCAGTGCCCGCAGTTTTTATTAAACATAACGTGGGATCTCC

ACGCGAATCTCGGGTACGTGTTCCGGACATGGTCTCTTCTCCGGTAGCGGCGGAGCTTCTACATCCGAGCCCTGC

TCCCATGCCTCCAGCGACTCATGGTCGCTCGGCAGCTCCTTGCTCCTAACAGTGGAGGCCAGACTTAGGCACAGC

ACGATGCCCACCACCACCAGTGTGCCGCACAAGGCCGTGGCGGTAGGGTATGTGTCTGAAAATGAGCTCGGGGAG

CGGGCTTGCACCGCTGACGCATTTGGAAGACTTAAGGCAGCGGCAGAAGAAGATGCAGGCAGCTGAGTTGTTGTG

TTCTGATAAGAGTCAGAGGTAACTCCCGTTGCGGTGCTGTTAACGGTGGAGGGCAGTGTAGTCTGAGCAGTACTC

GTTGCTGCCGCGCGCGCCACCAGACATAATAGCTGACAGACTAACAGACTGTTCCTTTCCATGGGTCTTTTCTGC

AG

ECMV IRES Sequence (SEQ ID NO: 50)

CCCCCCTCTCCCTCCCCCCCCCCTAACGTTACTGGCCGAAGCCGCTTGGAATAAGGCCGGTGTGCGTTTGTCTAT

ATGTTATTTTCCACCATATTGCCGTCTTTTGGCAATGTGAGGGCCCGGAAACCTGGCCCTGTCTTCTTGACGAGC

ATTCCTAGGGGTCTTTCCCCTCTCGCCAAAGGAATGCAAGGTCTGTTGAATGTCGTGAAGGAAGCAGTTCCTCTG

GAAGCTTCTTGAAGACAAACAACGTCTGTAGCGACCCTTTGCAGGCAGCGGAACCCCCCACCTGGCGACAGGTGC

CTCTGCGGCCAAAAGCCACGTGTATAAGATACACCTGCAAAGGCGGCACAACCCCAGTGCCACGTTGTGAGTTGG

ATAGTTGTGGAAAGAGTCAAATGGCTCTCCTCAAGCGTATTCAACAAGGGGCTGAAGGATGCCCAGAAGGTACCC

CATTGTATGGGATCTGATCTGGGGCCTCGGTGCACATGCTTTACATGTGTTTAGTCGAGGTTAAAAAACGTCTAG

GCCCCCCGAACCACGGGGACGTGGTTTTCCTTTGAAAAACACGATTGCTCGAATCACC

FMDV IRES (SEQ ID NO: 51)

AGCAGGTTTCCCCAACTGACACAAAACGTGCAACTTGAAACTCCGCCTGGTCTTTCCAGGTCTAGAGGGGTAACA

CTTTGTACTGTGTTTGGCTCCACGCTCGATCCACTGGCGAGTGTTAGTAACAGCACTGTTGCTTCGTAGCGGAGC

ATGACGGCCGTGGGAACTCCTCCTTGGTAACAAGGACCCACGGGGCCAAAAGCCACGCCCACACGGGCCCGTCAT

GTGTGCAACCCCAGCACGGCGACTTTACTGCGAAACCCACTTTAAAGTGACATTGAAACTGGTACCCACACACTG

GTGACAGGCTAAGGATGCCCTTCAGGTACCCCGAGGTAACACGCGACACTCGGGATCTGAGAAGGGGACTGGGGC

TTCTATAAAAGCGCTCGGTTTAAAAAGCTTCTATGCCTGAATAGGTGACCGGAGGTCGGCACCTTTCCTTTACAA

TTAATGACCCT

Example 14—CHO and Mouse Stable Site 1 Sequences—U.S. Pat. No. 7,771,997

211>6473
<212> DNA
<213> *Cricetulus griseus*
<400> 1

(SEQ ID NO: 52)

```
tctagaaaca aaaccaaaaa tattaagtca ggcttggctt caggtgctgg ggtggagtgc   60
tgacaaaaat acacaaattc ctggctttct aaggcttttt cggggattca ggtattgggt  120
gatggtagaa taaaatctg aaacataggt gatgtatctg ccatactgca tgggtgtgta  180
tgtgtgtgta tgtgtgtctg tgtgtgtgcc cagacagaaa taccatgaag gaaaaaaaca  240
cttcaaagac aggagagaag agtgacctgg gaaggactcc ccaatgagat gagaactgag  300
cacatgccag aggaggtgag gactgaacca ttcaacacaa gtggtgaata gtcctgcaga  360
cacagagagg gccagaagca ctcagaactc caggggtca ggagtggttc tctggaggct  420
tctgcccttg gaggttcctg aggaggaggc ttccatattg aaaatgtagt tagtggccgt  480
ttccattagt acagtgacta gagagagctg agggaccact ggactgaggc ctagatgctc  540
agtcagatgg ccatgaaagc ctagacaagc acttccgggt ggaaaggaaa cagcaggtgt  600
gaggggtcag gggcaagtta gtgggagagg tcttccagat gaagtagcag gaacggagac  660
gcactggatg gccccacttg tcaaccagca aaagcttgga tcttgttcta agaggccagg  720
gacatgacaa gggtgatctc ggttttaaa aggctttgtg ttacctaatc acttctatta  780
gtcagatact ttgtaacaca aatgagtact tggcctgtat tttagaaact tctgggatcc  840
tgaaaaaaca caatgacatt ctggctgcaa cacctggaga ctcccagcca ggccctggac  900
ccgggtccat tcatgcaaat actcagggac agattcttca ctaggtactg atgagctgtc  960
ttggatgcaa atgtggcctc ttcattttac tacaagtcac catgagtcag gaggtgctgt 1020
```

```
ttgcacagtg tgactaagtg atggagtgtt gactgcagcc attcccggcc ccagcttgtg   1080
agagagatcc ttttaaattg aaagtaagct caaagttacc acgaagccac acatgtataa   1140
actgtgtgaa taatctgtgc acatacacaa accatgtgaa taatctgtgt acatgtataa   1200
actgtgtgaa taatctgtgt gcagcctttc cttacctact accttccagt gatcaggttt   1260
ggactgcctg tgtgctactg gaccctgaat gtccccaccg ctgtcccctg tcttttacga   1320
ttctgacatt tttaataaat tcagcggctt cccctctgct ctgtgcctag ctataccttg   1380
gtactctgca ttttggtttc tgtgacattt ctctgtgact ctgctacatt ctcagatgac   1440
atgtgacaca gaaggtgttc cctctggaga catgtgatgt ccctgtcatt agtggaatca   1500
gatgccccca aactgttgtc cagtgtttgg gaaagtgaca cgtgaaggag gatcaggaaa   1560
agaggggtgg aaatcaagat gtgtctgagt atctcatgtc cctgagtggt ccaggctgct   1620
gacttcactc ccccaagtga gggaggccat ggtgagtaca cacacctcac acatactata   1680
tccaacacac acacacacac acacacacac acgcacgcac gcacgcacgc acgcacacat   1740
gcacacacac gaactacatt tcacaaacca catacgcata ttacacccca aacgtatcac   1800
ctatacatac cacacataca cacccctcca cacatcacac ataccaca cccacacaca   1860 gcacacacat acataggcac acattcacac accacacata tacatttgtg tatgcataca   1920
tgcatacaca cacaggcaca cagacaccac acacatgcat tgtgtacgca cacatgcata   1980
cacacacata ggcacacatt gagcacacac atacatttgt gtacgcacac tacatagaca   2040
tatatgcatt tgtatatgca cacatgcatg cacacataca taggcacaca tagagcacac   2100
acatacattt gtgtatgcac acatgcacac accaatcaca tgggaagact caggttcttc   2160
actaaggttc acatgaactt agcagttcct ggttatctcg tgaaacttgg aagattgctg   2220
tggagaagag gaagcgttgg cttgagccct ggcagcaatt aaccccgccc agaagaagta   2280
ggtttaaaaa tgagagggtc tcaatgtgga acccgcaggg cgccagttca gagaagagac   2340
ctacccaagc caactgagag caaaggcaga gggatgaacc tgggatgtag tttgaacctc   2400
tgtaccagct gggcttcatg ctatttttgtt atatctttat taaatattct tttagtttta   2460
tgtgcgtgaa taccttgctt gcataaatgt atgggcactg tatgtgttct tggtgccggt   2520
ggaggccagg agagggcatg gatcctccgg agctggcgtt tgagacagtt gtgacccaca   2580
gtgtggggtc tgggaactgg gtcttagtgt tccgcaagtg cagctggggc tcttaacctc   2640
tgagccatcc ctccagcttc aagaaactta ttttcttagg acatggggga agggatccag   2700
ggctttaggc ttgtttgttc agcaaatact cttttcgtgt attttgaatt ttatttatt   2760 ttactttttt gggatagaat cacattctgc agctcaggct gggcctgaac tcatcaaaat   2820
cctcctgtct cagtctacca ggtgataaga ttactgatgt gagcctggct ttgacaagca   2880
ctttagagtc cccagcccct ctggacactt gttccaagta taatatatat atatatatat   2940
atatatatat atatatatat atatattgtg tgtgtgtgtt tgtgtgtgta tgagacactt   3000
gctctaaggg tatcatatat atccttgatt tgcttttaat ttatttttta attaaaaatg   3060
attagctaca tgtcacctgt atgcgtctgt atcatctata tatccttcct tccttctctc   3120
tctttctctc ttcttcttct cacccccaag catctatttt caaatccttg tgccgaggag   3180
atgccaagag tctcgttggg ggagatggtg aggggcgat acaggggaag agcaggagga   3240 aaggggaca gactggtgtg ggtctttgga gagctcagga gaatagcagc gatcttccct   3300
gtccctggtg tcacctctta cagccaacac cattttgtgg cctggcagaa gagttgtcaa   3360
gctggtcgca ggtctgccac acaaccccaa tctggcccca agaaaaggca cctgtgtgtg   3420
```

```
actctggggt taaaggcgct gcctggtcgt ctccagctgg acttgaaact cccgtttaat 3480
aaagagttct gcaaaataat acccgcagag tcacagtgcc aggttcccgt gctttcctga 3540
agcgccaggc acgggttccc taggaaatgg ggccttgctt gccaagctcc cacggcttgc 3600
cctgcaaacg gcctgaatga tctggcactc tgcgttgcca ctgggatgaa atggaaaaaa 3660
gaaaaagaag aagtgtctct ggaagcgggc gcgctcacac aaacccgcaa cgattgtgta 3720
aacactctcc attgagaatc tggagtgcgg ttgccctcta ctggggagct gaagacagct 3780 agtggggcg gggggaggac cgtgctagca tccttccacg gtgctcgctg gctgtggtgc 3840
atgccgggaa ccgaaacgcg gaactaaagt caagtcttgc tttggtggaa ctgacaatca 3900
acgaaatcac ttcgattgtt ttcctctttt tactggaatt cttggatttg atagatgggg 3960
gaggatcaga ggggaggggg aggggcgggg agacggaggg aggaggggag gaggggagga 4020
ggggaggagg ggaggagggg aagggatgga ggaaaatact aacttttcta attcaacatg 4080
acaaagattc ggagaaagtg caccgctagt gaccgggagg aggaatgccc tattgggcat 4140
tatattccct gtcgtctaat ggaatcaaac tcttggttcc agcaccaagg attctgagcc 4200
tatcctattc aagacagtaa ctacagccca cacggaagag gctatacaac tgaagaaata 4260 aaatttcac tttatttcat ttctgtgact gcatgttcac atgtagagag ccacctgtgt 4320
ctaggggctg atgtgctggg cagtagagtt ctgagcccgt taactggaac aacccagaac 4380
tcccaccaca gttagagctt gctgagagag ggaggccctt ggtgagattt ctttgtgtat 4440
ttatttagag acagggtctc atactgtagt ccaagctagc ctccagctca cagaaattct 4500
cctgttccgg tttccaaagt actggagtta tgagtgtgtg ttaattgaac gctaagaatt 4560
tgctgattga agaaaacctc aagtgggttt ggctaatccc cacgacccca gaggctgagg 4620
caggaggaat gagagaattc aaggtttgcc agagccacag ggtgagctca atgtggagac 4680
tgtgagggtg agctcaatgt ggagactgtg agggtgagct caatgtggag actgtgaggg 4740
tgagctcaat gtggagactg tgagggtgag ctcaatgtgg agactgtgag ggtgagctca 4800
atgtggagac ctgtatcaag ataataatag tagtagtaac aatgcaggcg agggtgtggt 4860
tgagtggtag agcagttagt tgatttgaca tgcttgaggt ctcccggtcc atctgtggcc 4920
ctgcaacagg aagggaggga ggaagggggg gaacgagaga gaggaaagag agacagaagc 4980
taagataggg aatgagagag gaaggaagaa acgggaagaa attcagactc cttcctgagt 5040
tccgccaacg cctagtgaca tcctgtgcac accctaaggt ggcctttgtg tggcactggc 5100
ttgggtggtc gggaaaggca ttttcagctt gttgcagaac tgccacagta gcatgctggg 5160
tccgtgaaag tttctgcccg ttaacaagaa gtctctacta cttgtgacct caccagtgaa 5220
aatttcttta attgtctcct ggtgttctgg gttttgcatt tttgtttcta aggatacatt 5280
cctgggtgat gtcatgaagt ccccaaagac acagtggggc tgtgttggat tgggaaagat 5340
gatttatctg gggtgtcaaa aggaaaagaa gggaaacagg cacttgggaa aatgtcctcc 5400
cgcccacccg aattttggct tggcaaccgt ggtggaggag caagaaacac gtggacgttt 5460
gaggaggcat ggggtcctag gaggacagga agcagaagga gagagctggg ctgacagcct 5520
gcaggcattg cacagtttca gaaggagatt acagcatgac tgagttttta gggatccaac 5580
agggacctgg gtagagattc tgtgggctct gaggcaactt gacctcagcc agatggtatt 5640
tgaataacct gctcttagag ggaaaacaga catagcaaac agagccacgt ttagtgatga 5700
aactctcact ttgcctgagt catgtgcggc catgcccagg ggtcaggctg acactcaact 5760
caaaaacaag tgagaaattg aagacaatcc gtggtggcag ctactggaag ggccaccaca 5820
tccccagaaa gagtggagct gctaaaaagc catttgtgat aggcacagtt atcttgaatg 5880
```

-continued

```
catggagcag agattacgga aaaatcgaga atgttaatga ggcaacattc gagttgagtc   5940
attcagtgtg ggaaacccag acgcttccat cccctaaaag gaacatcttg ctctcagtca   6000
aaatggaaat aaaaattggg gcttgaattt ggcaaatgat tcagaactct gtgtaggtat   6060
tttcacacgc acagtggata attttcatgt tggagtttat ttgtgctaaa aggcagaaaa   6120
gggtaaaaag cacatcttaa gagttatgag gttctacgaa taaaaataat gttacttaca   6180
gctattcctt aattagtacc cccttccacc tgtggtaatt tcctgagata gtcagtgggg   6240
aaaagatctc tccttctctt ctttctcccc ctcccctcct ctccctccct ccctccctcc   6300
ctccctcctc tccctccctc cccctttcct tctttctttg ctccttctcc tctgcctcct   6360
tctcccttc ttcttcattt attctaagta gcttttaaca gcacaccaat tacctgtgta    6420
taacgggaaa acacaggctc aagcagctta gagaagattg atctgtgttc act          6473
```

<211> 7045
<212> DNA
<213> *Cricetulus griseus*
<400> 2

(SEQ ID NO: 53)

```
actagcgtgc aattcagagg tgggtgaaga taaaaggcaa acatttgagg ccatttcctt    60
atttggcacg gcacttagga agtggaacat gcctaatcta ctggtttgta ccacctttcc   120
ctataatgga ctgtttggga agctcctggg caaccgattc tggcatctca ttggtcagag   180
gcctgttaaa tggtactctt atttgcaaag aaggctgtaa cttgtagctt taaaagcctc   240
tcctcaagaa agaagggaga aaggatatgg ctagacatat ctaatagact taaccactgt   300
gaaaagcctt agtatgaatc agatagaacc tatttttaac tcagttttga aaaaaataat   360
ctttatattt atttgtgtgt gtgtgtgtgt gtgtgtgtgt gtgtgtgtgt gtgtgtgtgt   420
gaaccacatg tagcaggtgc tggaggaggc cagaagaggg caccagatct cctggaactg   480
acaccacaca tggttatgag ctgcctgatg tgggtgctgg gaactgaact ctcgtgttct   540
gcaagagcag caactgttct cttaactgat gagccatctc tccagccccc cccataattt   600
taattgttca ttttagtaaa ttttattcat aatcaattat cacagtataa acaatgatt   660
ttatatatat catatacata tcaaggatga cagtgagggg gatatgtgtg tgtgtgtgtg   720
tgtgtgtgtg tgtgtgtgtg tgtgttattt gtgtgtgtgc ttttttaagaa ggtgccatag   780
tcactgcatt tctctgaagg atttcaaagg aatgagacat gtctgtctgc caggaaccct   840
atcttcctct ttgggaatct gacccaaatg aggtattctg aggaactgaa tgaagagctc   900
aagtagcagt gtcttaaacc caaatgtgct gtctagagaa agtcaacgtc atcagtgagc   960
tgaggagaga tttactgagc ggaagacaag cgctctttga tttaagtggc tcgaacagtc  1020
acggctgtgg agtggagcct gtgctcaggt ctgaggcagt ctttgctagc cagctgtgat  1080
gagcagtgaa gaaagggtgg agatggaggc agggtgggag cagggctatg gttcagacta  1140
ggtatcgtga gcacaccagc tggttgactt gtggtctgtg ggtcaggcgt tgtaaacgcc  1200
ctcagggtca ggcagtcaca ttgcttgaag ctgaatgggt gaggcaacac agagagtgca  1260
aagaaggcaa agtaccacct cttccccgac ccaggtcact tctgggttat agctgagact  1320
ccggacagca tgcaaccagc tggttagagc ttcagggaaa acttgatgtc tgcatgttgc  1380
tatgaaatgt gattcggtac atctggagaa aatttataat gctggctcag tcaagcactg  1440
aacaaaggta ccttggcttt gggagctaca tgacattgac ttgtaggcag acttttttttt 1500
ttctgcccgc caattcccag ataaccaata tggaggctca atattaatta taaatgctcg  1560
```

-continued

```
gctgatagct caggcttgtt actagctaac tcttccaact taaatgaacc catttctatt 1620
atctacattc tgccacgtga ctttaccttg tacttcctgt ttcctctcct tgtctgactc 1680
tgcccttctg cttcccagag tccttagtct ggttctcctg cctaacctta tcctgcccag 1740
ctgctgacca agcatttata attaatatta agtctcccag tgagactctc atccagggag 1800
gacttgggtg ctcccccctc ctcattgcca tccgtgtctt cctcttccct cgcttccccc 1860
tcctcttcct gctcttcctc ctccacccct cctttcatag tattgatggc aagggtgttc 1920
tagaatggag gagtgcccat aggcatgcaa agaaaccagt taggatgctc tgtgaggggt 1980
tgtaatcata agcgatggac acaattcaag ccacagagtg aagacggaag gatgcactgt 2040
gctctagagc aacttctggg gcagaatcac agggtgagtt tctgacttga gggcgaagag 2100
gccacgagga agggagtgag tttgtctgag ctagaagcta cggcccacct cttggtagca 2160
gacctgccca caagcatgct tgttaatca tgtgggatct gattttcctc taaatctatg 2220
ttcaactctt aagaaaatgt gaattctcac attaaaattt agatatacgt cttttggtgg 2280
gggggtgta aaaatcctc aagaatatgg atttctgggg gccggagaga tggctcagag 2340
gttaagagaa ctggttgctc ttctagacat tctgagttca attcccagca accacatggt 2400
ggctcacaac catctgtaat gcgacctggt gccatcttct gacatgcatg gatacatgca 2460
ggcagaaagc tgtatacata gtaaattgat aaatcttttt ttaaaaagag tatggattct 2520
gccgggtgtt ggtggcgcac gccttttaatc ccagcactct ggaggcagag gcaggtggat 2580
ctctgtgagt tcgagaccag cctggtctat aagagctagt tccaggacag cctccaaagc 2640
cacagagaaa ccctgtctcg aaaaaccaaa aaaaaaaaaa aaaaaaaaa aaaaaaaga 2700
gtatggattc taagaaagcc gtaacagctg gagctgtgta cggagttcag cgtggtacta 2760
gaagaacaga cattcatgat gaaacacccc aggatttta cttagtatct agtttccatt 2820
gttgttttga daccggctct tatgctctcc aggctggcct caaactgctg atcttcccgc 2880
ctctacctct caagtcctgg gactacttgg ctcataaaac agttttttgtc gggctccctg 2940
aagttatggt tgtacaaacc gtggggtca atatactcac ttgggcagag agagaaggtc 3000
tgaatcccag acaatgactg catctcagga cagttgggaa gaggacaatg gcagaaggac 3060
ttagaaaaga tagactggag ggtggaaaag cagcaggaac agagaaacaa aacaggaagc 3120
ttgctatcca gggccactct ggagtcctgt ggcaagatgg aagcgggcta ggggaataca 3180
tttgtgctac tgtgtgtgtg tgtgtgtgtg tgtgtgtgtg tgtgtgtgat caatgcctat 3240
caatgttgaa gggaaatat gtataccaca ttgattctgg gagcaattct cagtatctgg 3300
cctagagaaa ggaatggccc ctgcagaata gacagagtga atggtgccct ttatcatttg 3360
ctaaagtgaa ggagaaataa acatccttcc atagagtttc aggtaaatga accccacagt 3420
tcatctgtgc cgtggtggag gcctggccaa cagttaaaaa gattagacac ggacaaagtc 3480
tgaaggaaac acctcgaata ggaagaggag agccacctca ttctgtaact ttcctcaagg 3540
ggaagatgtt ccaagagtgg gaataaatgg tcaaggggg gatttttaat taggaaaacg 3600
atttcctgta tcacttgtga aactggaggt tgatttgggg cataggacaa tagatttgat 3660
gctttgcaaa aagctgtttc aaagcagaga aatggaatag agacaattat gtagcgagga 3720
gggagggtgg ggcgaagatg gagacagaga agtggaagct gactttaggg aagaggaaca 3780
tagaccacag gggcggggcg ggggcaggg gcgggggggcg gggctcaaag gaggcagtgg 3840
gaacgttgct agtgttcgca gcgtaagcgt gaatgtgcaa gcgtcttttgt ggtgtgtgac 3900
caggagtagc gtggctggct tgtgtgctgc ttgtaatccc agtctttgag gtttccacac 3960
```

-continued

```
tgttccacag tgggtgtgat tttccctcgg agagcatgag ggctctgctt tccccacatc 4020
ctccccagcg ttcgttggta tttgtttcca agatgttagt gggtgagaca aagcctctct 4080
gttgatttgc ctttaacagg tgacaaaaaa agctcaacca ggagacattt ttgccttctt 4140
ggaaggtaat gctcccatgt agagcaatgg gacccatctc taaggtgagg ctactcttgc 4200
agtttgcacc cagctcttct gatgcaggaa ggaagttggt gggcaagcaa gactgtttgc 4260
ttcttgcgat ggacacattc tgcacacaaa ggctcaggag gggagaaggc tgtttgatgt 4320
ttagcactca ggaaggcccc tgatgcatct gtgattagct gtctccatct gtggagcaga 4380
cacggactaa ctaaaaacca gtgttttttaa attgtcaagc ctttaaggtg aggaaattga 4440
cttattgtgc tgggccatac gtagagcaag tgctctgcat tgggccaacc cccggctctg 4500
gtttctaggc accagaatgg cctagaacta actcacaatc ctcccattcc aggtctcagg 4560
tgctagaatg aaccactata ccagcctgcc tgcctgccta cctgccttcc taaatttaa 4620 atcatgggga gtaggggaga atacacttat cttagttagg gtttctattg ctgtgaagag 4680
acaccatgag catggcaact cttataaagg aaaacattta gttgggtggc agtttcagag 4740
gttttagtac attgtcatca tggctgggaa catgatggca tgcagacaga catggtgctg 4800
gagaaaggga tgagagtcct acatcttgca ggcaacagga cctcagctga cactggct 4860 ggtaccctga gcataggaaa cctcacagcc caccctcaca gtgacatatt tccttcaaca 4920
aagccatacc tcctaatagt gccactccct atgagatgac agggccaatt acattcaaac 4980
tgctataaca ctttaaagta tttattttt attattgtaa attatgtatg tagctgggtg 5040
gtggcagccg aggtgcacgc ctttaatccc agcacttggg aggcagaggc agatggatct 5100
ctgtgagttc aagaccagcc tggtctataa gagctagttg caaggaagga tatacaaaga 5160
acagttctag gatagccttc aaagccacag agaagtgctg tcttgaaaac caaaaattgt 5220
gctgggacct gtctctgctt tggttgcttc ccactccccc agagctggac tcttggtcaa 5280
cactgaatca gctgcaaaat aaactcctgg attcctctct tgtaacagga gcccgaagtc 5340
aggcgcccac ttgtcttctc gcaggattgc catagacttt ttctgtgtgc ccaccattcc 5400
agactgaagt agagatggca gtggcagaga ctgggaaggc tgcaacgaaa acaggaagtt 5460
attgcaccct gggaatagtc tggaaatgaa gcttcaaaac ttgcttcatg ttcagttgta 5520
cacagactca ctcccaggtt gactcacacg tgtaaatatt cctgactatg tctgcactgc 5580
ttttatctga tgcttccttc ccaaaatgcc aagtgtacaa ggtgagggaa tcacccttgg 5640
attcagagcc cagggtcgtc ctccttaacc tggacttgtc tttctccggc agcctctgac 5700
acccctcccc ccattttctc tatcagaagg tctgagcaga gttggggcac gctcatgtcc 5760
tgatacactc cttgtcttcc tgaagatcta acttctgacc cagaaagatg gctaaggtgg 5820
tgaagtgttt gacatgaaga cttggtctta agaactggag caggggaaaa aagtcggatg 5880
tggcagcatg tacccgaaat cccagaactg gggaggtaga gacggatgag tgcccggggc 5940
tagctggctg ctcagccagc ctagctgaat tgccaaattc caactcctat tgaaaaacct 6000
ttaccaaaca aacaaacaaa caaataataa caacaacaac aacaacaaac taccccatac 6060
aaggtgggcg gctcttggct cttgaggaat gactcaccca aacccaaagc ttgccacagc 6120
tgttctctgg cctaaatggg gtgggggtgg ggcagagaca gagacagaga gagacatgac 6180
ttcctgggct gggctgtgtg ctctaggcca ccaggaactt tcctgtcttg ctctctgtct 6240
ggcacagcca gagcaccagc acccagcagg tgcacacacc tccctccgtg cttcttgagc 6300
aaacacaggt gccttggtct gtctattgaa ccggagtaag ttcttgcaga tgtatgcatg 6360
gaaacaacat tgtcctggtt ttatttctac tgttgtgata aaaaccgggg aactccagga 6420
```

-continued

```
agcagctgag gcagaggcaa atgcaaggaa tgctgcctcc tagcttgctc cccatggctt   6480
gccgggcctg ctttctgcaa gcccttctct ccccattggc atgcctgaca tgaacagcgt   6540
ttgaaatgct ctcaaatgtc actttcaaag aaggcttctc tgatcttgct aactaaatca   6600
gaccatgttt caccgtgcat tatctttctg ctgtctgtct gtctgtctgt ctgtctatct   6660
gtctatcatc tatcaatcat ctatctatct atcttctatt tatctaccta tcattcaatc   6720
atctatcttc taactagtta tcatttattt atttgtttac ttacttttt tatttgagac    6780 agtatttctc tgagtgacag ccttggctgt cctggaaccc attctgtaac caggctgtcc   6840
tcaaactcac agagatccaa ctgcctctgc ctctctggtg ctggggttaa agacgtgcac   6900
caccaacgcc ccgctctatc atctatttat gtacttatta ttcagtcatt atctatcctc   6960
taactatcca tcatctgtct atccatcatc tatctatcta tctatctatc tatctatcta   7020
tctatcatcc atctataatc aattg                                         7045
```

20

<211> 6473
<212> DNA
<213> *Cricetulus griseus*
<400> 3

(SEQ ID NO: 54)

```
agtgaacaca gatcaatctt ctctaagctg cttgagcctg tgttttcccg ttatacacag     60
gtaattggtg tgctgttaaa agctacttag aataaatgaa gaagaaggg agaaggaggc    120 agaggagaag gagcaaagaa agaaggaaag ggggagggag ggagaggagg gagggaggga   180
ggagggaggg gagaggaggg gaggggagaa aagaagagaa ggagagatct ttccccact    240 gactatctca ggaaattacc acaggtggaa ggggtactaa attaaggaat agctgtaagt   300
aacattattt ttattcgtag aacctcataa ctcttaagat gtgctttta cccttttctg     360 cctttagca caaataaact ccaacatgaa aattatccac tgtgcgtgtg aaaataccta    420
cacagagttc tgaatcattt gccaaattca gccccaatt tttatttcca ttttgactga    480
gagcaagatg ttccttttag gggatggaag cgtctgggtt tcccacactg aatgactcaa   540
ctcgaatgtt gcctcattaa cattctcgat ttttccgtaa tctctgctcc atgcattcaa   600
gataactgtg cctatcacaa atggctttt agcagctcca ctctttctgg ggatgtggtg    660
gcccttccag tagctgccac cacggattgt cttcaatttc tcacttgttt ttgagttgag   720
tgtcagcctg accctgggc atggccgcac atgactcagg caaagtgaga gtttcatcac    780
taaacgtggc tctgtttgct atgtctgttt tccctctaag agcaggttat tcaaatacca   840
tctggctgag gtcaagttgc ctcagagccc acagaatctc tacccaggtc cctgttggat   900
ccctaaaaac tcagtcatgc tgtaatctcc ttctgaaact gtgcaatgcc tgcaggctgt   960
cagcccagct ctctccttct gcttcctgtc tccctaggac cccatgcctc ctcaaacgtc  1020
cacgtgtttc ttgctcctcc accacggttg ccaagccaaa attcgggtgg gcgggaggac  1080
attttcccaa gtgcctgttt cccttctttt ccttttgaca cccagataa atcatctttc   1140 ccaatccaac acagccccac tgtgtctttg gggacttcat gacatcaccc aggaatgtat  1200
ccttagaaac aaaaatgcaa aacccagaac accaggagac aattaaagaa attttcactg  1260
gtgaggtcac aagtagtaga gacttcttgt taacgggcag aaactttcac ggacccagca  1320
tgctactgtg gcagttctgc aacaagctga aaatgccttt cccgaccacc caagccagtg  1380
ccacacaaag gccaccttag ggtgtgcaca ggatgtcact aggcgttggc ggaactcagg  1440
aaggagtctg aatttcttcc cgtttcttcc ttcctctctc attccctatc ttagcttctg   1500
```

-continued

```
tctctctttc ctctctctcg ttccccccct tcctccctcc cttcctgttg cagggccaca 1560
gatggaccgg gagacctcaa gcatgtcaaa tcaactaact gctctaccac tcaaccacac 1620
cctcgcctgc attgttacta ctactattat tatcttgata caggtctcca cattgagctc 1680
accctcacag tctccacatt gagctcaccc tcacagtctc cacattgagc tcaccctcac 1740
agtctccaca ttgagctcac cctcacagtc tccacattga gctcaccctc acagtctcca 1800
cattgagctc accctgtggc tctggcaaac cttgaattct ctcattcctc ctgcctcagc 1860
ctctggggtc gtggggatta gccaaaccca cttgaggttt tcttcaatca gcaaattctt 1920
agcgttcaat taacacacac tcataactcc agtactttgg aaaccggaac aggagaattt 1980
ctgtgagctg gaggctagct tggactacag tatgagaccc tgtctctaaa taaatacaca 2040
aagaaatctc accaagggcc tccctctctc agcaagctct aactgtggtg ggagttctgg 2100
gttgttccag ttaacgggct cagaactcta ctgcccagca catcagcccc tagacacagg 2160
tggctctcta catgtgaaca tgcagtcaca gaaatgaaat aaagtgaaaa ttttatttct 2220
tcagttgtat agcctcttcc gtgtgggctg tagttactgt cttgaatagg ataggctcag 2280
aatccttggt gctggaacca agagtttgat tccattagac gacagggaat ataatgccca 2340
atagggcatt cctcctcccg gtcactagcg gtgcactttc tccgaatctt tgtcatgttg 2400
aattagaaaa gttagtattt tcctccatcc cttcccctcc tccctcctc ccctcctccc 2460 ctcctcccct cctccctccg tctccccgcc cctcccctcc ccctctgatc ctccccccatc 2520 tatcaaatcc aagaattcca gtaaaaagag gaaaacaatc gaagtgattt cgttgattgt 2580
cagttccacc aaagcaagac ttgactttag ttccgcgttt cggttcccgg catgcaccac 2640
agccagcgag caccgtggaa ggatgctagc acggtcctcc ccccgccccc actagctgtc 2700
ttcagctccc cagtagaggg caaccgcact ccagattctc aatggagagt gtttacacaa 2760
tcgttgcggg tttgtgtgag cgcgcccgct tccagagaca cttcttcttt ttctttttc 2820 catttcatcc cagtggcaac gcagagtgcc agatcattca ggccgtttgc agggcaagcc 2880
gtgggagctt ggcaagcaag gccccatttc ctagggaacc cgtgcctggc gcttcaggaa 2940
agcacgggaa cctggcactg tgactctgcg ggtattattt tgcagaactc tttattaaac 3000
gggagtttca gtccagctg gagacgacca ggcagcgcct ttaacccag agtcacacac 3060 aggtgccttt tcttggggcc agattggggt tgtgtggcag acctgcgacc agcttgacaa 3120
ctcttctgcc aggccacaaa atggtgttgg ctgtaagagg tgacaccagg gacagggaag 3180
atcgctgcta ttctcctgag ctctccaaag acccacacca gtctgtcccc ctttcctcct 3240
gctcttcccc tgtatcgccc cctcaccatc tcccccaacg agactcttgg catctcctcg 3300
gcacaaggat ttgaaaatag atgcttgggg gtgagaagaa gaagagagaa agagagagaa 3360
ggaaggaagg atatatagat gatacagacg catacaggtg acatgtagct aatcattttt 3420
aattaaaaaa taaattaaaa gcaaatcaag gatatatatg ataccttag agcaagtgtc 3480 tcatacacac acaaacacac acacacaata tatatatata tatatatata tatatatata 3540
tatatatata ttatacttgg aacaagtgtc cagaagggct ggggactcta aagtgcttgt 3600
caaagccagg ctcacatcag taatcttatc acctggtaga ctgagacagg aggattttga 3660
tgagttcagg cccagcctga gctgcagaat gtgattctat cccaaaaaag taaaataaaa 3720
taaaattcaa aatacacgaa aagagtattt gctgaacaaa caagcctaaa gccctggatc 3780 ccttcccccca tgtcctaaga aaataagttt cttgaagctg gagggatggc tcagaggtta 3840
agagccccag ctgcacttgc ggaacactaa gacccagttc ccagaccca cactgtgggt 3900
```

-continued

```
cacaactgtc tcaaacgcca gctccggagg atccatgccc tctcctggcc tccaccggca 3960
ccaagaacac atacagtgcc catacattta tgcaagcaag gtattcacgc acataaaact 4020
aaaagaatat ttaataaaga tataacaaaa tagcatgaag cccagctggt acagaggttc 4080
aaactacatc ccaggttcat ccctctgcct ttgctctcag ttggcttggg taggtctctt 4140
ctctgaactg gcgccctgcg ggttccacat tgagaccctc tcatttttaa acctacttct 4200
tctgggcggg gttaattgct gccagggctc aagccaacgc ttcctcttct ccacagcaat 4260
cttccaagtt tcacgagata accaggaact gctaagttca tgtgaacctt agtgaagaac 4320
ctgagtcttc ccatgtgatt ggtgtgtgca tgtgtgcata cacaaatgta tgtgtgtgct 4380
ctatgtgtgc ctatgtatgt gtgcatgcat gtgtgcatat acaaatgcat atatgtctat 4440
gtagtgtgcg tacacaaatg tatgtgtgtg ctcaatgtgt gcctatgtgt gtgtatgcat 4500
gtgtgcgtac acaatgcatg tgtgtggtgt ctgtgtgcct gtgtgtgtat gcatgtatgc 4560
atacacaaat gtatatgtgt ggtgtgtgaa tgtgtgccta tgtatgtgtg tgctgtgtgt 4620
gggtgtggta tgtgtgtgat gtgtggaggg gtgtgtatgt gtggtatgta taggtgatac 4680
gtttggggtg taatatgcgt atgtggtttg tgaaatgtag ttcgtgtgtg tgcatgtgtg 4740
cgtgcgtgcg tgcgtgcgtg cgtgtgtgtg tgtgtgtgtg tgtgtgtgtt ggatatagta 4800
tgtgtgaggt gtgtgtactc accatggcct ccctcacttg ggggagtgaa gtcagcagcc 4860
tggaccactc agggacatga gatactcaga cacatcttga tttccacccc tcttttcctg 4920
atcctccttc acgtgtcact ttcccaaaca ctggacaaca gtttggggc atctgattcc 4980 actaatgaca gggacatcac atgtctccag agggaacacc ttctgtgtca catgtcatct 5040
gagaatgtag cagagtcaca gagaaatgtc acagaaacca aaatgcagag taccaaggta 5100
tagctaggca cagagcagag gggaagccgc tgaatttatt aaaaatgtca gaatcgtaaa 5160
agacagggga cagcggtggg gacattcagg gtccagtagc acacaggcag tccaaacctg 5220
atcactggaa ggtagtaggt aaggaaaggc tgcacacaga ttattcacac agtttataca 5280
tgtacacaga ttattcacat ggtttgtgta tgtgcacaga ttattcacac agtttataca 5340
tgtgtggctt cgtggtaact ttgagcttac tttcaattta aaaggatctc tctcacaagc 5400
tggggccggg aatggctgca gtcaacactc catcacttag tcacactgtg caaacagcac 5460
ctcctgactc atggtgactt gtagtaaaat gaagaggcca catttgcatc caagacagct 5520
catcagtacc tagtgaagaa tctgtccctg agtatttgca tgaatggacc cgggtccagg 5580
gcctggctgg gagtctccag gtgttgcagc cagaatgtca ttgtgttttt tcaggatccc 5640
agaagtttct aaaatacagg ccaagtactc atttgtgtta caaagtatct gactaataga 5700
agtgattagg taacacaaag ccttttaaaa accgagatca cccttgtcat gtccctggcc 5760
tcttagaaca agatccaagc ttttgctggt tgacaagtgg ggccatccag tgcgtctccg 5820
ttcctgctac ttcatctgga agacctctcc cactaacttg cccctgaccc ctcacacctg 5880
ctgtttcctt tccacccgga agtgcttgtc taggctttca tggccatctg actgagcatc 5940
taggcctcag tccagtggtc cctcagctct ctcagtcac tgtactaatg gaaacggcca 6000
ctaactacat tttcaatatg gaagcctcct cctcaggaac ctccaagggc agaagcctcc 6060
agagaaccac tcctgacccc ctggagttct gagtgcttct ggccctctct gtgtctgcag 6120
gactattcac cacttgtgtt gaatggttca gtcctcacct cctctggcat gtgctcagtt 6180
ctcatctcat tggggagtcc ttcccaggtc actcttctct cctgtctttg aagtgttttt 6240
ttccttcatg gtatttctgt ctgggcacac acacagacac acatacacac acatacacac 6300
ccatgcagta tggcagatac atcacctatg tttcagattt ttattctacc atcacccaat 6360
```

-continued

```
acctgaatcc ccgaaaaagc cttagaaagc caggaatttg tgtattttttg tcagcactcc    6420 accccagcac ctgaagccaa gcctgactta atatttttgg ttttgtttct aga            6473
```

<211> 7045
<212> DNA
<213> *Cricetulus griseus*
<400> 4

(SEQ ID NO: 55)
```
caattgatta tagatggatg atagatagat agatagatag atagatagat agatagatga      60
tggatagaca gatgatggat agttagagga tagataatga ctgaataata agtacataaa     120
tagatgatag agcggggcgt tggtggtgca cgtctttaac cccagcacca gagaggcaga     180
ggcagttgga tctctgtgag tttgaggaca gcctggttac agaatgggtt ccaggacagc     240
caaggctgtc actcagagaa atactgtctc aaataaaaaa agtaagtaaa caaataaata     300
aatgataact agttagaaga tagatgattg aatgataggt agataaatag aagatagata     360
gatagatgat tgatagatga tagacagata gacagacaga cagacagaca gacagcagaa     420
agataatgca cggtgaaaca tggtctgatt tagttagcaa gatcagagaa gccttctttg     480
aaagtgacat ttgagagcat ttcaaacgct gttcatgtca ggcatgccaa tggggagaga     540
agggcttgca gaaagcaggc ccggcaagcc atggggagca agctaggagg cagcattcct     600
tgcatttgcc tctgcctcag ctgcttcctg gagttccccg gttttttatca caacagtaga     660 aataaaacca ggacaatgtt gtttccatgc atacatctgc aagaacttac tccggttcaa     720
tagacagacc aaggcacctg tgtttgctca agaagcacgg agggaggtgt gtgcacctgc     780
tgggtgctgg tgctctggct gtgccagaca gagagcaaga caggaaagtt cctggtggcc     840
tagagcacac agcccagccc aggaagtcat gtctctctct gtctctgtct ctgccccacc     900 cccacccccat ttaggccaga gaacagctgt ggcaagcttt gggtttgggt gagtcattcc     960
tcaagagcca agagccgccc accttgtatg gggtagtttg ttgttgttgt tgttgttatt    1020
atttgtttgt ttgtttgttt ggtaaaggtt tttcaatagg agttggaatt tggcaattca    1080
gctaggctgg ctgagcagcc agctagcccc gggcactcat ccgtctctac ctccccagtt    1140
ctgggatttc gggtacatgc tgccacatcc gactttttc ccctgctcca gttcttaaga    1200
ccaagtcttc atgtcaaaca cttcaccacc ttagccatct ttctgggtca gaagttagat    1260
cttcaggaag acaaggagtg tatcaggaca tgagcgtgcc ccaactctgc tcagaccttc    1320
tgatagagaa aatgggggga ggggtgtcag aggctgccgg agaaagacaa gtccaggtta    1380
aggaggacga ccctgggctc tgaatccaag ggtgattccc tcaccttgta cacttggcat    1440
tttgggaagg aagcatcaga taaaagcagt gcagacatag tcaggaatat ttacacgtgt    1500
gagtcaacct gggagtgagt ctgtgtacaa ctgaacatga agcaagtttt gaagcttcat    1560
ttccagacta ttcccagggt gcaataactt cctgttttcg ttgcagcctt cccagtctct    1620
gccactgcca tctctacttc agtctggaat ggtgggcaca cagaaaaagt ctatggcaat    1680
cctgcgagaa gacaagtggg cgcctgactt cgggctcctg ttacaagaga ggaatccagg    1740
agtttatttt gcagctgatt cagtgttgac caagagtcca gctctggggg agtgggaagc    1800
aaccaaagca gagacaggtc ccagcacaat ttttggtttt caagacagca cttctctgtg    1860
gctttgaagg ctatcctaga actgttcttt gtatatcctt ccttgcaact agctcttata    1920
gaccaggctg tcttgaact cacagagatc catctgcctc tgcctcccaa gtgctgggat    1980
taaaggcgtg cacctcggct gccaccaccc agctacatac ataatttaca ataataaaaa    2040
```

```
taaaatactt taaagtgtta tagcagtttg aatgtaattg gccctgtcat ctcataggga 2100
gtggcactat taggaggtat ggctttgttg aaggaaatat gtcactgtga gggtgggctg 2160
tgaggtttcc tatgctcagg gtaccagcca gtgtctcagc tgaggtcctg ttgcctgcaa 2220
gatgtaggac tctcatccct ttctccagca ccatgtctgt ctgcatgcca tcatgttccc 2280
agccatgatg acaatgtact aaaacctctg aaactgccac ccaactaaat gttttccttt 2340
ataagagttg ccatgctcat ggtgtctctt cacagcaata gaaaccctaa ctaagataag 2400
tgtattctcc cctactcccc atgatttaaa atttaggaag gcaggtaggc aggcaggcag 2460
gctggtatag tggttcattc tagcacctga gacctggaat gggaggattg tgagttagtt 2520
ctaggccatt ctggtgccta gaaaccagag ccgggggttg gcccaatgca gagcacttgc 2580
tctacgtatg gcccagcaca ataagtcaat ttcctcacct taaaggcttg acaatttaaa 2640
aacactggtt tttagttagt ccgtgtctgc tccacagatg gagacagcta atcacagatg 2700
catcaggggc cttcctgagt gctaaacatc aaacagcctt ctcccctcct gagcctttgt 2760
gtgcagaatg tgtccatcgc aagaagcaaa cagtcttgct tgcccaccaa cttccttcct 2820
gcatcagaag agctgggtgc aaactgcaag agtagcctca ccttagagat gggtcccatt 2880
gctctacatg ggagcattac cttccaagaa ggcaaaaatg tctcctggtt gagcttttt 2940 tgtcacctgt taaaggcaaa tcaacagaga ggctttgtct cacccactaa catcttggaa 3000
acaaatacca acgaacgctg gggaggatgt ggggaaagca gagccctcat gctctccgag 3060
ggaaaatcac acccactgtg gaacagtgtg gaaacctcaa agactgggat tacaagcagc 3120
acacaagcca gccacgctac tcctggtcac acaccacaaa gacgcttgca cattcacgct 3180
tacgctgcga acactagcaa cgttcccact gcctcctttg agcccgccc ccgcccctg 3240 cccccgccc cgcccctgtg gtctatgttc ctcttcccta aagtcagctt ccacttctct 3300
gtctccatct tcgccccacc ctccctcctc gctacataat tgtctctatt ccatttctct 3360
gctttgaaac agcttttgc aaagcatcaa atctattgtc ctatgcccca aatcaacctc 3420
cagtttcaca agtgatacag gaaatcgttt tcctaattaa aaatccccc tttgaccatt 3480 tattcccact cttggaacat cttccccttg aggaaagtta cagaatgagg tggctctcct 3540
cttcctattc gaggtgtttc cttcagactt tgtccgtgtc taatcttttt aactgttggc 3600
caggcctcca ccacggcaca gatgaactgt ggggttcatt tacctgaaac tctatggaag 3660
gatgtttatt tctccttcac tttagcaaat gataaagggc accattcact ctgtctattc 3720
tgcaggggcc attcctttct ctaggccaga tactgagaat tgctcccaga atcaatgtgg 3780
tatacatatt tccccttcaa cattgatagg cattgatcac acacacacac acacacacac 3840
acacacacac acacagtagc acaaatgtat tcccctagcc cgcttccatc ttgccacagg 3900
actccagagt ggccctggat agcaagcttc ctgttttgtt tctctgttcc tgctgctttt 3960
ccaccctcca gtctatcttt tctaagtcct tctgccattg tcctcttccc aactgtcctg 4020
agatgcagtc attgtctggg attcagacct tctctctctg cccaagtgag tatattgacc 4080
cccacggttt gtacaaccat aacttcaggg agcccgacaa aaactgtttt atgagccaag 4140
tagtcccagg acttgagagg tagaggcggg aagatcagca gtttgaggcc agcctggaga 4200
gcataagagc cggtctcaaa acaacaatgg aaactagata ctaagtaaaa atcctggggt 4260
gtttcatcat gaatgtctgt tcttctagta ccacgctgaa ctccgtacac agctccagct 4320
gttacggctt tcttagaatc catactcttt tttttttttt tttttttttt tttttttttgg 4380 tttttcgaga cagggtttct ctgtggcttt ggaggctgtc ctggaactag ctcttataga 4440
```

-continued

```
ccaggctggt ctcgaactca cagagatcca cctgcctctg cctccagagt gctgggatta    4500
aaggcgtgcg ccaccaacac ccggcagaat ccatactctt tttaaaaaaa gatttatcaa    4560
tttactatgt atacagcttt ctgcctgcat gtatccatgc atgtcagaag atggcaccag    4620
gtcgcattac agatggttgt gagccaccat gtggttgctg ggaattgaac tcagaatgtc    4680
tagaagagca accagttctc ttaacctctg agccatctct ccggccccca gaaatccata    4740
ttcttgagga ttttttacac ccccccccacc aaaagacgta tatctaaatt ttaatgtgag    4800
aattcacatt ttcttaagag ttgaacatag atttagagga aaatcagatc ccacatgatt    4860
aacaaagcat gcttgtgggc aggtctgcta ccaagaggtg ggccgtagct tctagctcag    4920
acaaactcac tcccttcctc gtggcctctt cgccctcaag tcagaaactc accctgtgat    4980
tctgccccag aagttgctct agagcacagt gcatccttcc gtcttcactc tgtggcttga    5040
attgtgtcca tcgcttatga ttacaacccc tcacagagca tcctaactgg tttctttgca    5100
tgcctatggg cactcctcca ttctagaaca cccttgccat caatactatg aaaggagggg    5160
tggaggagga agagcaggaa gaggaggggg aagcgaggga agaggaagac acggatggca    5220
atgaggaggg gggagcaccc aagtcctccc tggatgagag tctcactggg agacttaata    5280
ttaattataa atgcttggtc agcagctggg caggataagg ttaggcagga gaaccagact    5340
aaggactctg ggaagcagaa gggcagagtc agacaaggag aggaaacagg aagtacaagg    5400
taaagtcacg tggcagaatg tagataatag aaatgggttc atttaagttg gaagagttag    5460
ctagtaacaa gcctgagcta tcagccgagc atttataatt aatattgagc ctccatattg    5520
gttatctggg aattggcggg cagaaaaaaa aaagtctgcc tacaagtcaa tgtcatgtag    5580
ctcccaaagc caaggtacct ttgttcagtg cttgactgag ccagcattat aaattttctc    5640
cagatgtacc gaatcacatt tcatagcaac atgcagacat caagttttcc ctgaagctct    5700
aaccagctgg ttgcatgctg tccggagtct cagctataac ccagaagtga cctgggtcgg    5760
ggaagaggtg gtactttgcc ttcttttgcac tctctgtgtt gcctcaccca ttcagcttca    5820
agcaatgtga ctgcctgacc ctgagggcgt ttacaacgcc tgacccacag accacaagtc    5880
aaccagctgg tgtgctcacg atacctagtc tgaaccatag ccctgctccc accctgcctc    5940
catctccacc ctttcttcac tgctcatcac agctggctag caaagactgc ctcagacctg    6000
agcacaggct ccactccaca gccgtgactg ttcgagccac ttaaatcaaa gagcgcttgt    6060
cttccgctca gtaaatctct cctcagctca ctgatgacgt tgactttctc tagacagcac    6120
atttgggttt aagacactgc tacttgagct cttcattcag ttcctcagaa tacctcattt    6180
gggtcagatt cccaaagagg aagatagggt tcctggcaga cagacatgtc tcattccttt    6240
gaaatccttc agagaaatgc agtgactatg gcaccttctt aaaaagcaca cacacaaata    6300
acacacacac acacacacac acacacacac acacacacac atatccccct cactgtcatc    6360
cttgatatgt atatgatata tataaaatca ttgttttata ctgtgataat tgattatgaa    6420
taaaatttac taaaatgaac aattaaaatt atggggggggg ctggagagat ggctcatcag    6480 ttaagaaac agttgctgct cttgcagaac acgagagttc agttcccagc acccacatca    6540
ggcagctcat aaccatgtgt ggtgtcagtt ccaggagatc tggtgccctc ttctggcctc    6600
ctccagcacc tgctacatgt ggttcacaca cacacacaca cacacacaca cacacacaca    6660
cacacacaca caaataaata taagagattat ttttttcaaa actgagttaa aaataggttc    6720
tatctgattc atactaaggc ttttcacagt ggttaagtct attagatatg tctagccata    6780 tccttctctcc cttctttctt gaggagaggc ttttaaagct acaagttaca gccttctttg    6840
caaataagag taccatttaa caggcctctg accaatgaga tgccagaatc ggttgcccag    6900
```

-continued

```
gagcttccca aacagtccat tatagggaaa ggtggtacaa accagtagat taggcatgtt   6960
ccacttccta agtgccgtgc caaataagga aatggcctca aatgtttgcc ttttatcttc   7020
acccacctct gaattgcacg ctagt                                          7045
```

<211> 13515
<212> DNA
<213> *Cricetulus griseus*
<400> 5

```
                                                             (SEQ ID NO: 56)
tctagaaaca aaaccaaaaa tattaagtca ggcttggctt caggtgctgg ggtggagtgc     60
tgacaaaaat acacaaattc ctggctttct aaggcttttt cggggattca ggtattgggt    120
gatggtagaa taaaaatctg aaacataggt gatgtatctg ccatactgca tgggtgtgta    180
tgtgtgtgta tgtgtgtctg tgtgtgtgcc cagacagaaa taccatgaag gaaaaaaaca    240
cttcaaagac aggagagaag agtgacctgg gaaggactcc ccaatgagat gagaactgag    300
cacatgccag aggaggtgag gactgaacca ttcaacacaa gtggtgaata gtcctgcaga    360
cacagagagg gccagaagca ctcagaactc caggggggtca ggagtggttc tctggaggct   420
tctgcccttg gaggttcctg aggaggaggc ttccatattg aaaatgtagt tagtggccgt    480
ttccattagt acagtgacta gagagagctg agggaccact ggactgaggc ctagatgctc    540
agtcagatgg ccatgaaagc ctagacaagc acttccgggt ggaaaggaaa cagcaggtgt    600
gaggggtcag gggcaagtta gtgggagagg tcttccagat gaagtagcag gaacggagac    660
gcactggatg gccccacttg tcaaccagca aaagcttgga tcttgttcta agaggccagg    720
gacatgacaa gggtgatctc ggttttttaaa aggctttgtg ttacctaatc acttctatta    780
gtcagatact ttgtaacaca aatgagtact tggcctgtat tttagaaact tctgggatcc    840
tgaaaaaaca caatgacatt ctggctgcaa cacctgagac ctcccagcca ggccctggac    900
ccgggtccat tcatgcaaat actcagggac agattcttca ctaggtactg atgagctgtc    960
ttggatgcaa atgtggcctc ttcatttac tacaagtcac catgagtcag gaggtgctgt    1020
ttgcacagtg tgactaagtg atggagtgtt gactgcagcc attcccggcc ccagcttgtg   1080
agagagatcc ttttaaattg aaagtaagct caaagttacc acgaagccac acatgtataa   1140
actgtgtgaa taatctgtgc acatacacaa accatgtgaa taatctgtgt acatgtataa   1200
actgtgtgaa taatctgtgt gcagcctttc cttacctact accttccagt gatcaggttt   1260
ggactgcctg tgtgctactg gaccctgaat gtccccaccg ctgtcccctg tcttttacga   1320
ttctgacatt tttaataaat tcagcggctt cccctctgct ctgtgcctag ctataccttg   1380
gtactctgca ttttggtttc tgtgacattt tctctgtgact ctgctacatt tcagatgac    1440 atgtgacaca gaaggtgttc cctctggaga catgtgatgt ccctgtcatt agtgaatca    1500 gatgccccca aactgttgtc cagtgtttgg gaaagtgaca cgtgaaggag gatcaggaaa   1560
agaggggtgg aaatcaagat gtgtctgagt atctcatgtc cctgagtggt ccaggctgct   1620
gacttcactc ccccaagtga gggaggccat ggtgagtaca cacacctcac acatactata   1680
tccaacacac acacacacac acacacacac acgcacgcac gcacgcacgc acgcacacat   1740
gcacacacac gaactacatt tcacaaacca catacgcata ttacacccca aacgtatcac   1800
ctatacatac cacacataca caccccctcca cacatcacac acataccaca cccacacaca   1860
gcacacacat acataggcac acattcacac accacacata tacatttgtg tatgcataca   1920
tgcatacaca cacaggcaca cagacaccac acacatgcat tgtgtacgca cacatgcata   1980
```

-continued

```
cacacacata ggcacacatt gagcacacac atacatttgt gtacgcacac tacatagaca    2040
tatatgcatt tgtatatgca cacatgcatg cacacataca taggcacaca tagagcacac    2100
acatacattt gtgtatgcac acatgcacac accaatcaca tgggaagact caggttcttc    2160
actaaggttc acatgaactt agcagttcct ggttatctcg tgaaacttgg aagattgctg    2220
tggagaagag gaagcgttgg cttgagccct ggcagcaatt aaccccgccc agaagaagta    2280
ggtttaaaaa tgagagggtc tcaatgtgga acccgcaggg cgccagttca gagaagagac    2340
ctacccaagc caactgagag caaaggcaga gggatgaacc tgggatgtag tttgaacctc    2400
tgtaccagct gggcttcatg ctattttgtt atatctttat taaatattct tttagtttta    2460
tgtgcgtgaa taccttgctt gcataaatgt atgggcactg tatgtgttct tggtgccggt    2520
ggaggccagg agagggcatg gatcctccgg agctggcgtt tgagacagtt gtgacccaca    2580
gtgtggggtc tgggaactgg gtcttagtgt tccgcaagtg cagctggggc tcttaacctc    2640
tgagccatcc ctccagcttc aagaaactta ttttcttagg acatggggga agggatccag    2700
ggctttaggc ttgtttgttc agcaaatact cttttcgtgt attttgaatt ttattttatt    2760 ttacttttttt gggatagaat cacattctgc agctcaggct gggcctgaac tcatcaaaat    2820
cctcctgtct cagtctacca ggtgataaga ttactgatgt gagcctggct ttgacaagca    2880
ctttagagtc cccagccctt ctggacactt gttccaagta taatatatat atatatatat    2940
atatatatat atatatatat atatattgtg tgtgtgtgtt tgtgtgtgta tgagacactt    3000
gctctaaggg tatcatatat atccttgatt tgcttttaat ttatttttta attaaaaatg    3060
attagctaca tgtcacctgt atgcgtctgt atcatctata tatccttcct tccttctctc    3120
tctttctctc ttcttcttct cacccccaag catctatttt caaatccttg tgccgaggag    3180
atgccaagag tctcgttggg ggagatggtg aggggggcgat acaggggaag agcaggagga    3240 aaggggaca gactggtgtg ggtctttgga gagctcagga gaatagcagc gatcttccct    3300
gtccctggtg tcacctctta cagccaacac cattttgtgg cctggcagaa gagttgtcaa    3360
gctggtcgca ggtctgccac acaacccccaa tctggcccca agaaaaggca cctgtgtgtg    3420
actctggggt taaaggcgct gcctggtcgt ctccagctgg acttgaaact cccgtttaat    3480
aaagagttct gcaaataat acccgcagag tcacagtgcc aggttcccgt gctttcctga    3540
agcgccaggc acgggttccc taggaaatgg ggccttgctt gccaagctcc cacggcttgc    3600
cctgcaaacg gcctgaatga tctggcactc tgcgttgcca ctgggatgaa atggaaaaaa    3660 gaaaagaag aagtgtctct ggaagcgggc gcgctcacac aaacccgcaa cgattgtgta    3720
aacactctcc attgagaatc tggagtgcgg ttgccctcta ctggggagct gaagacagct    3780 agtggggcg gggggaggac cgtgctagca tccttccacg gtgctcgctg gctgtggtgc    3840
atgccgggaa ccgaaacgcg gaactaaagt caagtcttgc tttggtggaa ctgacaatca    3900
acgaaatcac ttcgattgtt ttcctctttt tactggaatt cttggatttg atagatgggg    3960
gaggatcaga gggggagggg agggggcgggg agacggaggg aggaggggag gaggggagga    4020
ggggaggagg ggaggagggg aagggatgga ggaaaatact aacttttcta attcaacatg    4080
acaaagattc ggagaaagtg caccgctagt gaccgggagg aggaatgccc tattgggcat    4140
tatattccct gtcgtctaat ggaatcaaac tcttggttcc agcaccaagg attctgagcc    4200
tatcctattc aagacagtaa ctacagccca cacggaagag gctatacaac tgaagaaata    4260
aaattttcac tttatttcat ttctgtgact gcatgttcac atgtagagag ccacctgtgt    4320
ctaggggctg atgtgctggg cagtagagtt ctgagcccgt taactggaac aacccagaac    4380
```

-continued

```
tcccaccaca gttagagctt gctgagagag ggaggccctt ggtgagattt ctttgtgtat    4440
ttatttagag acagggtctc atactgtagt ccaagctagc ctccagctca cagaaattct    4500
cctgttccgg tttccaaagt actggagtta tgagtgtgtg ttaattgaac gctaagaatt    4560
tgctgattga agaaaacctc aagtgggttt ggctaatccc cacgacccca gaggctgagg    4620
caggaggaat gagagaattc aaggtttgcc agagccacag ggtgagctca atgtggagac    4680
tgtgagggtg agctcaatgt ggagactgtg agggtgagct caatgtggag actgtgaggg    4740
tgagctcaat gtggagactg tgagggtgag ctcaatgtgg agactgtgag ggtgagctca    4800
atgtggagac ctgtatcaag ataataatag tagtagtaac aatgcaggcg agggtgtggt    4860
tgagtggtag agcagttagt tgatttgaca tgcttgaggt ctcccggtcc atctgtggcc    4920
ctgcaacagg aagggaggga ggaagggggg gaacgagaga gaggaaagag agacagaagc    4980
taagataggg aatgagagag gaaggaagaa acgggaagaa attcagactc cttcctgagt    5040
tccgccaacg cctagtgaca tcctgtgcac accctaaggt ggcctttgtg tggcactggc    5100
ttgggtggtc gggaaaggca ttttcagctt gttgcagaac tgccacagta gcatgctggg    5160
tccgtgaaag tttctgcccg ttaacaagaa gtctctacta cttgtgacct caccagtgaa    5220
aatttcttta attgtctcct ggtgttctgg gttttgcatt tttgtttcta aggatacatt    5280
cctgggtgat gtcatgaagt ccccaaagac acagtggggc tgtgttggat tgggaaagat    5340
gatttatctg gggtgtcaaa aggaaaagaa gggaaacagg cacttgggaa aatgtcctcc    5400
cgcccacccg aattttggct tggcaaccgt ggtggaggag caagaaacac gtggacgttt    5460
gaggaggcat ggggtcctag gaggacagga agcagaagga gagagctggg ctgacagcct    5520
gcaggcattg cacagtttca gaaggagatt acagcatgac tgagttttta gggatccaac    5580
agggacctgg gtagagattc tgtgggctct gaggcaactt gacctcagcc agatggtatt    5640
tgaataacct gctcttagag ggaaaacaga catagcaaac agagccacgt ttagtgatga    5700
aactctcact ttgcctgagt catgtgcggc catgcccagg ggtcaggctg acactcaact    5760
caaaaacaag tgagaaattg aagacaatcc gtggtggcag ctactggaag ggccaccaca    5820
tccccagaaa gagtggagct gctaaaaagc catttgtgat aggcacagtt atcttgaatg    5880
catggagcag agattacgga aaaatcgaga atgttaatga ggcaacattc gagttgagtc    5940
attcagtgtg ggaacccag acgcttccat cccctaaaag gaacatcttg ctctcagtca    6000
aaatggaaat aaaaattggg gcttgaattt ggcaaatgat tcagaactct gtgtaggtat    6060
tttcacacgc acagtggata attttcatgt tggagtttat ttgtgctaaa aggcagaaaa    6120
gggtaaaaag cacatcttaa gagttatgag gttctacgaa taaaaataat gttacttaca    6180
gctattcctt aattagtacc cccttccacc tgtggtaatt tcctgagata gtcagtgggg    6240
aaaagatctc tccttctctt ctttctcccc ctcccctcct ctccctccct ccctccctcc    6300
ctccctcctc tccctcccctc ccctttcct tctttctttg ctccttctcc tctgcctcct    6360 tctcccttc ttcttcattt attctaagta gcttttaaca gcacaccaat tacctgtgta    6420
taacgggaaa acacaggctc aagcagctta gagaagattg atctgtgttc actagcgtgc    6480
aattcagagg tgggtgaaga taaaaggcaa acatttgagg ccatttcctt atttggcacg    6540
gcacttagga agtggaacat gcctaatcta ctggtttgta ccacctttcc ctataatgga    6600
ctgtttggga agctcctggg caaccgattc tggcatctca ttggtcagag gcctgttaaa    6660
tggtactctt atttgcaaag aaggctgtaa cttgtagctt taaaagcctc tcctcaagaa    6720
agaagggaga aaggatatgg ctagacatat ctaatagact taaccactgt gaaaagcctt    6780
agtatgaatc agatagaacc tattttaac tcagttttga aaaaaataat ctttatattt    6840
```

```
             -continued
atttgtgtgt gtgtgtgtgt gtgtgtgtgt gtgtgtgtgt gtgtgtgtgt gaaccacatg   6900
tagcaggtgc tggaggaggc cagaagaggg caccagatct cctggaactg acaccacaca   6960
tggttatgag ctgcctgatg tgggtgctgg gaactgaact ctcgtgttct gcaagagcag   7020
caactgttct cttaactgat gagccatctc tccagccccc cccataattt taattgttca   7080
ttttagtaaa ttttattcat aatcaattat cacagtataa aacaatgatt ttatatatat   7140
catatacata tcaaggatga cagtgagggg gatatgtgtg tgtgtgtgtg tgtgtgtgtg   7200
tgtgtgtgtg tgtgttattt gtgtgtgtgc tttttaagaa ggtgccatag tcactgcatt   7260
tctctgaagg atttcaaagg aatgagacat gtctgtctgc caggaaccct atcttcctct   7320
ttgggaatct gacccaaatg aggtattctg aggaactgaa tgaagagctc aagtagcagt   7380
gtcttaaacc caaatgtgct gtctagagaa agtcaacgtc atcagtgagc tgaggagaga   7440
tttactgagc ggaagacaag cgctctttga tttaagtggc tcgaacagtc acggctgtgg   7500
agtggagcct gtgctcaggt ctgaggcagt ctttgctagc cagctgtgat gagcagtgaa   7560
gaaagggtgg agatggaggc agggtgggag cagggctatg gttcagacta ggtatcgtga   7620
gcacaccagc tggttgactt gtggtctgtg ggtcaggcgt tgtaaacgcc ctcagggtca   7680
ggcagtcaca ttgcttgaag ctgaatgggt gaggcaacac agagagtgca aagaaggcaa   7740
agtaccacct cttccccgac ccaggtcact tctgggttat agctgagact ccggacagca   7800
tgcaaccagc tggttagagc ttcagggaaa acttgatgtc tgcatgttgc tatgaaatgt   7860
gattcggtac atctggagaa aatttataat gctggctcag tcaagcactg aacaaaggta   7920
ccttggcttt gggagctaca tgacattgac ttgtaggcag acttttttttt ttctgcccgc   7980 caattcccag ataaccaata tggaggctca atattaatta taaatgctcg gctgatagct   8040
caggcttgtt actagctaac tcttccaact taaatgaacc catttctatt atctacattc   8100
tgccacgtga ctttaccttg tacttcctgt ttcctctcct tgtctgactc tgcccttctg   8160
cttcccagag tccttagtct ggttctcctg cctaaccttat cctgcccag ctgctgacca   8220 agcatttata attaatatta agtctcccag tgagactctc atccagggag gacttgggtg   8280
ctcccccctc ctcattgcca tccgtgtctt cctcttccct cgcttccccc tcctcttcct   8340
gctcttcctc ctccacccct cctttcatag tattgatggc aagggtgttc tagaatggag   8400
gagtgcccat aggcatgcaa agaaaccagt taggatgctc tgtgaggggt tgtaatcata   8460
agcgatggac acaattcaag ccacagagtg aagacggaag gatgcactgt gctctagagc   8520
aacttctggg gcagaatcac agggtgagtt tctgacttga gggcgaagag gccacgagga   8580
agggagtgag tttgtctgag ctagaagcta cggcccacct cttggtagca gacctgccca   8640
caagcatgct ttgttaatca tgtgggatct gattttcctc taaatctatg ttcaactctt   8700
aagaaaatgt gaattctcac attaaaattt agatatacgt cttttggtgg gggggtgta   8760 aaaaatcctc aagaatatgg atttctgggg gccggagaga tggctcagag gttaagaaa   8820 ctggttgctc ttctagacat tctgagttca attcccagca accacatggt ggctcacaac   8880
catctgtaat gcgacctggt gccatcttct gacatgcatg gatacatgca ggcagaaagc   8940
tgtatacata gtaaattgat aaatcttttt ttaaaaagag tatggattct gccgggtgtt   9000
ggtggcgcac gcctttaatc ccagcactct ggaggcagag gcaggtggat ctctgtgagt   9060
tcgagaccag cctggtctat aagagctagt tccaggacag cctccaaagc cacagagaaa   9120
ccctgtctcg aaaaccaaa aaaaaaaaa aaaaaaaaa aaaaaaaga gtatggattc   9180 taagaaagcc gtaacagctg gagctgtgta cggagttcag cgtggtacta aagaacaga   9240
```

```
                                                        -continued
cattcatgat gaaacacccc aggattttta cttagtatct agtttccatt gttgttttga    9300
gaccggctct tatgctctcc aggctggcct caaactgctg atcttcccgc ctctacctct    9360
caagtcctgg gactacttgg ctcataaaac agttttttgtc gggctccctg aagttatggt   9420
tgtacaaacc gtgggggtca atatactcac ttgggcagag agagaaggtc tgaatcccag    9480
acaatgactg catctcagga cagttgggaa gaggacaatg gcagaaggac ttagaaaaga   9540
tagactggag ggtggaaaag cagcaggaac agagaaacaa aacaggaagc ttgctatcca   9600
gggccactct ggagtcctgt ggcaagatgg aagcgggcta ggggaataca tttgtgctac   9660
tgtgtgtgtg tgtgtgtgtg tgtgtgtgtg tgtgtgtgat caatgcctat caatgttgaa    9720
ggggaaatat gtataccaca ttgattctgg gagcaattct cagtatctgg cctagagaaa   9780
ggaatggccc ctgcagaata gacagagtga atggtgccct ttatcatttg ctaaagtgaa    9840
ggagaaataa acatccttcc atagagtttc aggtaaatga accccacagt tcatctgtgc   9900
cgtggtggag gcctggccaa cagttaaaaa gattagacac ggacaaagtc tgaaggaaac   9960
acctcgaata ggaagaggag agccacctca ttctgtaact ttcctcaagg ggaagatgtt  10020
ccaagagtgg gaataaatgg tcaaggggg attttttaat taggaaaacg atttcctgta   10080
tcacttgtga aactggaggt tgatttgggg cataggacaa tagatttgat gctttgcaaa   10140
aagctgtttc aaagcagaga aatggaatag agacaattat gtagcgagga gggagggtgg  10200
ggcgaagatg gagacagaga agtggaagct gactttaggg aagaggaaca tagaccacag  10260
gggcggggcg gggggcaggg gcgggggggcg gggctcaaag gaggcagtgg gaacgttgct  10320
agtgttcgca gcgtaagcgt gaatgtgcaa gcgtctttgt ggtgtgtgac caggagtagc  10380
gtggctggct tgtgtgctgc ttgtaatccc agtctttgag gtttccacac tgttccacag  10440
tgggtgtgat tttccctcgg agagcatgag ggctctgctt tccccacatc ctccccagcg  10500
ttcgttggta tttgtttcca agatgttagt gggtgagaca aagcctctct gttgatttgc  10560
ctttaacagg tgacaaaaaa agctcaacca ggagacattt ttgccttctt ggaaggtaat  10620
gctcccatgt agagcaatgg gacccatctc taaggtgagg ctactcttgc agtttgcacc  10680
cagctcttct gatgcaggaa ggaagttggt gggcaagcaa gactgtttgc ttcttgcgat  10740
ggacacattc tgcacacaaa ggctcaggag gggagaaggc tgtttgatgt ttagcactca  10800
ggaaggcccc tgatgcatct gtgattagct gtctccatct gtggagcaga cacggactaa  10860
ctaaaaacca gtgttttttaa attgtcaagc ctttaaggtg aggaaattga cttattgtgc  10920
tgggccatac gtagagcaag tgctctgcat tgggccaacc cccggctctg gtttctaggc  10980
accagaatgg cctagaacta actcacaatc ctcccattcc aggtctcagg tgctagaatg  11040
aaccactata ccagcctgcc tgcctgccta cctgccttcc taaattttaa atcatgggga  11100
gtaggggaga atacacttat cttagttagg gtttctattg ctgtgaagag acaccatgag  11160
catgcaaact cttataaagg aaaacattta gttgggtggc agtttcagag gtttagtac   11220 attgtcatca tggctgggaa catgatggca tgcagacaga catggtgctg gagaaaggga  11280
tgagagtcct acatcttgca ggcaacagga cctcagctga gacactggct ggtaccctga  11340
gcataggaaa cctcacagcc caccctcaca gtgacatatt tccttcaaca aagccatacc  11400
tcctaatagt gccactccct atgagatgac agggccaatt acattcaaac tgctataaca  11460 cttttaaagta tttttatttttt attattgtaa attatgtatg tagctgggtg gtggcagccg  11520
aggtgcacgc ctttaatccc agcacttggg aggcagaggc agatggatct ctgtgagttc  11580
aagaccagcc tggtctataa gagctagttg caaggaagga tatacaaaga acagttctag  11640
gatagccttc aaagccacag agaagtgctg tcttgaaaac caaaaattgt gctgggacct  11700
```

-continued

```
gtctctgctt tggttgcttc ccactccccc agagctggac tcttggtcaa cactgaatca 11760
gctgcaaaat aaactcctgg attcctctct tgtaacagga gcccgaagtc aggcgcccac 11820
ttgtcttctc gcaggattgc catagacttt ttctgtgtgc ccaccattcc agactgaagt 11880
agagatggca gtggcagaga ctgggaaggc tgcaacgaaa acaggaagtt attgcaccct 11940
gggaatagtc tggaaatgaa gcttcaaaac ttgcttcatg ttcagttgta cacagactca 12000
ctcccaggtt gactcacacg tgtaaatatt cctgactatg tctgcactgc ttttatctga 12060
tgcttccttc ccaaaatgcc aagtgtacaa ggtgagggaa tcacccttgg attcagagcc 12120
cagggtcgtc ctccttaacc tggacttgtc tttctccggc agcctctgac accctcccc 12180 ccatttctc tatcagaagg tctgagcaga gttggggcac gctcatgtcc tgatacactc 12240
cttgtcttcc tgaagatcta acttctgacc cagaaagatg gctaaggtgg tgaagtgttt 12300
gacatgaaga cttggtctta agaactggag caggggaaaa aagtcggatg tggcagcatg 12360
tacccgaaat cccagaactg gggaggtaga gacggatgag tgcccggggc tagctggctg 12420
ctcagccagc ctagctgaat tgccaaattc caactcctat tgaaaaacct ttaccaaaca 12480
aacaaacaaa caaataataa caacaacaac aacaacaaac tacccatac aaggtggggcg 12540 gctcttggct cttgaggaat gactcaccca aaaccaaagc ttgccacagc tgttctctgg 12600
cctaaatggg gtggggtgg ggcagagaca gagacagaga gagacatgac ttcctgggct 12660
gggctgtgtg ctctaggcca ccaggaactt tcctgtcttg ctctctgtct ggcacagcca 12720
gagcaccagc acccagcagg tgcacacacc tccctccgtg cttcttgagc aaacacaggt 12780
gccttggtct gtctattgaa ccggagtaag ttcttgcaga tgtatgcatg gaaacaacat 12840
tgtcctggtt ttatttctac tgttgtgata aaaaccgggg aactccagga agcagctgag 12900
gcagaggcaa atgcaaggaa tgctgcctcc tagcttgctc cccatggctt gccgggcctg 12960
ctttctgcaa gcccttctct ccccattggc atgcctgaca tgaacagcgt ttgaaatgct 13020
ctcaaatgtc actttcaaag aaggcttctc tgatcttgct aactaaatca gaccatgttt 13080
caccgtgcat tatctttctg ctgtctgtct gtctgtctgt ctgtctatct gtctatcatc 13140
tatcaatcat ctatctatct atcttctatt tatctaccta tcattcaatc atctatcttc 13200
taactagtta tcatttattt attttgtttac ttactttttt tatttgagac agtatttctc 13260
tgagtgacag ccttggctgt cctggaaccc attctgtaac caggctgtcc tcaaactcac 13320
agagatccaa ctgcctctgc ctctctggtg ctggggttaa agacgtgcac caccaacgcc 13380
ccgctctatc atctatttat gtacttatta ttcagtcatt atctatcctc taactatcca 13440
tcatctgtct atccatcatc tatctatcta tctatctatc tatctatcta tctatcatcc 13500
atctataatc aattg                                                  13515
```

<210> 14553
<212> DNA
<213> *Mus musculus*
<400> 6

(SEQ ID NO: 57)

```
cttgaagaac acatgttttc caagagggag cacccatgtt ggaatgacaa tgtagttagt  60
gctcctctcc tgtaggttag tgctcctttg ctataggtaa gtgctcctct cctataggtc 120
agtgctcctc tcctataggt tagtgctcct ctcctatagg ttagtgctcc tctcctacag 180
gttagtgctc ctctgctcta ggttagtcct gctctcctat agtacctaga gagctagggc 240
aaatgggcta ggcccgaagt gcagagacaa acagctatgg aagactgggt aagcacttcc 300
```

-continued

```
aagctacgaa agagcagtgt gaagggtcag ggcttgtgca gttagtaggg gagatcttcc    360
agttgaagaa acagaagaac tgagagccac tgggtatcat cctcctgcgc catgccttcc    420
tggatactgc catgctccca ccttgatgat aatggaatga acctctgaac ctgtaagcca    480
gccccaatga aatattgttt ttatgagagt tgccttggtc atgctgtctg ttcacagcag    540 taaaaccct a aataaggcag aagttggtac cagtattgct gtgatagacc tgaccatgct    600
ttcctttgaa agaatgtgga tttggtgact ttggatttgc aacacagtgg aatgctttaa    660
atggagatta atgggtcatc aattcctagt aggaatatgg aagactttgt tgctgggagt    720
atttgaactg tgttgacctg gcctaagaga tttcaaagga gaagaatttc agaatgtggc    780
ataaagacag tttttgtggt attttggtga agaatgtggc tacttttttgc ccttgtctga    840 aaagtctgcc tgagactaaa gtgaagagaa tcagattaat tgcattgaca agggaagttt    900
gtggctgcgc tatctggaaa cttacagcca gcctcttgga cctcgggtga cttacgcaaa    960
tactcaggga cagagatgct tgactctgta ctgatgagtt gtcttggatg caaatatggg    1020
ctcttcattt gactacatgt cacgatgagt caggagctgc tctctccaga gtgtgacaaa    1080
gcgaggggat gctgacggta gctgttctag ctttgaaggt aagcctgcac ttatgctaaa    1140
gtcacacata cacgagccgg gtggagaacc tgtctgtgtg gagacacctt tcattacctg    1200
tggcatccag cctctcaagc ttggactgcc tgtgtgctcc tggactctgg aggtcccact    1260
gctctgtcct ctgctgctta tgatactgac attttaaaag aatccagtgg ttcccccctg    1320
tactcggtgt ctacttctac ctggatgttc ctcatttatg ttctgtgaca cttctctgtg    1380
actctgctgc attcctgggt gacatgtgga caccctgtcc ctttgcagac catgatgtca    1440
ctgtcactag tggaatcaga tgccccaagt gttgtcctgt gtttgggaac gtgacaggca    1500
gtacagaagc agaagaggaa gggtgaaaac ggaaatgtca cagcagcatc tgatgtgtgc    1560
ctcagtcacg catgctgctg attgaaacta ctcagcatga gagagggcca tggtgaatac    1620
acaaccctat acacactgtg tccatttctc tctctctctt acacagagag agagggagga    1680
gggggagggg gaggcggagg gggaggggga gggagaggga gtgggagagg gagagggaga    1740
gggagaggga gagggagagg gagagggaga gggagagttt aatgtctgtg aagagatacc    1800
atgaccaaag caactcttat aaaggacaac atttaattgg ggctggctta caggttcaga    1860
aattcagtcc attctcacca tggtgggaag catgcaggta gatgtggtgc tggaggaacc    1920
aagagttcta tatcctgatc tgaaggcagc caggagaaga ctgcctcttc tgcacagggc    1980
agagcttgag catagaacat caaagccctt ccccacactt cctccaacaa ggtcatacat    2040
acttcaacaa agacacacct cctaacggtg ccactccctg tggaccaacc atttaaacgc    2100
atgagtctat gagggtcaaa gctcttcaaa ccaccacact catgtacaca cacacacaca    2160
cacacacaca ctctcataca cacacacaca cacactcaca cacacacaca cacacacaca    2220
cacacacaca ccacacacac acacacacac agagttctat tttgcactgt ttcactgtca    2280
caaggttcta cttatctcag acacactgcc aggaattgtg tgggaagact ttcagtttct    2340
ttgggttcac atggacttag cagttcttgg tgatcctgaa agatttctgc agaaagaagc    2400
caaagtgttg agcccaaggc ctggccacac attagtcctg tctagatgaa caggggttta    2460
aaaataaggg ggcatcaagg tgaagccagc aggggctgac ttagagagga gacccaccca    2520
agccaactgc tcgaagtcaa aagcgatgaa tccccatatc cagctgtgcc cggtgctgtc    2580
ttgctacatc tttagtaaat gttctttttag ttgtatgcgt atgaatattt tgcttgcata    2640
tatttgtgta caccataggt gttcctaggg cctatggagg ccagaagagg gcatcagatc    2700
```

-continued

```
ctttggaact ggaattatag acacttgtta cccatagagt agattgtggg aaatgagcct    2760
ttagtcttcg agagcggcca gtgctcttaa cctttggtcg tttctccagg tctttgagac    2820
tttattttct tggacatcag gacaggatcc agggctttga gcttgtttct tcagccagct    2880
ttcttttcat gtatattaaa ttttatgtta ttttgctttc tttttcccca agacagaatc    2940
acactctata tagctcaggc tgggtttgaa ttcagtttcc ctgtctcagt ctaccgggta    3000
atatgattac agatgtgagt ctgactttgg tatcaaagtc cccagcccct ctggatatgt    3060
gttttaagga tatcagatat atccttgatt tgctttgaat tttcttttta gttacaacat    3120
aattagttcc gtgtcacctg aatatgtgta tgtcacctac atagtcttcc ttcttctctt    3180
cttccctctc ccaccttccc aggtacctgt ctgtcttcat atccttgtgc tgagagtctt    3240
gttgagggag atgatgaccg agacagagcc actgggaag ggagatgggc tagtgcaggt     3300
cttcagagag gagctcgtga atattgtagc ccctttagtc cctggcatgt cctcttgtat    3360
agccaccgcc atgctgtggc ctggcagaag tgaataagtt gtccagctgt tgacaggcct    3420
gccctccaga cccagtctga tcccaagaaa gggcatctgt gtctgtctct gaggccgtaa    3480
gtgctgcctg gttgtctcca gcttgacttg acactccctc cttaataaga gtaccacaga    3540
acagggtctg cagagtccct gggccaggtc cctgtgctgt cctggaatgc caggcgtgaa    3600
tttcctgtga agtaggactt tgctcgccaa gctcccacgg cttgcccttc agatagccag    3660
aattatctgg taccctgcat tgccgttcaa tacgcagagt atcactggaa gcgcgcgcgc    3720
gcacacacac acacacacac acacacacac acacacacac acacgcccac tccatcttta    3780
aaccccaccc cccagcaacg gcggtgtaaa cactctccat caggaagctg aaacgcagtt    3840
gccctctgct ggggagatga aggcagcttg ctggggcga ggaccgtgct agcaaccttc     3900
cctggtgcac acgggctctg gtgcatgacg ggaacggaaa cgcggaacta agtcagtcc    3960 tgctttttt ttttttttt tttttttt tttttttt ttttttttt ggcgttggtg          4020 gtggactgag tgacaatcag tgaaatcact taggttgttt ttctcttctt cgttgggttt    4080
gatagacggt gggagagggt cagaggagaa ggggagggat ggggagagag gaggaggga    4140 ggggcgggag gcgggggcg aggaaaacgt gctaacttct ccaatcctac aagacaaagg     4200
tttggagaaa gccgcactga gtgacccagc agaaggaatc caggaatgtc cgctggaatc    4260
tgactgttga ttccagcgcc atgcagagaa tctaggctgg taggaacatt ctttgtccta    4320
tccgacataa taactccaac caacacggaa aagaaaggct atacaagtga agaaatggca    4380
ttttcacttt catgactata caatcacttc caggtagtaa cacgtgtcta gcacagcggt    4440
tctcaacctg ggggtcacga tcccccactt ttctgcatat cagacatttt tacgttgtta    4500
ttcataacag tagcaaaatt gcagctatga agtaacaatg aaatgcattt atggtgcgtg    4560
tgtgtgtgtg tggggggggta tcaccttaac atttactgta agaaggttga gaatactgct    4620
ccagcagcta gtgtgttgga cttaggttct gggtatatta ttagcaatag ccaaccagaa    4680
tccccaccca ccacagcatt gaggcccat gcagggcttg ctgggagagg cactgataag     4740
acttctttat gtatttattt agagacgaat actcattagg taggccaagc tagcgtcaaa    4800
ctcatggcaa ttctcctcct ccagtttcct aagtactgga ctcaggagtg tgttgccatc    4860
atatacagta aggatttatt gactgaagaa aatctcaagt ggctttggtt aatccctact    4920
acgccagagg ctgaggcagg aggcgcgcaa ggtcaaggct tgcctgggct acatatagag    4980
tgagctcaat tttgacactt ggtgcggtgt tagtagtaat agtaaagatg aaggtgtggc    5040
tcaggtgggg ccggtgattg gacacacttg gggtctcctg gtccatctgc agctgtgcaa    5100
caggaagagc ggagaatgag aggaaagaga gaaaagacag aatgagagag agggaggaag    5160
```

```
agagaaaaag gaaagagag aggaaaggaa aaaggaaaat gaggaaagcg agaaagaaga    5220
aatgagaaag aggaaaggga gaaagaaatg agagagagag aagaaaagac agaatgcgag    5280
agagggagga agagagaaaa aaggaaagag agaggaaagg aaaaaggaaa atgaggaaag    5340
cgagaaagaa gaaatgagaa agaggaaagg gagaaagaaa tgagagagag aaaagaaaag    5400
acagaatgcg agagagggag gaagagagaa aaaggaaaag agagaggaag ggaaaaagga    5460
aaatgaggaa agcgagaaag aagaaatgag aaagaggaaa gggagaaaga aatgagagag    5520
agaaaagaaa agacagaatg cgagagaggg aggaagagag aaaaaggaaa agagagagga    5580
agggaaaaag gaaaatgagg aaagcgagaa agaagaaatg agaaagagga aagggagaaa    5640
gaaatgagag agagaaaaga aaagacagaa tgcgagagag ggaggaagag agaaaaagga    5700
aaagagagag gaagggaaaa tggaaaatga ggaaagcgag aaagaagaaa tgagaaagag    5760
gaaagggaga agaaatgag cgagataaaa gacagaattt gagagaggga ggaagaaata    5820
ggaaaagaga ggaaaggatg gagaaaagag agaaagaaag agatgaaa gagagaaagg    5880 agaaatgaaa tgagagagag agagagacac aaagagccag agagagaaga aaaaagggga    5940
aagagaaaga gaaagaggaa ggctcctctt ggacacatct tcctttatct ttccctgggg    6000
accgccaaag cctggtggca tactgtacat tctgtacact gttcattcaa aacaggctct    6060
gtcttaaaga tggtctgagc ggtcagaaaa gggtattgtt aacttgtttg caaaactgcc    6120
tcaggagagt gctgagtgcg tgaaagttgc tgcccgttaa ggagaagtct ctactacttg    6180
tgatctcacc atcgaaaatt tctttaattg tctcctggtg ttctgggttt tgcagttttg    6240
tttctaagga tacattcttg ggtgatgtca caaagtcccc aaagacacgg tggagctgtg    6300
ttagatgggg aaagacagtc tgctgaggat ttatctggaa ctgtcagaag gaaaagaagg    6360
taaatggggc acttgggaaa gtggcctcta gtttgacttc tggcttagca aaggttgtgg    6420
ggagataagg catacacagt agttagcagg aggcaacagg gtcctgggag gacgcgaggc    6480
agaaggagag gctgggctga cagcatgcaa tcattgcata gtctccaaag gagattgcaa    6540
catggctgag ttttcagagg tcctacagag cccgtggtag agattctgtg ggttctgaga    6600
caacttgact ttagccagat ggtatttgag taatctggga gagagaaaac agctacagca    6660
aacagggcca catttagtga cgaaactctc actttgactg ttgagtcatt tgcagtgggc    6720
cctgaggtca ggctggccct cagctcaaaa acaagcgagg aactgaagca attactcaga    6780
taatccacag ccacagccac tggaaagggc cacatcccca gagacagcac agcaggggtg    6840
ggggtggggc tatgagaaag ttagtgattg tagcagttat ctagaatgtg cggagcgag    6900 gaggttacac aaaaacctag aatgtcattc aatgtgggaa accgagaggc tcccaagccc    6960
taaaaggaac agtttgcttt cagccaaaat ggaaataaaa tttggggctt aaatctggca    7020
aatgattcag accttctgtg taggtgtctt taaatgcaca gcagattgat tttcatgttg    7080
gagtttattt gaactaaaag acagaaatgg tgaaaagcac acctgaagaa attgagatgc    7140
tatgaataaa atcatttact tacagctatc acttaattag tacctccttc caccttgctg    7200
atttattggg ctagtcaagg aagaaaagat cttccctcct ccttctctcc tcctcccct    7260 cctctcctcc tcccctcccc tccttgacct tcctctcctc cttttccctc ctccccctct    7320
tcttctcttc accccctcct cccctccccct cctctgtact cctcccctt cctcccaatc    7380 tcttttttct ccccccttctt ctctttctcc ccctcctct tccctcctct tcctccctcc    7440
ctccctcctc ctcctcatcc tcctcttcct cttcatcctc ttctccttcc tccctctcct    7500
cctcctcctt ttccagccct acctaccttc cctttcttct tcatttattc aaagtagctt    7560
```

-continued

```
tgaacagcac tactcggttt agttgtgtat aaaaggaaaa tgcaggtcca agcagcttgg  7620
ggaagattgc tttttgctct ctggaggcag atgatgacag ttcaagatca ttccttttgc  7680
tccatgtcac aggaaggggg acatgccgaa tctaccagtt tgcagccacc tacacaggat  7740
ccaccttcac ttctaaggaa atgtttggga agctacctac caaccacttc tggcatctca  7800
tgggctagag gactcttaaa tggcactctt atttgtttaa taaaggaggt tgtgacgtgt  7860
agttttaaat cccttccaca caacaattgc tactctctga ccaaaaaaga agggagacag  7920
gatacggcta ggtgtctagt agactttacc actttgaaaa gccttaatat aaatcaggta  7980
gatacatctt tttaacttat tcttgtaaag acaaaaacaa aactttattt ttatttgtgt  8040
gtatgcttgt gtgtgtgtgc ctgtgtgtat accacatgtc gctggtgccg gagaacacca  8100
gaagagggga cctgatctcc tggagctaaa gctatccatg gttctgagct gcctgatgtg  8160
ggtgctggga acagaactct ggtcttctgc aagagcaaca agcctcctct taactacgaa  8220
tctcctcccc atcccccaa atacatttaa ttattcattt tagcagcttt atttcgtaac  8280
tacttatcac agcataaaac aaggatttta tatatattac atgcaatcga ggataagagt  8340
tgagggagga tgcgtgtgct ccttctgggt gtctgtgctt ttgaagaatg taagcagtgc  8400
acaagggacc gaggcgtgcc tgtctgccag gagctgtctt cttcccttgg actctgagct  8460
gagtgcagtg ctccgaagaa gtaaaagacg acctcatgaa gcaatgtctt caacccaaac  8520
atgctgtcca gacaaagtcc agcttcatta gtgctctgag gagagactta ctgagcctca  8580
ggaaagcccc cctcagcatg gcgaaagtcc actttgattg aagtgactcg aaagccatgg  8640
cagtgcggcg gcgccgcgt ggagcttgtg ctcgagtcgg aagcggcatc tttgtcaggc  8700
ggctgtgatt agcacgggga ggcaggactg gagtgaagga agagttgggg gcggggctta  8760
gcgctctggt ctcctaagct gtagtcagcg cctcaagatt tgtaacctgc cttctgcctt  8820
cccagccagg cagtcaagtg gctccaagct gaagactgca aagtgcccct aaccttttgg  8880
ttatagcgag gctgaagaca ccgtgctctt tcatgaaagc cggatgtctg aaatccgatt  8940
tgataaatat ggataaaacg tataacgctc gatcaatcga atcgaaggag ctcacgattg  9000
gcaccacggc tttggggaca acagagtact gactcgttgg gaggacttgg atacttcccc  9060
tcctcttcca tctcttcccc tttcctcact tcctcctcct tccttctcca ttttctccct  9120
cttcactgtt tcttactatt tttacaaaag attttattta tttatttatt tatttattta  9180
tttatttatt tatttattta tttatttaat gtatgcgagt acactgtagc tgtcttcaga  9240
cacaccagaa gagggcgtca agttccatta gagatggttt cgagccacca tgtggttgct  9300
ggggcctctg gaaggaccgc cagtgctctt aacccctgag ccatttctcc agtacccttc  9360
tcaccgtttc tcttcaatct tcttcctctt ccttctccac tttccttgtc ttcttggttt  9420
cattatcttt ctcccttct tcctcttctc cccttcttcc tcctccactg tagttttcct  9480
tccctactct tttcctgcct ccctcctcct ccctctcat tcccctcct ctttcctcct  9540 tctccctcct cctccttcct tctccctctc ccctctcccc tctcccttct cccttctccc  9600
cctcctcttc ctctttctcc ttctccaccc ctcctgtcac agtatcaatg gcaagggtgt  9660
tctagaatgg aggagtgtcc cctaggcact aacgaaagcc agttaggatg ctctgagacg  9720
ggtacaattc agggagggcc gtggggatgg aagggttgtg ctgcgattca ttctggagca  9780 accccaggc agaatcatga ggttggttcc ggattcgcag ggcacaattc agaagaggaa  9840
ggtttcagga aggacgagtt tgtctgagat aggagttaca tctgatgtct tggcagcaga  9900
gccactgtac aagcgtgctt tattaaccac gtgggattaa atcttctttt aaatttattt  9960
tcaactctta aggaaacgtg aactttcaca ttcaaattta gacttgcagc tcttatgggg 10020
```

-continued

```
aaaaaaaggg gatcttaaga atattaagca taggcggctg gagagatggc tcagcggtta   10080
agagcactct ctgctctccc agaggtcctg agttcaattc ctagcaacca cataatagtt   10140
aacaacagtc tttaatgaat tctaatgccc tcttctggtg tgtctgaaga cagttacagt   10200
gtactcatat aaataaaata aagaaattta aaaaatgaa tattaggcat agattcctgg    10260
atcctaagaa agccatcaga gctggagcca tgtgtgggat cctgcttggt gctggagggg   10320
cagagttcat gcccccgggg tttttactta ttatcacatt ttcatcgttg ttttgaaaca   10380
gggtcttgtg tggtccaggc tggccttgaa ctcatctttc agcctctacc tcacaggttc   10440
tgggattact tggttcctaa aagtatctcc gtcaagctcc ctggtgttat ggctgtgcca   10500
accaggaggg tctatacact cgctcaggta gagggagaag atccgaatct ctgacaggga   10560
ctgctgcctc tcggggcaaa tggagtgaag acagcggca gaaggattta ggaaagatgg    10620
acgggagagt ggaaatgctg cagaagccag aaaacaaagc aggaagcctg ctgtccagtg   10680
gggctcaaga gcggagggat gcgaggggc tgcgcaggaa catttagcgt ctgcgtctat     10740
gggggtaggg gcggggtgcc agcacctagt cacctgaagg ggaaatgctt gcccagggag   10800
caggtctcag tagctgacct agagaaagga gcggcccta cagaggagac acgggtcact    10860
gtttgttaaa gtgaaggaga aataaatatt ctttcaaaga atcttaggtg agcccagttc   10920
atctgcgctg tggaggcctg gggaacagtt aaaaagaccc tgacacacac ccaaggcaaa   10980
caagcaacac acggctcctt ccgtaagggt ccatgattct ctgaagaatc agccccggaa   11040
tcagccccgg aatcaggtag tccgtaaaca caatgagtgt tttactctgc agaagtccag   11100
cctgctggcg tctcccatta ccaaaataga gggatagtca cgtgagctca ccggctcgat   11160
ttaaggcacg tggttttcca gggtagatga gctttggctt ctggaaccat tatgggcac    11220 gaaggatgga gccaggattt tttttttttt ttttttttc tattagcaat tgatttgctt   11280
gggcttggct ggacttgccc agttcttagg cccagtcttc ttaactgccg atctgaagtc   11340
tgtcatggag tcagcctagc cttctcactt cccttcagct cgaataggaa gaggaggtgc   11400
acaccagatg gtctgagagc agggataaat ggtgtgcctt tgtctttcag tatttcgtta   11460
ttttaagtag gaagatgctt ttctgtatta cattgcttgt gaaaccggaa gttgattcgg   11520
ggcacaggac aatggatttg gtgttttgca aggactgttt cagaagagag aggagtggaa   11580
gggtggttag agtgaggagt ggggtgggac gggatggggg aagagaagga agggccagac   11640
aggctaggta gggctgagag gaggcggtgg gaacttcttg agttagcgca gcagtaaact   11700
tggatgtgcg tgtatctttg tgatatatga cccggagccg tgtagctggc tccgatagta   11760
ctgctaatgt cagtgtcggg ggggggggt cccatactgt tccacagggg ctgcacattc     11820
ccatcgagag caggagggct cctctctcca tacatcctcg ccagcattcc ttgttgtttc   11880
tgtgatgaca gggggtggga tgaaatctct ctgttggttt gagagaccgt gaagaagctc   11940
aaccccagga cattttgcag tcttggaagg cagtgcctcc atgtggagcc gtggagccca   12000
tctctgagtc caggtcactc ttgcagttcg cactcagctc ttcagatgca ggagagacgt   12060
tggtgggaaa gcaagattgt ttgcttgttg agatagacac attctccaca caaaggctca   12120
cgtggggcaa aggctgattg acgtacagcg ttcaggaacg cctgtggtag agctatgatt   12180
agctgtctcc atctatgaag cagacaaaga gttataaaaa aaatcaatgt tttcaaattg   12240
tcaaactttt aacccgacag caagcgctct gtccctgggc taatccctag ccctggtttc   12300
ttgagatggg gtcttttgtg cactagactg gcctagaact cacgatctta gtgttccagc   12360
ctcccagctg ctgggatgag ccgctataac cagtctgcct gccttcctaa attttaagtg   12420
```

-continued

```
atgggaagtg ggggagaata cagtttaaag tatgcagatc tgagagcagg aacctggcaa 12480
agccaagggg ccggagttac aggcggctaa catgggtgct gggaactgac ccaggtcctt 12540
gagaggagca gtgtgtactc ttgaccaaac aggtccgtct ctccagtccc cgtagtatta 12600
aaaataggta ctacgggcat ggtggtgcac acctttaatc ccagcactag ggaggcagag 12660
gcaggtggat ttctgagttt gaggccagcc tggtctacaa aatgagttcc aggacagcca 12720
cggctataca gagaaaccct gtcttgaaaa caaacaaca acaaaatagg tactacaaag 12780
cgatgtaatt gtgctcaaac atgcaaaccg aggggactgt atgcataaga aagagaaaga 12840
cggccacact ggttctatct gggtgacagg aaatcagtat ttttattttt cacattcatt 12900
tttttgttgt tgttgttgac acagtgattt ttctatcaaa acattattt cttttatagt 12960 tccccctgagg agctgttttt aaagccgtgc tttgaaaaac cattgaagga gcagaggcag 13020
ggagactcct gtgtggcagt cggtgaagca ggccctctgc aggcaggctg gccctggact 13080
tgggagtctc tttccctccc tcctgtgctc aaatagcaaa tgtcaggctt caatgtagct 13140
agaaggttct agaatgatta agtttccaag gctgaagagc ttccctgttt gcctttcact 13200
tccctggaga ggtcgttgtg tgttccggag tctgcaaggt gcctttggtg atgcgggtgg 13260
ttcatctcgg gagattccgc ctggaggacc caagttcaag ccctgcctga gctacagagt 13320
gactttcagg tcttctgcgc aattcagtga gacccagtct acaaataaaa agtaaaaaga 13380
aggctgtgga tggaactcgg tggtagagtt ctgggtttac tccctagagg aggggagaag 13440
gaggaggagg gaggaggaag aggaagaaag aagaagagaa gggaagagga gaaggaaggg 13500
agggaagggg ctgacaagaa gagagaagag ggaggggggg gagggaaagg aagggggaaag 13560 gaagggaggg aaggggctga caagaagaga gaagagggag ggaggggagg gaaaggaagg 13620
ggaaagaaga gaagggtaag aagaaactgt tccaatggtc tgggccacag agtgatggcc 13680
ttttgtggtg atcagctgta atccttgatt tgacacaacc tagaatctgg gaagcgagtt 13740
tctgtgaagg agcattcaca ctggctggcc tgtgggcgtg catgtgggag actgtcataa 13800
ttaggttcat taatacagga agtcccagcc cactacaaat ggcttcgttc catacccaag 13860
agatgctaac tgtagacggt tggagaaagc aagcaagctg tggatacccc acgctctttc 13920
acctcggctc ctgggggggtg ggtgcactgt gtctcttggt attttaaagt cctgccttga 13980
cgtccctgct gtgacagact gtaactggaa ttgtgagctt tagtcctttta gttttctacg 14040 ttggtttttc tcaggatatt ttatcgcagt aacagaaaca agaccaggac acttgatctc 14100
ctctgatcaa cactgaagag ttacaaaaca ggctgaggaa acaaactttc ttctccctct 14160 ccccttctg tccctcccct tccttctcgc tccctccctt gccccctctc tccctgtctc 14220
tgtctctgtc tctgtctctg tctctgtctc tgtctctgcc tctcccctcc cctcccctcc 14280
ctctgtctct gtctctgtct ctgtctctgt ctctgtctct gtctctgtcc ctttctcctc 14340
tatctcctaa atggctggag gccatgctag ctcaatgttg aactttgaac acgtatttag 14400
gaaatctttg ttcttaacag ttctgaagtg ctgaagtggt ggtttagtct ctcggcctga 14460
caagctcact tcctctcact ctgtcttaat gaccaaatct gccatttccc taaaacagca 14520
caggctccag ctccaggttg ctccggagcg gag                                14553
```

Example 15-CHO Stable Site 2 Sequences—U.S. Pat. No. 9,816,110

<211> 4001
<212> DNA
<213> *Cricetulus griseus*
<400> 1

(SEQ ID NO: 58)

```
ccaagatgcc catcaactga ttaatagatg ataaaattat tgtacatttc agtgtaatat    60
tattcagttt ttaagaaaaa tgaaattatg taataagcat gtaaatggat atatcttgaa   120
acaaccattc cccattatat tacctaaaca ttgaaagtcc aaaatcatat gatcttttta   180
gtggatctac taatcttttg ctatatgtat tttattgaac tacccatgga tgtgagataa   240
ttggtaacaa cagcacatgg gagagcatgg gatcattcaa ggaagattag agagaatgca   300
tttttttagga gataatggag gagcaataga aaggattaaa tgaggttact gatgaaagtg   360
atggttagag aaggcaatat gaggagggat aactagcact tagggccttt tgaaaaagac   420
atagagaaaa tactattgta gaaacttcct ataattggtg tatagttata tacaccaaag   480
agctcagatg gagttaccct ataatggaaa tattaactac ttttatcac tgtgataaaa    540
catcctgaac agagcaacat agattgggaa gcatttactt tggcttacag ttctaacggg   600
ataaaaattc atgatgaaag aatgaatatg tcagcaaaca gcagtagcaa tggcctgaga   660
agcaggtgag agctcacatc ttgaagtgta agaatgtagc agagagaaca aactgcaaat   720
gaccagaaaa tgcttttgga tcagagccca taccctctg actgacttct ccagaaattc    780
tgaacaaata aaactcccca aacagagcca taactgaagg tccagtgtct gagactacta   840
ggggtatttc ttattcaaac cactacaatg gggtgggggg agcaatcctc caagtaggca   900
ctacacacag acaaataaaa actctagtaa ctggaatgga ttgacttatt tgaattactt   960
gccagtggag ctacatagag cacaattatt gtatttaaat tacctttat gatcttacaa  1020
aacttgacag taagatcata ttgctaaaga aaccacatat ttgaatcagg gaacatggtg  1080
atatctagtt gttcttcaac tggaaacttc atgctttctg cccagcattc atgttgctgg  1140
aaagagcaat gtacactacc agtgtagaaa ttaaatcatc aatcttatca agatgtggat  1200
cctataagtt acaataaaaa ttagcctgat aagatatccc caccagaaga atattcacat  1260
aaatgctatg ggagcaacaa gctatttct aaattagctt taatcctatt ctacaagaga    1320
gaatccatat ctagaatagt tatagggatc aagaacccat ggcttgattg gtcataggcc  1380
caatgggaga tcctaatatt attgttctac aaaatgaaaa taactcctaa tgacttgttg  1440
ctgcagtaat aagttagtat gttgctcaac tctcacaaga gaagttttgt cttacaataa  1500
atggcaatta aagcagcccc acaagattta tatcataccg atctcctcat ggcctatgca  1560
tctagaagct aggaaacaaa gaggaccca agagagacat acatggtccc cctggagaag  1620
gggaagggg caagacctcc aaagctaatt gggagcatgg gggagggag agggagttag  1680
aagaaagaga agggataaa aggagggaga ggaggacaag agagagaagg aagatctagt  1740
caagagaaga tagaggagag caagaaaaga gataccatag tagagggagc cttgtatgtt  1800
taaatagaaa actggcacta gggaattgtc caaagatcca caaggtccaa ctaataatct  1860
aagcaatagt cgagaggcta ccttaaaagc ctttctctga taatgagatt gatgactacc  1920
ttatatacca tcctagagcc ttcatccagt agctgatgga agcagaagca gacatctaca  1980
gctaaacact gagctagttg cagacaggga ggagtgatga gcaaagtcaa gaccaggctg  2040
gagaaacaca cagaaacagc agacctgaaa aaaatgttgc acatggaccc cagactgata  2100
gctgggagtc cagcatagga ctttttctaga aaccctgaat gaggatatca gtttggaggt  2160
```

-continued

```
ctggttaatc tatggggaca ctggtagtgg atcaatattt atccctagtt catgactgga    2220
atttgggtac ccattccaca tggaggaatt ctctgtcagc ctagacacat ggggaggtt     2280
ctaggtcctg ctccaaataa tgtgttagac tttgaagaac tcccttgaga agactcaccc    2340
tccctgggga gcagaaaggg gatgggatga gggttggtga gggacaggag aggaggggag    2400
ggtgagggaa ctgggattga caagtaaatg atgcttgttt ctaatttaaa tgaataaagg    2460
aaaagtaaaa gaagaaaaga aaacaggcca aagattata aagacagag gtggtgggtg      2520
actataaaga aacactatta tctaaataaa aacatgtcag aagcacacat gaacttatag    2580
tgtttatgaa agtatgtata ataactacat aatctcaagc caagaaaaaa atatcatctt    2640
tcagtgatga aggtgatttt atttctccca gaattaaagc caaagaccta atgaaagtaa    2700
ttatcttcaa aaggttgaaa atacatactt tgcaatacac agatctgcct agaaatctca    2760
tgttcacaat acacatgatg ctcaattgaa ttccattcaa tgttacagtt tagataaaca    2820
gtttgtagat aaactcacaa tgtatcattt cttttatttt tttgaccaaa cagcttctca    2880
tctgttattc agaataattc ctcgatggca ggatatccat cccaattggg ggaaggggag    2940
aatttgaaga aaacctagac cacatacata tttgccattg ggaaacaaag tctaaaatga    3000
tgttgttcac atcttctcta ctagtcctct ccccgtccca aagaaccttg gtatatgtgc    3060
ctcattttac agagagagga aagcaggaac tgagcatccc ttacttgcca tcctcaaccc    3120
aaaatttgca tcattgctca gctctgccct tctcatatga cagttacaag tcaaggcttc    3180
caaagtccct ctgtcatgtt tggtgtcaat agtttataca gatgacttca tgtcttcata    3240
tctaatgtct tatatagatt aatattaaac aatgttattt ctctaaccac attttaaatt    3300
aatttaaaaa tccattaatt gtgtctataa aatgcagaca gagtgctgag acacaatata    3360
agcctgatga tctgaatttg aaactcacac ccaccacatg gagaatcaac ttccaaaaat    3420
tttcctatta cttccacact tacaccattg tacaaacaca ataataatga acaaaatgaa    3480
atgaaataaa aaattaagtc tctgtaggta atgctactgt gcagcaaaag taaaaatggc    3540
agcttaagct tgctttatgg ttacactta ccatcttcca ttaattataa ggacttcaat     3600
catggcagaa ctatgctgtt attgtctcag tgtaacctaa ccaggtgttc cagatgttct    3660
taatgtggac acctaaacta tttgatattt gggttaagat ctttcctct ttcagaagaa     3720
acctcaggac agagggaatc ttgtctttta attttgagtc tgtagacttt ttccatttca    3780
aatatacatg aaacaagtga tgaagaaaat taatcaaaag gtgggaattg caatgatatt    3840
aggttcaata ttaagcttca atattatcat ggaatcgcct gttatacact gagtgtttgg    3900
caataaggga tttttagaag aaggagtttt tattctcaac aggttcctta agtttagctc    3960
aaataaatct aagcaatcca ctctagaatt aaatagtttc c                         4001
```

<211> 14931
<212> DNA
<213> Cricetulus griseus
<220>
<221> misc_feature
<222> (2176)...(2239)
<223> n is a, c, g, t or nucleotide is missing
<400> 4

(SEQ ID NO: 59)
```
catgtacact tatgcaagta tgatatggcc caacacagta ttttacacca attttatct     60
ataaaatata catgtacatc aaaatatatt attaataata acatcattat tctttcttc    120
caagtaataa acacatacac tgaaattttg gttcttgtgg ataattttaa tgaaacagga   180
aatgcaaatt tatcttagca tgtttacttc actttctttg catagataac cagtaatcac   240
attgatggat catgtagtga aatgtatttt taggtatcta aggaattttg gcttcgtttt   300
```

-continued

```
gtgcttgttg acactgaatt ctattcctaa caacagtgtg taaggattct gtctgatttc    360
ttttaccagt atttgtccat ttgcattttc tttattattc atggctgctg ttctagaaag    420
tggaaggtag tgtgtcaagt ctgtttaaca tgtttccctg atgatcagtg tcttaacacc    480
tctctgagta catgttggcc aatgtcgttt ctagacccat ctattcttgc ttgacttatc    540
ctggtacatg cctgccaaga aatttctcct catcctttct gtctcttcac tgatttactt    600
gatgtgtgga tttcacattg atcatatgga aatagaagat acaattttct ttattcacag    660
tttggaagac tttcaatctc atagatcatc attatttttt gctactgttc cctatgctat    720
ggtgaaattt ccatttgaat aattgcttaa acaattaaca agaaagaatc tattttact     780
tgcaataact tccatttcag aacatttact acactgttac tatatccaaa aactagtttt    840
atatatcatg tgagaaatga ctaattcata atttggccat gacattttt tcagaaacag     900
aaaaagtgac caatacatac acaatgctat aaatattaag acttcagcaa attaaatatt    960
tattcatgat atcacataaa attcatttat tatgttttat ttaaatgtgt ttttaaaaca   1020
gtggtatcac taaatattaa gttagatgtg tttatgtgct taatgaattt atattttaga   1080
atgttataag ttgtatatag tcaaatatgt aataaatttt atttttagg tctttctcat    1140
taaggtattt taatttggg tcccttttcc agagtgactc tagctcatga tgagttgaca    1200
taaaaactaa acagtacaaa atgtacattg cattcagtat tgcacttgat ctttgcactg   1260
aagtttgagt cagttcatac atttagtact tgggaagtac attaagctaa ctttcattgc   1320
tctggcaaaa tgctcgataa gataagagtc tattgtggaa agccatgca gcaggaaagt    1380
aagactgctg atgatgttta atccatagtc aagacgcaga aggagatgaa tgctggtatc   1440
caacattttt tgctgttcat tttctctaga accctagtcc ataaagatgt atgacttgca   1500
ttcaaaatgc gtcccttca gttgttcaac ttttctgtaa atatcctttc aggcatgtct    1560
agaagattgt ttcgcaaata cttctcaatc cattcaagtt gatagtgcag attaatcact   1620
gcagaataaa agcctgtaac ttggctcacg tgccaaggaa tatgcacact cctgacacat   1680
caataagtaa atcaaagtgt agcttttgcc tttaacattg ccagactat gtaatgttct    1740
gcacgttctt cctccatcac tttttattct aatggtgttt ccttgacatt gaatcacgct   1800
gtggaagctg cttagaatta acattgaaat ctactgatat atttatgatg cagcaattta   1860
gatttactat tttacttaga atttttata attgagagaa tataatattt tcacagttat    1920
ctatctgctg taaatagagg attttaaaaa aaatctctat aacttttttt tacaacacac   1980
agtaaaatta agttaaaatt taataaagtc actatgttga tttcaaagtg tgctacgccc   2040
acggtggtca cgcaggtgta gcagaagatg ccactaaggt gggctaaggc cgatgggttg   2100
gggtctgcgc tccctggaga tgagcccag gcggttccct ggcaatcagc tgcgatcatg    2160
atgcccgatg agccannnnn nnnnnnnnnn nnnnnnnnnn nnnnnnnnnn nnnnnnnnn     2220
nnnnnnnnnn nnnnnnnnnc tgggtgactt tatggaaaga atttgataga tttcatgatg   2280
tagaagaatt ttattaggct tattttacag gagactaaga ccctgggacc taagatatc    2340
tgggtcctga gaatcaggaa atgggtagag acgtggttga tggtatgaga cagattttag   2400
agaactctta gatcatgggc aatgaccgca atctgatgct tagaatagat catctataaa   2460
caattatgct gttcttttc tttctgttgt atgatctgat gatgtagccc ccttgccaag    2520
ttccctgatc ccccttgcca gttccctga ttgtaacagt atataagcat tgcttgagag    2580
catattcaac tacattgagt gtgtctgtct gtcatttcct cgccgattcc tgatttctcc   2640
ttgagccttt tccttgttc tccctcggtc ggtggtctcc acgagaggcg gtccgtggca   2700
```

-continued

```
aaagtgtata aatgttctaa aacatttgaa ctctaaaaca tgcaaaatga aaaattaaaa    2760
taaataaaca tgaaaattaa aatatattag ctgctaaaag ttaaacaata ctatataata    2820
ttttgttatt agaattcaaa atcacattag ttggatttaa tttgaacatt gcattctttc    2880
aataataatt tcaataaaaa aagtttcccc atgatagtag aaaataataa catatgtatc    2940
tatctattta tttaactaca catatatagc atttgtttca actaaaataa atgaatgagc    3000
aaagcaccta agtaattggt gtctattata tttatgaagc caatagtttc aaataaaatta   3060 tcatgcataa ggaggtattg caaatgttaa accttttttg aaacagatat tcccagttac    3120
agaaattata atttctaatc tttcctataa gtagaatgat gataattaat ataggccatt    3180
tgtaaataat gttcagatta aaatattctc tatttcacta gagaagaatg atattaaatg    3240
tattatattt tatttcccat tttgtttgca ccactattct atatccctca gcagtttaaa    3300
tttgtttcac catatgtgtg tgtgtttgta tcttaaatat ggcactaaaa ttagaataat    3360
ttaatataaa tctttaggag aaaagatatt gaattatttt atgttgatag gaaaatatct    3420
tttaattgtc caagaatact ttttcttcta ttttaggact gatcagaccc aggactaata    3480
ttttatatgt actaattcta tgtaccaaaa tatgttatta tctcatgaat tctgtctcaa    3540
tattgaggta ataaaaatag tccatcatga actttaaaat taaataatg attaattaat    3600 ttttattcat attttgtttg tatgaatggt tatacatcac atgtgtgcct ggtgactgtg    3660
aatgtcagga gaaggtatga aagccactgg aattggaata agagataata tttgagatgt    3720
tatgtgggtg ctgagaatta gacgcaagcc atcttcaaga atagccagca tactatacca    3780
ctgagtaatc cattcatccc tcaataatta tctttgtaga cagtaaatat atttctaaac    3840
tataaatgac cagaaaaatt aatgtattat taatgaagac attcatctca tgtgacacac    3900
ttcacctgtc taaatcagta acactctctc cactaattaa gattttctaa gtgcatgaca    3960
cttactattt ctaaagctgt ccaatggggg ccagtcccca gtcagcaccc agtgagataa    4020
tccatgaatg catttatatc ttaggaaaaa ttcttatcta tgtagtattt agaacatttt    4080
catgtgaggg gataaacaag gaagcacaga tgctttctga tagaaacttt ctctttaatt    4140
catctagaaa aaaaaaacct ctcaggaaaa tctctcttgc tctcctccca atgctctatt    4200
cagcatcttc tccctactta attctagatc ttttttctcta tgcctccttg ctgctgccct    4260
gctggctctg ctctatgcct ccccatgtca cttttctttg ctatctcacc gttaccttct    4320
ctgcctcact ctctgccttc ttctctgctt ctcacatggc caggctctgg acaattatag    4380
ttatatgtta cattctcata acacatgata tgtcacatag tttctctcag gctagggata    4440
tcacaatgac tggccaatga gcaagtggcc ttgcatgtag ctctaagttg gtgatggttc    4500
ccagacagta agtagccatt tggttgaaat ttgaggttgg gtagtacatg aagactgaat    4560
tttcttcaaa ctctggcctt gaaatagtaa aacaacacct atgaaaatga cgacctgtat    4620
ttgtctttag aggcaaccac atattgtctg cagggcctgc tttgaatttg ctctgaagtt    4680
agcttgtttg tgtaaaagga agaatcctat atcagcctga gaaatgtaaa atatcctagc    4740
atttcaagtc atcaaaatta tatggagagt ataaatcatc cttctgacta ttcatagtca    4800
tatttgtgtc caccaagtat aaaacacact accaaagggc tgtggaaaaa atcgccataa    4860
ctgttcttat tagggaggca tagcagtggg acctgaggaa gttacagcaa caaccagtca    4920
tccagtcaat aaccccatgg ctttgccact tggaggtacc caataatgtt tggctttgcc    4980
gagtaggact ccaacaaatt cagagggtca atttttaaat gctggttgtc actgctgaac    5040
agtcccattg ccctctgcat aattccacaa tggaaagctt tttacactga ttgccaatca    5100
ttaaacagcc tactcagcat aaacaggtat gatattattc tgcattttgt tacattacta    5160
```

-continued

```
gatgaattcc tatttcttcc tacaatagtg gaactgaaaa aagatacaca atcatactac    5220
ccctctacta atcttatgac ttatatcatt tcaattttca gaccataatg caaactattg    5280
accaaaacat gtgaagatga aaatagaaa tgtagaataa tattacatat aaaaagaaaa    5340
ggcggactta ttttgtttta tttcttagca tgcatagcaa tacatgattt gaggtttata    5400
taataaaggg acaataaatc ttcaagaaac ttaccccctac tgaattaaaa tattaaagaa    5460
ggtcacacat ttactcaaat atattagact actgggcaaa tagacatgaa aagtagagtt    5520
aatattgagg taggccttct gtgaaatgtc taaggaaatt atgtttcata cagtgtgtaa    5580
ccaagtggga atcatatcag aaagcagtca aaagcttata ttacaagtaa cagatgcttg    5640
gttatatgac ctcccagagc ttgactgtct atacacaaaa agtggtgtta ataaaactgt    5700
aatttgggct atgtttttt aaatggcttc accaacatga aaggaaggga atgagcatgt    5760
catggatgct tagagattat gcttccagca agaagaattg agctttggct cttattacag    5820
aaacatgaca aggtgtgagt tttatttatt agaaattata taatatttta agctggggac    5880
taaaaatttt attgaaacaa acaggcaagg gataggcatg tactagaagc aaaaatagga    5940
tgtcaatgct gtaatgttat tttttggacc aaaatagtat ttcctataga aatgacaatg    6000
atcttaggtt attattcttc ataaagatga caagttcaca agatatccta gttcattaaa    6060
atcgttttag tcatttaata gagtgctgtg atagattaca caaggaaag cacttacgat    6120 gagaaataat gatatccaca attatttct taattcttag aaacattcta ttgttatatc    6180
tcaatctcag aagccactta ttgctttatt attgaaacat atgaaattgt aagttatata    6240
ttgtctatgg tgacatttca aagaacatgt gacgtacagt gtagcacaga taaagaacat    6300
aactgcagct gaatcagtaa ctaaacttac atacattaaa tctgccatgt tggcaacagt    6360
gtgtgcacta ccaaaggatg tactaatgct cacgacactc ccctatgtca ccctttgttc    6420
atcattacat cataggtcta ttttgtttgc ttttgaaatc tagaccaagt cttttgtgtc    6480
tttccaagca cagagctcat taatttacct catagacttg ttaaacttct tctggttcat    6540
caattgaata gaaatactca ctactaatta tgtgagaccc tgccagtacc atagcacatg    6600
gataattttt acataaaaca tgcatacaag taagattatt cagactgaac atgaatttta    6660
gagaaatcag gaaggagtat atgggagtgg ttggagtgag actagagaaa tgtaattaaa    6720
ctataatctc aatacaaaga tctactaagc aaaaacatg aaacattgtc attcaagtga    6780
aacatcagtc ttcaaattgg aaagatattt ttactaggaa aatgtctggt agatggttat    6840
tatctagaaa acacaaaaat tagaaaacgg taaacttta taaaagaat aatacaatga    6900 gactacatga aaagttctta actaatgaaa caaatatctt gaaacttttt tcttaaaagt    6960
ttaatatcaa taaccatcat ggaaattcaa attaaaacta tttacatatt accctgaaa    7020 taataactaa tacccaataa aaataatata aacaaaaat ggcaatgcat gccatcatgg    7080
atttgggaga gagaatgttc attgcagttc tgaatggata ctggtgccac cacggtgaaa    7140
atctctgtat aggtccttcc aaaagctgaa aatagacata tcacaagacc tgccacacat    7200
ttttcaagca ataccccaaa ggactctacc tgactgcaga gacactttct cataaaatat    7260
tattgttgat ctattcataa tatctggaaa atagaaacag ccaagatgcc catcaactga    7320
ttaatagatg ataaaattat tgtacatttc agtgtaatat tattcagttt ttaagaaaaa    7380
tgaaattatg taataagcat gtaaatggat atatcttgaa acaaccattc cccattatat    7440
tacctaaaca ttgaaagtcc aaaatcatat gatctttta gtggatctac taatcttttg    7500
ctatatgtat tttattgaac tacccatgga tgtgagataa ttggtaacaa cagcacatgg    7560
```

-continued

```
gagagcatgg gatcattcaa ggaagattag agagaatgca ttttttagga gataatggag   7620
gagcaataga aaggattaaa tgaggttact gatgaaagtg atggttagag aaggcaatat   7680
gaggagggat aactagcact tagggccttt tgaaaaagac atagagaaaa tactattgta   7740
gaaacttcct ataattggtg tatagttata tacaccaaag agctcagatg gagttaccct   7800
ataatggaaa tattaactac tttttatcac tgtgataaaa catcctgaac agagcaacat   7860
agattgggaa gcatttactt tggcttacag ttctaacggg ataaaaattc atgatgaaag   7920
aatgaatatg tcagcaaaca gcagtagcaa tggcctgaga agcaggtgag agctcacatc   7980
ttgaagtgta agaatgtagc agagagaaca aactgcaaat gaccagaaaa tgcttttgga   8040
tcagagccca tacccctctg actgacttct ccagaaattc tgaacaaata aaactcccca   8100
aacagagcca taactgaagg tccagtgtct gagactacta ggggtatttc ttattcaaac   8160
cactacaatg gggtggggg agcaatcctc caagtaggca ctacacacag acaaataaaa   8220
actctagtaa ctggaatgga ttgacttatt tgaattactt gccagtggag ctacatagag   8280
cacaattatt gtatttaaat tacccttat gatcttacaa aacttgacag taagatcata   8340
ttgctaaaga aaccacatat ttgaatcagg gaacatggtg atatctagtt gttcttcaac   8400
tggaaacttc atgctttctg cccagcattc atgttgctgg aaagagcaat gtacactacc   8460
agtgtagaaa ttaaatcatc aatcttatca agatgtggat cctataagtt acaataaaaa   8520
ttagcctgat aagatatccc caccagaaga atattcacat aaatgctatg ggagcaacaa   8580
gctattttct aaattagctt taatcctatt ctacaagaga gaatccatat ctagaatagt   8640
tatagggatc aagaacccat ggcttgattg gtcataggcc caatgggaga tcctaatatt   8700
attgttctac aaaatgaaaa taactcctaa tgacttgttg ctgcagtaat aagttagtat   8760
gttgctcaac tctcacaaga gaagttttgt cttacaataa atggcaatta aagcagcccc   8820
acaagattta tatcataccg atctcctcat ggcctatgca tctagaagct aggaaacaaa   8880 gaggaccta agagagacat acatggtccc cctggagaag gggaaggggg caagacctcc   8940
aaagctaatt gggagcatgg gggaggggag agggagttag aagaaagaga agggataaa    9000 aggagggaga ggaggacaag agagagaagg aagatctagt caagaagaa tagaggagag   9060 caagaaaaga gataccatag tagagggagc cttgtatgtt taaatagaaa actggcacta   9120
gggaattgtc caaagatcca caaggtccaa ctaataatct aagcaatagt cgagaggcta   9180
ccttaaaagc ctttctctga taatgagatt gatgactacc ttatatacca tcctagagcc   9240
ttcatccagt agctgatgga agcagaagca gacatctaca gctaaacact gagctagttg   9300
cagacaggga ggagtgatga gcaaagtcaa gaccaggctg gagaaacaca cagaaacagc   9360
agacctgaaa aaaatgttgc acatggaccc cagactgata gctgggagtc cagcatagga   9420 ctttttctaga aaccctgaat gaggatatca gtttggaggt ctggttaatc tatggggaca   9480
ctggtagtgg atcaatattt atccctagtt catgactgga atttgggtac ccattccaca   9540
tggaggaatt ctctgtcagc ctagacacat ggggaggt ctaggtcctg ctccaaataa     9600
tgtgttagac tttgaagaac tcccttgaga agactcaccc tccctggga gcagaagg    9660 gatgggatga gggttggtga gggacaggag aggagggag ggtgagggaa ctgggattga   9720
caagtaaatg atgcttgttt ctaatttaaa tgaataaagg aaaagtaaaa gaagaaaaga   9780
aaacaggcca aagattata aaagacagag gtggtgggtg actataaaga aacactatta   9840
tctaaataaa aatatgtcag aagcacacat gaacttatag tgtttatgaa agtatgtata   9900
ataactacat aatctcaagc caagaaaaaa atatcatctt tcagtgatga aggtgatttt   9960
atttctccca gaattaaagc caaagaccta atgaaagtaa ttatcttcaa aaggttgaaa  10020
```

-continued

```
atacatactt tgcaatacac agatctgcct agaaatctca tgttcacaat acacatgatg   10080
ctcaattgaa ttccattcaa tgttacagtt tagataaaca gtttgtagat aaactcacaa   10140
tgtatcattt ctttttattt tttgaccaaa cagcttctca tctgttattc agaataattc   10200
ctcgatggca ggatatccat cccaattggg ggaaggggag aatttgaaga aaacctagac   10260
cacatacata tttgccattg ggaaacaaag tctaaaatga tgttgttcac atcttctcta   10320
ctagtcctct ccccgtccca agaaccttg gtatatgtgc ctcattttac agagagagga    10380
aagcaggaac tgagcatccc ttacttgcca tcctcaaccc aaaatttgca tcattgctca   10440
gctctgccct tctcatatga cagttacaag tcaaggcttc caaagtccct ctgtcatgtt   10500
tggtgtcaat agtttataca gatgacttca tgtcttcata tctaatgtct tatatagatt   10560
aatattaaac aatgttattt ctctaaccac attttaaatt aatttaaaaa tccattaatt   10620
gtgtctataa aatgcagaca gagtgctgag acacaatata agcctgatga tctgaatttg   10680
aaactcacac ccaccacatg gagaatcaac ttccaaaaat tttcctatta cttccacact   10740
tacaccattg tacaaacaca ataataatga acaaaatgaa atgaaataaa aaattaagtc   10800
tctgtaggta atgctactgt gcagcaaaag taaaaatggc agcttaagct tgctttatgg   10860 ttacactta ccatcttcca ttaattataa ggacttcaat catggcagaa ctatgctgtt    10920
attgtctcag tgtaacctaa ccaggtgttc cagatgttct taatgtggac acctaaacta   10980
tttgatattt gggttaagat ctttccctct ttcagaagaa acctcaggac agagggaatc   11040
ttgtctttta attttgagtc tgtagacttt ttccatttca aatatacatg aaacaagtga   11100
tgaagaaaat taatcaaaag gtgggaattg caatgatatt aggttcaata ttaagcttca   11160
atattatcat ggaatcgcct gttatacact gagtgtttgg caataaggga tttttagaag   11220
aaggagtttt tattctcaac aggttcctta agtttagctc aaataaatct aagcaatcca   11280
ctctagaatt aaatagtttc ctaagggcac agctatgaat agagctcaat ttacatataa   11340
aattttgttc accatttatg tcattccagt tttcattagt acaaggaaaa tacaaaatat   11400
ttagatgtca atatcaagtg aatagttcat ctccttttt aatatatatc acctaaatca    11460
ccattttctc agaaaaatct ggcctgaagt tctgtctgga acttcaacat gaaaaatatg   11520
cacagcttgc tattataaat cctagttgat ttttaagatt catgtctggt gtctgactca   11580 gagggggccag aggctagaca aatatttttt gaatcttcat tgtgaagatt tttaatgatt   11640
attttaatat aaataacaaa gatgatggat aatgtaactt tgtacagttc atagacgctg   11700
aactactttg tgcttaaaat gttagttccc tatcataaat gataggtgat aagtgtatgt   11760
ttaatacttt ccctctgagc tatattcatg tactagagaa ttattttaaa catgaaaaga   11820
ctgtgtttat agtctcagct cctgagaact ggtccaacct taggcaggtg aatgccagga   11880
gcaacgtttt tcttctacag aggatgcttt gctgccaagc aacctggttg tgtggaaatg   11940 ttccttttt aatcaagttt aaagggtctt catcatgctg ttgctccaca tattttcagg    12000
ttagagcttg gtccttggag tattatcttt taccagaaaa ttcatagtat tctttcaata   12060
actaacaact aaacttttcg ataaaaaaga attggaattt caattttaaa gcctgagtaa   12120
aattcttgtg aatcaggata ttttatttta agtcttatct tttaaaaagt tattttattt   12180
tttaaaaaat tataatatac tttcataatt tccctccttc actttctttt acaaacactt   12240
ctatagatca ccatgtgttt ttttttttac atttatggcc tctttctgtt cattgttatt   12300
acatacaaat agtcttgcct atagaagaac accacaattt gttacctgat aacaaattat   12360
caacccttaa aacctacaaa ctattgatat tactgaaaag actatactta tagatgtaaa   12420
```

-continued

```
gatatatgtg tgtgcacata tatagataca catatatgta ggatttttaa ttttagattt 12480
tagacatcaa aattatttat atgactgaga aactagacac tataaatgag cattcagtat 12540
tcaacaccgt gattttagat attgtcacaa tgacagaaaa ttttcttata gaaaatttta 12600
agttttgtga ttgctctgtg cacttagtga agtctcacag aaaaagaatc atagtatttt 12660
tagtttataa taaaaagtac atataattaa aatggttggc acaaacaac atttgagcat 12720 ttttcctatt tactatcaag tagtatcatt ttgaaataat aatttgacta gtttcaaaaa 12780
tgaaaacaaa atttaaacta aatgcctaat ctagcctgat aacatttta tgaatgaaat 12840 tattcaatag tgttatcaat taggggccca aaacttttcc taaaataaaa cttttaatt 12900 ttttccattt ttatttaaat tagaaacaaa attgttttac atgtaaatca gagtttcctc 12960
accctcccct tctccctgtc cctcactaac accctacttg tcccatacca tttctgctcc 13020
ccagggaggg tgaggccttc catggggaaa cttcagagtc tgtctatcct ttcggatagg 13080
gcctaggccc tcacccattt gtctaggcta aggctcacaa agtttactcc tatgctagtg 13140
ataagtactg atctactaca agagacacca tagatttcct aggcttcctc actgacaccc 13200
atgttcatgg ggtctggaac aatcatatgc tagtttccta ggtatcagtc tggggaccat 13260
gagctccccc ttgttcaggt caactgtttc tgtgggtttc accaccctgg tcttgactgc 13320
tttgctcatc actcctccct ttctgtaact gggttccagt acaattccgt gtttagctgt 13380
gggtgtctac ttctactttc atcagcttct gggatggagc ctctaggata gcatacaatt 13440
agtcatcatc tcattatcag ggaagggcat ttaaagtagc ctctccattg ttgcttggat 13500
tgttagttgg tgtcatcttt gtagatctct ggacatttcc ctagtgccag atatctcttt 13560
aaacctacaa gactacctct attatggtat ctcttttctt gctctcgtct attcttccag 13620
acaaaatctt cctgctccct tatattttcc tctcccctcc tcttctcccc ttctcattct 13680
cctagatcca tcttcccttc ccccatgctc ccaagagaga tgttgctcag gagatcttgt 13740
tccttaaccc ttttcttggg gatctgtctc tcttagggtt gtccttgttt cctagcttct 13800
ctggaagtgt ggattgtaag ctggtaatca tttgctccat gtctaaaatc catatatgag 13860
tgatgtttgt ctttttgtga ctgggttacc tcactcaaaa tggtttcttc catatgtctg 13920
tggatttcaa tagcacaaac aacatacagt atcttgggc aacactaacc aaacaagtga 13980
aagaccagta tagcaagaac tttgagttta aagaaagaaa ttaaagaaga taccagaaaa 14040
tggaaagatc tcccatgctc tttgataggc agaatcaaca tagtaaaaat ggcaatcttg 14100
ccaaaatcca tctacagact caatgcaatc cccattaaat accagcacac ttcttcacag 14160
acctgaaaga ataatactta actttatatg gagaaacaaa agacccagga taggccaaac 14220
aaccctgtac aatgaaggca cttccagagg catccccatc cctgacttca agctctatta 14280
tagagtaata atcctgaaaa cagcttggta atggcacaaa aatagacagg tagaccaatg 14340
gaattgagtt gaaaaccctg atattaaccc acatatctat gaacacctga ctttgacaaa 14400
gaagctaagg ttatacaatg taagaaagaa agcatcttca acaaatcgtg ctggcataac 14460
tggatgctgg catgtagaag actgcagata gatccatgtc taatgccatg cacaaaactt 14520
aagtccaaat ggatcaaaaa cctcaacata aatccagcca cactgaacct catagaagag 14580
aaagtgggaa gtatccttga ataaattggt acaggagacc acatcttgaa cttaacacca 14640
gtagcacaga caatcagatc aataatcaat aaatgggacc tcctgaaact gagaagcttc 14700
tgtaaggcaa tggataagtc aacaggacaa aatggcagcc cacggaatgg gaaaagatat 14760
tcaccaatcc tatatctgac agagggctgc tctctatttg caaagaacac aataagctag 14820
```

-continued

```
tttttaaaac accaattaat ccgattataa agttgggtag agaactaaat aaagaattgt   14880
taacagagca atctaacttg gcagaaagac acataagaaa gtgctcacca t             14931
```

It is to be understood that the description, specific examples and data, while indicating exemplary embodiments, are given by way of illustration and are not intended to limit the present inventions. Various changes and modifications within the present invention, including combining embodiments in whole and in part, will become apparent to the skilled artisan from the discussion, disclosure and data contained herein, and thus are considered part of the inventions.

---

SEQUENCE LISTING

```
Sequence total quantity: 59
SEQ ID NO: 1            moltype = DNA  length = 2211
FEATURE                 Location/Qualifiers
misc_feature            1..2211
                        note = CapVP1
source                  1..2211
                        mol_type = genomic DNA
                        organism = Adeno-associated virus - 1
SEQUENCE: 1
atggctgccg atggttatct tccagattgg ctcgaggaca acctctctga gggcattcgc   60
gagtggtggg acttgaaacc tggagccccg aagcccaaag ccaaccagca aaagcaggac   120
gacggccggg gtctggtgct tcctggctac aagtacctcg gacccttcaa cggactcgac   180
aaggggagc ccgtcaacgc ggcggacgca gcggccctcg agcacgacaa ggcctacgac   240
cagcagctca aagcgggtga caatccgtac ctgcggtata accacgccga cgccgagttt   300
caggagcgtc tgcaagaaga tacgtctttt gggggcaacc tcgggcgagc agtcttccag   360
gccaagaagc gggttctcga acctctcggt ctggttgagg aaggcgctaa gacggctcct   420
ggaaagaaac gtccggtaga gcagtcgcca caagagccag actcctcctc gggcatcggc   480
aagacaggcc agcagcccgc taaaaagaga ctcaattttg gtcagactgg cgactcagag   540
tcagtccccg atccacaacc tctcggagaa cctccagcaa cccccgctgc tgtgggacct   600
actacaatgc cttcaggcgg tggcgcacca atggcagaca ataacgaagg cgccgacgga   660
gtgggtaatg cctcaggaaa ttggcattgc gattccacat ggctgggcga cagagtcatc   720
accaccagca cccgcacctg ggccttgccc acctacaata accacctcta caagcaaatc   780
tccagtgctt caacggggc cagcaacgac aaccactact tcggctacag caccccctgg   840
gggtattttg atttcaacag attccactgc cactttttcac cacgtgactg gcagcgactc   900
atcaacaaca attggggatt ccggcccaag agactcaact tcaaactctt caacatccaa   960
gtcaaggagg tcacgacgaa tgatggcgtc acaaccatcg ctaataacct taccagcacg   1020
gttcaagtct tctcggactc ggagtaccag cttccgtacg tcctcggctc tgcgcaccag   1080
ggctgcctcc ctccgttccc ggcggacgtg ttcatgattc cgcaatacgg ctacctgacg   1140
ctcaacaatg gcagccaagc cgtgggacgt tcatcctttt actgcctgga atatttccct   1200
tctcagatgc tgagaacggg caacaacttt accttcagct acacctttga ggaagtgcct   1260
ttccacagca gctacgcgca cagccagagc ctgaccggc tgatgaatcc tctcatcgac   1320
caataccctgt attacctgaa cagaactcaa aatcagtccg gaagtgccca aaacaaggac   1380
ttgctgtttt gccgtgggtc tccagctggc atgtctgttc agcccaaaaa ctggctacct   1440
ggaccctgtt atcggcagca gcgcgtttct aaaacaaaaa cagacaacaa caacagcaat   1500
tttacctgga ctggtgcttc aaaatataac catcaatggg gtgaatccat catcaaccct   1560
ggcactgcta tggcctcaca caaagacgac gaagacaagt tctttcccat gagcggtgtc   1620
atgattttg gaaaagagag cgccgagct tcaaacactg cattggacaa tgtcatgatt   1680
acagacgaag aggaaattaa agccactaac cctgtggcca ccgaaagatt tgggaccgtg   1740
gcagtcaatt tccagagcag cagcacagac cctgcgaccg gagatgtgca tgctatggga   1800
gcattacctg gcatggtgtg gcaagataga gacgtgtacc tgcagggtcc catttgggcc   1860
aaaattcctc acacagatgg acactttcac ccgtctcctc ttatgggcgg cttttggacte   1920
aagaacccgc ctcctcagat cctcatcaaa aacacgcctg ttcctgcgaa tcctccggcg   1980
gagttttcag ctacaaagtt tgcttcattc atcacccaat actccacagg acaagtgagt   2040
gtggaaattg aatgggagct gcagaaagaa aacagcaagc gctggaatcc cgaagtgcag   2100
tacacatcca attatgcaaa atctgccaac gttgatttta ctgtggacaa caatggactt   2160
tatactgagc ctcgcccccat tggcacccgt taccttaccc gtcccctgta a             2211

SEQ ID NO: 2            moltype = DNA  length = 1872
FEATURE                 Location/Qualifiers
misc_feature            1..1872
                        note = Rep78
source                  1..1872
                        mol_type = genomic DNA
                        organism = Adeno-associated virus - 1
SEQUENCE: 2
atgccgggct tctacgagat cgtgatcaag gtgccgagcg acctggacga gcacctgccg   60
ggcatttctg actcgtttgt gagctgggtg gccgagaagg aatgggagct gccccggat   120
tctgacatgg atctgaatct gattgagcag gcacccctga ccgtgccga gaagctgcag   180
cgcgacttcc tggtccaatg gcgccgcgtg agtaaggccc cggaggccct cttctttgtt   240
cagttcgaga agggcgagtc ctacttccac ctccatattc tggtgagac cacggggtc   300
aaatccatgg tgctgggccg cttcctgagt cagattaggg acaagctggt gcagaccatc   360
taccgcggga tcgagccgac cctgcccaac tggttcgcgt tgaccaagac gcgtaatgcc   420
gccggagggg ggaacaaggt ggtggacgag tgctacatcc caactacct cctgcccaag   480
actcagcccg agctgcagtg ggcgtggact aacatggagg agtatataag cgcctgtttg   540
```

```
aacctggccg agcgcaaacg gctcgtggcg cagcacctga cccacgtcag ccagacccag   600
gagcagaaca aggagaatct gaaccccaat tctgacgcgc ctgtcatccg gtcaaaaacc   660
tccgcgcgct acatggagct ggtcgggtgg ctggtggacc ggggcatcac ctccgagaag   720
cagtggatcc aggaggacca ggcctcgtac atctccttca acgccgcttc caactcgcgc   780
tcccagatca aggccgctct ggacaatgcc ggcaagatca tggcgctgac caaatccgcc   840
cccgactacc tggtaggccc cgctccgccc gcggacatta aaaccaaccg catctaccgc   900
atcctggagc tgaacggcta cgaacctgcc tacgccggct ccgtcttcct cggctgggcc   960
cagaaaaggt tcgggaagcg caacaccatc tggctgtttg gccgccacac cacgggcaag  1020
accaacatcg cggaagccat cgcccacgcc gtgcccttct acggctgcgt caactggacc  1080
aatgagaact tcccccttcaa tgattgcgtc gacaagatgg tgatctgcat gggaggggc  1140
aagatgacgc ccaaggtcgt ggagtccgcc aaggccattc tcggcggcag caaggtgcgc  1200
gtggaccaaa agtgcaagtc gtccgcccag atcgaccccca ccccccgtgat cgtcacctcc  1260
aacaccaaca tgtgcgccgt gattgacggg aacagccgcc ccttcgagca ccagcagccg  1320
ttgcaggacc ggatgttcaa attttgaactc acccgccgtc tggagcatga ctttggcaag  1380
gtgacaaagc aggaagtcaa agagttcttc cgctgggcgc aggatcacgt gaccgaggtg  1440
gcgcatgagt tctacgtcag aaaggggtgga gccaacaaaa gacccgcccc cgatgacgcg  1500
gataaaagcg agcccaagcg ggcctgcccc tcagtcgcgg atccatcgac gtcagacgcg  1560
gaaggagctc cggtggactt tgccgacagg taccaaaaca atgttctcg tcacgcgggc  1620
atgcttcaga tgctgtttcc ctgcaagaca tgcgagagaa tgaatcagaa tttcaacatt  1680
tgcttcacgc acgggacgag agactgttca gagtgcttcc ccggcgtgtc agaatctcaa  1740
ccggtcgtca gaaagaggac gtatcggaaa ctctgtgcca ttcatcatct gctggggcgg  1800
gctcccgaga ttgcttgctc ggcctgcgat ctggtcaacg tggacctgga tgactgtgtt  1860
tctgagcaat aa                                                       1872

SEQ ID NO: 3             moltype = DNA  length = 1866
FEATURE                  Location/Qualifiers
misc_feature             1..1866
                         note = Rep78
source                   1..1866
                         mol_type = genomic DNA
                         organism = Adeno-associated virus - 2
SEQUENCE: 3
atgccggggt tttacgagat tgtgattaag gtccccagcg accttgacga gcatctgccc    60
ggcatttctg acagctttgt gaactgggtg gccgagaagg aatgggagtt gccgccagat   120
tctgacatgg atctgaatct gattgacagc gcaccccgtca ccgtggccga gaagctgcag   180
cgcgactttc tgacgaatg cgcgcgtgtg agtaagccc cggaggccct tttcttgtg    240
caatttgaga agggagagag ctacttccac atgcacgtgc tcgtgaaaac caccggggtg   300
aaaatccatg ttttgggacg tttcctgagt cagattcgcg aaaaactgat tcagagaatt   360
taccgcggga tcgagccgac tttgccaaac tggttcgcg tcacaaagac cagaaatggc   420
gccggaggcg ggaacaaggt ggtggatgag tgctacatcc ccaattactt gctccccaaa   480
acccagcctg agctccagtg ggcgtggact aatatggaac agtatttaag cgcctgtttg   540
aatctcacga gcgtaaacg gttggtgcg cagcatctga cgcacgtgtc gcagacgcag   600
gagcagaaca aagagaatca gaatcccaat tctgatgcgc cggtgatcag atcaaaaact   660
tcagccaggt acatggagct ggtcgggtgg ctcgtggaca agggggattac ctcggagaag   720
cagtggatcc aggaggacca ggcctcatac atctccttca atgcggcctc caactcgcgc   780
tcccaaatca aggctgcctt ggacaatgcg ggaaagatta tgagcctgac taaaaccgcc   840
cccgactacc tggtgggcca cagcccgtg gaggacatta ccagcaatcg gatttataaa   900
attttggaac taaacgggta cgatcccccaa tatgcggctt ccgtcttctct gggatgggcc   960
acgaaaaagt tcggcaagag gaacaccatc tggctgtttg gcctgcaac taccgggaag  1020
accaacatcg cggaggccat agcccacact gtgcccttct acgggtgcgt aaactggacc  1080
aatgagaact tcccccttcaa cgactgtgtc gacaagatgg tgatctgcat ggaggaggg  1140
aagatgaccc caaggtcgt ggagtcggcc aaagcattc tcggaggaag caaggtgcgc  1200
gtggaccaga aatgcaagtc ctcggcccag atagacccga ctcccgtgat cgtcacctcc  1260
aacaccaaca tgtgcgccgt gattgacggg aactcaacga ccttgaaaca ccagcagccg  1320
ttgcaagacc ggatgttcaa attttgaactc acccgcccgtc tggatcatga ctttgggaag  1380
gtcaccaagc aggaagtcaa agactttttc cggtgggcaa aggatcacgt ggttgaggtg  1440
gagcatgaat tctacgtcaa aaaggggtgga gccaagaaaa gacccgcccc cagtgacgca  1500
gatataagtg agcccaaacg ggtgcgcgag tcagttgcgc agccatcgac gtcagacgcg  1560
gaagcttcga tcaactacgc agacaggtac caaaacaagt gttctcgtca cgtgggcatg  1620
aatctgatgc tgtttcccctg cagacaatgc gagagaatga tcagaattc aaatatctgc  1680
ttcactcacg gacagaaaga ctgtttagag tgctttcccg tgtcagaatc tcaacccgtt  1740
tctgtcgtca aaaaggcgta tcagaaactg tgctacattc atcatatcat gggaaaggtg  1800
ccagacgctt gcactgcctg cgatctggtc aatgtggatt tggatgactg catctttgaa  1860
caataa                                                              1866

SEQ ID NO: 4             moltype = DNA  length = 1194
FEATURE                  Location/Qualifiers
misc_feature             1..1194
                         note = Rep52
source                   1..1194
                         mol_type = genomic DNA
                         organism = Adeno-associated virus - 2
SEQUENCE: 4
atggagctgg tcgggtggct cgtgacaag gggattacct cggagaagca gtggatccag    60
gaggaccagg cctcatacat ctccttcaat gcggcctcca actcgcggtc ccaaatcaag   120
gctgccttga caatgcggg aaagattatg agcctgacta aaccgcccc cgactacctg   180
gtgggccagc agcccgtgga ggacattcc agcaatcgga tttataaaat tttggaacta   240
aacgggtacg atccccaata tgcggcttcc gtctttctgg gatgggccac gaaaaagttc   300
ggcaagagga acaccatctg gctgtttggg cctgcaacta ccgggaagac caacatcgcg   360
```

```
gaggccatag cccacactgt gcccttctac gggtgcgtaa actgaccaa tgagaacttt     420
cccttcaacg actgtgtcga caagatggtg atctggtggg aggaggggaa gatgaccgcc     480
aaggtcgtgg agtcggccaa agccattctc ggaggaagca aggtgcgcgt ggaccagaaa     540
tgcaagtcct cggcccagat agacccgact cccgtgatcg tcacctccaa caccaacatg     600
tgcgccgtga ttgacgggaa ctcaaacgac ttcgaacacc agcagccgtt gcaagaccgg     660
atgttcaaat ttgaactcac ccgccgtctg gatcatgact ttgggaaggt caccaagcag     720
gaagtcaaag acttttccg gtgggcaaag gatcacgtgg ttgaggtgga gcatgaattc     780
tacgtcaaaa agggtggagc caagaaaaga cccgccccca gtgacgcaga tataagtgag     840
cccaaacggg tgcgcgagtc agttgcgcag ccatcgacgt cagacgcgga agcttcgatc     900
aactacgcag acaggtacca aaacaaatgt tctcgtcacg tgggcatgaa tctgatgctg     960
tttccctgca gacaatgcga gagaatgaat cagaattcaa atatctgctt cactcacgga    1020
cagaaagact gtttagagtg ctttcccgtg tcagaatctc aacccgtttc tgtcgtcaaa    1080
aaggcgtatc agaaactgtg ctacattcat catatcatgg gaaaggtgcc agacgcttgc    1140
actgcctgcg atctggtcaa tgtggatttg gatgactgca tctttgaaca ataa          1194

SEQ ID NO: 5                 moltype = DNA   length = 2208
FEATURE                      Location/Qualifiers
misc_feature                 1..2208
                             note = CapVP1
source                       1..2208
                             mol_type = genomic DNA
                             organism = Adeno-associated virus - 2
SEQUENCE: 5
atggctgccg atggttatct tccagattgg ctcgaggaca ctctctctga aggaataaga     60
cagtggtgga agctcaaacc tggcccacca ccaccaaagc ccgcagagcg cataaggac     120
gacagcaggg gtcttgtgct tcctgggtac aagtacctcg gacccttcaa cggactcgac    180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa gacggctccg    420
ggaaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg accccagcc tctcggacag ccaccagcag cccctctgg tctgggaact    600
aatacgatgg ctacaggcag tggcgcacca atggcagaca ataacgaggg cgccgacgga    660
gtgggtaatt cctcgggaaa ttggcattgc gattccacat ggatgggcga cagagtcatc    720
accaccagca cccgaacctg gcctgccca cctacaacaa ccacctcta caacaaatt     780
tccagccaat caggagcctc gaacgacaat cactactttg gctacagcac ccttggggg    840
tattttgact tcaacagatt ccactgccac ttttcaccac gtgactggca agactcatc    900
aacaacaact gggattccga cccaagaga tcaacttca gctctttaa cattcaagtc    960
aaagaggtca cgcagaatga cggtacgacg cgattgccaa taaccttac cagcacggtt    1020
caggtgttta ctgactcgga gtaccagctc ccgtacgtcc tcggctcggc gcatcaagga    1080
tgcctcccgc cgttcccagc agacgtcttc atggtgccag tatggata cctcaccctg    1140
aacaacggga gtcaggcagt aggacgctct tcattttact gcctggagta cttttcctct    1200
cagatgctgc gtaccggaaa caacttttacc ttcagctaca cttttgagga cgttcctttc    1260
cacagcagct acgctcacag ccagagtctg gaccgtctca tgaatcctct catcgaccag    1320
tacctgtatt acttgagcag aacaaacact ccaagtggaa ccaccacgca gtcaaggctt    1380
cagttttctc aggccggagc gagtgacatt cgggaccagt cggggaactg gcttcctgga    1440
ccctgttacc gccagcagcg agtatcaaaa acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt tcctcagag cggggttctc    1620
atcttttggga gcaaggctc agagaaaaca aatgtgaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca ttttcacccc tctcccctca tgggtggatt ggacttaaa    1920
cacccctcctc cacagattct catcaagaac ccccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatccga attcagtac    2100
acttccaact caacaagtc tgttaatgtg gacttactgg tggacactaa tggcgtgtat    2160
tcagagcctc gcccattgg caccagatac ctgactcgta tctgtaa              2208

SEQ ID NO: 6                 moltype = DNA   length = 1797
FEATURE                      Location/Qualifiers
misc_feature                 1..1797
                             note = CapVP2
source                       1..1797
                             mol_type = genomic DNA
                             organism = Adeno-associated virus - 2
SEQUENCE: 6
acggctccgg gaaaaagag gccggtagag cactctcctg tggagccaga ctcctcctcg     60
ggaaccggaa aggcgggcca gcagcctgca agaaaaagat tgaattttgg tcagactgga    120
gacgcagact cagtacctga ccccagcct ctcggacagc caccagcagc ccctctggt     180
ctgggaacta atacgatggc tacaggcagt ggcgcaccaa tggcagacaa taacgagggc    240
gccgacggag tgggtaattc ctcgggaaat tggcattgcg attccacatg gatgggcgac    300
agagtcatca ccaccagcac ccgaacctgg cctgccca cctacaacaa ccacctctac    360
aaacaaattt ccagccaatc aggagcctcg aacgacaatc actactttgg ctacagcacc    420
ccttgggggt attttgactt caacagattc cactgccact tttcaccacg tgactggcaa    480
agactcatca caacaactg gggattccga cccaagagac tcaacttcaa gctctttaac    540
attcaagtca agaggtcac gcagaatgac ggtacgacga cgattgccaa taaccttacc    600
```

```
agcacggttc aggtgtttac tgactcggag taccagctcc cgtacgtcct cggctcggcg 660
catcaaggat gcctcccgcc gttcccagca gacgtcttca tggtgccaca gtatggatac 720
ctcaccctga acaacgggag tcaggcagta ggacgctctt catttactg cctggagtac 780
tttccttctc agatgctgcg taccggaaac aactttacct tcagctacac ttttgaggac 840
gttcctttcc acagcagcta cgctcacagc cagagtctgg accgtctcat gaatcctctc 900
atcgaccagt acctgtatta cttgagcaga acaaacactc caagtggaac caccacgcag 960
tcaaggcttc agttttctca ggccggagcg agtgacattc gggaccagtc taggaactgg 1020
cttcctggac cctgttaccg ccagcagcga gtatcaaaga catctgcgga taacaacaac 1080
agtgaatact cgtggactgg agctaccaag taccacctca atggcagaga ctctctggtg 1140
aatccgggcc cggccatggc aagccacaag gacgatgaag aaaagttttt tcctcagagc 1200
ggggttctca tctttgggaa gcaaggctca gagaaaacaa atgtggacat tgaaaaggtc 1260
atgattacag acgaagagga aatcaggaca accaatcccg tggctacgga gcagtatggt 1320
tctgtatcta ccaacctcca gagaggcaac agacaagcta ctaccgcaga tgtcaacaca 1380
caaggcgttc ttccaggcat ggtctggcag gacagagatg tgtaccttca ggggcccatc 1440
tgggcaaaga ttccacacac ggacggacat tttcacccct ctcccctcat gggtggattc 1500
ggacttaaac acccctcctc cacagattct atcaagaaca ccccggtacc tgcgaatcct 1560
tcgaccacct tcagtgcggc aaagtttgct tccttcatca cacagtactc cacgggacag 1620
gtcagcgtgg agatcgagtg ggagctgcag aaggaaaaca gcaaacgctg gaatcccgaa 1680
attcagtaca cttccaacta caacaagtct gttaatgtgg actttactgt ggacactaat 1740
ggcgtgtatt cagagcctcg ccccattggc accagatacc tgactcgtaa tctgtaa 1797

SEQ ID NO: 7              moltype = DNA  length = 1602
FEATURE                   Location/Qualifiers
misc_feature              1..1602
                          note = CapVP3
source                    1..1602
                          mol_type = genomic DNA
                          organism = Adeno-associated virus - 2
SEQUENCE: 7
atggctacag gcagtggcgc accaatggca gacaataacg agggcgccga cggagtgggt 60
aattcctcgg gaaattggca ttgcgattcc acatggatgg cgacagagt catcaccacc 120
agcacccgaa cctgggccct gcccacctac aacaaccacc tctacaaaca aatttccagc 180
caatcaggag cctcgaacga caatcactac tttggctaca gcccccttg ggggtatttt 240
gacttcaaca gattccactg ccactttca ccacgtgact ggcaaagact catcaacaac 300
aactgggga tccgacccaa gagactcaac ttcaagctct ttaacattca agtcaaagag 360
gtcacgcaga atgacggtac gacgacgatt gccaataacc ttaccagcac ggttcaggtg 420
tttactgact cggagtacca gctcccgtac gtcctcggct cggcgcatca aggatgcctc 480
ccgccgttcc cagcagacgt cttcatggtg ccacagtatg gatacctcac cctgaacaac 540
gggagtcagg cagtaggacg ctcttcattt tactgcctga gtactttcc ttctcagatg 600
ctgcgtaccg gaaacaactt taccttcagc tacactttg aggacgttcc tttccagagc 660
agctacgctc acagccagag tctggaccgt ctcatgaatc ctctcatcga ccagtacctg 720
tattacttga gcagaacaaa cactccaagt ggaaccacca cgcagtcaag gcttcagttt 780
tctcaggccg gagcgagtga cattcgggac cagtctagga actggcttcc tggaccctgt 840
taccgccagc agcgagtatc aaagacatct gcggataaca acaacagtga atactcgtgg 900
actggagcta ccaagtacca cctcaatggc agagactctc tggtgaatcc gggcccggcc 960
atggcaagcc acaaggacga tgaagaaaag ttttttcctc agagcggggt tctcatcttt 1020
gggaagcaag gctcagagaa aacaaatgtg gacattgaaa aggtcatgat tacagacgaa 1080
gaggaaatca ggacaaccaa tcccgtggct acggagcagt atggttctgt atctaccaac 1140
ctccagagag gcaacagaca agctactacc gcagatgtca acacacaagg cgttcttcca 1200
ggcatggtct ggcaggacag agatgtgtac cttcaggggc ccatctggc aaagattcca 1260
cacacggacg gacattttca cccctctccc ctcatgggtg gattcggact taaacaccct 1320
cctccacaga ttctcatcaa gaacaccccg gtacctgcga atccttcgac cacccttcagt 1380
gcggcaaagt ttgcttcctt catcacacag tactccacgg gacaggtcag cgtggagatc 1440
gagtgggagc tgcagaagga aaacagcaaa cgctggaatc cgaaattca gtacacttcc 1500
aactacaaca agtctgttaa tgtggacttt actgtggaca ctaatggcgt gtattcagag 1560
cctcgcccca ttggcaccag atacctgact cgtaatctgt aa 1602

SEQ ID NO: 8              moltype = DNA  length = 615
FEATURE                   Location/Qualifiers
misc_feature              1..615
                          note = CapAAP
source                    1..615
                          mol_type = genomic DNA
                          organism = Adeno-associated virus - 2
SEQUENCE: 8
ctggagacgc agactcagta cctgaccccc agcctctcgg acagccacca gcagcccct 60
ctggtctggg aactaatacg atggctacag gcagtggcgc accaatggca gacaataacg 120
agggcgccga cggagtgggt aattcctcgg gaaattggca ttgcgattcc acatggatgg 180
cgacagagt catcaccacc agcacccgaa cctgggccct gcccacctac aacaaccacc 240
tctacaaaca aatttccagc caatcaggag cctcgaacga caatcactac tttggctaca 300
gcccccttg ggggtatttt gacttcaaca gattccactg ccactttca ccacgtgact 360
ggcaaagact catcaacaac aactgggga tccgacccaa gagactcaac ttcaagctct 420
ttaacattca agtcaaagag gtcacgcaga atgacggtac gacgacgatt gccaataacc 480
ttaccagcac ggttcaggtg tttactgact cggagtacca gctcccgtac gtcctcggct 540
cggcgcatca aggatgcctc ccgccgttcc cagcagacgt cttcatggtg ccacagtatg 600
gatacctcac cctga 615

SEQ ID NO: 9              moltype = DNA  length = 1875
FEATURE                   Location/Qualifiers
```

| misc_feature | 1..1875 |
| | note = Rep78 |
| source | 1..1875 |
| | mol_type = genomic DNA |
| | organism = Adeno-associated virus - 3 |

SEQUENCE: 9

```
atgccggggt tctacgagat tgtcctgaag gtcccgagtg acctggacga gcgcctgccg   60
ggcatttcta actcgtttgt taactgggtg gccgagaagg aatgggacgt gccgccggat  120
tctgacatgg atccgaatct gattgagcag gcaccctga ccgtggccga aaagcttcag  180
cgcgagttcc tggtggagtg gcgccgcgtg agtaaggccc cggaggccct cttttttgtc  240
cagttcgaaa agggggagac ctacttccac ctgcacgtgc tgattgagac catcggggtc  300
aaatccatgt tggtcggccg ctacgtgagc cagattaaag agaagctggt gacccgcatc  360
taccgcgggg tcgagccgca gcttccgaac tggttcgcgt tgaccaaaac gcgaaatggc  420
gccgggggcg ggaacaaggt ggtggacgac tgctacatcc ccaactacct gctccccaag  480
acccagcccg agctccagtg ggcgtggact aacatggacc agtatttaag cgcctgtttg  540
aatctcgcgg agcgtaaacg gctggtggcg cagcatctga cgcacgtgtc gcagacgcag  600
gagcagaaca aagagaatca gaaccccaat tctgacgcgc cggtcatcag gtcaaaaacc  660
tcagccaggt acatggagct ggtcggcctg ctggtggaca gtcagaaaag  720
caatggattc aggaggacca ggcctcgtac atctccttca acgccgcctc caactcgcgg  780
tcccagatca aggccgcgct ggacaatgcc tccaagatca tgagcctgac aaagacggct  840
ccggactacc tggtgggcag caacccgccg aggacatta ccaaaaatcg gatctaccaa  900
atcctgagc tgaacgggta cgatccgcag tacgcgggct ccgtcttcct gggctgggcg  960
caaaagaagt tcgggaagag gaacaccatc tggctctttg gccggccac gacgggtaaa 1020
accaacatcg cggaagccat cgcccacgcc gtgcccttct acggctgcgt aaactggacc 1080
aatgagaact ttcccttcaa cgattgcgtc gacaagatgt tgatctggtg gaggagggc 1140
aagatgacgg ccaaggtcgt ggagagcgcc aaggccatc tgggcggaag caaggtgcgc 1200
gtggaccaaa agtgcaagtc atcggcccag atcgaaccca ctcccgtgat cgtcacctcc 1260
aacaccaaca tgtgcgccgt gattgacggg aacagcacca ccttcgagca tcagcagccg 1320
ctgcaggacc ggatgtttga atttgaactt acccgccgtt tggaccatga ctttgggaag 1380
gtcaccaaac aggaagtaaa ggactttttc cggtgggctt ccgatcacgt gactgacgtg 1440
gctcatgagt tctacgtcag aaaggggtgga gctaagaaac gccccgcctc caatgacgcg 1500
gatgtaagcg agccaaaacg ggagtgcacg tcacttgcgc agccgacaac gtcagacgcg 1560
gaagcaccgg cggactacgc ggacaggtac caaaacaaat gttctcgtca cgtgggcatg 1620
aatctgatgc ttttttccctg taaaacatgc gagagaatga atcaaatttc caatgtctgt 1680
tttacgcatg gtcaaagaga ctgtgggggaa tgcttccctg aatgtcaga atctcaaccc 1740
gtttctgtcg tcaaaaagaa gacttatcag aaactgtgtc caattcatca tatcctggga 1800
agggcacccg agattgcctg ttcggcctgc gatttggcca atgtggactt ggatgactgt 1860
gtttctgagc aataa                                                  1875
```

| SEQ ID NO: 10 | moltype = DNA length = 2211 |
| FEATURE | Location/Qualifiers |
| misc_feature | 1..2211 |
| | note = CapVP1 |
| source | 1..2211 |
| | mol_type = genomic DNA |
| | organism = Adeno-associated virus - 3 |

SEQUENCE: 10

```
atggctgctg acggttatct tccagattgg ctcgaggaca accttctga aggcattcgt   60
gagtggtggg ctctgaaacc tggagtccct caacccaaag cgaaccaaca acaccaggac  120
aaccgtcggg tcttgtgct tccgggttac aaatacctcg acccggtaa cggactcgac  180
aaaggagagc cggtcaacga ggcggacgcg gcagccgtc aacacgacaa agcttacgac  240
cagcagctca aggccggtga acaccccgtac ctcaagtaca accacgccga cgccgagttt  300
caggagcgtc ttcaagaaga tacgtctttt gggggcaacc ttggcagagc agtcttccag  360
gccaaaaga ggatccttga gcctcttggt ctggttgagg aagcagctaa acggctcct  420
ggaaaagg gggctgtaga tcagtctcct caggaaccgg actcatcatc tggtgttggc  480
aaatcgggca aacagcctgc cagaaaaga ctaaatttcg gtcagactgg agactcagag  540
tcagtcccag accctcaacc tctcggagaa ccaccagcag ccccacaag tttgggatct  600
aatacaatgt cttcaggcgg tggcgcacca atggcagaca ataacgaggg tgccgatgga  660
gtgggtaatt cctcaggaaa ttggcattgc gattccaat ggctgggcga cagagtcatc  720
accaccagca ccagaaacct ggccctgccc cttacaaca accatctcta caagcaaatc  780
tccagccaat caggagcttc aaacgacaac cactactttg gctacagcac cccttggggg  840
tatttgact ttaacagatt ccactgccac ttctcaccac gtgactggca gcgactcatt  900
aacaacaact ggggattccg gcccaagaaa ctcagcttca agctcttcaa catccaagtt  960
agagggtca cgcagaacga tggcacgacg actattgcca ataaccttac cagcacggtt 1020
caagtgttta cggactcgga gtatcagctc ccgtacgtgc tcgggtcggc gaccaaggcc 1080
tgtctcccgc cgtttccagc ggacgtcttc atggtccctc agtatggata cctcaccctg 1140
aacaacggaa gtcaagcggt gggacgctca tcctttacct gctgagta cttcccttcg 1200
cagatgctaa ggactggaaa taacttccaa gccagtata ccttcgagga tgtaccttt 1260
cacagcagct acgctcacag ccagagtttg gatcgcttga tgaatcctct tattgatcag 1320
tatctgtact acctgaacag aacgcaagga caacctctg aacaaccaa ccaatcacgg 1380
ctgctttta gccaggctgg gcctcagtct atgtctttgc aggccagaaa ttggctacct 1440
gggccctgct accggcaaca gagacttca aagactgcta cgacaacaa caacagtaac 1500
tttccttga cagcggccag caaatatcat ctcaatggcc gcgactcgct ggtgaatcca 1560
ggaccagcta tggcccagtca caaggacgat gaagaaaaat tttcccctat gcacggcaat 1620
ctaatattg caaagaagg gacaacggca gtaacgcag aattagataa tgtaatgatt 1680
acggatgaag aagagattcg taccaccaat cctgtggcaa cagagcagta tggaactgtg 1740
gcaaataact tgcagagctc aaatacagct cccacgactg aactgtcaa tcatcagggg 1800
gccttacctg gcatggtgtg gcaagatcgt gacgtgtacc ttcaaggacc tatctgggca 1860
aagattcctc acacggatgg acactttcat ccttctcctg tgatgggagg ctttggactg 1920
```

```
aaacatccgc ctcctcaaat catgatcaaa aatactccgg taccggcaaa tcctccgacg   1980
actttcagcc cggccaagtt tgcttcattt atcactcagt actccactgg acaggtcagc   2040
gtggaaattg agtgggagct acagaaagaa aacagcaaac gttggaatcc agagattcag   2100
tacacttcca actacaacaa gtctgttaat gtggacttta ctgtagacac taatggtgtt   2160
tatagtgaac ctcgccctat tggaacccgg tatctcacac gaaacttgtg a            2211

SEQ ID NO: 11          moltype = DNA   length = 1872
FEATURE                Location/Qualifiers
misc_feature           1..1872
                       note = Rep78
source                 1..1872
                       mol_type = genomic DNA
                       organism = Adeno-associated virus - 4
SEQUENCE: 11
atgccggggt tctacgagat cgtgctgaag gtgcccagcg acctggacga gcacctgccc     60
ggcatttctg actcttttgt gagctgggtg gccgagaagg aatgggagct gccgccggat    120
tctgacatgg acttgaatct gattgagcag gcacccctga ccgtgccgga aaagctgcaa    180
cgcgagttcc tggtcgagtg gcgccgcgtg agtaaggccc cggaggccct cttctttgtc    240
cagttcgaga aggggacag ctacttccac ctgcacatcc tggtggagac cgtgggcgtc     300
aaatccatgg tggtgggccg ctacgtgagc cagattaaag agaagctggt gacccgcatc    360
taccgcgggg tcgagccgca gcttccgaac tggttcgcgg tgaccaagac gcgtaatggc    420
gccggaggcg ggaacaaggt ggtggacgac tgctacatcc ccaactacct gctccccaag    480
acccagcccg agctccagtg ggcgtggact aacatggacc agtatataag cgcctgtttg    540
aatctcgcgg agcgtaaacg gctggtggcg cagcatctga cgcacgtgtc gcagacgcag    600
gagcagaaca aggaaaacca gaaccccaat tctgacgcgc cggtcatcag gtcaaaaacc    660
tccgccaggt acatggagct ggtcgggtgg ctggtggatc ac gtcagaaaag            720
caatggatcc aggaggacca ggcgtcctac atctccttca acgccgcctc caactcgcgg    780
tcacaaatca aggccgcgct ggacaatgcc tccaaaatca tgagcctgac aaagacgggct   840
ccggactacc tggtgggcca gaacccgccg gaggacattt ccagcaaccg catctaccga    900
atcctcgaga tgaacgggta cgatccgcag tacgcggcct ccgtcttcct gggctgggcg    960
caaaagaagt tcgggaagag gaacaccatc tggctctttg gccggccac gacgggtaaa    1020
accaacatcg cggaagccat cgccacgccg gtgcccttct acggcgcgt gaactggacc    1080
aatgagaact ttccgttcaa cgattgcgtc gacaagatgg tgatctggtg ggaggagggc    1140
aagatgacgg ccaaggtcgt agagagcgcc aaggccatct gggcggaaa caaggtcgc     1200
gtggaccaaa agtgcaagtc atcgcccaag atcgacccaa ctccgtgat cgtcacctcc    1260
aacaccaaca tgtgcgcggt catcgacgga aactcgacca ccttcgagca ccaacaacca   1320
ctccaggacc ggatgttcaa gttcgagctc accaagcgcc tggagcacga ctttggcaag   1380
gtcaccaagc aggaagtcaa agacttttc cggtgggcgt cagatcacgt gaccgaggtg    1440
actcacgagt tttacgtcag aaagggtgga gctagaaaga ggcccgcccc caatgacgca   1500
gatataagtg agcccaagcg gcctgtccg tcagttgcgc agccatcgac gtcagacgcg    1560
gaagctccgg tggactacgc ggacaggtac caaaacaaat gttctcgtca cgtgggtatg   1620
aatctgatgc ttttttcctg ccggcaatgc gagagaatga atcagaatgt ggacatttgc   1680
ttcacgcacg gggtccatgga ctgtgccgag tgcttccccg tgtcagaatc tcaacccgtg   1740
tctgtcgtca gaaagcggac gtatcagaaa ctgtgtccga ttcatcacat catgggggag   1800
gcgcccgagg tggcctgctc ggcctgcgaa ctggccaatg tggacttgga tgactgtgac   1860
atggaacaat aa                                                       1872

SEQ ID NO: 12          moltype = DNA   length = 2205
FEATURE                Location/Qualifiers
misc_feature           1..2205
                       note = CapVP1
source                 1..2205
                       mol_type = genomic DNA
                       organism = Adeno-associated virus - 4
SEQUENCE: 12
atgactgacg gttaccttcc agattggcta gaggacaacc tctctgaagg cgttcgagag      60
tggtgggcgc tgcaacctgg agcccctaaa cccaaggcaa atcaacaaca tcaggacaac     120
gctcggggtc ttgtgcttcc gggttacaaa tacctcggac ccgcaacgg actcgacaag     180
ggggaacccg tcaacgcagc ggacgcggca gccctgcgagc acgacaaggc ctacgaccag    240
cagctcaagg ccggtgacaa cccctacctc aagtacaacc acgccgacgc ggagttccaa    300
cagcggcttc agggcgacac atcgtttggg gcaacctcg gcagcagt cttccaggcc       360
aaaaagaggg ttcttgaacc tcttggtctg gttgagcaag cgggtgagac ggctcctgga    420
aagaagagac cgttgattga atccccccag cagcccgact cctccacggg tatcggcaaa    480
aaaggcaagc agccggctaa aaagaagctc gttttcgaag acgaaactgg acgaggcgac    540
ggacccctg agggatcaac ttccggagcc atgtctgatg acagtgagat gcgtgcagca    600
gctggcggag ctgcagtcga gggcggacaa ggtgccgatg agtgggtaa tgcctcgggt   660
gattggcatt gcgattccac ctggtctgag ggccacgtca cgaccaccag caccagaacc   720
tgggtcttgc ccacctacaa caaccaccte tacaagcgac tcggagagag cctgcagtcg   780
aacacctaca acgattctc caccccctgg ggatactttg acttcaacg cttccactgc    840
cacttctcac cacgtgactg gcagcgactc atcaacaaca ctggggcat gcgacccaaa    900
gccatgcggg tcaaaatctt caacatccag gtcaaggagg tcacgacgtc gaacggcgag    960
acaacggtgg ctaataacct taccagcacg gttcagatct tgcggactc gtcgtacgaa    1020
ctgccgtacg tgatggatgc gggtcaagag ggcagcctgc ctccttttcc caacgacgtc   1080
tttatggtgc cccagtacgg ttacctgacg ctgaatgacg gcagccaacg cgcagcaacag   1140
actgacagaa atgccttcta ctgcctggag tactttcctt cgcagatgct gcggactggc   1200
aacaactttg aaattacgta cagttttgag aaggtgcctt tccactcgat gtacgcgcac   1260
agccagagtc tggaccggct gatgaaccct ctcatcgacc agtacctgtg gggactgcaa   1320
tcgaccacca ccggaaccac cctgaatgcc gggactgcca ccaccaactt taccaagctg   1380
cggcctacca actttttccaa ctttaaaaag aactggctgc ccgggccttc aatcaagcag   1440
```

```
cagggcttct caaagactgc caatcaaaac tacaagatcc ctgccaccgg gtcagacagt   1500
ctcatcaaat acgagacgca cagcactctg gacggaagat ggagtgccct gaccccggga   1560
cctccaatgg ccacggctgg acctgcggac agcaagttca gcaacagcca gctcatcttt   1620
gcggggccta aacagaacgg caacacggcc accgtacccg ggactctgat cttcacctct   1680
gaggaggagc tggcagccac caacgccacc gatacgacca tgtggggcaa cctacctggc   1740
ggtgaccaga gcaacagcaa cctgccgacc gtggacagac tgacagcctt gggagccgtg   1800
cctggaatgt tctggcaaaa cagagacatt tactaccagg gtcccatttg ggccaagatt   1860
cctcataccg atggacactt tcaccctca ccgctgattg gtgggtttgg gctgaaacac   1920
ccgcctcctc aaatttttat caagaacacc ccggtacctg cgaatcctgc aacgaccttc   1980
agctctactc cggtaaactc cttcattact cagtacagca ctggccaggt gtcggtgcag   2040
attgactggg agatccagaa ggagcggtcc aaacgctgga accccgaggt ccagtttacc   2100
tccaactacg gacagcaaaa ctctctgttg tgggctcccg atgcggctgg gaaatacact   2160
gagcctaggc ctatcggtac ccgctacctc acccaccacc tgtaa                  2205

SEQ ID NO: 13          moltype = DNA  length = 1833
FEATURE                Location/Qualifiers
misc_feature           1..1833
                       note = Rep78
source                 1..1833
                       mol_type = genomic DNA
                       organism = Adeno-associated virus - 5
SEQUENCE: 13
atggctacct tctatgaagt cattgttcgc gtcccatttg acgtggagga acatctgcct    60
ggaatttctg acagctttgt ggactgggta actggtcaaa tttgggagct gcctccagag   120
tcagatttaa atttgactct ggttaacag cctcagttga cggtggctga tagaattcgc    180
cgcgtgttcc tgtacgagtg gaacaaattt tccaagcagg agtccaaatt ctttgtgcag    240
tttgaaaagg gatctgaata ttttcatctg cacacgcttg tggagacctc cggcatctct    300
tccatggtcc tcggccgcta cgtgagtcag attcgcgccc agctggtgaa agtggtcttc    360
cagggaattg aaccccagat caacgactgg gtcgccatca ccaaggtaaa gaagggcgga    420
gccaataagg tggtggattc tgggtatatt cccgcctaca ctgtcgccgaa ggtccaaccg    480
gagcttcagt gggcgtggac aaacctggac gagtataaat tggccgccct gaatctggag    540
gagcgcaaac ggctcgtcgc gcagtttctg cagaatcct cgcagcgctc gcaggaggcg    600
gcttcgcagc gtgagttctc ggctgacccg gtcatcaaaa gcaagacttc ccagaaatac    660
atggcgctcg tcaactggct cgtggagcac ggcatcactt ccgagaagca gtggatccag    720
gaaaatcagg agagctacct ctccttcaac tccaccggca actctcggag ccagatcaag    780
gccgcgctcg acaacgcgac caaaattatg agtctgacaa aaagcgcggt ggactacctc    840
gtggggagct ccgttcccga ggacatttca aaaaacagaa tctggcaaat ttttgagatg    900
aatggctacg accggcctta cgcgggatcc atcctctacg gctggtgtca gcgctccttc    960
aacaagagga cacgcgtctg gctctacgga ccgccacga ccggcaagac caatatcgcg   1020
gaggccatcg cccacactgt gcccttttac ggctgcgtga actggaccaa tgaaaacttt   1080
ccctttaatg actgtgtgga caaaatgctc atttggtggg aggagggaaa gatgaccaac   1140
aaggtggttg aatccgccaa ggccatcctg gggggctcaa aggtgcgggt cgatcagaaa   1200
tgtaaatcct ctgttcaaat tgattctacc cctgtcatta aacttccaa tacaaacatg   1260
tgtgtggtgg tggatgggaa ttccacgacc tttgaacacc agcagccgct ggaggaccgc   1320
atgttcaaat ttgaactgac taagcggctc cgccagatt ttggcaagat tactaagcag   1380
gaagtcaagg acttttttgc ttgggcaaag gtcaatcagg tgccggtgac tcacgagttt   1440
aaagttccca gggaattggc gggaactaaa gggcggaga aatctctaaa acgcccactg   1500
ggtgacgtca ccaatactag ctataaaagt ctggagaagc gggccaggct ctcatttgtt   1560
cccgagacgc ctcgcagttc agacgtgact gttgatcccg ctcctctgcg accgctcaat   1620
tggaattcaa ggtatgattg caaatgtgac tatcatgctc aatttgacaa catttctaac   1680
aaatgtgatg aatgtgaata tttgaatcgg gcaaaatg gatgtatctg tcacaatgta   1740
actcactgtc aaatttgtca tgggattccc ccctgggaa aggaaacttt gtcagatttt   1800
ggggattttg acgatgccaa taagaacagt taa                                1833

SEQ ID NO: 14          moltype = DNA  length = 2175
FEATURE                Location/Qualifiers
misc_feature           1..2175
                       note = CapVP1
source                 1..2175
                       mol_type = genomic DNA
                       organism = Adeno-associated virus - 5
SEQUENCE: 14
atgtcttttg ttgatcaccc tccagattgg ttggaagaag ttggtgaagg tcttcgcgag    60
ttttttgggc ttgaagcggg cccaccgaaa ccaaaaccga tcagcagca tcaagatcaa   120
gcccgtggtc ttgtgctgcc tggttataac tatctcggac ccggaaacgg tctcgatcga    180
ggagagcctg tcaacagggc agacgaggtc gcgcgagagc acgacatctc gtacaacgag    240
cagcttgagg cgggagacaa cccctacctc aagtacaacc acgcggacgc cgagtttcag    300
gagaagctcg ccgacgacac atccttcggg ggaaacctcg gaaaggcagt ctttcaggcc    360
aagaaaaggg ttctcgaacc ttttggcctg gttgaagagg gtgctaagac ggccccctac    420
ggaaagcgga tagacgacca cttttccaaaa agaagaaggg ctcggaccga agaggactcc    480
aagcccttcca cctcgtcaga cgccgaagct ggacccagcg atccagca gctgcaaatc    540
ccagcccaac cagcctcaag tttgggagct gatacaatgt ctgcgggagg tggcggccca    600
ttgggcgaca taaccaagg tgccgatgga gtgggcaatg cctcgggaga ttggcattgc    660
gatcccacgt ggatggggca cagagtcgtc accaagtcca ccaggaccga gatatggcag    720
cattggatgc gcaagcggta caagaagttc acggaagaga cagcaagcgg cggtgctgcc    780
agctacaaca accaccagta ccgagagatc aaaagcggct ccgtcacggg aagcaacgtc    840
aacgcctact ttgatacag cacccctggg ggtactttg actttaaccg cttccacagc    900
cactggagcc ccgagactg gcaaagacta atcaacaact actgggtgtt cagccccgg    960
tccctcagag tcaaaatctt caacattcaa gtcaaagagg tcacggtgca ggactccacc    960
accaccatcg ccaacaacct cacctccacc gtccaagtgt ttacggacga cgactaccag   1020
```

-continued

| | |
|---|---|
| ctgccctacg tcgtcggcaa cgggaccgag ggatgcctgc cggccttccc tccgcaggtc | 1080 |
| tttacgctgc cgcagtacgg ttacgcgacg ctgaaccgcg acaacacaga aaatcccacc | 1140 |
| gagaggagca gcttcttctg cctagagtac tttcccagca agatgctgag aacgggcaac | 1200 |
| aactttgagt ttacctacaa ctttgaggag gtgcccttcc actccagctt cgctcccagt | 1260 |
| cagaacctgt tcaagctggc caacccgctg gtggaccagt acttgtaccg cttcgtgagc | 1320 |
| acaaataaca ctggcggagt ccagttcaac aagaactggg ccgggagata cgccaacacc | 1380 |
| tacaaaaact ggttcccggg gcccatgggc cgaaccagg gctggaacct gggctccggg | 1440 |
| gtcaaccgcg ccagtgtcag cgccttcgcc acgaccaata ggatggagct cgagggcgcg | 1500 |
| agttaccagg tgcccccgca gccgaaccgg atgaccaaca acctccaggg cagcaacacc | 1560 |
| tatgccctgg agaacactat gatcttcaac agccagccgg cgaacccggg caccaccgcc | 1620 |
| acgtacctcg agggcaacat gctcatcacc agcgagagcg agacgcagcc ggtgaaccgc | 1680 |
| gtggcgtaca acgtcggcgg gcagatggcc accaacaacc agagctccac cactgccccc | 1740 |
| gcgaccggca cgtacaacct ccaggaaatc gtgcccggca gcgtgtggat ggagagggac | 1800 |
| gtgtacctcc aaggacccat ctgggccaag atcccagaga cggggtgcga ctttcaccc | 1860 |
| tctccggcca tgggcggatt cggactcaaa caccaccgc ccatgatgct catcaagaac | 1920 |
| acgcctgtgc ccgaaaatat caccagcttc tcggacgtgc ccgtcagcag cttcatcacc | 1980 |
| cagtacagca ccgggcaggt caccgtggag atggagtggg agctcaagaa ggaaaactcc | 2040 |
| aagaggtgga acccagagat ccagtacaca aacaactaca acgacccca gtttgtggac | 2100 |
| tttgcccgg acagcaccgg ggaatacaga accaccgac ctatcggaac ccgatacctt | 2160 |
| acccgacccc tttaa | 2175 |

| SEQ ID NO: 15 | moltype = DNA  length = 1872 |
|---|---|
| FEATURE | Location/Qualifiers |
| misc_feature | 1..1872 |
| | note = Rep78 |
| source | 1..1872 |
| | mol_type = genomic DNA |
| | organism = Adeno-associated virus - 6 |

SEQUENCE: 15

| | |
|---|---|
| atgccggggt tttacgagat tgtgattaag gtccccagcg accttgacga gcatctgccc | 60 |
| ggcattctg acagctttgt gaactggggtg gccgagaagg aatgggagtt gccgccagat | 120 |
| tctgacatgg atctgaatct gattgagcag gcacccctga ccgtggccga gaagctgcag | 180 |
| cgcgacttcc tggtccagtg gcgccgcgtg agtaaggccc cggaggccct cttctttgtt | 240 |
| cagttcgaga agggcgagtc ctacttccac tccatattc tggtggagac cacgggggtc | 300 |
| aaatccatgg tgctgggccg cttcctgagt cagattaggg acaagctggt gcagaccatc | 360 |
| taccgcggga tcgagccgac cctgcccaac tggttcgcgg tgaccaagac gcgtaatggc | 420 |
| gccgaggggg gaacaaggt ggtggacgag tgctacatcc caactacct cctgcccaag | 480 |
| actcagcccg agctgcagtg ggcgtggact aacatggagg agtatataag cgcgtgttta | 540 |
| aacctggcg agcgcaaacg gctcgtggcg cacgacctga cccacgtcag ccagacccag | 600 |
| gagcagaaca aggagaatct gaaccccaat tctgacgcgc ctgtcatccg gtcaaaaacc | 660 |
| tccgcacgct acatggagct ggtcgggtgg ctggtggacc ggggcatcac ctccgagaag | 720 |
| cagtggatcc aggaggacca ggcctcgtac atctccttca acgccgcctc caactcgcgg | 780 |
| tccagatca aggccgctct ggacaatgcc ggcaagatca tggcgctgac caaatccgtg | 840 |
| cccgactacc tggtaggccc cgctccgccc gccgacatta aaaccaaccg catttaccgg | 900 |
| atcctggagc tgaacggcta cgaccctgcc tacgccggct ccgtctttct cggctgggcc | 960 |
| cagaaaaggt tcgaaaacg caacaccatc tggctgtttg gccgccac cacgggcaag | 1020 |
| accaacatcg cggaagccat cgcccacgcc gtgcccttct acggctgcgt caactggacc | 1080 |
| aatgagaact ttcccttcaa cgattgcgtc gacaagatgg tgatctggtg ggaggagggc | 1140 |
| aagatgacgg ccaaggtcgt ggagtccgcc aaggccattc tcggcggcag caaggtgcgc | 1200 |
| gtggaccaaa agtgcaagtc gtccgcccag atcgatccca ccccgtgat cgtcacctcc | 1260 |
| aacaccaaca tgtgcgccgt gattgacggg aacagcacca ccttcgagca ccagcagccg | 1320 |
| ttgcaggacc ggatgttcaa atttgaactc accccgccgtc tggagcatga ctttggcaag | 1380 |
| gtgacaaagc aggaagtcaa agagttcttc cgctgggcgc aggatcacgt gaccgaggtg | 1440 |
| gcgcatgagt tctacgtcag aaaggggtgga gccaacaaga gacccgcccc cgatgacgcg | 1500 |
| gataaaagcg agcccaagcg ggcctgcccc tcagtcgcgg atccatcgac gtcagacgcg | 1560 |
| gaaggagctc cggtgactt tgccgacagg taccaaaaca aatgttctcg tcacgcgggc | 1620 |
| atgcttcaga tgctgtttcc ctgcaaaaca tgcgagagaa tgaatcagaa ttcaacatt | 1680 |
| tgcttcacgc acgggaccag agactgttca gaatgttcc ccggcgtgtc agaatctcaa | 1740 |
| ccggtcgtca gaaagaggac gtatcggaaa ctctgtgcca ttcatcatct gctgggcggg | 1800 |
| gctccccgaga ttgcttgctc ggcctgcgat ctggtcaacg tggatctgga tgactgtgtt | 1860 |
| tctgagcaat aa | 1872 |

| SEQ ID NO: 16 | moltype = DNA  length = 2211 |
|---|---|
| FEATURE | Location/Qualifiers |
| misc_feature | 1..2211 |
| | note = CapVP1 |
| source | 1..2211 |
| | mol_type = genomic DNA |
| | organism = Adeno-associated virus - 6 |

SEQUENCE: 16

| | |
|---|---|
| atggctgccg atggttatct tccagattgg ctcgaggaca acctctctga ggcattcgc | 60 |
| gagtggtggg acttgaaacc tggagccccg aaacccaaag ccaaccagca aaagcaggac | 120 |
| gacggccggg gtctggtgct tcctggctac aagtacctcg accccttcaa cggactcgac | 180 |
| aagggggagc ccgtcaacgc ggcggatgca gcggccctcg agcacgacaa ggcctacgac | 240 |
| cagcagctca aagcgggtga caatccgtac ctgcggtata accacgccga cgccgagttt | 300 |
| caggagcgtc tgcaagaaga tacgtctttt gggggcaacc tcgggcgagc agtcttccag | 360 |
| gccaagaaga gggttctcga acctttggt ctggttgagg aaggtgctaa gacggctcct | 420 |
| ggaaagaaac gtccggtaga gcagtcgcca aagagccag actcctcctc gggcattggc | 480 |
| aagacaggcc agcagcccgc taaaaagaga ctcaattttg gtcagactgg cgactcagag | 540 |

```
tcagtcccg   acccacaacc   tctcggagaa   cctccagcaa   ccccgctgc    tgtgggacct    600
actacaatgg  cttcaggcgg   tggcgcacca   atggcagaca   ataacgaagg   cgccgacgga    660
gtgggtaatg  cctcaggaaa   ttggcattgc   gattccacat   ggctgggcga   cagagtcatc    720
accaccagca  cccgaacatg   ggccttgccc   acctataaca   accacctcta   caagcaaatc    780
tccagtgctt  caacggggc    cagcaacgac   aaccactact   tcggctacag   cacccctgg     840
gggtattttg  atttcaacag   attccactgc   catttctcac   cacgtgactg   cagcgactc     900
atcaacaaca  attggggatt   ccggcccaag   agactcaact   tcaagctctt   caacatccaa    960
gtcaaggagg  tcacgacgaa   tgatggcgtc   acgaccatcg   ctaataacct   taccagcacg   1020
gttcaagtct  tctcggactc   ggagtaccag   ttgccgtacg   tcctcggctc   tgcgcaccag   1080
ggctgcctcc  ctccgttccc   ggcggacgtg   ttcatgattc   cgcagtacgg   ctacctaacg   1140
ctcaacaatg  gcagccaggc   agtgggacgg   tcatccttt    actgcctgga   atatttccca   1200
tcgcagatgc  tgagaacggg   caataacttt   accttcagct   acaccttcga   ggacgtgcct   1260
ttccacagca  gctacgcgca   cagccagagc   ctggaccggc   tgatgaatcc   tctcatcgac   1320
cagtacctgt  attacctgaa   cagaactcag   aatcagtccg   gaagtgccca   aacaaggac    1380
ttgctgttta  gccggggtc    tccagctggc   atgtctgttc   agcccaaaaa   ctggctacct   1440
ggaccctgtt  accggcagca   gcgcgtttct   aaaacaaaaa   cagacaacaa   caacagcaac   1500
tttacctgga  ctggtgcttc   aaaatataac   cttaatgggc   gtgaatctat   aatcaaccct   1560
ggcactgcta  tggcctcaca   caaagacgac   aaagacaagt   tctttcccat   gagcggtgtc   1620
atgattttg   gaaaggagag   cgccggagct   tcaaacactg   cattggacaa   tgtcatgatc   1680
acagacgaag  aggaaatcaa   agccactaac   ccgtggcca    ccgaaagatt   tgggactgtg   1740
gcagtcaatc  tccagagcag   cagcacagac   cctgcgaccg   gagatgtgca   tgttatggga   1800
gccttacctg  gaatggtgtg   gcaagacaga   gacgtatacc   tgcagggtcc   tatttgggga   1860
aaaattcctc  acacgatgg    acactttcac   ccgtctcctc   tcatgggcgg   ctttggactt   1920
aagcaccgc   ctcctcagat   cctcatcaaa   aacacgcctg   ttcctgcgaa   tcctccggca   1980
gagttttcg   ctacaaagtt   tgcttcattc   atcacccagt   attccacagg   acaagtgagc   2040
gtggagattg  aatgggagct   gcagaaagaa   aacagcagct   gctggaatcc   cgaagtgcag   2100
tatacatcta  actatgcaaa   atctgccaac   gttgatttca   ctgtggacaa   caatggactt   2160
tatactgagc  ctcgcccat    ggcacccgt    acctcaccc    gtcccctgta   a            2211

SEQ ID NO: 17           moltype = DNA  length = 1872
FEATURE                 Location/Qualifiers
misc_feature            1..1872
                        note = Rep78
source                  1..1872
                        mol_type = genomic DNA
                        organism = Adeno-associated virus - 7
SEQUENCE: 17
atgccgggtt  tctacgagat   cgtgatcaag   gtgccgagcg   acctggacga   gcacctgccg     60
ggcatttctg  actcgtttgt   gaactgggtg   gccgagaagg   aatggagct    gccccgcgga    120
tctgacatgg  atctgaatct   gatcgagcag   gcacccctga   ccgtggccga   gaagctgcag    180
cgcgacttcc  tggtccaatg   gcgccgcgtg   agtaaggccc   cggaggccct   gttctttgtt    240
cagttcgaga  agggcgagag   ctacttccac   cttcacgttc   tggtggagac   cacggggtc     300
aagtccatgg  tgctaggccg   cttcctgagt   cagattcggg   agaagctgat   ccagaccatc    360
taccgcgggg  tcgagcccac   gctgcccaac   tggttcgcgg   tgaccaagac   gcgtaatggc    420
gccggcgggg  ggaacaaggt   ggtggacgag   tgctacatcc   caactacct    cctgcccaag    480
acccagcccg  agctgcagtg   ggcgtggact   aacatggagg   agtatataag   cgcgtgtttg    540
aacctggccg  aacgcaaacg   gctcgtggcg   cagcacctga   cccacgtacg   ccagacgcag    600
gagcagaaca  aggagaatct   gaaccccaat   tctgacgcgc   ccgtgatcag   gtcaaaaacc    660
tccgcgcgct  acatggagct   ggtcgggtgg   ctggtggacc   ggggcatcac   ctccgagaag    720
cagtggatcc  aggaggacca   ggcctcgtac   atctccttca   acgccgcctc   caactcgcgg    780
tcccaatca   aggccgcgct   ggacaatgcc   ggcaagatca   tggcgctgac   caaatccgcc    840
cccgactacc  tggtggggcc   ctcgctgccc   gcggacatta   aaaccaaccg   catctaccgc    900
atcctggagc  tgaacgggta   cgatcctgcc   tacgccggct   ccgtctttct   cggctgggcc    960
cagaaaaagt  tcgggaagcg   caacaccatc   tggctgtttg   gcccgccac    caccggcaag   1020
accaacattg  cggaagccat   cgcccacgcc   gtgcccttct   aaggctggcc   caactggacc   1080
aatgagaact  ttccccttcaa  cgattgcgtc   gacaagatgg   tgatctggtg   ggaggagggc   1140
aagatgacgg  ccaaggtcgt   ggagtccgcc   aaggccattc   tcggcggcag   caaggtgcgc   1200
gtggaccaaa  agtgcaagtc   gtccgcccag   atcgaccca    ccccgtgat    cgtcacctcc   1260
aacaccaaca  tgtgcgccgt   gattacggga   aacagcacca   ccttcgagca   acagcagccg   1320
ttgcaggacc  ggatgttcaa   atttgaactc   accgcgtc     tggagcacga   ctttggcaag   1380
gtgacgaagc  aggaagtcaa   agagttcttc   cgctgggcca   gtgatcacgt   gaccgaggtg   1440
gcgcatgagt  tctacgtcag   aaagggcgga   gccagcaaaa   gacccgccc    cgatgacgcg   1500
gatataagcg  agcccaagcg   ggcctgcccc   tcagtcgcgg   atccatcgac   gtcagacgcg   1560
gaaggagtc   cggtggactt   tgccgacagg   taccaaaaca   aatgttctcg   tcacgcgggc   1620
atgattcaga  tgctgtttcc   ctgcaaaacg   tgcgagagaa   tgaatcagaa   tttcaacatt   1680
tgcttcacac  acggggtcag   agactgttta   gagtgtttcc   ccggcgtgtc   agaatctcaa   1740
ccggtcgtca  gaaaaaagac   gtatcggaaa   ctctgcgcga   ttcatcatct   gctggggcgg   1800
gcgcccgaga  ttgcttgctc   ggcctgcgac   ctggtcaacg   tggacctgga   cgactgcgtt   1860
tctgagcaat  aa                                                               1872

SEQ ID NO: 18           moltype = DNA  length = 2214
FEATURE                 Location/Qualifiers
misc_feature            1..2214
                        note = CapVP1
source                  1..2214
                        mol_type = genomic DNA
                        organism = Adeno-associated virus - 7
SEQUENCE: 18
atggctgccg  atggttatct   tccagattgg   ctcgaggaca   acctctctga   gggcattcgc     60
```

-continued

```
gagtggtggg acctgaaacc tggagccccg aaacccaaag ccaaccagca aaagcaggac    120
aacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctca aagcgggtga caatccgtac ctgcggtata accacgccga cgccgagttt    300
caggacgtc tgcaagaaga tacgtcattt gggggcaacc tcgggcgagc agtcttccag     360
gccaagaagc gggttctcga acctctcggt ctggttgagg aaggcgctaa gacggctcct    420
gcaaagaaga gaccggtaga gccgtcacct cagcgttccc ccgactcctc cacgggcatc    480
ggcaagaaag ccagcagcc cgccagaaag agactcaatt tcggtcagac tggcgactca    540
gagtcagtcc ccgaccctca acctctcgga gaacctccag cagcgccctc tagtgtggga    600
tctggtacag tggctgcagg cggtggcgca ccaatggcag acaataacga aggtgccgac    660
ggagtgggta atgcctcagg aaattggcat tgcgattcca catggctggg cgacagagtc    720
attaccacca gcacccgaac ctgggccctg cccacctaca caaccacct ctacaagcaa     780
atctccagtg aaactgcagg tagtaccaac gacaacacct acttcggcta cagcaccccc    840
tggggtgtat ttgactttaa cagattccac tgccacttct caccacgtga ctggcagcga    900
ctcatcaaca caactgggg attccggccc aagaagctgc ggttcaagct cttcaacatc     960
caggtcaagg aggtcacgac gaatgacggc gttacgacca tcgctaataa ccttaccagc   1020
acgattcagg tattctcgga ctcggaatac cagctgccgt acgtcctcgg ctctgcgcac   1080
cagggctgcc tgcctccgtt cccggcggca tgtcttcatga ttcctcagta cggctacctg  1140
actctcaaca atggcagtca gtctgtggga cgttcctcct tctactgcct ggagtacttc   1200
ccctctcaga tgctgagaac gggcaacaac tttgagttca gctacagctt cgaggacgtg   1260
cctttccaca gcagctacgc acacagccag agcctggacc ggctgatgaa tcccctcatc   1320
gaccagtact tgtactacct ggcagaaca cagagtaacc caggaggcac agctggcaat    1380
cgggaactgc agttttacca gggcgggcct tcaactatgg ccgaacaagc caagaattgg   1440
ttacctggac cttgcttccg gcaacaaaga gtctccaaaa cgctggatca aaacaacaac   1500
agcaactttg cttggactgg tgccaccaaa tatcacctga acggcagaaa ctcgttggtt   1560
aatccggcg tcgccatggc aactcacaag gacgacgaag accgcttttt cccatccagc   1620
ggagtcctga ttttttggaaa aactggagca actaacaaaa ctacattgga aaatgtgtta   1680
atgacaaatg aagaagaaat tcgtcctact aatcctgtag ccacgaaga atacgggata     1740
gtcagcagca acttacaagc ggctaatact gcagcccaga cacaagttgt caacaaccag   1800
ggagccttac ctggcatggt ctggcagaac cgggacgtgt acctgcaggg tcccatctgg   1860
gccaagattc ctcacacgga tggcaacttt caccccgtctc ctttgatggg cggctttgga   1920
cttaaacatc cgcctcctca gatcctgatc aagaacactc ccgttccgc taatcctccg   1980
gaggtgttta ctcctgccaa gtttgcttcg ttcatcacac agtacagcac cggacaagtc   2040
agcgtggaaa tcgagtggga gctgcagaag gaaaacagca agcgctggaa ccggagatt    2100
cagtacacct ccaactttga aaagcagact ggtgtggact ttgccgttga cagccagggt   2160
gtttactctg agcctcgccc tattggcact cgttacctca cccgtaatct gtaa          2214

SEQ ID NO: 19       moltype = DNA  length = 1878
FEATURE             Location/Qualifiers
misc_feature        1..1878
                    note = Rep78
source              1..1878
                    mol_type = genomic DNA
                    organism = Adeno-associated virus - 8
SEQUENCE: 19
atgccgggct tctacgagat cgtgatcaag gtgccgagcg acctggacga gcacctgccg    60
ggcatttctg actcgtttgt gaactgggtg gccgagaagg aatgggagct gccccccggat    120
tctgacatgg atcggaatct gatcgagcag gcacccctga ccgtggccga gaagctgcag    180
cgcgacttcc tggtccaatg gcgccgcgtg agtaaggccc cggaggccct cttctttgtt    240
cagttcgaga agggcgagag ctactttcac ctgcacgttc tggtcgagac cacggggtc     300
aagtccatgt gctaggccg cttcctgagt cagattcagg aaaagcttgg tccagaccat    360
ctacccgcgg ggtcgagccc caccttgccc aactggttcg cggtgaccaa agacgcggta    420
atggcgccgg cggggggaa caaggtggtg gacgagtgct acatccccaa ctacctcctg     480
cccaagactc agcccgagct gcagtgggcg tggactaaca tggaggagta tataagcgcg    540
tgcttgaacc tggccgagc caaacggctc gtggcgcagc acctgaccca cgtcagccag    600
acgcaggagc agaacaagga gaatctgaac cccaattctg acgcgccgt gatcaggtca    660
aaaacctccg cgcgctatat ggagctggtc gggtggctgg tggaccgggg catcaccctcc   720
gagaagcagt ggatccagga ggaccaggcc tcgtacatct ccttcaacgc cgcctccaac    780
tcggtctccc agatcaaggc cgcgctggac aatgccggca agatcatggc gctgaccaaa    840
tccgcgcccg actacctggt ggggcctcg ctgcccgcgg acattaccca gaaccgcatc    900
taccgcatcc tcgctctcaa cggctacgac cctgcctacg ccggctccgt cttctctcggc    960
tgggctcaga aaagtcggg gaaacgcaac catctcggc tgtttggacc cgccaccacc    1020
ggcaagacca cattgcgga agcatcgcc cacgccgtgc ccttctacgg ctgcgtcaac    1080
tggaccaatg agaactttcc cttcaatgat tgcgtcgaca agtggtgat ctggtgggca    1140
gagggcaaga tgacgccaa ggtcgtggag tccgccaagg ccattctcgg cggcagcaag    1200
gtgcgcgtgg accaaaagtg caagtcgtcc gcccagatcg accccacccc cgtgatcgtc    1260
acctccaaca ccaacatgtg cgccgtgatt gacgggaaca gcaccacctt cgagcaccag    1320
cagcctctcc aggaccggat gttaagttc gaactcaccg ccgtctggga gcacgacttt    1380
ggcaaggtga caaagcagga agtcaaagag ttcttccgct ggccagcagt gtcacgtgacc    1440
gaggtggcgc atgagtttta cgtcagaaag ggcggagcca gcaaagcac cgcccccgat    1500
gacgcggata aaagcgagcc caagcgggcc tgccctcag tcgcggatcc atcgacgtca    1560
gacgcggaag gagctccggt ggactttgcc gacaggtacc aaaacaaatg ttctcgtcac    1620
gcgggcatgc ttcagatgct gtttccctgc aaaacgtgcg agagaatgaa tcagaatttc    1680
aacattgct tcacacacgg tgtcagagac tgctcagagt gtttcccgg tgttcccgg       1740
tctcaaccgg tcgtcagaaa gaggacgtat cggaaactgt gtcgcattca tcatctgctg   1800
gggcgggctc ccgagattgc ttgctcggcc tgcgatctgg tcaacgtgaa cctggatgac    1860
tgtgttcctg agcaataa                                                 1878

SEQ ID NO: 20       moltype = DNA  length = 2217
```

```
FEATURE              Location/Qualifiers
misc_feature         1..2217
                     note = CapVP1
source               1..2217
                     mol_type = genomic DNA
                     organism = Adeno-associated virus - 8
SEQUENCE: 20
atggctgccg atggttatct tccagattgg ctcgaggaca acctctctga gggcattcgc   60
gagtggtggg cgctgaaacc tggagccccg aagcccaaag ccaaccagca aaagcaggac  120
gacggccggg gtctggtgct tcctggctac aagtacctcg gacccttcaa cggactcgac  180
aaggggggagc ccgtcaacgc ggcggacgca gcggccctcg agcacgacaa ggcctacgac  240
cagcagctgc aggcgggtga caatccgtac ctgcggtata accacgccga cgccgagttt  300
caggagcgtc tgcaagaaga tacgtctttt ggggggcaacc tcgggcgagc agtcttccag  360
gccaagaagc gggttctcga acctctcggt ctggttgagg acggctaa gacggctcct  420
ggaaagaaga gaccggtaga gccatcaccc cagcgttctc cagactcctc tacgggcatc  480
ggcaagaaag ccaacagcc cgccagaaaa agactcaatt ttggtcagac tggcgactca  540
gagtcagttc cagaccctca acctctcgga gaacctccag cagcgccctc tggtgtggga  600
cctaatacaa tggctgcagg cggtggcgca ccaatggcga ataacaagga aggcgccgac  660
ggagtgggta gttcctcggg aaattggcat tgcgattcca catggctggg cgacagagtc  720
atcaccacca gcacccgaac ctgggccctg cccacctaca acaaccacct ctacaagcaa  780
atctccaacg gacatcggg aggagccacc aacgacaaca cctacttcgg ctacagcacc  840
ccctggggt attttgactt taacagattc cactgccact tttcaccacg tgactggcag  900
cgactcatca caacaactg gggattccgc cccaagagac tcagcttcaa gctcttcaac  960
atccaggtca aggaggtcac gcagaatgaa ggcaccaaga ccatcgccaa taacctcacc 1020
agcaccatcc aggtgtttac ggactcggag taccagctgc cgtacgttct cggctctgcc 1080
caccagggct gcctgcctcc gttcccggcg gacgtgttca tgattcccca gtacggctac 1140
ctaacactca acaacggtag tcaggccgtg ggacgctcct ccttctactg cctggaatac 1200
tttcctccgc agatgctgag aaccggcaac aacttccagt ttacttacac cttcgaggac 1260
gtgcctttcc acagcagcta cgcccacagc cagagcttgg accggctgat gaatcctctg 1320
attgaccagt acctgtacta cttgtctcgg actcaaacaa caggaggcac ggcaaatacg 1380
cagactctgg gcttcagcca aggtgggcct aatacaatgg ccaatcaggc aaagaactgg 1440
ctgccaggac cctgttaccg ccaacaacgt gtctcaacga caaccgggca aaacaacaat 1500
agcaactttg cctggactgc tgggaccaaa taccatctga atggaagaaa ttcattggct 1560
aatcctggca tcgctatggc aacacacaaa gacgacgagg agcgttttt tcccagtaac 1620
gggatcctga ttttttggcaa acaaaatgct gccagagaca atgcggatta cagcgatgtc 1680
atgctcacca gcgaggaaga aatcaaaacc actaacctg tggctacaga ggaatacggt 1740
atcgtggcag ataacttgca gcagcaaaac acggctcctc aaattggaac tgtcaacagc 1800
caggggggcct acccggtat ggtctggcag aaccgggacg tgtacctgca gggtcccatc 1860
tgggccaaga ttcctcacac ggacggcaac ttccacccgt ctccgctgat gggcggcttt 1920
ggcctgaaac atcctccgcc tcagatcctg atcaagaaca cgcctgtacc tgcggatcct 1980
ccgaccacct tcaaccagtc aaagctgaac tctttcatca cgcaatacag caccggacag 2040
gtcagcgtgg aaattgaatg ggagctgcag aaggaaaaca gcaagcgctg gaaccccgag 2100
atccagtaca cctccaacta ctacaaatct acaagtgtgg actttgctgt taatacagaa 2160
ggcgtgtact ctgaaccccg ccccattggc acccgttacc tcacccgtaa tctgtaa    2217

SEQ ID NO: 21         moltype = DNA   length = 2211
FEATURE              Location/Qualifiers
misc_feature         1..2211
                     note = CapVP1
source               1..2211
                     mol_type = genomic DNA
                     organism = Adeno-associated virus - 9
SEQUENCE: 21
atggctgccg atggttatct tccagattgg ctcgaggaca accttagtga aggaattcgc   60
gagtggtggg ctttgaaacc tggagccccc t caacccaagg caaatcaaca acatcaagac  120
aacgctcgag gtcttgtgct tccgggttac aaataccttg acccggcaa cggactcgac  180
aaggggggagc cggtcaacgc agcagacgcg cggcccctcg agcacgacaa ggcctacgac  240
cagcagctca aggccggaga caacccgtac ctcaagtaca accacgccga cgccgagttc  300
caggagcggc tcaaagaaga tacgtctttt ggggggcaacc tcgggcgagc agtcttccag  360
gccaaaaaga ggcttcttga acctctcggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag cccctcagg tgtgggatct  600
cttacaatgg cttcaggtgg tggcgcacca gtggcagaca ataacgaagg tgccgatgga  660
gtgggtagtt cctcgggaaa ttggcattgc gattccacat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcacccc  840
tggggggtatt ttgacttcaa cagattccac tgccactttt caccacgtga ctggcagcga  900
ctcatcaaca acaactgggg attccggcct aagcgactca acttcaagct tttcaacatt  960
caggtcaaag aggttacgga caacaatgga gtcaagacca tcgccaataa ccttaccagc 1020
acggtccagg tcttcacgga ctcagactat cagctcccgt acgtgctcgg tcggctcac 1080
gagggctgcc tcccgccgtt cccagcggac gttttcatga ttcctcagta cgggtatctg 1140
acgcttaatg atggaagcca ggcgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaagagac tattaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
```

-continued

```
ggacctgcta tggccagcca caaagaagga gaggaccgtt tctttccttt gtctggatct      1620
ttaattttg gcaaacaagg aactggaaga acaacgtgg atgcggacaa agtcatgata        1680
accaacgaag aagaaattaa aactactaac ccggtagcaa cggagtccta tggacaagtg      1740
gccacaaacc accagagtgc ccaagcacag gcgcagaccg gctgggttca aaaccaagga     1800
atacttccgg gtatggtttg gcaggacaga gatgtgtacc tgcaaggacc catttgggcc     1860
aaaattcctc acacggacgg caactttcac ccttctccgc tgatgggagg gtttggaatg     1920
aagcacccgc ctcctcagat cctcatcaaa aacacacctg tacctgcgga tcctccaacg     1980
gccttcaaca aggacaagct gaactctttc atcacccagt attctactgg ccaagtcagc     2040
gtggagatcg agtgggagct gcagaaggaa aacagcaagc gctggaaccc ggagatccag     2100
tacacttcca actattacaa gtctaataat gttgaatttg ctgttaatac tgaaggtgta     2160
tatagtgaac cccgcccat tggcaccaga tacctgactc gtaatctgta a               2211

SEQ ID NO: 22              moltype = DNA  length = 1869
FEATURE                    Location/Qualifiers
misc_feature               1..1869
                           note = Rep78
source                     1..1869
                           mol_type = genomic DNA
                           organism = Adeno-associated virus - 10
SEQUENCE: 22
atgccgggct tctacgagat cgtgatcaag gtgccgagcg acctggacga gcacctgccg      60
ggcatttctg actcgtttgt gaactgggtg gccgagaagg aatggagct cccccggat      120
tctgacatgg atcggaatct gatcgagcag gcaccctga ccgtggccga gaagctgcag     180
cgcgacttcc tggtccactg gcgccgcgtg agtaaggccc cggaggccct cttctttgtt     240
cagttcgaga agggcgagtc ctactttcac ctgcacgttc tggtcgagac cacggggtc     300
aagtccatgg tcctgggccg cttcctgagt cagatccaga caggctggt cagagaccatc    360
taccgcgggg tagagcccac gctgcccaac tggttcgcgg tgaccaagac gcgaaatggc    420
gccggcgggg gaacaaggt ggtggacgag tgctacatcc caactacct cctgcccaag      480
acgcagcccg agctgcagtg ggcgtggact aacatggagg agtatataag cgcgtgtctg    540
aacctgccgg agcgtaaacg gctcgtggcg cagcacctga cccacgtcag ccagacgcag    600
gagcagaaca aggagaatct gaacccgaat tctgacgcgc ccgtgatcag gtcaaaaacc    660
tccgcgcgct acatggagct ggtcgggtgg ctggtggacc ggggcatcac ctccgagaag    720
cagtggatcc aggaggacca ggcctcgtac atctccttca cgccgcctc caactcgcgg    780
tcccagatca aggccgcgct ggacaatgcc ggaaagatca tggcgtgac caaatccgcg    840
cccgactacc tggtaggccc gtccttaccc gcggacatta aggccaaccg catctaccgc   900
atcctggagc tcaacggcta cgaccccgcc tacgccggct ccgtcttcct gggctgggcg   960
cagaaaaagt tcggtaaaag gaatacaatt tggctgttcg ggcccgccac caccggcaag  1020
accaacatcg cggaagccat cgcccacgcc gtgcccttct acggctgcgt caactggacc 1080
aatgagaact ttccccttcaa cgattgcgtc gacaagatgg tgatctgtca ggaggagggc 1140
aagatgaccg ccaaggtcgt ggagtccgcc aaggccattc tgggcggaag caaggtgcgc 1200
gtcgaccaaa agtgcaagtc ctcggcccag atcgacccca cgcccgtgat cgtcacctcc 1260
aacaccaaca tgtgcgccgt gatcgacggg aacagcacca ccttcgagca ccagcagccc 1320
ctgcaggacc gcatgttcaa gttcgaggctc accgcgctg tggagcacga ctttggcaag 1380
gtgaccaagc aggaagtcaa agagttcttc cgctgggctc aggatcacgt gactgaggtg 1440
acgcatgagt tctacgtcag aaagggcgga gccaccaaaa gacccgcccc cagtgacgcg 1500
gatataagcg agcccaagcg ggcctgcccc tcagttgcgg agccatcgac gtcagacgcg 1560
gaagcaccgg tggactttgc ggacaggtac caaaacgaat gttctcgtca cgcgggcatg 1620
cttcagatgc tgtttccctg caagacatgc gagagaatga atcagaattt caacgtctgc 1680
ttcacgcacg gggtcagaga ctgctcagag tgcttccccg gcgcgtcaga atctcaacct 1740
gtcgtcagaa aaagacgta tcagaaactg tgcgcgattc atcatctgct ggggcgggca 1800
cccgagattg cgtgttcggc ctgcgatctc gtcaacgtgg acttggatga ctgtgtttct 1860
gagcaataa                                                         1869

SEQ ID NO: 23              moltype = DNA  length = 2217
FEATURE                    Location/Qualifiers
misc_feature               1..2217
                           note = CapVP1
source                     1..2217
                           mol_type = genomic DNA
                           organism = Adeno-associated virus - 10
SEQUENCE: 23
atggctgctg acggttatct tccagattgg ctcgaggaca acctctctga gggcattcgc    60
gagtggtggg acctgaaacc tggagccccc aagcccaagg ccaaccagca gaagcaggac   120
gacggccggg gtctggtgct tcctggctac aagtacctcg gacccttcaa cggactcgac   180
aagggggagc cgtcaacgc ggcggacgca gcgccctcg agcacgacaa ggcctacgac    240
cagcagctca aagcgggtga caatccgtac ctgcggtata accacgccga cgccgagttt   300
caggagcgtc tgcaagaaga tacgtctttt ggggcaacc tcgggcgagc agtcttccag    360
gccaagaagc gggttctcga acctctcggt ctggttgagg aagctgctaa gacggctcct   420
ggaaagaaga gaccggtaga accgtcacct cagcgttccc ccgactcctc cacgggcatc   480
ggcaagaaag ccagcagcc cgctaaaaag agactgaact ttgggcagac tggcgagtca   540
gagtcagtcc ccgaccctca accaatcgga gaaccaccag caggccctc tggtctggga    600
tctggtacaa tggctgcagg cggtggcgct ccaatggcag acaataacga aggcgccgac    660
ggagtgggta gttcctcagg aaattggcat tgcgattcca tggctggg cgacagagtc     720
atcaccacag aacccgaac ctgggcctg cccacctaca caaccaccct ctacaagcaa    780
atctccaacg gacatcggg aggaagcacc aacgacaaca cctacttcgg ctacagcacc    840
ccctggggt atttttgactt caacagattc cactgccact tctcaccacg tgactggcag    900
cgactcatca caacaactg gggattccgg ccaaaaagac tcagcttcaa gcttcaac     960
atccaggtca aggaggtcac gcagaatgaa ggcaccaaga ccatcgccaa taaccttacc  1020
agcacgattc aggtatttac ggactcggaa taccagctgc cgtacgtcct cggctccgcg  1080
```

```
caccagggct gcctgcctcc gttcccggcg gatgtcttca tgattcccca gtacggctac   1140
ctgacactga acaatggaag tcaagccgta ggccgttcct ccttctactg cctggaatat   1200
tttccatctc aaatgctgcg aactggaaac aattttgaat tcagctacac cttcgaggac   1260
gtgcctttcc acagcagcta cgcacacagc cagagcttgg accgactgat gaatcctctc   1320
attgaccagt acctgtacta cttatccaga actcagtcca caggaggaac tcaaggtacc   1380
cagcaattgt tattttctca agctgggcct gcaaacatgt cggctcaggc caagaactgg   1440
ctgcctggac cttgctaccg gcagcagcga gtctccacga cactgtcgca aaacaacaac   1500
agcaactttg cttggactgg tgccaccaaa tatcacctga acggaagaga ctctctggtg   1560
aatcccggtg tcgccatggc aacccacaag gacgacgagg aacgcttctt cccgtcgagc   1620
ggagtcctga tgtttggaaa acagggtgct ggaagagaca atgtggacta cagcagcgtt   1680
atgctaacaa gcgaagaaga aattaaaacc actaaccctg tagccacaga acaaatcggt   1740
gtggtggctg caaacttgca gcaagccaat cagggcctta ttgtgggaaa tgtcaacagc   1800
caaggagcct tacctggcat ggtctggcag aaccgagacg tgtacctgca gggtcccatc   1860
tgggccaaga ttcctcacac ggacggcaac tttcacccgt ctcctctgat gggcggcttt   1920
ggacttaaac acccgcctcc acagatcctg atcaagaaca cgccggtacc tgcggatcct   1980
ccaacaacgt tcagccaggc gaaattgct tccttcatca cgcagtacag caccggacag   2040
gtcagcgtgg aaatcgagtg ggagctgcag aaggagaaca gcaaacgctg gaacccgag    2100
attcagtaca cttcaaacta ctacaaatct acaaatgtga actttgctgt caatacagag   2160
ggaacttatt ctgagcctcg ccccattggt actcgttatc tgacacgtaa tctgtaa      2217

SEQ ID NO: 24             moltype = DNA   length = 1869
FEATURE                   Location/Qualifiers
misc_feature              1..1869
                          note = Rep78
source                    1..1869
                          mol_type = genomic DNA
                          organism = Adeno-associated virus - 11
SEQUENCE: 24
atgccgggct tctacgagat cgtgatcaag gtgccgagcg acctggacga gcacctgccg    60
ggcatttctg actcgtttgt gaactgggtg gccgagaagg aatgggagct gccccggat   120
tctgacatgg atcggaatct gatcgagcag gcaccctga ccgtggccga gaagctgcag   180
cgcgacttcc tggtccactg gcgcgcgcgt agtaaggccc cggaggccct cttctttgtt   240
cagttcgaga agggcgagtc ctacttccac ctccacgttc tcgtcgagac cacggggtc    300
aagtccatgg tcctgggccg cttcctgagt cagatcagag acaggctggt gcagatcca    360
taccgcgggg tcgagcccac gctgcccaac tggttcgcgg tgaccaagac gcgaaatggc   420
gccggcgggg gaacaaggt ggtggacgag tgctacatcc caactacct cctgcccaag    480
acccagcccg agctgcagtg ggcgtggact aacatggagg agtatataag cgcgtgtcta   540
aacctcgcgg agcgtaaacg gctcgtggcg cagcacctga cccacgtcag ccagacgcag   600
gagcagaaca aggagaatct gaacccgaat tctgacccgg ccgtgatcgg gtcaaaaacc   660
tccgcgcgct acatggagct ggtcgggtgg ctggtggacc ggggcatcac ctccgagaag   720
cagtggatcc aggaggacca ggcctcgtac atctccttca acgccgcctc caactcgcgg   780
tcccagatca aggccgcgct ggacaatgcc ggaaagatca tggcgctgac caaatcccgc    840
cccgactacc tggtaggccc gtccttaccc gcggacatta aggccaaccg catctaccgc   900
atcctggagc tcaacggcta cgaccccgcc tacgccggct ccgtcttcct gggctgggcg   960
cagaaaaagt tcgtaaacg caacaccatc tggctgtttg gccccgccac caccggcaag  1020
accaacatcg cggaagccat agcccacgcc gtgcccttct acgctgcgt gaactggacc   1080
aatgaaact ttcccttcaa cgattgcgtc gacaagatgg tgatctgtg gagggaggc   1140
aagatgaccg ccaaggtcgt ggagtccgcc aaggccattc tgggcggaag caaggtgcgc   1200
gtggaccaaa agtgcaagtc ctcggcccag atcgacccca cgcccgtgat cgtcacctcc   1260
aacaccaaca tgtgcgccgt gatcgacggg aacagcacca ccttcgagca ccagcagccg   1320
ctgcaggacc gcatgttcaa gttcgagctc acccgccgtc tggagcacga cttggcaag   1380
gtgaccaagc aggaagtcaa agagttcttc cgctgggctc aggatcacgt gactgaggtg   1440
gcgcatgagt tctacgtcag aaagggcgga gccaccaaaa gacccgcccc cagtgacgcg   1500
gatataagca gcccaagcg ggcctgcccc tcagttccgg agccatcgac gtcagacgcg   1560
gaagcaccgg tggactttgc ggacaggtac caaaacaagt tctctcgtca cgcgggcatg   1620
cttcagatgc tgtttccctg caagacatgc gagagaatga atcagaattt caacgtctgc   1680
ttcacgcacg gggtcagaga ctgctcagag tgcttccccg cgcgtcaga atctcaaccc   1740
gtcgtcagaa aaagacgta tcagaaactg tgcgcgattc atcatctgct ggggcgggca   1800
cccgagattg cgtgttcggc ctgcgatctc gtcaacgtgg acttggatga ctgtgtttct   1860
gagcaataa                                                          1869

SEQ ID NO: 25             moltype = DNA   length = 2202
FEATURE                   Location/Qualifiers
misc_feature              1..2202
                          note = CapVP1
source                    1..2202
                          mol_type = genomic DNA
                          organism = Adeno-associated virus - 11
SEQUENCE: 25
atggctgctg acggttatct tccagattgg ctcgaggaca acctctctga gggcattcgc    60
gagtggtggg acctgaaacc tggagccccg aagcccaagg ccaaccagca gaagcaggac   120
gacgccgggg tctggtgct tcctggctac aagtacctcg gacccttcaa cggactcgac   180
aagggggagc ccgtcaacgc ggcggacgca gcggccctcg agcacgacaa ggcctacgac   240
cagcagctca aagcgggtga caatccgtac ctgcggtata accgcgagtt t             300
caggagcgtc tgcaagaaga tacgtctttt gggggcaacc tcgggcgagc agtcttccag    360
gccaagaaga gggtactcga acctctgggc ctggttgaag aagtgctaa aacgctcct    420
ggaagagaa gaccgttaga gtcaccacaa gagcccgact cctcctcggg catcggcaaa    480
aaaggcaaac aaccagccag aaagaggctc aactttgaag gagactctgg agccggagac   540
ggacccctg aaggatcaga taccagcgcc atgtcttcag acattgaaat gcgtgcagca   600
```

```
ccgggcggaa atgctgtcga tgcgggacaa ggttccgatg gagtgggtaa tgcctcggtg    660
gattggcatt gcgattccac ctggtctgag ggcaaggtca caacaacctc gaccagaacc    720
tgggtcttgc ccacctacaa caaccacttg tacctgcgtc tcggaacaac atcaagcagc    780
aacacctaca acgattctc caccccctgg ggatattttg acttcaacag attccactgt    840
cacttctcac cacgtgactg gcaaagactc atcaacaaca actgggggact acgaccaaaa    900
gccatgcgcg ttaaaatctt caatatccaa gttaaggagg tcacaacgtc gaacggcgag    960
actacggtcg ctaataacct taccagcacg gttcagatat ttgcggactc gtcgtatgag   1020
ctcccgtacg tgatggacgc tggacaagag gggagcctgc ctcctttccc caatgacgtg   1080
ttcatggtgc tcaatatgg ctactgtggc atcgtgactg gcgagaatca gaaccaaacg   1140
gacagaaacg cttctactg cctggagtat tttccttcgc aaatgttgag aactggcaac   1200
aactttgaaa tggcttacaa cttttgagaag gtgccgttcc actcaatgta tgctcacagc   1260
cagagcctgg acagactgat gaatcccctc ctggaccagt acctgtggca cttacagtcg   1320
actacctctg gagagactct gaatcaaggc aatgcagcaa ccacatttgg aaaaatcagg   1380
agtggagact ttgcctttta cagaaagaac tggctgccaa ggctttgtgt caacagcag   1440
agattctcaa aaactgccag tcaaaattac aagattcctg ccagcggggg caacgctctg   1500
ttaaagtatg acacccacta taccttaaac aaccgctgga gcaacatcgc gcccggacct   1560
ccaatggcca cagccggacc ttcggatggg gacttcagta acgcccagct tatattccct   1620
ggaccatctg ttaccggaaa tacaacaact tcagccaacc atctgttgtt tacatcagaa   1680
gaagaaattg ctgccaccaa cccaagagac acgacatgt tggccagat tgctgacaat   1740
aatcagaatg ctacaactgc tcccataacc ggcaacgtga ctgctatggg agtgctgcct   1800
ggcatggtgt ggcaaaacag agacatttac taccaagggc caatttgggc caagatccca   1860
cacgcggggt gacattttca tccttcaccg ctgattgctg ggtttggact gaaacaccccg   1920
cctcccccaga tattcatcaa gaacactccc gtacctgcca atcctgcgac aaccttcact   1980
gcagccagtg ggactcttt catcacacaa tacagcaccg gccaggtcgc tgttcagatt   2040
gaatgggaaa ttgaaaagga acgctccaaa cgctggaatc ctgaagtgca gtttacttca   2100
aactatggga accagtcttc tatgttgtgg gctcctgata caactgggaa gtatacagag   2160
ccgcgggtta ttggctctcg ttatttgact aatcatttgt aa                      2202

SEQ ID NO: 26          moltype = DNA  length = 1866
FEATURE                Location/Qualifiers
misc_feature           1..1866
                       note = Rep78
source                 1..1866
                       mol_type = genomic DNA
                       organism = Adeno-associated virus - 12
SEQUENCE: 26
atgccggggt tctacgaggt ggtgatcaag gtgcccagcg acctggacga gcacctgccc     60
ggcatttctg actcctttgt gaactgggtg gccgagaagg aatgggagtt gccccccgat    120
tctgacatgg atcagaatct gattgacag gcaccccctga ccgtggccga gaagctgcag    180
cgcgagttcc tggtggaatg gcgccgagtg agtaaattc tggaggccaa gttttttgtg    240
cagtttgaaa aggggggactc gtactttcat ttgcatattc tgattgaaat taccggcgtg    300
aaatccatgg tggtgggccg ctacgtgagt cagattagga taaactgat ccagcgcatc    360
taccgcgggg tcgagcccca gctgcccaac tggttcgtga tcacaaagac ccgaaatgct    420
gccggaggcg ggaacaaggt ggtggacgag tgctacatcc ccaactacct gctcccaag    480
gtccagcccg agcttcagtg ggcgtggact aacatgagg agtatataag cgcctgtttg    540
aacctcgcg agcgtaaacg gctcgtgcg cagcacctga cgcacgtctc ccagacccag    600
gagggcgaca aggagaatct gaaccccgaat tctgacgcgc cggtgatccg gtcaaaaacc    660
tccgccaggt acatggagct ggtcgggtgg ctggtggaca agggcatcac gtccgagaag    720
cagtggatcc aggaggacca ggcctcgtac atctccttca acgcggcctc caactcccgg    780
tcgcagatca aggcggccct ggacaatgcc tccaaaatca tgagcctcac caaaacggct    840
ccggactatc tcatcgggca gcagccccgtg ggggacatta ccaccaaccg gatctacaaa    900
atcctggaac tgaacgggta cgaccccaag tacgccgcct ccgtcttcct cggctgggcc    960
cagaaaaagt ttggaaagcg caacaccatc tggctgtttg gcccgccac caccggcaag   1020
accaacatcg cggaagccat cgcccacgcg gtcccttct acggctgcgt caactggacc   1080
aatgaaact tcccttcaa cgactgcgtc gacaaaatgg tgattgggtt ggaggagggc   1140
aagatgaccg ccaaggtcgt agagtccgcc aaggccattg ggcgcgcag caaggtcgcc   1200
gtggaccaaa aatgcaaggc ctctgcgcag atcgacccca ccccgtgat gcctcacctcc   1260
aacaccaaca tgtgcgccgt gattgacggg aacagcacca ccttcgagca ccagcagccc   1320
ctgcaggacc ggatgttcaa gttttaactc acccgccgcc tcgaccacga ctttggccag   1380
gtcaccaaggc aggaagtcaa ggactttttc cggtggggcg ctgatcacgt gactgacgtg   1440
gctcatgagt tttacgtcac aaagggggtgga gctaagaaaa ggcccgcccc ctctgacgag   1500
gatataagcg agcccaagcg gccgcgcgtg tcatttgcgc agccgagac gtcagacgcg   1560
gaagctcccg gagacttcgc cgacaggtac caaaacaaat gttctcgtca cgcgggtatg   1620
ctgcagatgc tctttccctg caagacgtgc gagagaatga atcagaattc caacgtctgc   1680
ttcacgcacg gtcagaaaga ttgcggggag tgctttcccg gttcagaatc tcaaccggtt   1740
tctgtcgtca gaaaaacgta tcagaaactg tgcatccttc atcagctccg ggggcacccc   1800
gagatcgcct gctctgcttg cgaccaactc aaccccgatt ggacgattg ccaatttgag   1860
caataa                                                             1866

SEQ ID NO: 27          moltype = DNA  length = 2229
FEATURE                Location/Qualifiers
misc_feature           1..2229
                       note = CapVP1
source                 1..2229
                       mol_type = genomic DNA
                       organism = Adeno-associated virus - 12
SEQUENCE: 27
atggctgctg acgttatct tccagattgg ctcgaggaca acctctctga aggcattcgc     60
gagtggtggg cgctgaaacc tggagctcca caacccaagg ccaaccaaca gcatcaggac    120
```

```
aacggcaggg gtcttgtgct tcctgggtac aagtacctcg gacccttcaa cggactcgac   180
aagggagagc cggtcaacga ggcagacgcc gcggccctcg agcacgacaa ggcctacgac   240
aagcagctcg agcaggggga caacccgtat ctcaagtaca accacgccga cgccgagttc   300
cagcagcgct tggcgaccga cacctctttt ggggcaacc tcgggcgagc agtcttccag   360
gccaaaaaga ggattctcga gcctctgggt ctggttgaag agggcgttaa aacggctcct   420
ggaaagaaac gcccattaga aaagactcca aatcggccga ccaacccgga ctctgggaag   480
gccccggcca agaaaaagca aaaagacggg gaaccagccg actctgctag aaggacactc   540
gactttgaag actctggagc aggagacgga ccccctgagg gatcatcttc cggagaaatg   600
tctcatgatg ctgagatgcg tgcggcgcca ggcggaaatg ctgtcgaggc gggacaaggt   660
gccgatggag tgggtaatgc ctccgaactg attccacctg gtcagaggc                720
cgagtcacca ccaccagcac ccgaacctgg gtcctaccca cgtacaacaa ccacctgtac   780
ctgcgaatcg gaacaacggc caacagcaac acctacaacg gattctccac cccctgggga   840
tactttgact ttaaccgctt ccactgccac ttttcccac gcgactggca gcgactcatc    900
aacaacaact ggggactcag gccgaaatcg atgcgtgtta aaatcttcaa catacaggtc   960
aaggaggtca cgacgtcaaa cggcgagact acggtcgcta ataaccttac cagcacggtt  1020
cagatctttg cggattcgac gtatgaactc ccatacgtga tggacgccgg tcaggagggg  1080
agcttttcctc cgtttcccaa cgacgtcttt atggttcccc aatacggata ctgcggagtt  1140
gtcactggaa aaaaccagaa ccagacagac agaaatgcct tttactgcct ggaatacttt  1200
ccatcccaaa tgctaagaac tggcaacaat tttgaagtca gttaccaatt tgaaaaagtt  1260
cctttccatt caatgtacgc gcacagccag agcctggaca gaatgatgaa tcctttactg  1320
gatcagtacc tgtggcatct gcaatcgacc actaccggaa attcccttaa tcaaggaaca  1380
gctaccacca cgtacgggaa aattaccact ggagacttgt cctactacag gaaaaactgg  1440
ttgcctggag cctgcattaa acaacaaaaa ttttcaaaga atgccaatca aaactacaag  1500
attcccgcca gcggggggaga cgcccttttta aagtatgaca cgcataccac tctaaatggg  1560
cgatggagta acatggctcc tggacctcca atggcaaccg caggtgccgg ggactcggat  1620
tttagcaaca gccagctgat ctttgccgga cccaatccga gcggtaacac gaccacatct  1680
tcaaacaatt tgttgtttac ctcagaaagg gagattgcca caacaaaccc acgagacacg  1740
gacatgtttg cacagattgc agataataat caaaatgcca ccaccgcccc tcacatcgct  1800
aacctggacg ctatggaat tgttcccgga atggtctggc aaaacagaga catctactac  1860
cagggccta tttgggccaa ggtccctcac acggacgagc actttcaccc ttcgccgctg  1920
atggggaggat ttggactgaa acacccgcct ccacagattt tcatcaaaaa cacccccgta  1980
cccgccaatc ccaatactac ctttagcgct gcaaggatta attctttcct gacgcagtac  2040
agcaccggac aagttgccgt tcagatcgac tgggaaattc agaaggagca ttccaaacgc  2100
tggaatcccg aagttcaatt tacttcaaac tacggcactc aaaattctat gctgtgggct  2160
cccgacaatg ctggcaacta ccacgaactc cgggctattg ggtcccgttt cctcacccac  2220
cacttgtaa                                                          2229

SEQ ID NO: 28          moltype = DNA   length = 1872
FEATURE                Location/Qualifiers
misc_feature           1..1872
                       note = Rep78
source                 1..1872
                       mol_type = genomic DNA
                       organism = Adeno-associated virus - 13
SEQUENCE: 28
atgccgggat tctacgagat tgtcctgaag gtgcccagcg acctggacga gcacctgcct    60
ggcattcctg actcttttgt aaactgggtg gcggagaagg aatgggagct gccgccggat   120
tctgacatgg atctgaatct gattgagcag gcacccctaa ccgtggccga aaagctgcaa   180
cgcgaattcc tggtcgagtg gcgccgcgtg agtaaggccc cggaggccct cttctttgtt   240
cagttcgaga aggggggacag ctacttccac ctacacattc tggtggagac cgtgggcgtg   300
aaatccatgg tggtggggccg ctacgtgagc cagattaaag agaagctggt gacccgcatc   360
taccgcgggg tcgagccgca gcttccgaac tggttcgcgg tgaccaagac gcgtaatggc   420
gccggaggcg ggaacaaggt ggtggacgac tgctacatcc caactacctt gctccccaag   480
acccagcccg agctccagtg ggcgtggact aatatggacc agtatttaag cgcctgtttg   540
aatctcgcga agcgtaaacg gctggtggcg cagcatctga cgcacgtgtc gcagacgcag   600
gagcagaaca aagagaacca gaatcccaat tctgacgcgc cggtcgatcag atcaaaaacc   660
tccgcgaggt acatgagct ggtcgggtgg ctggtggacc gcgggatcac gtcagaaaag   720
caatggatcc aggaggacca ggcctcttac atctccttca acgccgcctc caactcgcgg   780
tcacaaatca aggccgcact ggacaatgcc tccaaattta tgacctgac aaaaacggct   840
ccggactacc tggtgggaaa caacccgccg gaggacatta ccagcaaccg gatctacaaa   900
atcctcgaga tgaacgggta cgatccgcag tacgcggcct ccgtcttcct gggctggggcg   960
caaaagaagt tcgggaagag gaacaccatc tggctctttg gccggccac gacgggtaaa  1020
accaacatcg ctgaagctat cgcccacgcc gtgccctttt acggctgcgt gaactggacc  1080
aatgagaact ttccgttcaa cgattgcgtc gacaagatgg tgatctgttag gactgaggtg  1140
aagatgacgg ccaaggtcgt ggagtccgcc aaggccattc tgggcggaag caaggtcgcg  1200
gtggaccaaa agtgcaagtc atcggcccag atcgaccaa ctcccgtcat cgtcacctcc  1260
aacaccaaca tgtgcgcggt catcgacgga aattccacca cctccgagca ccaacaacca  1320
ctccaagacc ggatgttcaa gttcgagctc accaagcgc tggacacga ctttggcaag  1380
gtcaccaagc aggaagtcaa ggacttttc cggtggggcg cagatcacgt gactgaggtg  1440
tctcacgagt tttacgtcag aaagggtgga gctagaaaga ggcccgcccc caatgacgca  1500
gatataagtg agcccaagcg ggcctgtccg tcagttgcgc agccatcgac gtcagacgcg  1560
gaagctccgg tggactacgc ggacaggtac caaaacaaat gttctcgtca cgtgggcatg  1620
aatctgatgc tttttccctg ccggcaatgc gagagaatga atcagaatgt ggacatttgc  1680
ttcacgcacg gggtcatgga ctgtgcgag tgcttcccgg tgtcagaatc tcaacccgtg  1740
tctgtcgtca gaaagcggac atatcagaaa ctgtgtccga ttcatcacat catgggggag  1800
gcgcccgagg tggcttgttc ggcctgcgat ctggccaatg tggacttgga tgactgtgac  1860
atggagcaat aa                                                      1872

SEQ ID NO: 29          moltype = DNA   length = 2202
```

```
FEATURE              Location/Qualifiers
misc_feature         1..2202
                     note = CapVP1
source               1..2202
                     mol_type = genomic DNA
                     organism = Adeno-associated virus - 13
SEQUENCE: 29
atgactgacg gttaccttcc agattggcta gaggacaacc tctctgaagg cgttcgagag    60
tggtgggcgc tgcaacctgg agcccctaaa cccaaggcaa atcaacaaca tcaggacaac   120
gctcggggtc ttgtgcttcc gggttacaaa tacctcggac ccggcaacgg acttgacaag   180
ggggaacccg tcaacgcagc ggacgcggca gccctcgaac acgacaaggc ctacgaccag   240
cagctcaagg ccggtgacaa ccccctacct caagtacaac cgccgacgc cgagtttcag    300
gagcgtcttc aagaagatac gtcttttggg ggcaacctcg gacgagcagt cttccaggcc   360
aaaaagagga tccttgagcc tctgggtctg gttgaggaag ggctaagac ggctcctcga    420
aaaaagagac ctgtagagca atctccagca gaaccggact cctcttcggg catcggcaaa   480
tcaggccagc agcccgctag aaaaagactg aatttggtc agactggcga cacagagtca    540
gtcccagacc ctcaaccact cggacaacct cccgcagccc cctctggtgt gggatctact   600
acaatggctt caggcggtgg cgcaccaatg gcagacaata acgagggtgc cgatggagtg   660
ggtaattcct caggaaattg gcattgcgat tcccaatggc tggcgacag agtcatcacc    720
accagcaccc gcacctgggc cctgcccacc tacaacaatc acctctacaa gcaaatctcc   780
agccaatcag gagccaccaa cgacaaccac tactttggct acagcacccc ctgggggtat   840
tttgacttca acagattcca ctgccacttt tcaccacgtg actggcaaag actcatcaac   900
aacaactggg gattccgacc caagagactc aacttcaagc tctttaacat tcaagtcaaa   960
gaggtcacgc agaatgacgg tacgacgacg attgccaata accttaccag cacggttcag  1020
gtgtttactg actccgagta ccagctcccg tacgtcctcg gctcggcgca tcagggatgc  1080
ctcccgccgt tcccagcaga cgtcttcatg gtcccacagt atggatcct caccctgaac   1140
aacgggagtc aggcggtagg acgctcttcc ttttactgcc tggagtactt tccttctcag  1200
atgctgcgta ctggaaacaa cttttcagttt agctacactt tgaagacgt gcctttccac   1260
agcagctacg ctcacagcca aagtctggac cgtctcatga tcctctgat cgaccagtac   1320
ctgtactatc tgaacaggac acaaacagcc agtggaactc acagtctcg gctactgttt  1380
agccaagctg acccaccag tatgtctctt caagctaaaa actggctgcc tggaccttgc   1440
tacagacagc agcgtctgtc aaagcaggca acgacaaca acaacagcaa ctttccctgg   1500
actggtgcca ccaaatatca tctgaatggc cgggactcat tggtgaaccc gggccctgct  1560
atggccagtc acaaggatga caaagaaaag ttttttcccca tgcatggaac cctgatattt  1620
ggtaaagaag gaacaaatgc caacaacgcg gatttggaaa atgtcatgat tacagatgaa  1680
gaagaaatcc gcaccaccaa tcccgtggct acggagcagt acgggactgt gtcaaataat   1740
ttgcaaaact caaacgctgg tccaactact ggaactgtca atcaccaagg agcgttacct  1800
ggtatggtgt ggcaggatcg agacgtgtac ctgcagggac ccatttgggc caagattcct  1860
cacaccgatg gacactttca tccttctcca ctgatgggag gttttgggct caaacaccg   1920
cctcctcaga tcatgatcaa aaacactccc gttccagcca atcctccac aaactttagt   1980
gcggcaaagt ttgcttcctt catcacacag tactccacgg ggcaggtcag cgtggagatc  2040
gagtgggagc tgcagaagga aacagcaaa cgctggaatc cgaaattca gtacacttcc   2100
aactacaaca aatctgttaa tgtggacttt actgtggaca ctaatggtgt gtattcagag  2160
cctcgcccca ttggcaccag ataccctgact cgtaatctgt aa                    2202

SEQ ID NO: 30        moltype = DNA  length = 141
FEATURE              Location/Qualifiers
misc_feature         1..141
                     note = ITR Sequence
source               1..141
                     mol_type = genomic DNA
                     organism = Adeno-associated virus
SEQUENCE: 30
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggttcc t                                              141

SEQ ID NO: 31        moltype = DNA  length = 1866
FEATURE              Location/Qualifiers
misc_feature         1..1866
                     note = Rep2 Sequence  Contains Rep78 and Rep52
source               1..1866
                     mol_type = genomic DNA
                     organism = Adeno-associated virus
SEQUENCE: 31
atgccggggt tttacgagat tgtgattaag gtccccagcg accttgacga gcatctgccc    60
ggcatttctg acagctttgt gaactgggtg gccgagaagg aatgggagtt gccgccagat   120
tctgacatgg atctgaatct gattgagcag gcacccctga ccgtggccga aagctgcag   180
cgcgactttc tgacggaatg gcgccgtgtg agtaaggccc cggaggccct tttctttgtg   240
caatttgaga agggagagag ctacttccac atgcacgtgc tcgtggaaac caccggggtg   300
aaatccatgt ttttgggacg ttttcctgagt cagattcgcg aaaaactgat tcagagaatt   360
taccgcggga tcgagccgac tttgccaaac tggttcgcgg tcacaaagac cagaaatggc   420
gccggaggcg gaacaaggt ggtggatgag tgctacatcc caattactt gctcccaaa      480
acccagctcg gctccagtg ggcgtggact aatatgaac agtatttaag cgcctgtttg     540
aatctcacgg agcgtaaacg gttggtggc cagcatctga cgcacgtgtc cagacgcag    600
gagcagaaca agagaatca gaatcccaat tctgatgcgc cggtgatcag atcaaaaact    660
tcagccaggt acatggagct ggtcgggtgg ctcgtggaca ggggattac ctcggagaag   720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
```

```
cccgactacc tggtgggcca gcagccgtg gaggacattt ccagcaatcg gatttataaa   900
attttggaac taaacgggta cgatccccaa tatgcggctt ccgtcttcct gggatgggcc   960
acgaaaaagt tcggcaagag gaacaccatc tggctgtttg gcctgcaac taccgggaag  1020
accaacatcg cggaggccat agcccacact gtgcccttct acgggtgcgt aaactggacc  1080
aatgaaact ttcccttcaa cgactgtgtc gacaagatgg tgatctggtg ggaggagggg  1140
aagatgaccg ccaaggtcgt ggagtcggca aaagccattc tcggaggaag caaggtgcgc  1200
gtggaccaga aatgcaagtc ctcggcccag atagacccga ctcccgtgat cgtcacctcc  1260
aacaccaaca tgtgcgccgt gattgacggg aactcaacga ccttcgaaca ccagcagccg  1320
ttgcaagacc ggatgttcaa atttgaactc acccgccgtc tggatcatga ctttgggaag  1380
gtcaccaagc aggaagtcaa agactttttc cggtgggcaa aggatcacgt ggttgaggtg  1440
gagcatgaat tctacgtcaa aaaggggtgga gccaagaaaa gacccgcccc cagtgacgca  1500
gatataagtg agcccaaacg ggtgcgcgag tcagttgcgc agccatcgac gtcagacgcg  1560
gaagcttcga tcaactacgc agacaggtac caaaacaaat gttctcgtca cgtgggcatg  1620
aatctgatgc tgtttcccctg cagacaatgc gagagaatga atcagaattc aaatatctgc  1680
ttcactcacg gacagaaaga ctgtttagag tgctttcccg tgtcagaatc tcaacccgtt  1740
tctgtcgtca aaaaggcgta tcagaaactg tgctacattc atcatatcat gggaaaggtg  1800
ccagacgctt gcactgcctg cgatctggtc aatgtggatt ggatgactg catctttgaa  1860
caataa                                                             1866

SEQ ID NO: 32            moltype = DNA  length = 2208
FEATURE                  Location/Qualifiers
misc_feature             1..2208
                         note = Cap2 Sequence   contains sequentially VP1, VP2, AAP,
                         VP3
source                   1..2208
                         mol_type = genomic DNA
                         organism = Adeno-associated virus
SEQUENCE: 32
atggctgccg atggttatct tccagattgg ctcgaggaca ctctctctga aggaataaga   60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca accacgccga cgcggagttt  300
caggagcgcc ttaaagaaga tacgtctttt gggggcaacc tcggacgagc agtcttccag  360
gcgaaaaaga gggttcttga acctctgggc ctggttgagg aacctgttaa gacggctccg  420
ggaaaaaaga ggccggtaga gcactctcct gtggagccag actcctcctc gggaaccgga  480
aaggcgggcc agcagcctgc aagaaaaaga ttgaattttg gtcagactgg agacgcagac  540
tcagtacctg accccagcc tctcggacag ccaccagcag cccctctgg tctgggaact  600
aatacgatgg ctacaggcag tggcgcacca atggcagaca ataacgaggg cgccgacgga  660
gtgggtaatt cctcgggaaa ttggcattgc gattccacat ggatgggcga cagagtcatc  720
accaccagca cccgaacctg ggcctgcc acctacaaca accacctcta caaacaaatt  780
tccagccaat caggagcctc gaacgacaat cactactttg gctacagcac cccttggggg  840
tattttgact tcaacagatt ccactgccac tttccaccgg atggtggca aagactcatc  900
aacaacaact ggggattccg acccaagaga ctcaacttca agctctttaa cattcaagtc  960
aaagaggtca cgcagaatga cggtacgacg acgattgcca ataacctta cagcacggtt 1020
caggtgttta ctgactcgga gtaccagctc ccgtacgtcc tcggctcggc gcatcaagga 1080
tgcctcccgc cgttcccagc agacgtcttc atggtgccaa agtatggata cctcacccctg 1140
aacaacggga gtcaggcagt aggacgctct tcatttact gcctggagta ctttcctctt 1200
cagatgctgc gtaccggaaa caactttacc ttcagctaca cttttgagga cgttcctttc 1260
cacagcagct acgctcacag ccagagtctg gaccgtctca tgaatcctct catcgaccag 1320
tacctgtatt acttgagcag aacaaaacact ccaagtgaa ccaccacga gtcaaggctt 1380
cagttttctc aggccggagc gagtgacatt cggaccagt ctaggaactg gcttcctgga 1440
ccctgttacc gccagcagcg agtatcaaag acatctgcgg ataacaacaa cagtgaatac 1500
tcgtggactg gagctaccaa gtaccacctc aatggcagag actctctggt gaatccggc 1560
ccggccatgg caagccacaa ggacgatgaa gaaaagtttt ttcctcagag cgggttctc 1620
atctttggga gcaaggctc agagaaaaca aatgtggaca ttgaaaaggt catgattaca 1680
gacgaagagg aaatcaggac aaccaatccc gtggctacgg agcagtatgg ttctgtatct 1740
accaacctcc agagaggcaa cagacaagca gctaccgcag atgtcaacac acaaggcgtt 1800
cttccaggca tggtctggca ggacagagat gtgtaccctg aggggcccat ctgggcaaag 1860
attccacaca cggacggaca ttttcacccc tctcccctca tgggtggatt cggacttaaa 1920
caccctcctc cacagattct catcaagaac acccccggtac ctgcgaatcc ttcgaccacc 1980
ttcagtgcgg caaagtttgc ttccttcatc acacagtact ccacgggaca ggtcagcgtg 2040
gagatcgagt gggagctgca gaaggaaaac agcaaacgct ggaatcccga aattcagtac 2100
acttccaact acaacaagtc tgttaatgtg gactttactg tggacactaa tggcgtgtat 2160
tcagagcctc gcccccattgg caccagatac ctgactcgta atctgtaa              2208

SEQ ID NO: 33            moltype = DNA  length = 2175
FEATURE                  Location/Qualifiers
misc_feature             1..2175
                         note = Cap5 Sequence   contains sequentially VP1, VP2, AAP,
                         VP3
source                   1..2175
                         mol_type = genomic DNA
                         organism = Adeno-associated virus
SEQUENCE: 33
atggcttttg ttgatcaccc tccagattgg ttggaagaag ttggtgaagg tcttcgcgag   60
ttttttgggc ttgaagcggg cccaccgaaa ccaaaaccca atcagcagca tcaagatcaa   120
gcccgtggtc ttgtgctgcc tggttataac tatctcggac ccgaaacgg tctcgatcga   180
ggagagcctg tcaacagggc agacgaggtc gcgcgagagc acgacatctc gtacaacgag   240
```

```
cagcttgagg cgggagacaa cccctacctc aagtacaacc acgcggacgc cgagtttcag    300
gagaagctcg ccgacgacac atccttcggg ggaaacctcg gaaaggcagt ctttcaggcc    360
aagaaaaggg ttctcgaacc ttttggcctg gttgaagagg gtgctaagac ggcccctacc    420
ggaaagcgga tagacgacca ctttccaaaa agaaagaagg ctcggaccga agaggactcc    480
aagccttcca cctcgtcaga cgccgaagct ggacccagca gatcccagca gctgcaaatc    540
ccagcccaac cagcctcaag tttgggagct gatacaatgt ctgcgggagg tggcggccca    600
ttgggcgaca ataaccaagg tgccgatgga gtgggcaatg cctcgggaga ttggcattgc    660
gattccacgt ggatggggga cagagtcgtc accaagtcca cccgaacctg ggtgctgccc    720
agctacaaca accaccagta ccgagagatc aaaagcggct ccgtcgacgg aagcaacgcc    780
aacgcctact ttggatacag caccccctgg gggtactttg actttaaccg cttccacagc    840
cactggagcc cccgagactg gcaaagactc atcaacaact actggggctt cagaccccgg    900
tccctcagag tcaaaatctt caacattcaa gtcaaagagg tcacggtgca ggactccacc    960
accaccatcg ccaacaacct cacctccacc gtccaagtgt ttacggacga cgactaccag   1020
ctgcccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa ctttgaggag gtgcccttcc actccagctt cgctcccagt   1260
cagaacctct tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg gctggaacct gggctccggg   1440
gtcaaccgcg ccagtgtcag cgccttcgcc acgaccaata ggatgctt cgagggcgcg    1500
agttaccagg tgccccgca gccgaacggc atgaccaaca gcagcaacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca acgtcggcgg gcagatggcc accaacaacc agagctccac cactgccccc   1740
gcgaccggca cgtacaacct ccaggaaatc gtgcccggca gcgtgtggat ggagagggac   1800
gtgtacctcc aaggacccat ctgggccaag atcccagaga cggggggcgca ctttcacccc   1860
tctccggcca tgggcggatt cggactcaaa caccccaccg ccatgatgct catcaagaac   1920
acgcctgtgc ccgaaaatat caccagcttc tcggacgtgc ccgtcagcag cttcatcacc   1980
cagtacagca cggggcaggt cacgtgaggaag atggagtgg agctcaagaa ggaaaactcc   2040
aagaggtgga acccagagat ccagtacaca aacaactaca acgacccca gtttgtggac   2100
tttgccccgg acagcaccgg ggaatacaga agcaccagac ctatcggaac ccgatacctt   2160
acccgacccc tttaa                                                    2175

SEQ ID NO: 34         moltype = DNA   length = 5336
FEATURE               Location/Qualifiers
misc_feature          1..5336
                      note = E2A Full Sequence
source                1..5336
                      mol_type = genomic DNA
                      organism = Adeno-associated virus
SEQUENCE: 34
cgaccgcacc ctgtgacgaa agccgcccgc aagctgcgcc cctgagttag tcatctgaac     60
ttcggcctgg gcgtctctgg gaagtaccac agtggtggga gcgggacttt cctggtacac    120
cagggcagcg ggccaactac ggggattaag gttattacga ggtgtggtgg taatagccgc    180
ctgttcgagg agaattcggt ttcggtgggc gcggattccg ttgacccggg atatcatgtg    240
gggtcccgcg ctcatgtagt ttattcgggt tgagtagtct tgggcagctc cagccgcaag    300
tcccatttgt ggctggtaac tccacatgta gggcgtggga atttccttgc tcataatggc    360
gctgacgaca ggtgctggcg ccgggtgtgg ccgctggaga tgacgtagtt ttcgcgctta    420
aatttgagaa agggcgcgaa actagtcctt aagagtcagc gcgcagtatt tgctgaagag    480
agcctccgcg tcttccagcg tgcgccgaag ctgatcttcg cttttgtgat acaggcagt    540
gcgggtgagg gagcgcagag acctgttttt tattttcagc tcttgttctt ggccctgct    600
ttgttgaaat atagcataca gagtgggaaa aatcctattt ctaagctcgc gggtcgatac    660
gggttcgttg ggcgccagac gcagcgctcc tcctcctgct gctgccgccg ctgtggattt    720
cttgggcttt gtcagagtct tgctatccgg tcgccttgc ttctgtgtga ccgctgctgt    780
tgctgccgct gccgctgccg ccggtgcagt aggggctgta gagatgacgg tagtaatgca    840
ggatgttacg ggggaaggcc acgccgtgat ggtagagaag aaagcggcgg gcgaaggaga    900
tgttgccccc acagtcttgc aagcaagcaa ctatggcgtt cttgtgcccg cgccacgagc    960
ggtagccttg gcgctgttgt tgctcttggg ctaacgcgg cggctgctta gacttaccgg   1020
ccctggttcc agtggtgtcc catctacggt tgggtcgggg aacaggcagt gccggcgggg   1080
cctgaggagc ggaggttgta gcgatgctgg gaacggttgc caatttctgg ggcgccggcg   1140
aggggaatgc gaccgagggt gacggtgttt cgtctgacac ctcttcggcc tcggaagctt   1200
cgtctaggct gtcccagtct tccatcatct cctcctcctc gtccaaaacc tcctctgcct   1260
gactgtccca gtattcctcc tcgtccgtgg gtggcgggca gctgctgctc agctcttttt   1320
tgggtgccat cctgggaagc aagggccgc ggctgctgat agggctgcgg cggcggggg    1380
attgggttga gctcctcgcc ggactggggg tccaggtaaa ccccccgtcc ctttcgtagc    1440
agaaactctt ggcgggcttt gttgatggct tgcaattggc caaggatgtg gccctgggta    1500
atgacgcagg cggtaagctc cgcatttggc gggcgggatt ggtcttcgta gaacctaatc    1560
tcgtgggcgt ggtagtcctc aggtacaaat ttgcgaaggt aagcgacgt ccacagcccg     1620
ggagtgagtt tcaaccccgg agccgcggac ttttcgtcag gcgagggacc ctgcagctca    1680
aaggtaccga taatttgact ttcgctaagc agttgcgaat tgcagaccag ggagcggtgc    1740
ggggtgcata ggttgcagcg acagtgacac tccagtaggc cgtcaccgct cacgtcttcc    1800
atgatgtcgg agtggtaggc aaggtagttg gctagctgca gaaggtagca gtgacccaa    1860
agcggcggag ggcattcacg gtacttaatg gcacacaaagt gctaggaag gcacagcag    1920
gtggcgggca gaattcctga acgctctagg ataaagttcc taaagttttg caacatgctt    1980
tgactggtga agtctggcag accctgttgc agggttttaa gcaggcgttc ggggaagata    2040
atgtccgcca ggtgcgcggc cacggagcgc tcgttaagg ccgtccatag gtccttcaag    2100
ttttgcttta gcagcttctg cagctccttt aggttgcgct cctccaggca ttgctgccac    2160
acgcccatgg ccgtttgcca ggtgtagcac agaaataagt aaacgcagtc gcggacgtag   2220
```

```
tcgcggcgcg cctcgccctt gagcgtggaa tgaagcacgt tttgcccgag gcggttttcg 2280
tgcaaaattc caaggtagga gaccaggttg cagagctcca cgttggaaat tttgcaggcc 2340
tggcgcacgt agcccggcg aaaggtgtag tgcaacgttt cctctagctt gcgctgcatc 2400
tccgggtcag caaagaaccg ctgcatgcac tcaagctcca cggtaacaag cactgcggcc 2460
atcattagct tgcgtcgctc ctccaagtcg gcaggctgcg gcgtctcaag ccagcgcgcg 2520
agctgctcat cgccaactgc gggtaggccc tcctcggttt gttcttgcaa gtttgcatcc 2580
ctctccaggg gtcgtgcacg gcgcacgatc agctcgctca tgactgtgct cataaccttg 2640
gggggtaggt taagtgccgg gtaggcaaag tgggtgacct cgatgctgcg tttcagcacg 2700
gctaggcgcg cgttgtcacc ctcaagttcc accagcactc cacagtgact ttcattttcg 2760
ctgttttctt gttgcagagc gtttgccgcg cgtttctcgt cgcgtccaag accctcaaag 2820
atttttggca cttcgtcgag cgaggcgata tcaggtatga cagcgccctg ccgcaaggcc 2880
agctgcttgt ccgctcggct gcggttggca cggcaggata ggggtatctt gcagttttgg 2940
aaaaagatgt gataggtggc aagcacctct ggcacggcaa atacggggta gaagttgagg 3000
cgcgggttgg gctcgcatgt gccgttttct tggcgttttgg gggtacgcg cggtgagaac 3060
aggtggcgtt cgtaggcaag gctgacatcc gctatggcga ggggcacatc gctgcgctct 3120
tgcaacgcgt cgcagataat ggcgcactgg cgctgcagat gcttcaacag cacgtcgtct 3180
cccacatcta ggtagtcgcc atgcctttgg tcccccgcc cgacttgttc ctcgtttgcc 3240
tctgcgtcgt cctggtcttg cttttatcc tctgttgata ctgagcgatc ctcgtcgtct 3300
tcgcttacaa aacctgggtc ctgctcgata atcacttcct cctcctcaag cggggggtgcc 3360
tcgacgggga aggtggtagg cgcgttgcg gcatcggtgg aggcggtggt ggcgaactca 3420
aagggggcgg ttaggctgtc ctccttctcg actgactcca tgatcttttt ctgcctatag 3480
gagaaggaaa tggccagtcg ggaagaggag cagcgcgaaa ccaccccga gcgcggacgc 3540
ggtgcggcgc gacgtccacc aaccatggag gacgtgtcgt cccgtcgcc gtcgccgccg 3600
cctccccgcg cgccccaaa aaagcggctg aggcggcgtc tcgagtccga ggacgaagaa 3660
gactcgtcac aagatgcgct ggtgccgcgc acacccagcc cgcggccatc gacctcgacg 3720
gcggatttgg ccattgcgtc caaaaagaaa aagaagcgcc cctctcccaa gcccgagcgc 3780
ccgccatccc cagaggtgat cgtggacagc gaggaagaaa gagaagatgt ggcgctacaa 3840
atggtgggtt tcagcaaccc accggtgcta atcaagcacg gcaagggagg taagcgcacg 3900
gtgcggcggc tgaatgaaga cgacccagtg gcgcggggta tgcggacgca agaggaaag 3960
gaagagtcca gtgaagcgga aagtgaaagc acggtgataa acccgctgag cctgccgatc 4020
gtgtctgcgt gggagaaggg catgaggct gcgcgcgcgt tgatggacaa gtaccacgtg 4080
gataacgatc taaaggcaaa cttcaagcta ctgcctgacc aagtgaagc tctggcggcc 4140
gtatgcaaga cctggctaaa cgaggagcac cgcgggttgc agctgacctt caccagcaac 4200
aagacctttg tgacgatgat ggggcgattc ctgcaggcgt acctgcagtc gtttgcgagg 4260
gtaacctaca agcaccacga gcccacgggc tgcgcgttgt ggctgcaccg ctgcgctgag 4320
atcgaaggcg agcttaagtg tctacacggg agcattatg taaataagga gcacgtgatt 4380
gaaatggatg tgacgagcga aaacgggcag cgcgcgctga aggagcagtc tagcaaggcc 4440
aagatcgtga agaaccggtg gggccgaaat gtggtgcaga tctccaacac cgacgcaagg 4500
tgctgcgtgc atgacgcggc ctgtccggcc aatcagtttt ccggcaagtc ttgcggcatg 4560
ttcttctctg aaggcgcaaa ggctcaggtg gctttttaagc agatcaaggc tttcatgcag 4620
gcgctgtatc ctaacgccca gaccgggcac ggtcaccttc tgatgccact acggtgcgag 4680
tgcaactcaa gcctgggca tgcaccctt ttggggaaggc agctaccaaa gttgactccg 4740
ttcgccctga gcaacgcgga ggacctggac gcggatctga tctccgacaa gagcgtgctg 4800
gccagcgtgc accaccggcc gctgatagtg ttccagtgct gcaaccctgt gtatcgcaac 4860
tcgcgcgcgc agggcggagg ccccaactgc gacttcaaga tatcggcgcc cgacctgcta 4920
aacgcgttgg tgatggtgcg cagcctgtgg agtgaaaact tcaccgagct gccgcggatg 4980
gttgtgcctg agttaagtg gagcactaaa caccagtac gcaacgttgc cctgccagtg 5040
gcgcatagcg atgcgcggca gaaccccttt gattttaaaa cggcgcagac ggcaagggtg 5100
gggggtaaat aatcacccga gagtgtacaa ataaaaacat ttgcctttat tgaaagtgtc 5160
tcctagtaca ttattttac atgtttttca agtgacaaaa agaagtggcg ctcctaatct 5220
gcgcactgtg gctgcggaag tagggcgagt ggcgctccag gaagctgtag agctgttcct 5280
ggttgcgacg caggtggc tgtacctggg gactgttaag catggagttg ggtacc 5336
SEQ ID NO: 35         moltype = DNA   length = 1590
FEATURE               Location/Qualifiers
misc_feature          1..1590
                      note = Adenovirus - E2A ORF Sequence
source                1..1590
                      mol_type = unassigned DNA
                      organism = unidentified
SEQUENCE: 35
atggccagtc gggaagagga gcagcgcgaa accaccccg agcgcggacg cggtgcggcg  60
cgacgtccac caaccatgga ggacgtgtcg tcccgtcgc gtcgccgcc gcctcccgc  120
gcgccccaa aaaagcggct gaggcggcgt tcgagtccga ggacgaaga agactcgtca  180
caagatgcgc tggtgccgcg cacacccagc ccgcggccat cgacctcgac ggcggatttg  240
gccattgcgt ccaaaaagaa aaagaagcgc cctctcccca agcccgagcg cccgccatcc  300
ccagaggtga tcgtggacag cgaggaagaa agagaagatg tggcgctaca aatggtgggt  360
ttcagcaacc caccggtgct aatcaagcac ggcaaggag taagcgcac ggtgcggcgg  420
ctgaatgaag acgacccagt ggcgcggggt atgcggacgc aagaggaaaa ggaagagtcc  480
agtgaagcgg aaagtgaaag cacggtgata aacccgctga gcctgccgat cgtgtctgcg  540
tgggagaagg gcatgaggc tgcgcgcgcg ttgatggaca gtaccacgt ggataacgat  600
ctaaaggcaa acttcaagct actgcctgac caagtgaag ctctggcggc cgtatgcaag  660
acctggctaa acgaggagca ccgcgggttg cagctgacct tcaccagcaa caagaccttt  720
gtgacgatga tggggcgatt cctgcaggcg tacctgcagt cgtttgcaga ggtaacctac  780
aagcaccacg agcccacggg ctgcgcgttg tggctgcacc gctgcgctga gatcgaaggc  840
gagcttaagt gtctacacgg gagcattatg taaataagg agcacgtgat tgaaatggat  900
gtgacgagcg aaaacgggca gcgcgcgctg aaggagcagt ctagcaaggc caagatcgtg  960
aagaaccggt ggggccgaaa tgtggtgcag atctccaaca ccgacgcaag gtgctgcgtg 1020
catgacgcgg cctgtccggc caatcagttt tccggcaagt cttgcggcat gttcttctct 1080
```

```
gaaggcgcaa aggctcaggt ggcttttaag cagatcaagg ctttcatgca ggcgctgtat   1140
cctaacgccc agaccgggca cggtcacctc ctgatgccac tacgctgcga gtgcaactca   1200
aagcctgggc atgcacccct tttgggaagg cagctaccaa agttgactcc gttcgccctg   1260
agcaacgcgg aggacctgga cgcggatctg atctccgaca agagcgtgct ggccagcgtg   1320
caccacccgg cgctgatagt gttccagtgc tgcaaccctg tgtatcgcaa ctcgcgcgcg   1380
cagggcggag gccccaactg cgacttcaag atatcggcgc ccgacctgct aaacgcgttg   1440
gtgatggtgc gcagcctgtg gagtgaaaac ttcaccgagc tgccgcggat ggttgtgcct   1500
gagtttaagt ggagcactaa acaccagtat cgcaacgtgt ccctgccagt ggcgcatagc   1560
gatgcgcggc agaaccccct tgattttaa                                     1590

SEQ ID NO: 36          moltype = DNA    length = 3201
FEATURE                Location/Qualifiers
misc_feature           1..3201
                       note = Adenovirus - E4 Full Sequence
source                 1..3201
                       mol_type = unassigned DNA
                       organism = unidentified
SEQUENCE: 36
cccgggcgtt ttagggcgga gtaacttgca tgtattggga attgtagttt ttttaaaatg     60
ggaagtgacg tatcgtggga aaacggaagt gaagatttga ggaagttgtg ggttttttgg    120
cttcgtttc tgggcgtagg ttcgcgtgcg gttttctggg tgttttttgt ggactttaac    180
cgttacgtca tttttagtc ctatatatac tcgctctgta cttggcccttt tttacactgt    240
gactgattga gctggtgccg tgtcgagtgg tgttttttaa taggtttttt tactggtaag    300
gctgactgtt atggctgccg ctgtggaagc gctgtatgtt gttctggagc gggagggtgc    360
tatttgcct aggcaggagg gttttcagg tgtttatgtg ttttctctc ctattaattt    420
tgttatacct cctatggggg ctgtaatgtt gtctctacgc ctgcgggtat gtattccccc    480
gggctatttc ggtcgctttt tagcactgac cgatgttaac caacctgatg tgtttaccga    540
gtcttacatt atgactccgg acatgaccga ggaactgtcg gtggtgcttt taatcacgg    600
tgaccagttt ttttacggtc acgccggcat ggccgtagtc cgtcttatgc ttataagggt    660
tgtttttcct gttgtaagac aggcttctaa tgtttaaatg ttttttttt tgttattta    720
ttttgtgttt aatgcaggaa cccgcagaca tgtttgagag aaaaatggtg tcttttttctg   780
tggtggttcc ggaacttacc tgcctttatc tgcatgagca tgactacgat gtgcttgctt    840
ttttgcgcga ggctttgcct gattttttga gcagcacctt gcatttttata tcgccgccca    900
tgcaacaagc ttacataggg gctacgctgg ttagcatagc tccgagtatg cgtgtcataa    960
tcagtgtggg ttcttttttgtc atggttcctg gcggggaagt ggcgcgctg gtccgtgcag   1020
acctgcacga ttatgttcag ctggccctgc gaagggacct acgggatcgc ggtattttgg    1080
ttaatgttcc gcttttgaat cttatacagg tctgtgagga acctgaattt ttgcaatcat    1140
gattcgctgc ttgaggctga aggtggaggg cgctctggag cagattttta caatggccgg    1200
acttaatatt cggatttgc ttagagacat attgataagg tggcagatg aaaattatt    1260
gggcatggtt gaaggtgctg gaatgtttat agaggagatt caccctgaag ggtttagcct    1320
ttacgtccac ttggacgtga gggcagtttg cctttttggaa gccattgtgc aacatcttac    1380
aaatgccatt atctgttctt tggctgtaga gtttgaccac gccaccggag gggagcgcgt    1440
tcacttaata gatcttcatt ttgagtttt ggataatttt ttggaataaa aaaaaaaaa    1500
catggttctt ccagctcttc ccgctcctcc cgtgtgtgac tcgcagaacg aatgtgtagg    1560
ttggctgggt gtgcttatt ctgcggtggt ggatgtatc agggcagcgg cgcatgaagg    1620
agtttacata gaacccgaag ccaggggggcg cctggatgct tgagagagt ggatatacta    1680
caactactac acagagcgag ctaagcgacg agaccgacag cgcagatctg tttgtcacgc    1740
ccgcacctgg ttttgcttca ggaaaatga ctacgtccgg cgttccattt ggcatgacac    1800
tacgaccaac acgatctcgg ttgtctcggc gcactccgta cagtagggat cgcctacctc    1860
cttttgagac agagacccgc gctaccatac tggaggatca tccgctgctg cccgaatgta    1920
acactttgac aatgcacaac gtgagttacg tgcgaggtct tccctgcagt gtggggattta    1980
cgctgattca ggaatgggtt gttccctggg atatggttct gacgcgggag gagcttgtaa    2040
tcctgaggaa gtgtatgcac gtgtgcctgt gttgtgccaa cattgatatc atgacgagca    2100
tgatgatcca tggttacgag tcctgggctc tccactgtca ttgttccagt cccggttccc    2160
tgcagtgcat agccggcggg caggtttttgg ccagctggtt taggatggtg gtggatggcg    2220
ccatgtttaa tcagaggttt atatggtacc gggaggtggt gaattacaac atgccaaag    2280
aggtaatgtt tatgtccagc gtgttttatga ggggtcgcca cttaatctac ctgcgcttgt    2340
ggtatgatgg ccacgtgggt tctgtggtcc ccgccatgag ctttgataca gcgccttgc    2400
actgtgggat tttgaacaat attgtggtgc tgtgctgcag ttactgtgct gatttaagtg    2460
agatcagggt gcgctgctgt gcccgagga caaggcgtct catgctgcgg gcggtgcgaa    2520
tcatcgctga ggagaccact gccatgttgt attcctgcag gacggagcgg cggcggcagc    2580
agttattcg cgcgctgctg cagcaccacc gccctatcct gatgcacgat tatgactcta    2640
cccccatgta ggcgtggact tccccttcgc cgccgttga gcaaccgcaa gttggacagc    2700
agcctgtggc tcagcagctg gacagcgaca tgaacttaag cgagctgccc gggagttta    2760
ttaatatcac tgatgagcgt ttggctcgac aggaaaccgt gtggaatata acacctaaga    2820
atatgtctgt tacccatgat atgatgcttt taaggccag ccggggagaa aggactgtgt    2880
actctgtgtg ttgggaggga ggtggcaggt tgaatactag ggttctgtga gtttgattaa    2940
ggtacggtga tcaatataag ctatgtggtg gtggggctat actactgaat gaaaaatgac    3000
ttgaaattt ctgcaattga aaaataaaca cgttgaaata taacatgaca caggttcacg    3060
attctttatt cctgggcaat gtaggagaag gtgtaagagt tggtagcaaa agtttcagtg    3120
gtgtatttc cactttccca ggaccatgta aaagacatag agtaagtgct tacctcgcta    3180
gtttctgtgg attcactaga a                                               3201

SEQ ID NO: 37          moltype = DNA    length = 885
FEATURE                Location/Qualifiers
misc_feature           1..885
                       note = Adenovirus - E4 Orf6 Sequence
source                 1..885
                       mol_type = unassigned DNA
```

```
                        organism = unidentified
SEQUENCE: 37
atgactacgt ccggcgttcc atttggcatg acactacgac caacacgatc tcggttgtct      60
cggcgcactc cgtacagtag ggatcgccta cctcctttg agacagagac ccgcgctacc      120
atactggagg atcatccgct gctgcccgaa tgtaacactt tgacaatgca caacgtgagt    180
tacgtgcgag gtcttccctg cagtgtggga tttacgctga ttcaggaatg ggttgttccc    240
tgggatatgg ttctgacgcg ggaggagctt gtaatcctga ggaagtgtat gcacgtgtgc    300
ctgtgttgtg ccaacattga tatcatgacg agcatgatga tccatggtta cgagtcctgg    360
gctctccact gtcattgttc cagtcccggt tccctgcagt gcatagccgg cggcaggtt     420
ttggccagct ggtttaggat ggtggttggat ggcgccatgt ttaatcagag gtttatatgg   480
taccggggagg tggtgaatta caacatgcca aaagaggtaa tgtttatgtc cagcgtgttt   540
atgaggggtc gccacttaat ctacctgcgc ttgtggtatg atggccacgt gggttctgtg    600
gtccccgcca tgagctttgg atacagcgcc ttgcactgtg ggattttgaa caatattgtg    660
gtgctgtgct gcagttactg tgctgattta agtagatac ggtgcgctg ctgtgcccgg      720
aggacaaggc gtctcatgct gcgggcggtg cgaatcatcg ctgaggagac cactgccatg    780
ttgtattcct gcaggacgga gcggcggcgg cagcagttta ttcgcgcgct gctgcagcac    840
caccgcccta tcctgatgca cgattatgac tctacccca tgtag                    885

SEQ ID NO: 38           moltype = DNA    length = 743
FEATURE                 Location/Qualifiers
misc_feature            1..743
                        note = Adenovirus - VA Sequence
source                  1..743
                        mol_type = unassigned DNA
                        organism = unidentified
SEQUENCE: 38
cgtaatccgt agatgtacct ggacatccag gtgatgccgg cggcggtggt ggaggcgcgc    60
ggaaagtcgc ggacgcggtt ccagatgttg cgcagcggca aaaagtgctc catggtcggg    120
acgctctggc cggtgaggcg tgcgcagtcg ttgacgctct agaccgtgca aaaggagagc    180
ctgtaagcgg gcactcttcc gtggtctggt ggataaattc gcaagggtat catggcggac    240
gaccggggtt cgaaccccgg atccggccgt ccgccgtgat ccatgcggtt accgcccgcg    300
tgtcgaaccc aggtgtgcga cgtcagacaa cggggggagcg ctcctttgg cttccttcca    360
ggcgcggcgg ctgctgcgct agctttttg gccactggcc gcgcgcggcg taagcggtta    420
ggctggaaag cgaaagcatt aagtggctcg ctccctgtag ccggagggtt attttccaag   480
ggttgagtcg caggaccccc ggttcgagtc tcgggccggg cgggactgcgg cgaacgggag   540
tttgcctccc cgtcatgcaa gacccccgctt gcaaattcct ccggaaacag ggacgagccc  600
cttttttgct tttcccagat gcatccggtg ctgcggcaga tgcgcccccc tcctcagcag   660
cggcaagagc aagagcagcg gcagacatgc agggcaccct ccccttctcc taccgcgtca    720
ggaggggcaa catcctacat cga                                            743

SEQ ID NO: 39           moltype = DNA    length = 870
FEATURE                 Location/Qualifiers
misc_feature            1..870
                        note = Ad5 E1A
source                  1..870
                        mol_type = genomic DNA
                        organism = Human mastadenovirus C
SEQUENCE: 39
atgagacata ttatctgcca cggaggtgtt attaccgaag aaatggccgc cagtcttttg    60
gaccagctga tcgaagaggt actggctgat aatcttccac ctcctagcca ttttgaacca   120
cctaccttc acgaactgta tgatttagac gtgacgggcc ccgaagatcc caacgaggag    180
gcggtttcgc agattttcc cgactctgta atgttggcgg tgcaggaagg gattgactta    240
ctcactttc cgccggcgcc cggttctccg gagccgcctc accttttccg gcagcccgag   300
cagccggagc agagagcctt gggtccggtt tctatgccaa accttgtacc ggaggtgatc    360
gatcttacct gccacgaggc tggctttcca cccagtgacg acgaggatga agagggtgag    420
gagtttgtgt tagattatgt ggagcaccc gggcacggtt gcaggtcttg tcattatcac    480
cggaggaata cgggggaccc agatattatg tgttcgcttt gctatatgag gacctgtggc    540
atgtttgtct acagtcctgt gtctgaacct gagcctgagc ccgagccaga accggagcct    600
gcaagaccta cccgccgtcc taaaatggcg cctgctatcc tgagacgcgg gacatcacct    660
gtgtctagag aatgcaatag tagtacggat agctgtgact ccggtccttc taacacacct    720
cctgagatac accggtggt cccgctgtgc ccattaaac cagttgccgt gagagttggt    780
gggcgtcgcc aggctgtgga atgtatcgag gacttgctta acgagcctgg gcaaccttg     840
gacttgagct gtaaacgccc caggccataa                                     870

SEQ ID NO: 40           moltype = DNA    length = 732
FEATURE                 Location/Qualifiers
misc_feature            1..732
                        note = Ad5 E1A
source                  1..732
                        mol_type = genomic DNA
                        organism = Human mastadenovirus C
SEQUENCE: 40
atgagacata ttatctgcca cggaggtgtt attaccgaag aaatggccgc cagtcttttg    60
gaccagctga tcgaagaggt actggctgat aatcttccac ctcctagcca ttttgaacca   120
cctaccttc acgaactgta tgatttagac gtgacgggcc ccgaagatcc caacgaggag    180
gcggtttcgc agattttcc cgactctgta atgttggcgg tgcaggaagg gattgactta    240
ctcactttc cgccggcgcc cggttctccg gagccgcctc accttttccg gcagcccgag   300
cagccggagc agagagcctt gggtccggtt tctatgccaa accttgtacc ggaggtgatc    360
gatcttacct gccacgaggc tggctttcca cccagtgacg acgaggatga agagggtcct   420
```

```
gtgtctgaac ctgagcctga gcccgagcca gaaccggagc ctgcaagacc tacccgccgt    480
cctaaaatgg cgcctgctat cctgagacgc ccgacatcac ctgtgtctag agaatgcaat    540
agtagtacgg atagctgtga ctccgtcct tctaacacac ctcctgagat acacccggtg     600
gtcccgctgt gccccattaa accagttgcc gtgagagttg gtgggcgtcg ccaggctgtg    660
gaatgtatcg aggacttgct taacgagcct gggcaacctt tggacttgag ctgtaaacgc    720
cccaggccat aa                                                        732

SEQ ID NO: 41             moltype = DNA   length = 531
FEATURE                   Location/Qualifiers
misc_feature              1..531
                          note = Ad5 E1B_19K
source                    1..531
                          mol_type = genomic DNA
                          organism = Human mastadenovirus C
SEQUENCE: 41
atggaggctt gggagtgttt ggaagatttt tctgctgtgc gtaacttgct ggaacagagc     60
tctaacagta cctcttggtt ttggaggttt ctgtggggct catcccaggc aaagttagtc    120
tgcagaatta aggaggatta caagtgggaa tttgaagagc ttttgaaatc ctgtggtgag    180
ctgtttgatt cttgaatct gggtcaccag gcgcttttcc aagagaaggt catcaagact     240
ttggattttt ccacaccggg gcgcgctgcg gctgctgttg cttttttgag ttttataaag    300
gataaatgga gcgaagaaac ccatctgagc gggggtacc tgctggattt tctgccatg      360
catctgtgga gagcggttgt gagacacaag aatcgcctgt tactgttgtc ttccgtccgc    420
ccggcgataa taccgacgga ggagcagcag cagcagcagg aggaagccag gcggcggcgg    480
caggagcaga gcccatggaa cccgagagcc ggcctggacc ctcgggaatg a             531

SEQ ID NO: 42             moltype = DNA   length = 1491
FEATURE                   Location/Qualifiers
misc_feature              1..1491
                          note = Ad5 E1B_55K
source                    1..1491
                          mol_type = genomic DNA
                          organism = Human mastadenovirus C
SEQUENCE: 42
atggagcgaa gaaacccatc tgagcggggg gtacctgctg attttctgg ccatgcatct       60
gtggagagcg gttgtgagac acaagaatcg cctgctactg ttgtcttccg tccgcccggc    120
gataataccg acggaggagc agcagcagca gcaggaggaa gccaggcggc ggcggcagga    180
gcagagccca tggaacccga gagccggcct ggaccctcgg gaatgaatgt tgtacaggtg    240
gctgaactgt atccagaact gagacgcatt ttgacaatta gaggatgg gcagggcta       300
aaggggtaa agagggagcg gggggcttgt gaggctacag gaatctagct                360
tttagcttaa tgaccagaca ccgtcctgag tgtattactt tcaacagat caaggataat    420
tgcgctaatg agcttgatct gctggcgcag aagtattcca tagagcagct gaccacttac    480
tggctgcagc caggggatga ttttgaggag ctattaggg tatatgcaaa ggtggcactt     540
aggccagatt gcaagtacaa gatcagcaaa ctttgtaaata tcaggaattg ttgctacatt    600
tctgggaacc gggccgaggt ggagatagat acgaggata gggtggcctt tagatgtagc     660
atgataaata tgtggccggg ggtgcttggc atggacgggg tggttattat gaatgtaagg    720
tttactggcc ccaattttag cggtacggtt ttcctgcca ataccaacct tatcctacac      780
ggtaagct tctatgggtt taacaatacc tgtgtgaag cctggaccga tgtaaggtt          840
cggggctgtg ccttttactg ctgctgaag ggggtggtgt gtcgcccaa agcagggct        900
tcaattaaga aatgcctctt tgaaaggtgt accttgggta tcctgtctga gggtaactcc    960
agggtgcgcc acaatgtggc ctccgactgt ggttgcttca tgctagtgaa aagcgtggct   1020
gtgattaagc ataacatggt atgtggcaac tgcgaggaca gggcctctca gatgctggag  1080
tgctcggacg gcaactgtca cctgctgaag accattcacg tagccagcca ctctcgcaag   1140
gcctggccag tgtttgagca taacatactg acccgctgtt ccttgcattt gggtaacagg   1200
agggggtgt cctaccttta ccaatgcaat ttgagtcaca ctaagatatt gcttgagccc    1260
gagagcatgt ccaaggtgaa cctgaacggg gtgtttgaca tgaccatgaa gatctggaag   1320
gtgctgaggt acgatgagac ccgcaccagg tgcagaccct gcgagtgtgg cggtaaacat   1380
attaggaacc agcctgtgat gctggatgtg accgaggagc tgaggcccga tcacttggtg   1440
ctggcctgca cccgcgctga gtttggctct agcgatgaag atacagattg a             1491

SEQ ID NO: 43             moltype = DNA   length = 1590
FEATURE                   Location/Qualifiers
misc_feature              1..1590
                          note = Ad5 E2A orf
source                    1..1590
                          mol_type = genomic DNA
                          organism = Human mastadenovirus C
SEQUENCE: 43
atggccagtc gggaagagga gcagcgcgaa accacccccg agcgcggacg cggtgcggcg      60
cgacgtccac caaccatgga ggacgtgtcg tccccgtcgc cgtccgccgcc gcctccccgc   120
gcgccccaa aaaagcggct gaggcggcgt ctcgagtccg aggacgaaga agactcgtca    180
caagatcgc tggtgccgcg cacacccagc ccgcggccat cgacctcgac ggcggatttg    240
gccattgcgt tccaaaagaa aaagaagcgc ccctctccca gcccgagcg cccgccatcc    300
ccagaggtga tcgtggacag cgaggaagaa agagaagatg tggcgctaca aatggtgggt    360
ttcagcaacc taccggtgct aatcaagcac gcaaggagg gtaaccgcac ggtgcggcg     420
ctgaatgaag cgacccagt ggcgcgggt atgcggacgc aagaggaaaa ggaagagtcc    480
agtgaagcgg aaagtgaaag cacggtgata aacccgctga gcctgccgat cgtgtctgcg    540
tgggagaagg gcatggaggc tgcgcgcgcg ttgatggaca gtaccacgt ggataacgat    600
ctaaaggcaa acttcaagct actgcctgac caagtggaag ctctgcggc cgtatgcaag    660
acctggctaa acgaggagca ccgcgggttg cagctgacct tcaccagcaa caagccctt    720
```

```
gtgacgatga tggggcgatt cctgcaggcg tacctgcagt cgtttgcaga ggtaacctac   780
aagcaccacg agcccacggg ctgcgcgttg tggctgcacc gctgcgctga gatcgaaggc   840
gagcttaagt gtctacacgg gagcattatg ataaataagg agcacgtgat tgaaatggat   900
gtgacgagcg aaaacgggca gcgcgcgctg aaggagcagt ctagcaaggc caagatcgtg   960
aagaaccggt ggggccgaaa tgtggtgcag atctccaaca ccgacgcaag gtgctgcgtg  1020
catgacgcgg cctgtccggc caatcagttt tccggcaagt cttgcggcat gttcttctct  1080
gaaggcgcaa aggctcaggt ggcttttaag cagatcaagg ctttcatgca ggcgctgtat  1140
cctaacgccc agaccgggca cggtcacctt ctgatgccac tacggtgcga gtgcaactca  1200
aagcctgggc atgcaccctt tttgggaagg cagctaccaa agttgactcc gttcgccctg  1260
agcaacgcgg aggacctgga cgcggatctg atctccgaca agagcgtgct ggccagcgtg  1320
caccacccgg cgctgatagt gttccagtgc tgcaaccctg tgtatcgcaa ctcgcgcgcg  1380
cagggcggag gccccaactg cgacttcaag atatcggcgc ccgacctgct aaacgcgttg  1440
gtgatggtgc gcagcctgtg gagtgaaaac ttcaccgagc tgccgcggat ggttgtgcct  1500
gagtttaagt ggagcactaa acaccagtat cgcaacgtgt ccctgccagt ggcgcatagc  1560
gatgcgcggc agaaccccct tgattttaa                                   1590

SEQ ID NO: 44           moltype = DNA   length = 453
FEATURE                 Location/Qualifiers
misc_feature            1..453
                        note = Ad5 E4A
source                  1..453
                        mol_type = genomic DNA
                        organism = Human mastadenovirus C
SEQUENCE: 44
atgactacgt ccggcgttcc atttggcatg acactacgac caacacgatc tcggttgtct    60
cggcgcactc cgtacagtag ggatcgccta cctccttttg agacagagac ccgcgctacc   120
atactggagg atcatccgct gctgcccgaa tgtaacactt tgacaatgca caacgcgtgg   180
acttcccctt cgccgcccgt tgagcaaccg caagttggac agcagcctgt ggctcagcag   240
ctggacagcg acatgaactt aagcgagctg cccggggagt ttattaatat cactgatgag   300
cgtttggctc gacaggaaac cgtgtggaat ataaaccta agaatatgtc tgttacccat   360
gatatgatgc ttttttaaggc cagccgggga gaaaggactg tgtactctgt gtgttgggag   420
ggaggtggca ggttgaatac tagggttctg tga                              453

SEQ ID NO: 45           moltype = DNA   length = 885
FEATURE                 Location/Qualifiers
misc_feature            1..885
                        note = Ad5 E4A
source                  1..885
                        mol_type = genomic DNA
                        organism = Human mastadenovirus C
SEQUENCE: 45
atgactacgt ccggcgttcc atttggcatg acactacgac caacacgatc tcggttgtct    60
cggcgcactc cgtacagtag ggatcgccta cctccttttg agacagagac ccgcgctacc   120
atactggagg atcatccgct gctgcccgaa tgtaacactt tgacaatgca caacgtgagt   180
tacgtgcgag tcttccctg cagtgtggga tttacgctga ttcaggaatg ggttgttccc   240
tgggatatgt ttctgacgcg ggaggagctt gtaatcctga ggaagtgtat gcacgtgtgc   300
ctgtgttgtg ccaacattga tatcatgacg agcatgatgt ccatggtta cgagtcctgg   360
gctctccact gtcattgttc cagtcccggt tccctgcagt gcatagccgg cgggcaggtt   420
ttggccagct ggtttaggat ggtggtggat ggcgccatgt taatcagag gtttatatgg   480
taccgggagg tggtgaatta caacatgcca aaagaggtaa tgtttatgtc cagcgtgttt   540
atgaggggtc gccacttaat ctacctgcgc ttgtggtatg atggccacgt gggttctgtg   600
gtccccgcca tgagctttgg atacagcgcc ttgcactgtg ggattttgaa caatattgtg   660
gtgctgtgct gcagttactg tgctgattta agtgagatca gggtgcgctg ctgtgcccgg   720
aggacaaggc gtctcatgct gcgggcggtg cgaatcatcg ctgaggagac cactgccatg   780
ttgtattcct gcaggacgga gcggcggcgg cagcagttta ttcgcgcgct gctgcagcac   840
caccgcccta tcctgatgca cgattatgac tctaccccca tgtag                885

SEQ ID NO: 46           moltype = DNA   length = 743
FEATURE                 Location/Qualifiers
misc_feature            1..743
                        note = Synthetic: Ad5 VA
source                  1..743
                        mol_type = other DNA
                        organism = synthetic construct
SEQUENCE: 46
tcgatgtagg atgttgcccc tcctgacgcg gtaggagaag gggagggtgc cctgcatgtc    60
tgccgctgct cttgctcttg ccgctgctga ggagggggc gcatctgccg cagcaccgga   120
tgcatctggg aaaagcaaaa aagggggctcg tccctgtttc cggaggaatt tgcaagcggg   180
gtcttgcatg acggggaggc aaaccccgcg tcgccgcagt ccggccggcc cgagactcga   240
accggggtc ctgcgactca acccttgaa aataaccctc cggctacagg gagcgagcca   300
cttaatgctt tcgcttttcca gcctaaccgc ttaccgcgcg cgcggccagt ggccaaaaaa   360
gctagcgcag cagccgccgc gcctggaagg aagccaaaag gagcgctccc ccgttgtctg   420
acgtcgcaca cctgggttcg acacgcgggc ggtaaccgca tggatcacgg cggacggccg   480
gaccgggggt tcgaacccg gtcgtccgcc atgatacct tgcgaattta tccaccagac   540
cacggaagag tgcccgctta caggctctct ttttgcacgg tctagagcgt caacgactgc   600
gcacgcctca ccggccagag cgtcccgacc atggagcact ttttgccgct gcgcaacatc   660
tggaaccgcg tccgcgactt tccgcgcgcc tccaccaccg ccgccggcat cacctggatg   720
tccaggtaca tctacggatt acg                                         743
```

| SEQ ID NO: 47 | moltype = DNA  length = 588 |
|---|---|
| FEATURE | Location/Qualifiers |
| misc_feature | 1..588 |
| | note = Synthetic: CMV Promoter |
| source | 1..588 |
| | mol_type = other DNA |
| | organism = synthetic construct |

SEQUENCE: 47

```
tagttattaa tagtaatcaa ttacggggtc attagttcat agcccatata tggagttccg   60
cgttacataa cttacggtaa atggcccgcc tggctgaccg cccaacgacc cccgcccatt  120
gacgtcaata atgacgtatg ttcccatagt aacgccaata gggactttcc attgacgtca  180
atgggtggag tatttacggt aaactgccca cttggcagta catcaagtgt atcatatgcc  240
aagtacgccc cctattgacg tcaatgacgg taaatggccc gcctggcatt atgcccagta  300
catgacctta tgggactttc ctacttggca gtacatctac gtattagtca tcgctattac  360
catggtgatg cggttttggc agtacatcaa tgggcgtgga tagcggtttg actcacgggg  420
atttccaagt ctccacccca ttgacgtcaa tgggagtttg ttttggcacc aaaatcaacg  480
ggactttcca aaatgtcgta caactccgcc ccattgacgc aaatgggcg gtaggcgtgt  540
acggtggag gtctatataa gcagagctcg tcgacgttta gtgaaccg              588
```

| SEQ ID NO: 48 | moltype = DNA  length = 40 |
|---|---|
| FEATURE | Location/Qualifiers |
| misc_feature | 1..40 |
| | note = Synthetic: 2xTet Operator Sequence |
| source | 1..40 |
| | mol_type = other DNA |
| | organism = synthetic construct |

SEQUENCE: 48

```
tccctatcag tgatagagat ctccctatca gtgatagaga                          40
```

| SEQ ID NO: 49 | moltype = DNA  length = 827 |
|---|---|
| FEATURE | Location/Qualifiers |
| misc_feature | 1..827 |
| | note = Synthetic: hCMV Intron Sequence |
| source | 1..827 |
| | mol_type = other DNA |
| | organism = synthetic construct |

SEQUENCE: 49

```
gtaagtaccg cctatagagt ctataggccc accccctggg cttcttatgc atgctatact   60
gtttttggct tggggtctat acaccccgc ttcctcatgt tataggtgat ggtatagctt  120
agcctatagg tgtgggttat tgaccattat tgaccactcc cctattggtg acgatacttt  180
ccattactaa tccataacat ggctctttgc cacaactctc tttattggct atatgccaat  240
acactgtcct tcagagactg acacggactc tgtattttta caggatgggg tctcattta   300
tatttacaaa ttcacatata caaccaccac gtccccagtg cccgcagttt ttattaaaca  360
taacgtggga tctccacgcg aatctcgggt acgtgttccg gacatggtct cttctccggt  420
agcggcggag cttctacatc cgagccctgc tccccatgcct ccagcgactc atggtcgctc  480
ggcagctcct tgctcctaac agtggaggcc agacttaggc acagcacgat gcccaccacc  540
accagtgtgc cgcacaaggc cgtggcggta gggtatgtgt ctgaaaatga gctcggggag  600
cgggcttgca ccgctgacgc atttggaaga cttaaggcag cggcagaaga agatgcaggc  660
agctgagttg ttgtgttctg ataagagtca gaggtaactc ccgttgcggt gctgttaacg  720
gtggagggca gtgtagtctg agcagtactc gttgctgccg cgcgcgccac cagacataat  780
agctgacaga ctaacagact gttcctttcc atgggtcttt tctgcag               827
```

| SEQ ID NO: 50 | moltype = DNA  length = 583 |
|---|---|
| FEATURE | Location/Qualifiers |
| misc_feature | 1..583 |
| | note = Synthetic: ECMV IRES Sequence |
| source | 1..583 |
| | mol_type = other DNA |
| | organism = synthetic construct |

SEQUENCE: 50

```
ccccctctc cctccccccc ccctaacgtt actggccgaa gccgcttgga ataaggccgg   60
tgtgcgtttg tctatatgtt atttttccacc atattgccgt cttttggcaa tgtgagggcc  120
cggaaacctg gccctgtctt cttgacgagc attcctaggg gtctttcccc tctcgccaaa  180
ggaatgcaag gtctgttgaa tgtcgtgaag gaagcagttc ctctggaagc ttcttgaaga  240
caaacaacgt ctgtagcgac cctttgcagg cagcggaacc cccaccctgg cgacaggtgc  300
ctctgcggcc aaaagccacg tgtataagat acacctgcaa aggcggcaca ccccagtgc  360
cacgttgtga gttggatagt tgtggaaaga gtcaaatggc tctcctcaag cgtattcaac  420
aaggggctga aggatgccca aaggtacccc cattgtatgg gatctgatct ggggcctcgg  480
tgcacatgct ttacatgtgt ttagtcgagg ttaaaaaacg tctaggcccc ccgaaccacg  540
gggacgtggt tttcctttga aaaacacgat tgctcgaatc acc                   583
```

| SEQ ID NO: 51 | moltype = DNA  length = 461 |
|---|---|
| FEATURE | Location/Qualifiers |
| misc_feature | 1..461 |
| | note = Synthetic: FMDV IRES |
| source | 1..461 |
| | mol_type = other DNA |
| | organism = synthetic construct |

SEQUENCE: 51

```
agcaggtttc cccaactgac acaaaacgtg caacttgaaa ctccgcctgg tctttccagg   60
tctagagggg taacactttg tactgtgttt ggctccacgc tcgatccact ggcgagtgtt  120
agtaacagca ctgttgcttc gtagcggagc atgacggccg tgggaactcc tccttggtaa  180
caaggaccca cggggccaaa agccacgccc acacgggccc gtcatgtgtg caaccccagc  240
acggcgactt tactgcgaaa cccactttaa agtgacattg aaactggtac ccacacactg  300
gtgacaggct aaggatgccc ttcaggtacc ccgaggtaac acgcgacact cgggatctga  360
gaaggggact ggggcttcta taaaagcgct cggtttaaaa agcttctatg cctgaatagg  420
tgaccggagg tcggcacctt tcctttacaa ttaatgaccc t                      461
```

| SEQ ID NO: 52 | moltype = DNA  length = 6473 |
|---|---|
| FEATURE | Location/Qualifiers |
| source | 1..6473 |
| | mol_type = genomic DNA |
| | organism = Cricetulus griseus |

SEQUENCE: 52
```
tctagaaaca aaaccaaaaa tattaagtca ggcttggctt caggtgctgg ggtggagtgc   60
tgacaaaaat acacaaattc ctggctttct aaggcttttt cggggattca ggtattgggt  120
gatggtagaa taaaaatctg aaacataggt gatgtatctg ccatactgca tgggtgtgta  180
tgtgtgtgta tgtgtgtctg tgtgtgtgcc cagacagaaa taccatgaag gaaaaaaaca  240
cttcaaagac aggagagaag agtgacctgg gaaggactcc ccaatgagat gagaactgag  300
cacatgccag aggaggtgag gactgaacca ttcaacacaa gtggtgaata gtcctgcaga  360
cacagagagg gccagaagca ctcagaactc caggggtca tcggtgttc tctggaggct    420
tctgcccttg gaggttcctg aggaggaggc ttccatattg aaaatgtagt tagtggccgt  480
ttccattagt acagtgacta gagagagctg agggaccact ggactgaggc ctagatgctc  540
agtcagatgc ccatgaaagc ctagacaagc acttccgggt ggaaaggaaa cagcaggtgt  600
gaggggtcag gggcaagtta gtgggagagg tcttccaggt gaagtagcag gaacggagac  660
gcactggatg gccccacttg tcaaccagca aaagcttgga tcttgttcta agaggccagg  720
gacatgacaa gggtgatctc ggttttaaa aggcttgtg ttacctaatc acttctatta    780
gtcagatact ttgtaacaca aatgagtact tggcctgtat tttagaaact tctgggatcc  840
tgaaaaaaca caatgacatt ctggctgcaa cacctggaga ctcccagcca ggccctgaca  900
ccgggtccat tcatgcaaat actcaggac agattcttca ctaggtactg atgagctgtc    960
ttggatgcaa atgtggcctc ttcattttac tacaagtcac catgagtcag gaggtgctgt 1020
ttgcacagtg tgactaagtg atggagtgtt gactgcagcc attcccggcc ccagcttgtg 1080
agagagatcc ttttaaattg aaagtaagct caaagttacc acgaagccac acatgtataa 1140
actgtgtgaa taatctgtgc acatacacaa accatgtgaa taatctgtgt acatgtataa 1200
actgtgtgaa taatctgtgt gcagcctttc cttacctact accttccagt gatcaggttt 1260
ggactgcctg tgtgctactg gaccctgaat gtccccaccg ctgtccctg tcttttacga  1320
ttctgacatt tttaataaat tcagcggctt ccctctgct ctgtgcctag ctaccttg    1380
gtactctgca tttggtttc tgtgacattt tctgtgact ctgctacatt ctcagatgc    1440
atgtgacaca gaaggtgttc cctctggaga catgtgatgt ccctgtcatt agtggaatca 1500
gatgccccca aactgttgtc cagtgtttgg gaaagtgaca cgtgaaggag gatcaggaaa 1560
agaggggtgg aaatcaagat gtgtctgagt atctcatgtc cctgagtggt ccaggctgct 1620
gacttcactc ccccaagtga gggaggccat ggtgagtaca cacacctcac acatactata 1680
tccaacacac acacacacac acacacacac acgcacgcac gcacgcacgc acgcacacat 1740
gcacacacac gaactacatt tcacaaacca catacgcata ttacacccca aacgtatcac 1800
ctatacatac cacacataca cacccctcca cacatcacac acataccaca cccacacaca 1860
gcacacacat acataggcac acattcacac accacacata tacatttgtg tatgcataca 1920
tgcatacaca cacaggcaca cagacaccac acacatgcat tgtgtacgca cacatgcata 1980
cacacacata ggcacacatt gagcacacac atacatttgt gtacgcacac tacatagaca 2040
tatatgcatt tgtatatgca cacatgcatg cacacataca taggcacaca tagagcacac 2100
acatacattt gtgtatgcac acatgcacac accaatcaca tgggaagact caggttcttc 2160
actaaggttc acatgaactt agcagttcct ggttatctcg tgaaacttgg aagattgctc 2220
tggagaagag gaagcgttgg cttgagccct ggcagcaatt aaccccgccc agaagaagta 2280
ggtttaaaaa tgagagggtc tcaatgtgga accgcaggg cgccagttca gagaagagac  2340
ctacccaagc caactgagag caaaggcaga gggatgaagt ctggtgtag tttgaacctc   2400
tgtaccagct gggcttcatg ctatttgtt atatctttat taaatattct tttagtttta   2460
tgtgcgtgaa taccttgctt gcataaatgt atgggcactg tatgtgttct tggtgccggt 2520
ggaggccagg agagggcatg gatcctccgg agctggcgtt tgagacagtt gtgacccaca 2580
gtgtggggtc tgggaactgg gtcttagtgt tccgcaagtg cagctgggc tcttaacctc   2640
tgagccatcc ctccagcttc aagaaactta tttttcttag acatggggga agggatccag 2700
ggctttaggc ttgtttgttc agcaaatact ctttcgtgt atttgaatt ttatttttat    2760
ttactttttt gggatagaat cacattctgc agctcaggct gggcctgaac tcatcaaat   2820
cctcctgtct cagtctacca ggtgataaga ttactgatgt gagcctggct ttgacaagca 2880
ctttagagtc cccagccctt ctggacactt gttccaagta taatatatat atatatatat 2940
atatatatat atatatatat atatattgtg tgtgtgtgtt tgtgtgtgta tgagacactt 3000
gctctaaggg tatcatatat atccttgatt tgcttttaat ttatttttta attaaaaatg 3060
attagctaca tgtcacctgt atgcgtcgt atcatctata tatccttcct tccttctctc   3120
tcttttctct ttcttcttct caccccaag catctatttt caaatccttg tgccgaggag   3180
atgccaagag tctcgttggg ggagatggtg agggggcgat acagggggag agcaggagga 3240
aaggggggaca gactggtgtg ggtctttgga gagtcagga gaatagcagc gatcttccct   3300
gtccctggtg tcacctctta cagccaacac catttgtgg cctggcagaa gagttgtcaa   3360
gctggtcgca ggtctgccac acaacccaa tctggcccca agaaaaggca cctgtgtgtg 3420
actctggggt taaaggcgct gcctggtcgt ctccagctgg acttgaaact cccgtttaat 3480
aaagagttct gcaaaataat acccgcagag tcacagtgcc aggttcccgt gctttcctga 3540
agcgccaggc acgggttccc taggaaatgg ggccttgctt gccaagctcc cacggcttgc 3600
cctgcaaacg gcctgaatga tctggcactc tgcgttgcca ctgggatgaa atggaaaaaa 3660
gaaaagaag aagtgtctct ggaagcgggc gcgctcacac aaacccgcaa cgattgtgta   3720
aacactctcc attgagaatc tggagtgcgg ttgccctcta ctggggagct gaagacagct 3780
agtggggggcg gggggaggac cgtgctagca tccttccacg gtgctcgctg gctgtggtgc 3840
```

```
atgccgggaa ccgaaacgcg gaactaaagt caagtcttgc tttggtggaa ctgacaatca   3900
acgaaatcac ttcgattgtt ttcctctttt tactggaatt cttggatttg atagatgggg   3960
gaggatcaga gggggagggg aggggcgggg agacggaggg aggaggggag gaggggagga   4020
ggggaggagg ggaggagggg aagggatgga ggaaaatact aacttttcta attcaacatg   4080
acaaagattc ggagaaagtg caccgctagt gaccgggagg aggaatgccc tattgggcat   4140
tatattccct gtcgtctaat ggaatcaaac tcttggttcc agcaccaagg attctgagcc   4200
tatcctattc aagacagtaa ctacagccca cacggaagag gctatacaac tgaagaaata   4260
aaattttcac tttatttcat ttctgtgact gcatgttcac atgtagagag ccacctgtgt   4320
ctaggggctg atgtgctggg cagtagagtt ctgagcccgt taactggaac aacccagaac   4380
tcccaccaca gttagagctt gctgagagag ggaggcccct ggtgagattt ctttgtgtat   4440
ttatttagag acagggtctc atactgtagt ccaagctagc ctccagctca cagaaattct   4500
cctgttccgg tttccaaagt actggagtta tgagtgtgtg taattgaac gctaagaatt    4560
tgctgattga agaaaacctc aagtgggttt ggctaatccc cacgacccca gaggctgagg   4620
caggaggaat gagagaattc aaggtttgcc agagccacag ggtgagctca atgtggagac   4680
tgtgagggtg agctcaatgt ggagactgtg agggtgagct caatgtggag actgtgaggg   4740
tgagctcaat gtggagactg tgagggtgag ctcaatgtgg agactgtgag ggtgagctca   4800
atgtggagac ctgtatcaag ataataatag tagtagtaac aatgcaggcg agggtgtggt   4860
tgagtggtag agcagttagt tgatttgaca tgcttgaggt ctcccggtcc atctgtggac   4920
ctgcaacagg aagggaggga ggaaggggg gaacgagaga gaggaaagag agacagaagc    4980
taagataggg aatgagagag gaaggaagaa acgggaagaa attcagactc cttcctgagt   5040
tccgccaacg cctagtgaca tcctgtgcac acccctaaggt ggcctttgtg tggcactggc   5100
tgggtggtc gggaaaggca ttttcagctt gttgcagaac tgccacagta gcatgctggg    5160
tccgtgaaag tttctgcccg ttaacaagaa gtctctacta cttgtgacct caccagtgaa   5220
aatttctttta attgtctcct ggtgttctgg gttttgcatt tttgtttcta aggatacatt   5280
cctgggtgat gtcatgaagt ccccaaagac acagtggggc tgtgttggat tgggaaagat   5340
gatttatctg gggtgtcaaa aggaaaagaa gggaaacagg cacttgggaa aatgtcctcc   5400
cgcccacccg aattttggct tggcaaccgt ggtggaggag caagaaacac gtggacgttt   5460
gaggaggcat ggggtcctag gaggacagga agcagaagga gagagctggg ctgacagcct   5520
gcaggcattg cacagtttca gaaggagatt acagcatgac tgagttttta gggatccaac   5580
agggacctgg gtagagattc tgtgggctct gaggcaactt gacctcagcc agatggtatt   5640
tgaataacct gctcttagag ggaaaacaga catagcaaac agagccacgt ttagtgatga   5700
aactctcact ttgcctgagt catgtgcggc catgcccagg ggtcaggctg acactcaact   5760
caaaaacaag tgagaaattg aagacaatcc gtggtggcag ctactggaag gccaccaca   5820
tccccagaaa gagtggagct gctaaaaagc catttgtgat aggcacagtt atcttgaatg   5880
catggagcag agattacgga aaaatccaga atgttaatga ggcaacattc gagttgagtc   5940
attcagtgtg ggaaacccag acgcttccat cccctaaaag gaacatcttg ctctcagtca   6000
aaatggaaat aaaaattggg gcttgaattt ggcaaatgat tcagaactct gtgtaggtat   6060
tttcacacgc acagtggata atttttcatgt tggagtttat ttgtgctaaa aggcagaaaa   6120
gggtaaaaag cacatcttaa gagttatgag gttctacaaa taaaaataat gttacttaca   6180
gctattcctt aattagtacc cccttccacc tgtggtaatt tcctgagata gtcagtgggg   6240
aaaagatctc tccttctctt cttttctccc ctcccctcct ctccctccct ccctccctcc   6300
ctccctcctc tccctccctc ccctttcct tctttctttg ctccttctcc tctgcctcct    6360
tctcccttc ttcttcattt attctaagta gcttttaaca gcacccaat tacctgtgta    6420
taacgggaaa acacaggctc aagcagctta gagaagattg atctgtgttc act          6473
```

SEQ ID NO: 53       moltype = DNA  length = 7045
FEATURE              Location/Qualifiers
source               1..7045
                      mol_type = genomic DNA
                      organism = Cricetulus griseus
SEQUENCE: 53

```
actagcgtgc aattcagagg tgggtgaaga taaaaggcaa acatttgagg ccatttcctt     60
atttggcacg gcacttagga agtggaacat gcctaatcta ctggttttgta ccacttttcc   120
ctataatgga ctgtttggga agctcctggg caaccgattc tggcatctca ttggtcagag   180
gcctgttaaa tggtactctt attttgcaaag aaggctgtaa cttgtagctt taaaagcctc   240
tcctcaagaa agaagggaga aaggatatgg ctagacatat ctaatagact taaccactgt   300
gaaaagcctt agtatgaatc agatagaacc tattttaaac tcagttttga aaaaaataat   360
ctttatattt atttgtgtgt gtgtgtgtgt gtgtgtgtgt gtgtgtgtgt gtgtgtgtgt   420
gaaccacatg tagcaggtgc tggaggaggc cagaagaggg caccagatct cctggaactg   480
acaccacaca tggttatgag ctgcctgatg tgggtgctgg gaactgaact ctcgtgttct   540
gcaagagcag caactgttct cttaactgat gagccatctc tccagccccc ccataatttt   600
taattgttca ttttagtaaa ttttattcat aatcaattat cacagtataa acaatgatt    660
ttatatatat catatacata tcaaggatga cagtgagggg gatatgtgtg tgtgtgtgtg   720
tgtgtgtgtg tgtgtgtgtg tgtgttattt gtgtgtgtc tttttaagaa ggtgacatag    780
tcactgcatt tctctgaagg atttcaaagg aatgagacat gtctgtctgc caggaaccct   840
atcttcctct ttgggaatct gacccaaatg aggtattctg aggaactgaa tgaagagctc   900
aagtagcagt gtcttaaacc caaatgtgct gtctagagaa agtcaacgtc atcagtgagc   960
tgaggagaga tttactgagc ggaagacaag cgctctttga tttaagtggc tcgaacagtc  1020
acggctgttg agtggagcct gtgctcaggt ctgaggcagt ctttgctagc cagctgtgat  1080
gagcagtgaa gaaagggtgg agatggaggc agggtgggaa cagggctatg gttcagacta  1140
ggtatcgtga gcacaccagc tggttgactt gtggtctgtg ggtcaggcgt tgtaaacgcc  1200
ctcagggtca ggcagtcaca ttgcttgaag ctgaatgggt gaggcaacac agagagtgca  1260
aagaaggcaa agtaccacct cttccccgac ccaggtcact tctgggttat agctgagact  1320
ccggacagca tgcaaccagc tcagggaaa acttgatgtc tgcatgttgc                1380
tatgaaatgt gattcggtac atctggaaaa aatttataat gctggctcag tcaagcactg  1440
aacaaaggta ccttggcttt gggagctaca tgacattgac ttgtaggcag acttttttt   1500
ttctgcccgc caattcccag ataaccaata tggaggctca atattaatta taaatgctcg  1560
gctgatagct caggcttgtt actagctaac tcttccaact taaatgaacc catttctatt  1620
atctacattc tgccacgtga cttttacctg tacttcctgt ttcctctcct tgtctgactc  1680
```

```
tgcccttctg cttcccagag tccttagtct ggttctcctg cctaaccttta tcctgcccag    1740
ctgctgacca agcatttata attaatatta agtctcccag tgagactctc atccagggag    1800
gacttgggtg ctccccctc ctcattgcca tccgtgtctt cctcttcctt cgcttccccc     1860
tcctcttcct gctcttcctc ctccacccct cctttcatag tattgatggc aagggtgttc    1920
tagaatggag gagtgcccat aggcatgcaa agaaaccgat taggatgctc tgtgagggt     1980
tgtaatcata agcgatggac acaattcaag ccacagagtg aagacggaag gatgcactgt    2040
gctctagagc aacttctggg gcagaatcac agggtgagtt tctgacttga gggcgaagag    2100
gccacgagga agggagtgag tttgtctgag ctagaagcta cggcccacct cttggtagca    2160
gacctgccca caagcatgct ttgttaatca tgtgggatct gattttcctc taaatctatg    2220
ttcaactctt aagaaaatgt gaattctcac attaaaattt agatatacgt cttttggtgt    2280
ggggggtgta aaaaatcctc aagaatatgg atttctgggg gccggagaga tggctcagag    2340
gttaagagaa ctggttgctc ttctagacat tctgagttca attcccagca accacatggt    2400
ggctcacaac catctgtaat gcgacctggt gccatcttct gacatgcatg gatacatgca    2460
ggcagaaagc tgtatacata gtaaattgat aaatctttt ttaaaaagag tatggattct     2520
gccgggtgtt ggtggcgcac gccttaatc ccagcactct ggaggcagag gcaggtggat     2580
ctctgtgagt tcgagaccag cctggtctat aagagctagt tccaggacag cctccaaagc    2640
cacagagaaa ccctgtctcg aaaaaaccaaa aaaaaaaaaa aaaaaaaaaa aaaaaaaga    2700
gtatggattc taagaaagcc gtaacagctg gagctgtgta cggagttcag cgtggtacta    2760
gaagaacaga cattcatgat gaaacacccc aggattttta cttagtatct agtttccatt    2820
gttgttttga gaccggctct tatgctctcc aggctggcct caaactgctg atcttcccgc    2880
ctctacctct caagtcctgg gactacttgg ctcataaaac agttttttgtc gggctccctg    2940
aagttatggt tgtacaaacc gtgggggtca atatactcac ttgggcagag agagaaggtc    3000
tgaatcccag acaatgactg catctcagga cagttgggaa gaggacaatg gcagaaggac    3060
ttagaaaaga tagactggag ggtggaaaag cagcaggaac agagaaacaa aacaggaagc    3120
ttgctatcca gggccactct ggagtcctgt ggcaagatgg aagcgggcta ggggaataca    3180
tttgtgctac tgtgtgtgtg tgtgtgtgtg tgtgtgtgat caatgcctat                3240
caatgttgaa gggaaatat gtataccaca ttgattctgg gagcaattct cagtatctgc     3300
cctagagaaa ggaatggccc ctgcagaata gacagagtga atggtgccct ttatcatttg    3360
ctaaagtgaa ggagaaataa acatccttcc atagagtttc aggtaaatga accccacagt    3420
tcatctgtgc cgtggtggag gcctggccaa cagttaaaaa gattagacac ggacaaagtc    3480
tgaaggaaac acctcgaata ggaagaggag agccacctca ttctgtaact ttcctccaagg    3540
ggaagatgtt ccaagagtgg gaataaatgg tcaaaggggg gattttttaat taggaaaacg    3600
atttcctgta tcacttgtga aactggaggt tgatttgggg cataggacaa tagatttgat    3660
gctttgcaaa aagctgtttc aaagcagaga aatggaatag agacaattat gtagcgagga    3720
gggagggtgg ggcgaagatg gagacagaga agtggaagct gactttaggg aagaggaaca    3780
tagaccacag gggcggggcg gggggcaggg gcggggggcg gggctcaaag gaggcagtgg    3840
gaacgttgct agtgttcgca gcgtaagcgt gaatgtgcaa gcgtctttgt ggtgtgtgac    3900
caggagtagc gtggctggct tgtgtgctgc ttgtaatccc agtcttgtag gtttccacac    3960
tgttccacag tgggtgtgat tttcctcgg agagcatgag ggctctgctt tccccacatc     4020
ctccccagcg ttcgttggta tttgtttcca agatgttagt gggtgagaca aagcctctct    4080
gttgatttgc ctttaacagg tgacaaaaaa agctcaacca ggagacattt ttgccttctt    4140
ggaaggtaat gctcccatgt agagcaatgg gacccatctc taaggtgagg ctactcttgc    4200
agtttgcacc cagctcttct gatgcaggaa ggaagttggt gggcaagcaa gactgttgc     4260
ttcttgcgat ggacacattc tgcacacaaa ggctcaggag gggagaaggc tgtttgatgt    4320
ttagcactca ggaaggcccc tgatgcatct gtgattagct gtctccatct gtggagcaga    4380
cacggactaa ctaaaaacca gtgttttttaa attgtcaagc ctttaaggtg aggaaattga    4440
cttattgtgc tgggccatac gtagagcaag tgctctgcag cccggcctg                4500
gtttctaggc accagaatgg cctagaacta actcacaatc ctcccattcc aggtctcagg    4560
tgctagaatg aaccactata ccagcctgcc tgcctgccta cctgccttcc taaattttaa    4620
atcatgggga gtaggggaga atacacttat cttagttagg gtttctattg ctgtgaagag    4680
acaccatgag catggcaact cttataaagg aaaacattta gttgggtggc agtttcagag    4740
gttttagtac attgtcatca tggctgggaa catgatggca tgcagacaga catggtgctg    4800
gagaaaggga tgagagtcct acatcttgca ggcaacagga cctcagctga cactggct     4860
ggtaccctga gcataggaaa cctcacagcc caccctcaca gtgacatatt tccttcaaca    4920
aagccatacc tcctaatagt gccactccct atgagatgac agggccaatt acattcaaac    4980
tgctataaca ctttaaagta ttttatttttt attattgtaa attatgtatg tagctgggtg    5040
gtggcagccg aggtgcacgc ctttaatccc agcacttggg aggcagaggc agatggatct    5100
ctgtgagttc aagaccagcc tggtctataa gagctagttg caaggaagga tatacaaaga    5160
acagttctag gatagccttc aaagccacag agaaagtcgt tcttgaaaac caaaaattgt    5220
gctgggacct gtctctgctt tggttgcttc ccactccccc agagctggac tcttggtcaa    5280
cactgaatca gctgcaaaat aaactcctgg attcctctct gtaacaggaa gcccgaagtc    5340
aggcgcccac ttgtcttctc gcaggattgc catagacttt ttctgtgtgc ccaccattcc    5400
agactgaagt agagatggca gtggcagaga ctgggaaggc tgcaacgaaa acaggaagtt    5460
attgcaccct gggaaatgtc tggaaatgaa gcttcaaaac ttgcttcatg ttcagttgta    5520
cacagactca ctcccaggtt gactcacacg tgtaaatatt cctgactatg tctgcactgc    5580
ttttatctga tgcttccttc ccaaaatgcc aagtgtacaa ggtgagggaa tcacccttgg    5640
attcagagcc cagggtcgtc ctccttaacc tggacttgtc tttctccggc agcctctgac    5700
accctcccc ccattttctc tatcagaagg tctgagcaga gttgggcac gctcatgtcc      5760
tgatacactc cttgtcttcc tgaagatcta acttctgacc cagaaagatg gctaaggtg     5820
tgaagtgttt gacatgaaga cttggtctta agaactggag cagggaaaa agtcggatg      5880
tggcagcatg tacccgaaat cccagaactg ggaggtaga cagggatgag tgcccggggc    5940
tagctggctg ctcagccagc ctagctgaat tgccaaattc caactcctat tgaaaaacct   6000
ttaccaaaca aacaaacaaa caataataaa caacaacaac aacaacaaac tacccatac     6060
aaggtgggcg gctcttggct cttgaggaat gactcaccca aacccaaagc ttgccacagc    6120
tgttctctgg cctaaatggg gtgggggtgg ggcagagaga gagacagaga gagacatgac    6180
ttcctgggct gggctgtgtg ctctaggcca ccaggaactt tcctgtcttg ctctctgtct    6240
ggcacagcca gagcaccagc acccagcagg tgcacacacc tccctccgtg cttcttgagc    6300
aaacacaggt gccttggtct gtctattgaa ccggagtaag ttcttgcaga tgtatgcatg    6360
gaaacaacat tgtcctggtt ttatttctac tgttgtgata aaaaccgggg aactccagga    6420
```

```
agcagctgag gcagaggcaa atgcaaggaa tgctgcctcc tagcttgctc cccatggctt   6480
gccgggcctg ctttctgcaa gcccttctct ccccattggc atgcctgaca tgaacagcgt   6540
ttgaaatgct ctcaaatgtc actttcaaag aaggcttctc tgatcttgct aactaaatca   6600
gaccatgttt caccgtgcat tatctttctg ctgtctgtct gtctgtctgt ctgtctatct   6660
gtctatcatc tatcaatcat ctatctatct atcttctatt tatctaccta tcattcaatc   6720
atctatcttc taactagtta tcatttattt atttgtttac ttacttttttt tatttgagac   6780
agtatttctc tgagtgacag ccttggctgt cctggaaccc attctgtaac caggctgtcc   6840
tcaaactcac agagatccaa ctgcctctgc ctctctggtg ctggggttaa agacgtgcac   6900
caccaacgcc ccgctctatc atctatttat gtacttatta ttcagtcatt atctatcctc   6960
taactatcca tcatctgtct atccatcatc tatctatcta tctatctatc tatctatcta   7020
tctatcatcc atctataatc aattg                                         7045

SEQ ID NO: 54           moltype = DNA  length = 6473
FEATURE                 Location/Qualifiers
source                  1..6473
                        mol_type = genomic DNA
                        organism = Cricetulus griseus
SEQUENCE: 54
agtgaacaca gatcaatctt ctctaagctg cttgagcctg tgttttcccg ttatacacag     60
gtaattggtg tgctgttaaa agctacttag aataaatgaa gaagaaaggg agaaggaggc    120
agaggagaag gagcaaagaa agaaggaaag ggggagggag ggagaggagg gagggaggga    180
gggagggagg gagaggaggg gagggggaga aagaagagaa gggagagatc tttcccccact    240
gactatctca ggaaattacc acaggtggaa ggggtactaa attaaggaat agctgtaagt    300
aacattattt ttattcgtag aacctcataa ctcttaagat gtgctttttta ccctttttctg    360
ccttttagca caaataaact ccaacatgaa aattatccac tgtgcgtgtg aaaatacccta    420
cacagagttc tgaatcattt gccaaattca agccccaatt tttattttcca ttttgactga    480
gagcaagatg ttcctttttag gggatggaag cgtctgggtt tcccacactg aatgactcaa    540
ctcgaatgtt gcctcattaa cattctcgat ttttccgtaa tctctgctcc atgcattcaa    600
gataactgtg cctatcacaa atggctttttt agcagctcca ctctttctgg ggatgtggtg    660
gcccttccag tagctgccac cacggattgt cttcaatttc tcacttgttt ttgagttgag    720
tgtcagcctg accctgggc atggccgcac atgactcagg caaagtgaga gtttcatcac    780
taaacgtggc tctgtttgct atgtctgttt tccctctaag agcaggttat tcaaatacca    840
tctggctgag gtcaagttgc ctcagagccc acagaatctc tacccaggtc cctgttggat    900
ccctaaaaac tcagtcatgc tgtaatctcc ttctgaaact gtgcaatgcc tgcaggctgg    960
cagcccagct ctctccttct gcttcctgtc ctcctaggac cccatgcctc ctcaaacgtc   1020
cacgtgtttc ttgctcctcc accacggttg ccaagccaaa attcgggtgg gcgggaggac   1080
attttcccaa gtgcctgttt cccttctttt ccttttgaca ccccagataa atcatctttc   1140
ccaatccaac acagccccac tgtgtctttg gggacttcat gacatcaccc aggaatgtat   1200
ccttagaaac aaaaatgcaa aacccagaac accaggagac aattaaagaa attttcactg   1260
gtgaggtcac aagtagtaga gacttcttgt taacgggcag aaactttcac ggacccagca   1320
tgctactgtg gcagttctgc aacaagctga aaatgccttt cccgaccacc caagccagtg   1380
ccacacaaag gccaccttag ggtgtgcaca ggatgtcact aggcgttggc ggaactcagg   1440
aaggagtcg aatttcttcc cgtttcttcc ttcctctctc attccctatc ttagcttctg   1500
tctctctttc ctctctctcg ttcccccccct tctccctcc cttcctgttg cagggccaca   1560
gatggaccgg gagacctcaa gcatgtcaaa tcaactaact gctctaccac tcaaccacac   1620
cctcgcctgc attgttacta ctactattat tatcttgata caggtctcca cattgagctc   1680
accctcacag tctccacatt gagctcaccc tcacagtctc cacattgagc tcaccctcac   1740
agtctccaca ttgagctcac cctcacagtc tccacattga gctcaccctc acagtctcca   1800
cattgagctc accctgtggc tctggcaaac cttgaattct ctcattcctc ctgcctcagc   1860
ctctggggtc gtgggggatta gccaaaccca cttgaggttt tcttcaatca gcaaattctt   1920
agcgttcaat taacacacac tcataactcc agtactttgg aaaccggaac aggagaattt   1980
ctgtgagctg gaggctagct tggactacag tatgagaccc tgtctctaaa taaatacaca   2040
aagaaatctc accaagggcc tccctctctc agcaagctct aactgtgtg ggagttctgg   2100
gttgttccga ttaacgggct cagaactcta ctgcccagca catcagcccc tagacacagg   2160
tggctctcta catgtgaaca tgcagtcaca gaaatgaaat aaagtgaaaa ttttatttct   2220
tcagttgtat agcctcttcc gtgtgggctg tagttactgt cttgaatagg ataggctcag   2280
aatccttggt gctggaacca agagtttgat tccattagac cagggaatat aatgcccca   2340
atagggcatt cctcctcccg gtcactagcg gtgcactttc tccgaatctt tgtcatgttg   2400
aattagaaaa gttagtattt tcctccatcc ctttcccctcc tccctcctcc ccctcctcc   2460
ctcctccccc cctcctctcg tctccccgcc cctcccctcc cctctgatcc ctcccccatc   2520
tatcaaatcc aagaattcca gtaaaaagag gaaaacaatc gaagtgattt cgttgattgt   2580
cagttccacc aaagcaagac ttgactttag ttccgcgttt cggttccgg catgcaccac   2640
agccagcgag caccgtggaa ggatgctagc acggtcctcc cccgcccccc actagctgtc   2700
ttcagctccc cagtagagggg caaccgcact ccagattctc aatggagagt gtttacacaa   2760
tcgttgcggg tttgtgtgag cgcgcccgct tccagagaca cttcttcttt ttcttttttc   2820
catttcatcc cagtggcaac gcagagtgcc agatcattca ggcgtttgc agggcaagcc   2880
gtgggagctt ggcaagcaag gccccatttc ctagggaacc cgtgcctggc gcttcaggaa   2940
agcacgggaa cctggcactg tgactctgcg ggtattattt tgcagaactc tttattaaac   3000
gggagtttca agtccagctg gagacgacca ggcagcgctc ttaacccccag agtcacacac   3060
aggtgccttt tcttgggggcc agattgggggt tgtgtggcag acctgcgacc agcttgacaa   3120
ctcttctgcc aggccacaaa atggtgttgg ctgtaagagg tgacaccagg gacagggaag   3180
atcgctgcta ttctcctgag ctctccaaag acccacacca gtctgtcccc ctttcctcct   3240
gctcttcccc tgtatcgccc cctcaccatc tcccccaacg agactcttgg catctcctcg   3300
gcacaaggat ttgaaaatag atgcttgggg gtgagagaga agaggagaaa agagagagaa   3360
ggaaggaagg atatatagat gatacagacg catacaggtg acatgtagct aatcatttttt   3420
aattaaaaaa taaattaaaa gcaaatcaag gatatatatg ataccccttag agcaagtgtc   3480
tcatacacac acaaacacac acacacaata tatatatata tatatatata tatatatata   3540
tatatatata ttatacttgg aacaagtgtc cagaagggct ggggactcta aagtgcttgt   3600
caaagccagg ctcacatcag taatcttatc acctggtaga ctgagacagg aggattttga   3660
```

```
tgagttcagg cccagcctga gctgcagaat gtgattctat cccaaaaaag taaaataaaa    3720
taaaattcaa aatacacgaa aagagtattt gctgaacaaa caagcctaaa gccctggatc    3780
ccttccccca tgtcctaaga aaataagttt cttgaagctg agggatggc tcagaggtta     3840
agagcccag ctgcacttgc ggaacactaa gacccagttc ccagacccca cactgtgggt     3900
cacaactgtc tcaaacgcca gctccggagg atccatgccc tctcctggcc tccaccggca    3960
ccaagaacac atacagtgcc catacattta tgcaagcaag gtattcacgc acataaaact    4020
aaaagaatat ttaataaaga tataacaaaa tagcatgaag cccagctggt acagaggttc    4080
aaactacatc ccaggttcat ccctctgcct ttgctctcag ttggcttggg taggtctctt    4140
ctctgaactg gcgccctgcg ggttccacat tgagaccctc tcattttta acctacttct    4200
tctgggcggg gttaattgct gccagggctc aagccaacgc ttcctcttct ccacagcaat    4260
cttccaagtt tcacgagata accaggaact gctaagttca tgtgaacctt agtgaagaac    4320
ctgagtcttc ccatgtgatt ggtgtgtgca tgtgtgcata cacaaatgta tgtgtgtgct    4380
ctatgtgtgc ctatgtatgt gtgcatgcat gtgtgcatat acaaatgcat atatgtctat    4440
gtagtgtgcg tacacaaatg tatgtgtgtg ctcaatgtgt gcctatgtgt gtgtatgcat    4500
gtgtgcgtac acaatgcatg tgtggtgt ctgtgtgcct gtgtgtgtat gcatgtatgc      4560
atacacaaat gtatatgtgt ggtgtgtgaa tgtgtgccta tgtatgtgtg tgctgtgtgt    4620
gggtgtggta tgtgtgtgat gtgtggaggg gtgtgtatgt gtggtatgta taggtgatac    4680
gtttggggtg taatatgcgt atgtggtttg tgaaatgtag ttcgtgtgtg tgcatgtgtg    4740
cgtgcgtgcg tgcgtgcgtg cgtgtgtgtg tgtgtgtgtg tgtgtgtgtt ggatatagta    4800
tgtgtgaggt gtgtgtactc accatggcct ccctcacttg ggggagtgaa gtcagcagcc    4860
tggaccactc agggacatga gatactcaga cacatcttga tttccacccc tcttttcctg    4920
atcctccttc acgtgtcact ttcccaaaca ctggacaaca gtttggggc atctgattcc     4980
actaatgaca gggacatcac atgtctccag agggaacacc ttctgtgtca catgtcatct    5040
gagaatgtag cagagtcaca gagaaatgtc acagaaacca aaatgcagag taccaaggta    5100
tagctaggca cagagcagag gggaagccgc tgaatttatt aaaaatgtca gaatcgtaaa    5160
agacaggggga cagcggtggg gacattcagg gtccagtagc acacaggcag tccaaacctg    5220
atcactggaa ggtagtaggt aaggaaaggc tgcacacaga ttattcacac agtttataca    5280
tgtacacaga ttattcacat ggtttgtgta tgtgcacaga ttattcacac agtttataca    5340
tgtgtggctt cgtggtaact ttgagcttac tttcaattta aaaggatctc tctcacaagc    5400
tggggccggg aatggctgca gtcaacactc catcacttag tcacactgtg caaacagcac    5460
ctcctgactc atggtgactt gtagtaaaat gaagaggcca catttgcatc caagacagct    5520
catcagtacc tagtgaagaa tctgtccctg agtatttgca tgaatggacc cgggtccagg    5580
gcctggctgg gagtctccag gtgttgcagc cagaatgtca ttgtgttttt tcaggatccc    5640
agaagtttct aaaatacagg ccaagtactc atttgtgtta caaagtatct gactaataga    5700
agtgattagg taaacaaaag ccttttaaaa accgagatca cccttgtcat gtccctggcc    5760
tcttagaaca agatccaagc ttttgctggt tgacaagtgg ggccatccag tgcgtctccg    5820
ttcctgctac ttcatctgga agacctctcc cactaacttg cccctgaccc ctcacacctg    5880
ctgtttcctt tccaccgga agtgcttgtc taggctttca tggccatctg actgagcatc       5940
taggcctcag tccagtggtc cctcagctct ctctagtcac tgtactaatg gaaacggcca    6000
ctaactacat tttcaatatg gaagcctcct cctcaggaac ctccaagggc agaagcctcc    6060
agagaaccac tcctgacccc ctggagttct gagtgcttct ggccctctct gtgtctgcag    6120
gactattcac cacttgtgtt gaatggttca gtcctccacct cctctggcat gtgctcagtt    6180
ctcatctcat tggggagtcc ttcccaggtc actcttctct cctgtctttg aagtgtttt      6240
ttccttcatg gtatttctgt ctgggcacac acacagacac acatacacac acatacacac    6300
ccatgcagta tggcagatac atccacctatg tttcagattt ttattctacc atcacccaat    6360
acctgaatcc ccgaaaaagc cttagaaagc caggaatttg tgtattttg tcagcactcc      6420
accccagcac ctgaagccaa gcctgactta atattttttgg ttttgtttct aga           6473

SEQ ID NO: 55          moltype = DNA   length = 7045
FEATURE                Location/Qualifiers
source                 1..7045
                       mol_type = genomic DNA
                       organism = Cricetulus griseus
SEQUENCE: 55
caattgatta tagatggatg atagatagat agatagatag atagatagat agatagatga       60
tggatagaca gatgatggat agttagagga tagataatga ctgaataata agtacataaa     120
tagatgatag agcggggcgt tggtggtgca cgtctttaac cccagcacca gagaggcaga    180
ggcagttgga tctctgtgag tttgaggaca gcctggttac agaatgggtt ccaggacagc    240
caaggctgtc actcagagaa atactgtctc aaataaaaaa agtaagtaaa caaataaata    300
aatgataact agttagaaga tagatgattg aatgataggt agataaatag aagatagata    360
gatagatgat tgatagatga tagacagata gacagacaga cagacagaca gacagcagaa    420
agataatgca cggtgaaaca tggtctgatt tagttagcaa gatcagagaa gccttctttg    480
aaagtgacat ttgagagcat tcaaacgct gttcatgtca ggcatgccaa tggggagaga      540
agggcttgca gaaagcaggc ccggcaagcc atggggagca agctaggagg cagcattcct    600
tgcatttgcc tctgcctcag ctgcttcctg gagttccccg gttttatca caacagtaga    660
aataaaacca ggacaatgtt gtttccatgc atacatctgc aagaacttac tccggttcaa    720
tagacagacc aaggcacctg tgtttgctca agaagcacgg agggagggtgt gtgcacctgc    780
tgggtgctgg tgctctggct gtgccagaca gagagcaaga caggaaagtt cctggtgtcc    840
tagcacacac agcccagccc aggaagtcat gtctctctct gtctctgtct ctgccccacc    900
cccaccccat ttaggccaga gaacagctgt ggcaagcttt gggtttgggt gagtcattcc    960
tcaagagcca agagccgcc acttgtatg gggtagtttg ttgttgtgt tgttgttatt      1020
atttgtttgt ttgtttgttt ggtaaaggtt tttcaatagg agttggaatt tggcaattca    1080
gctaggctgg ctgagcagcc agctagcccc gggcactcat ccgtctctac ctccccagtt    1140
ctgggatttc gggtacatgc tgccacatcc gacttttttc ccctgctcca gttcttaaga    1200
ccaagtcttc atgtcaaaca cttcaccacc ttagccatct ttctgggtca gaagttagat    1260
cttcaggaag acaaggagtg tatcaggaca tgagcgtgcc ccaactctgc tcagaccttc    1320
tgatagaaa aatgggggga ggggtgtcag aggctgccgg agaaagacaa gtccaggtta     1380
aggaggacga ccctgggctc tgaatccaag ggtgattccc tcaccttgta cacttggcat    1440
tttgggaagg aagcatcaga taaaagcagt gcagacatag tcaggaatat ttacacgtgt    1500
```

```
gagtcaacct gggagtgagt ctgtgtacaa ctgaacatga agcaagtttt gaagcttcat   1560
ttccagacta ttcccagggt gcaataactt cctgttttcg ttgcagcctt cccagtctct   1620
gccactgcca tctctacttc agtctggaat ggtgggcaca cagaaaaagt ctatggcaat   1680
cctgcgagaa gacaagtggg cgcctgactt cgggctcctg ttacaagaga ggaatccagg   1740
agtttatttt gcagctgatt cagtgttgac caagagtcca gctctggggg agtgggaagc   1800
aaccaaagca gagacaggtc ccagcacaat ttttggtttt caagacagca cttctctgtg   1860
gctttgaagg ctatcctaga actgttcttt gtatatcctt ccttgcaact agctcttata   1920
gaccaggctg gtcttgaact cacagagatc catctgcctc tgcctcccaa gtgctgggat   1980
taaaggcgtg cacctcggct gccaccaccc agctacatac ataatttaca ataataaaaa   2040
taaaatactt taaagtgtta tagcagtttg aatgtaattg gccctgtcat ctcatagga    2100
gtggcactat taggaggtat ggctttgttg aaggaaatat gtcactgtga gggtgggctg   2160
tgaggtttcc tatgctcagg gtaccagcca gtgtctcagc tgaggtcctg ttgcctgcaa   2220
gatgtaggac tctcatccct ttctccagca ccatgtctgt ctgcatgcca tcatgttccc   2280
agccatgatg acaatgtact aaaacctctg aaactgccac ccaactaaat gttttccttt   2340
ataagagttg ccatgctcat ggtgtctctt cacagcaata gaaacccta ctaagataag    2400
tgtattctcc cctactcccc atgatttaaa atttaggaag gcaggtaggc aggcaggcag   2460
gctggtatag tggttcattc tagcacctga gacctggaat gggaggattg tgagttagtt   2520
ctaggccatt ctggtgccta gaaaccagag ccgggggttg gcccaatgca gagcacttgc   2580
tctacgtatg gcccagcaca ataagtcaat ttcctcacct taaaggcttg acaatttaaa   2640
aacactggtt tttagttagt ccgtgtctgc tccacagatg gagacagcta atcacagatg   2700
catcaggggc cttcctgagt gctaaacatc aaacagcctt ctccctcct gagcctttgt    2760
gtgcagaatg tgtccatcgc aagaagcaaa cagtcttgct tgccaccaa cttccttcct    2820
gcatcagaag agctgggtgc aaactgcaag agtagcctca ccttagagat gggtcccatt   2880
gctctacatg ggagcattac cttccaagaa ggcaaaaatg tctcctggtt gagcttttt    2940
tgtcacctgt taaaggcaaa tcaacagaga ggctttgtct cacccactaa catcttggaa   3000
acaaatacca acgaacgctg ggaggatgt ggggaaagca gagccctcat gctctccgag    3060
ggaaaatcac acccactgtg gaacagtgtg gaaacctcaa agactgggat tacaagcagc   3120
acacaagcca gccacgctac tcctggtcac acaccacaaa gacgcttgca cattcacgct   3180
tacgctgcga acactagcaa cgttcccact gcctcctttg agcccgccc ccgcccctg     3240
ccccccgccc cgcccctgtg gtctatgttc ctcttcctca aagtcagctt ccacttctct   3300
gtctccatct tcgccccacc ctccctcctc gctacataat tgtctctatt ccatttctct   3360
gctttgaaac agctttttgc aaagcatcaa atctattgtc ctatgcccca atcaacctc    3420
cagtttcaca agtgatacag gaaatcgttt tcctaattaa aaatcccccc tttgaccatt   3480
tattcccact cttggaacat cttcccctttg aggaaagtta cagaatgagg tggctctctt   3540
cttcctattc gaggtgtttc cttcagactt tgtccgtgtc taatctttt aactgttggc    3600
caggcctcca ccacggcaca gatgaactgt ggggttcatt tacctgaaac tctatggaag   3660
gatgtttatt tctccttcac tttagcaaat gataaagggc accattcact ctgtctattc   3720
tgcaggggcc attccttct ctaggccaga tactgagaat tgctcccaga atcaatgtgg    3780
tatacatatt tccccttcaa cattgatagg cattgatcac acacacacac acacacacac   3840
acacacacac acacagtagc acaaatgtat tccctagcc cgcttccatc ttgccacagg    3900
actccagagt ggcctggat agcaagcttc ctgttttgtt tctctgttcc tgctgctttt    3960
ccaccctcca gtctatcttt tctaagtcct tctgccattg tcctcttccc aactgtcctg   4020
agatgcctgc attgtctggg attcagacct tctctctctg cccaagtgag tatattgacc   4080
cccacggttt gtacaaccat aacttcaggg agcccgacaa aaactgtttt atgagccaag   4140
tagtcccagg acttgagagg tagaggcggg aagatcagca gtttgaggcc agcctggaga   4200
gcataagagc cggtctcaaa acaacaatgg aaactagata ctaagtaaaa atcctggggt   4260
gtttcatcat gaatgtctgt tcttctagta ccacgctaca ctccgtacac agctccagct   4320
gttacggctt tcttagaatc catactcttt ttttttttt tttttttttt ttttttttgg   4380
ttttttcgaga cagggtttct ctgtggcttt ggaggctgtc ctggaactag ctcttataga   4440
ccaggctggt ctcgaactca cagagatcca cctgcctctg cctccagagt gctgggatta   4500
aaggcgtgcg ccaccaacac ccggcagaat ccatactctt tttaaaaaa gatttatcaa    4560
tttactatgt atacagcttt ctgcctgcat gtatccatgc atgtcagaag atggcaccag   4620
gtcgcattac agatggttgt gagccaccat gtggttgctg ggaattgaac tcagaatgtc   4680
tagaagagca accagttctc ttaacctctg agccatctct ccggccccca gaaatccata   4740
ttcttgagga ttttttacac ccccccccacc aaaagacgta tatctaaatt ttaatgtgag   4800
aattcacatt ttcttaagag ttgaacatag atttagagga aaatcagatc ccacatgatt   4860
aacaaagcat gcttgtgggc aggtctgcta ccaagaggtg ggccgtagct tctagctcag   4920
acaaactcac tcccttcctc gtggcctctt cgccctcaag tcagaaactc accctgtgat   4980
tctgccccag aagttgctct agagcacagt gcatccttcc gtcttcactc tgtggcttga   5040
attgtgtcca tcgcttatga ttacaacccc tcacagagca tcctaactgg tttcttgca    5100
tgcctatggg cactcctcca ttctagaaca cccttgccat caatactatg aaaggagggg   5160
tggaggagga agagcaggaa gaggaggggg aagcgaggga agaggaagac acggatggca   5220
atgaggaggg gggagcaccc aagtcctccc tggatgagag tctcactggg agacttaata   5280
ttaattataa atgcttggtc agcagctggg caggataagg ttaggcagga gaaccagact   5340
aaggactctg ggaagcagaa gggcagagtc agacaaggag aggaaacagg aagtacaagg   5400
taaagtcacg tggcagaatg tagataatag aaatgggttc atttaagttg gaagagttag   5460
ctagtaacaa gcctgagcta tcagccgagc atttataatt aatattgagc ctccatattg   5520
gttatctggg aattggcggg cagaaaaaaa aaagtctgcc tacaagtcaa tgtcatgtag   5580
ctcccaaagc caaggtacct ttgttcagtg cttgactgag ccagcattat aattttctc    5640
cagatgtacc gaatcacatt tcatagcaac atgcagacat caagtttttcc ctgaagctct   5700
aaccagctgt tgcatgctg tccggagtct cagctataac ccagaagtga cctgggtcgg    5760
ggaagaggtg gtactttgcc ttctttgcac tctctgtgtt gcctcaccca ttcagcttca   5820
agcaatgtga ctgcctgacc ctgagggcgt ttacaacgcc tgacccacag accacaagtc   5880
aaccaggtgg tgtgctcacg atacctagtc tgaaccatgc cctgctccc accctgcctc    5940
catctccacc ctttcttcac tgctcatcac agctggctag caaagactgc cttcagacctg   6000
agcacaggct ccactccaca gccgtgactg ttcgagccac ttaaatcaaa gagcgcttgt   6060
cttccgctca gtaaatctct cctcagctca ctgatgacgt tgactttctc tagacagcac   6120
atttgggttt aagacactgc tacttgagct cttcattcag ttcctcagaa tacctcattt   6180
gggtcagatt cccaaagagg aagatagggt tcctggcaga cagacatgtc tcattccttt   6240
```

```
gaaatccttc agagaaatgc agtgactatg gcaccttctt aaaaagcaca cacacaaata   6300
acacacacac acacacacac acacacacac acacacacac atatccccct cactgtcatc   6360
cttgatatgt atatgatata tataaaatca ttgttttata ctgtgataat tgattatgaa   6420
taaaatttac taaaatgaac aattaaaatt atgggggggg ctggagagat ggctcatcag   6480
ttaagagaac agttgctgct cttgcagaac acgagagttc agttcccagc acccacatca   6540
ggcagctcat aaccatgtgt ggtgtcagtt ccaggagatc tggtgccctc ttctggcctc   6600
ctccagcacc tgctacatgt ggttcacaca cacacacaca cacacacaca cacacacaca   6660
cacacacaca caaataaata taagattat tttttttcaaa actgagttaa aaataggttc   6720
tatctgattc atactaaggc ttttcacagt ggttaagtct attagatatg tctagccata   6780
tcctttctcc cttctttctt gaggagaggc ttttaaagct acaagttaca gccttctttg   6840
caaataagag taccatttaa caggcctctg accaatgaga tgccagaatc ggttgcccag   6900
gagcttccca aacagtccat tatagggaaa ggtggtacaa accagtagat taggcatgtt   6960
ccacttccta agtgccgtgc caaataagga aatggcctca aatgtttgcc ttttatcttc   7020
acccacctct gaattgcacg ctagt                                         7045

SEQ ID NO: 56          moltype = DNA   length = 13515
FEATURE                Location/Qualifiers
source                 1..13515
                       mol_type = genomic DNA
                       organism = Cricetulus griseus
SEQUENCE: 56
tctagaaaca aaaccaaaaa tattaagtca ggcttggctt caggtgctgg ggtggagtgc     60
tgacaaaaat acacaaattc ctggcttttct aaggcttttt cggggattca ggtattgggt    120
gatggtagaa taaaaatctg aaacataggt gatgtatctg ccatactgca tgggtgtgta    180
tgtgtgtgta tgtgtgtctg tgtgtgtgcc cagacagaaa taccatgaag gaaaaaaaca    240
cttcaaagac aggagagaag agtgacctgg gaaggactcc ccaatgagat ggaaactgag    300
cacatgccag aggaggtgag gactgaacca ttcaacacaa gtggtgaata gtcctgcaga    360
cacagagagg gccagaagca ctcagaactc caggggtca ggagtggttc tctgaaggct     420
tctgcccttg gaggttcctg aggaggaggc ttccatattg aaaatgtagt tagtggccgt    480
ttccattagt acagtgacta gagagagctg agggaccact ggactgaggc ctagatgctc    540
agtcagatgg ccatgaaagc ctagacaagc acttccgggt ggaaaggaaa cagcaggtgt    600
gaggggtcag gggcaagtta gtgggagagg tcttccagat gaagtagcag gaacggagac    660
gcactgcatg gcccccacttg tcaaccagca aaagcttgga tcttgttcta agaggccagg    720
gacatgacaa gggtgatctc ggttttttaaa aaggcttgtg ttacctaatc acttctatta    780
gtcagatact ttgtaacaca aatgagtact tggcctgcat tttagaaact tctgggatcc    840
tgaaaaaaca caatgacatt ctggctgcaa cacctggaga ctcccagcca ggccctggac    900
ccgggtccat tcatgcaaat actcaggac agattcttca ctaggtactg atgagctgtc     960
ttggatgcaa atgtggcctc ttcattttac tacaagtcac catgagtcag gaggtgctgt   1020
ttgcacagtg tgactaagtg atggagtgtt gactgcagcc attcccggcc ccagcttgtg   1080
agagagatcc ttttaaattg aaagtaagct caaagttacc acgaagccac acatgtataa   1140
actgtgtgaa taatctgtgc acatacacaa accatgtgaa taatctgtgt acatgtataa   1200
actgtgtgaa taatctgtgt gcagcctttc cttacctact accttccagt gatcaggttt   1260
ggactgcctg tgtgctactg gaccctgaat gtcccccacg ctgtccccctg tcttttacga   1320
ttctgacatt tttaataaat tcagcggctt cccctctgct ctgtgcctag ctataccttg   1380
gtactctgca ttttggtttc tgtgacattt ctctgtgact ctgctacatt tcagatgac    1440
atgtgacaca gaaggtgttc cctctggaga catgtgatgt ccctgtcatt agtggaatca   1500
gatgccccca aactgttgtc cagtgttttgg gaaagtgaca cgtgaaggag gatcaggaaa   1560
agagggggtgg aaatcaagat gtgtctgagt atctcatgtc cctgagtggt ccaggctgct   1620
gacttcactc ccccaagtga gggaggccat ggtgagtaca cacacctcac acatactata   1680
tccaacacac acacacacac acacacacac acgcacgcac gcacgcacgc acgcacacat   1740
gcacacacac gaactacatt tcacaaacca catacgcata ttacaccca aacgtatcac    1800
ctatacatac cacacataca cacccctcca cacatcacac acataccaca cccacacaca   1860
gcacacacat acataggcac acattcacac accacacata tacatttgtg tatgcataca   1920
tgcatacaca cacaggcaca cagacaccac acacatgcat tgtgtacgca cacatgcata   1980
cacacacata ggcacacatt gagcacacac atacatttgt gtacgcacac tacatagaca   2040
tatatgcatt tgtatatgca cacatgcatg cacacataca taggcacaca tagagcacac   2100
acatacattt gtgtatgcac acatgcacac accaatcaca tgggaagact caggttcttc   2160
actaaggttc acatgaactt agcagttcct ggttatctcg tgaaacttgg aagattgctg   2220
tggagaagag gaagcgttgg cttgagcct ggcagcaatt aacccgcc agaagaagta     2280
ggtttaaaaa tgagagggtc tcaatgtgga acccgcaggg cgccagttca gagaagagac   2340
ctacccaagc caactgagag caaaggcaga gggatgaacc tgggatgtag tttgaacctc   2400
tgtaccagct gggcttcatg ctatttgttt atatctttat taaatattct tttagtttta   2460
tgtgcgtgaa taccttgctt gcataaatgt atgggcactg tatgtgttct tggtgccggt   2520
ggaggccagg agagggcatt gatcctccgg agctggcgtt tgagacagtt gtgaccaca   2580
gtgtggggtc tgggaactgg gtcttagtgt tccgcaagtg cagctgggc tcttaacctc     2640
tgagccatcc ctccagcttc aagaaactta ttttcttagg acatggggga agggatccag   2700
ggctttagcc ttgtttgttc agcaaatact cttttcgtgt attttgaatt ttatttttatt   2760
ttactttttt gggatagaat cacattctgc agctcaggct gggcctgaac tcatcaaaat   2820
cctcctgtct cagtctacca ggtgataaga ttactgatgt gagcctgcct ttgacaagca   2880
ctttagagtc cccagcccctt ctggacactt gttccaagta taatatatat atatatatat   2940
atatatatat atatatatat atatattgtg tgtgtgtgtt tgtgtgtgta tgagacactt   3000
gctctaaggg tatcatatat atccttgatt tgcttttaat ttattttta attaaaatg    3060
attagctaca tgtcacctgt atgcgtctgt atcatctata tatccttcct tccttctctc   3120
tcttttctct ttctttttct caccccccaag catctatttt caaatcttt tgccgaggag   3180
atgccaagag tctcgttggg ggagatggtg aggggggcgat acaggggaag agcaggagga   3240
aaggggggaca gactggtgtg ggtctttgga gagctcagga gaatagcagc gatcttccct   3300
gtccctggtg tcacctctta cagccaacac catttttgtgg cctggcagaa gagttgtcaa   3360
gctggtcgca ggtctgccac acaaccccaa tctggcccca agaaaggca cctgtgtgtg    3420
actctggggt taaaggcgct gcctggtcgt ctccagctgg acttgaaact cccgtttaat   3480
```

```
aaagagttct gcaaaataat acccgcagag tcacagtgcc aggttcccgt gctttcctga 3540
agcgccaggc acgggttccc taggaaatgg ggccttgctt gccaagctcc cacggcttgc 3600
cctgcaaacg gcctgaatga tctggcactc tgcgttgcca ctgggatgaa atggaaaaaa 3660
gaaaaagaag aagtgtctct ggaagcgggc gcgctcacac aaacccgcaa cgattgtgta 3720
aacactctcc attgagaatc tggagtgcgg ttgccctcta ctggggagct gaagacagct 3780
agtgggggcg gggggaggac cgtgctagca tccttccacg gtgctcgctg gctgtggtgc 3840
atgccgggaa ccgaaacgcg gaactaaagt caagtcttgc tttggtggaa ctgacaatca 3900
acgaaatcac ttcgattgtt ttcctctttt tactggaatt cttggatttg atagatgggg 3960
gaggatcaga gggggagggg aggggcgggg agacggaggg aggaggggag gagggaggag 4020
ggggaggagg ggaggagggg aagggatgga ggaaaatact aacttttcta attcaacatg 4080
acaaagattc ggagaaagtg caccgctagt gaccggaggg aggaatgccc tattgggcat 4140
tatattccct gtcgtctaat ggaatcaaac tcttggttcc agcaccaagg attctgagcc 4200
tatcctattc aagacagtaa ctacagccca cacggaaagg gctatacaac tgaagaaata 4260
aaattttcac tttatttcat ttctgtgact gcatgttcac atgtagagag ccacctgtgt 4320
ctaggggctg atgtgctggg cagtagagtt ctgagcccgt taactggaac aacccagaac 4380
tcccaccaca gttagagctt gctgagagag ggaggccctt ggtgagattt ctttgtgtat 4440
ttatttagag acagggtctc atactgtagt ccaagctagc ctccagctca cagaaattct 4500
cctgttccgg tttccaaagt actggagtta tgagtgtgtg ttaattgaac gctaagaatt 4560
tgctgattga agaaaacctc aagtgggttt ggctaatccc cacgacccca gaggctgagg 4620
caggaggaat gagagaattc aaggtttgcc agagccacag ggtgagctca atgtggagac 4680
tgtgagggtg agctcaatgt ggagactgtg agggtgagct caatgtggag actgtgaggg 4740
tgagctcaat gtggagactg tgaggtgagc tcaatgtgga ggtgagctca 4800
atgtggagac ctgtatcaag ataataatag tagtagtaac aatgcaggcg agggtgtggt 4860
tgagtggtag agcagttagt tgatttgaca tgcttgaggt ctcccggtcc atctgtggcc 4920
ctgcaacagg aagggaggga ggaaggggggg gaacagagag aggaaagag agacagaagc 4980
taagataggg aatgagagag gaaggaagaa acgggaagag attcagactc cttcctgagt 5040
tccgccaacg cctagtgaca tcctgtgcac accctaaggt ggcctttgtg tggcactggc 5100
ttgggtggtc gggaaaggca ttttcagctt gttgcagaac tgccacagta gcatgctggg 5160
tccgtgaaag tttctgcccg ttaacaagaa gtctctacta cttgtgacct caccagtgaa 5220
aatttcttta attgtctcct ggtgttctgg gttttgtcta tttgtttcta aggatacatt 5280
cctgggtgat gtcatgaagt ccccaaagac acagtggggc tgtgttggat tgggaaagat 5340
gatttatctg gggtgtcaaa aggaaaagaa gggaaacagg cacttgggaa aatgtcctcc 5400
cgcccacccg aattttggct tggcaaccgt ggtggaggag caagaaacac gtggacgttt 5460
gaggaggcat ggggtcctag gaggacagga agcagcaagga gagagctggg ctgacagcct 5520
gcaggcattg cacagtttca gaaggagatt acagcatgac tgagttttta gggatccaac 5580
agggacctgg gtagagattc tgtgggctct gaggcaactt gacctcagcc agatgggtatt 5640
tgaataacct gctcttagag ggaaaacaga catagcaaac agagccacgt ttagtgatga 5700
aactctcact ttgcctgagt catgtgcggc catgcccagg ggtcaggctg acactcaact 5760
caaaaacaag tgaaaattg aagacaatcc gtggttgcag ctactggaag ggccaccaca 5820
tccccagaaa gagtggagct gctaaaaagc catttgtgat aggcacagtt atcttgaatg 5880
catggagcag agattacgga aaaatcgaga atgttaatga ggcaacattc gagttgagtc 5940
attcagtgtg ggaaacccag acgcttccat ccctaaaag gaacatcttg ctctcagtca 6000
aaatggaaat aaaaattggg gcttgaattt ggcaaatgat tcagaactct gtgtaggtat 6060
tttcacacgc acagtggata atttcatgt tggagtttat ttgtgctaaa aggcagaaaa 6120
gggtaaaag cacatcttaa gagttatgag gttctacgaa taaaaataat gttacttaca 6180
gctattcctt aattagtacc cccttccacc tgtggtaatt tcctgagata gtcagtgggg 6240
aaaagatctc tccttctctt cttttctccc ctcccctcct ctccctcccta cctccctcc 6300
ctccctcctc tccctccctc ccccttttcct tcttttcttg ctccttctcc tctgcctcct 6360
tctccctttc ttcttcattt attctaagta gcttttaaca gcacaccaat tacctgtgta 6420
taacgggaaa acacaggctc aagcagctta gagaagattc atctgtgttc actagcgtgc 6480
aattcagagg tgggtgaaga taaaaggcaa acatttgagg ccatttcctt atttggcacg 6540
gcacttagga agtggaacat gcctaatcta ctggtttgta ccaccctccc ctataatgca 6600
ctgtttggga agctcctggg caaccgattc tggcatctca ttggtcagag gcctgttaaa 6660
tggtactctt atttgcaaag aaggctgtaa cttgtagctt taaaagcctc tcctcaagaa 6720
agaaggagaa aaggatatgg ctagacatat ctaatagact taaccactgt gaaaagcctt 6780
agtatgaatc agatagaacc tattttaac tcagttttga aaaaaataat ctttatattt 6840
atttgtgtgt gtgtgtgtgt gtgtgtgtgt gtgtgtgtgt gtgtgtgtgt gaaccacatg 6900
tagcaggtgc tggaggaggc cagaagaggg caccagatct cctggaactg acaccacaca 6960
tggttatgag ctgcctgatg tgggtctgg gaactgaact ctcgtgttct gcaagagcag 7020
caactgttct cttaactgat gagccatctc tccagccccc cccataattt taattgttca 7080
ttttagtaaa ttttattcat aatcaattat cacagtataa aacaatgatt ttatatatat 7140
catatacata tcaaggatga cagtgagggg gatatgtgtg tgtgtgtgtg tgtgtgtgtg 7200
tgtgtgtgtg tgtgttattt gtgtgtgtgc ttttaagaa ggtgccatag tcactgcatt 7260
tctctgaagg atttcaaagg aatgagacat gtctgtctgc caggaacctc atcttcctct 7320
ttgggaatct gacccaaatg aggtattctg aggaactgaa tgaagagctc aagtagcagt 7380
gtcttaaacc caaatgtgct gtctagagaa agtcaacgtc atcagtgagc tgaggagaga 7440
tttactgagc ggaagacaag cgctctttga tttaagtggc tcgaacagtc acggctgtgg 7500
agtggagcct gtgctcaggt ctgaggcagt cttttgctagc cagctgtgat gagcagtgaa 7560
gaaagggtgg agatgaggc agggtgggag caggggtatg gttcagacta ggtatcgtga 7620
gcacaccagc tggttgactt gtggtctgtg ggtcaggcgt tgtaaacgcc ctcagggtca 7680
ggcagtcaca ttgcttgaag ctgaatgggt gaggcaacac agagagtgca aagaaggcaa 7740
agtaccacct cttcccgac ccaggtcact tctgggttat agctgagact ccggacagca 7800
tgcaaccagc tggttagagc ttcagggaaa acttgatgtc tgcatgttgc tatgaaatgt 7860
gattcggtac atctggaaga aatttataat gctggctcag tcaagcactg aacaaaggta 7920
ccttggcttt gggagctaca tgacattgac ttgtaggcag acttttttt ttctgcccgc 7980
caattcccag ataaccaata tggaggctca atattaatta taaatgctcg gctgatagct 8040
caggcttgtt actagctaac tcttccaact taaatgaacc catttctatt atctacattc 8100
tgccacgtga ctttaccttg tacttcctgt ttcctctcct tgtctgactc tgcccttctg 8160
cttcccagag tccttagtct ggttctcctg cctaaccttra tcctgcccag ctgctgacca 8220
```

```
agcatttata attaatatta agtctcccag tgagactctc atccaggag gacttgggtg   8280
ctcccccctc ctcattgcca tccgtgtctt cctcttccct cgcttccccc tcctcttcct   8340
gctcttcctc ctccacccct cctttcatag tattgatggc aagggtgttc tagaatggag   8400
gagtgcccat aggcatgcaa agaaaccagt taggatgctc tgtgagggt tgtaatcata    8460
agcgatggac acaattcaag ccacagagtg aagacgagg gatgcactgt gctctagagc    8520
aacttctggg gcagaatcac agggtgagtt tctgacttga gggcgaagag gccacgagga   8580
agggagtgag tttgtctgag ctagaagcta cggcccacct cttggtagca gacctgccca   8640
caagcatgct ttgttaatca tgtgggatct gattttcctc taaatctatg ttcaactctt   8700
aagaaaatgt gaattctcac attaaaattt agatatacgt cttttggtgg gggggtgta    8760
aaaaatcctc aagaatatgg atttctgggg gccggagaga tggctcagag gttaagagaa   8820
ctggttgctc ttctagacat tctgagttca attcccagca accacatggt ggctcacaac   8880
catctgtaat gcgacctggt gccatcttct gacatgcatg gatacatgca ggcagaaagc   8940
tgtatacata gtaaattgat aaatcttttt ttaaaaagag tatggattct gccgggtgtt   9000
ggtggcgcac gccttttaatc ccagcactct ggaggcagga gcaggtggat ctctgtgagt   9060
tcgagaccag cctggtctat aagagctagt tccaggacag cctccaaagc cacagagaaa   9120
ccctgtctcg aaaaaccaaa aaaaaaaaaa aaaaaaaaa aaaaaaaga gtatggattc    9180
taagaaagcc gtaacagctg gagctgtgta cggagttcag cgtggtacta aagaacaga    9240
cattcatgat gaaacacccc aggattttta cttagtatct agtttccatt gttgttttga   9300
gaccggctct tatgctctcc aggctggcct caaactgctg atcttcccgc ctctacctct   9360
caagtcctgg gactacttgg ctcataaaac agtttttgtc gggctccctg aagttatggt   9420
tgtacaaacc gtgggggtca atatactcac ttgggcagag agagaaggtc tgaatcccag   9480
acaatgactg catctcagga cagttgggaa gaggacaatg gcagaaggac ttagaaaaga   9540
tagactggag ggtggaaaag cagcaggaac agagaaacaa aacaggaagc ttgctatcca   9600
gggccactct ggagtcctgt ggcaagatgg aagcgggcta ggggaataca tttgtgctac   9660
tgtgtgtgtg tgtgtgtgtg tgtgtgtgtg tgtgtgtgat caatgcctat caatgttgaa   9720
ggggaaatat gtataccaca ttgattctgg gagcaattct cagtatctgg cctagagaaa   9780
ggaatggccc ctgcagaata gacagagtga atggtgccct ttatcatttg ctaaagtgaa   9840
ggagaaataa acatccttcc atagagtttc aggtaaatga accccacagt tcatctgtgc   9900
cgtggtggag gcctggccaa cagttaaaaa gattagacac ggacaaagtc tgaaggaaac   9960
acctcgaata ggaagaggag agccacctca ttctgtaact ttcctcaagg ggaagatgtt  10020
ccaagagtgg gaataaatgg tcaaggggg gattttaat taggaaaacg atttcctgta    10080
tcacttgtga aactggaggt tgatttgggg cataggacaa tagatttgat gctttgcaaa  10140
aagctgtttc aaagcagaga aatgaatag agacaattat gtagcgagga gggagggtgg   10200
ggcgaagatg gagacagaga agtggaagct gactttaggg aagaggaaca tagaccacag  10260
ggggcggggcg gggggcaggg gcgggggcg caaagg gaggcagtgg gaacgttgct     10320
agtgttcgca gcgtaagcgt gaatgtgcaa gcgtctttgt ggtgtgtgac caggagtagc  10380
gtggctggct tgtgtgctgc ttgtaatccc agtctttgag gttcacac tgttccacag    10440
tgggtgtgat tttccctcgg agagcatgag ggctctgctt tccccacatc ctccccagcg  10500
ttcgttggta tttgtttcca agatgttagt gggtgagaca aagcctctct gttgatttgc  10560
ctttaacagg tgacaaaaaa agctcaacca ggagacattt ttgccttctt ggaaggtaat  10620
gctcccatgt agagcaatgg gacccatctc taaggtgagg ctactcttgc agtttgcacc  10680
cagctcttct gatgcaggaa ggaagttggt gggcaagcaa gactgtttgc ttcttgcgat  10740
ggacacattc tgcacacaaa ggctcaggag gggagaagc tgtttgatgt ttagcactca    10800
ggaaggcccc tgatgcatct gtgattagct gtctccatct gtggagcaga cacggactaa  10860
ctaaaaacca gtgtttttaa attgtcaagc ctttaaggtg aggaaattga cttattgtgc   10920
tgggccatac gtagagcaag tgctctgcat tgggccaacc cccggctctg gtttctaggc  10980
accagaatgg cctagaacta actcacaatc ctcccattcc aggtctcagg tgctagaatg  11040
aaccactata ccagcctgcc tgcctgccta cctgccttcc taaatttaa atcatgggga   11100
gtagggagga atacacttat cttagttagg gtttctattg ctgtgaagag acaccatgag  11160
catgcaaact cttataaagg aaaacattta gttgggtggc agtttcagag gttttagtac  11220
attgtcatca tggctgggaa catgatgcca tgcagacaga catggtgctg gagaaaggga  11280
tgagagtcct acatcttgca ggcaacagga cctcagctga gacactggct ggtaccctga  11340
gcataggaaa cctcacagcc caccctcaca gtgacatatt tccttcaaca aagccatacc  11400
tcctaatagt gccactccct atgagatgac agggccaatt acattcaaac tgctataaca  11460
ctttaaagta tttttattttt attattgtaa attatgtagg tagctgggtg gtggcagccg  11520
aggtgcacgc ctttaatccc agcacttggg aggcagaggc agatggatct ctgtgagttc  11580
aagaccagcc tggtctataa gagctagttg caaggaagga tatacaaaga acagttctag  11640
gatagccttc aaagccacag agaagtgctg tcttgaaaac caaaaattgt gctgggacct  11700
gtctctgctt tggttgcttc ccactccccc agagctggac tcttggtcaa cactgaatca  11760
gctgcaaaat aaactcctgg attcctctct tgtaacagga gcccgaagtc aggcgcccac  11820
ttgtcttctc gcaggattgc catagacttt ttctgtgtgc ccaccattcc agactgaagt  11880
agagatggca gtggcagaga ctgggaaggc tgcaacgaaa acaggaagtt attgcaccct  11940
gggaatagtc tggaaatgaa gcttcaaaac ttgcttcatg ttcagttgta cacagactca  12000
ctcccaggtt gactcacacg tgtaaatatt cctgactatg tctgcactgc ttttatctga  12060
tgcttcctttc ccaaaatgcc aagtgtacaa ggtgagggaa tcacccttgg attcagagcc  12120
cagggtcgtc ctccttaacc tggacttgtc tttctccggc agcctctgac accctcccc   12180
ccattttctc tatcagaagg tctgagcaga gttgggcac gctcatgtcc tgatacactc    12240
cttgtcttcc tgaagatcta acttctgacc cagaaagatg gctaaggtgg tgaagtgttt  12300
gacatgaaga cttggtctta agaactggag caggggaaa aagtcggatg ttgcagcatg    12360
tacccgaaat cccagaactg ggaggtagaa gacggatgag tgcccggggc tagctggctg  12420
ctcagccagc ctagctgaat tgccaaattc caactcctat tgaaaaacct ttaccaaaca  12480
aacaaacaaa caaataataa caacaacaac aacaacaaac tacccccatac aaggtgggcg  12540
gctcttggct cttgaggaat gactcaccca aacccaaagc ttgccacagc tgttctctgg  12600
cctaaatggg gtgggggtgg ggcagagaca gagacagaga gaacagatgac ttcctgggct  12660
gggctgtgtg ctctaggcca ccaggaactt tcctgtcttg ctctctgtct ggcacagcca  12720
gagcaccagc acccagcagg tgcacacacc tccctccgtg cttcttgagc aaacacaggt  12780
gccttggtct gtctattgaa ccggagtaag ttccttgcaga tgtatgcatg gaaacaacat  12840
tgtcctggtt ttatttctac tgttgtgata aaaccgggg aactccagga agcagctgag    12900
gcagaggcaa atgcaaggaa tgctgcctcc tagcttgctc cccatggctt gccgggcctg  12960
```

```
ctttctgcaa gcccttctct ccccattggc atgcctgaca tgaacagcgt ttgaaatgct   13020
ctcaaatgtc actttcaaag aaggcttctc tgatcttgct aactaaatca gaccatgttt   13080
caccgtgcat tatctttctg ctgtctgtct gtctgtctgt ctgtctatct gtctatcatc   13140
tatcaatcat ctatctatct atcttctatt tatctaccta tcattcaatc atctatcttc   13200
taactagtta tcatttattt atttgtttac ttacttttt tatttgagac agtatttctc    13260
tgagtgacag ccttggctgt cctggaaccc attctgtaac caggctgtcc tcaaactcac   13320
agagatccaa ctgcctctgc ctctctggtg ctggggttaa agacgtgcac caccaacgcc   13380
ccgctctatc atctatttat gtacttatta ttcagtcatt atctatcctc taactatcca   13440
tcatctgtct atccatcatc tatctatcta tctatctatc tatctatcta tctatcatcc   13500
atctataatc aattg                                                    13515
```

SEQ ID NO: 57          moltype = DNA   length = 14553
FEATURE                Location/Qualifiers
source                 1..14553
                       mol_type = genomic DNA
                       organism = Mus musculus
SEQUENCE: 57

```
cttgaagaac acatgttttc caagagggag cacccatgtt ggaatgacaa tgtagttagt    60
gctcctctcc tgtaggttag tgctcctttg ctataggtaa gtgctcctct cctataggtc   120
agtgctcctc tcctataggt tagtgctcct ctcctatagg ttagtgctcc tctcctacag   180
gttagtgctc ctctgctcta ggttagtcct gctctcctat agtacctaga gagctagggc   240
aaatgggcta ggcccgaagt gcagagacaa acagcagttg aagactgggt aagcacttcc   300
aagctacgaa agagcagtgt gaagggtcag ggcttgtgca gttagtaggg gagatcttcc   360
agttgaagaa acagaagaac tgagagccac tgggtatcat cctcctgcgc catgccttcc   420
tggatactgc catgctccca ccttgatgat aatggaatga acctctgaac ctgtaagcca   480
gccccaatga aatattgttt ttatgagagt tgccttgtgc atgctgtctg ttcacagcag   540
taaaacccta aataaggcag aagttggtac cagtattgct gtgatagacc tgaccatgct   600
ttcctttgaa agaatgtgga tttggtgact ttggattgc aacacagtgg aatgctttaa   660
atggagatta atgggtcatc aattcctagt aggaatatgg aagactttgt tgctgggagt   720
atttgaactg tgttgacctg gcctaagaga tttcaaagga gaagaatttc agaatgtggc   780
ataaagacag tttttgtggt attttggtga agaatgtggc tactttttgc ccttgtctga   840
aaagtctgcc tgagactaaa gtgaagagaa tcagattaat tgcattgaca agggaagttt   900
gtggctgcgc tatctggaaa cttacagcca gcctcttgga cctcgggtga cttacgcaaa   960
tactcaggga cagagatgct tgactctgta ctgatgagtt gtcttggatg caaatatggg  1020
ctcttcattt gactacatgt cacgatgagt caggagctgc tctctccaga gtgtgacaaa  1080
gcgaggggat gctgacggta gctgttctag ctttgaaggt aagcctgcac ttatgctaaa  1140
gtcacacata cacgagccgg gtggagaacc tgtctgtgtg gagacacctt tcattacctg  1200
tggcatccag ccctctcaag cttggactgc tgtgtgctcc tggactctgg aggtcccact  1260
gctctgtcct ctgctgctta tgatactgac attttaaaag aatccagtgg ttccccctg   1320
tactcggtgt ctacttctac ctggatgttc ctcatttatg ttctgtgaca cttctctgtg  1380
actctgctgc attcctgggt gacatgtgga caccctgtcc ctttgcagac catgatgtca  1440
ctgtcactag tggaatcaga tgccccaagt gttgtcctgt gtttgggaac gtgacaggca  1500
gtacagaagc agaagaggaa gggtgaaaac ggaaatgtca cagcagcatc tgatgtgtgc  1560
ctcagtcacg catgctgctg attggaacta ctcagcatga gagagggcca tggtgaatac  1620
acaaccctat acacactgtg tccatttctc tctctctctt acacagagag agagggagga  1680
gggggagggg gaggcggagg gggagggga gggagagga gtgggagagg gagagggaga    1740
gggagagaga gaggagaga gagagggaga aagagatacc                         1800
atgaccaaag caactcttat aaaggacaac atttaattgg ggctggctta caggttcaga  1860
aattcagtcc attctcacca tggtgggaag catgcaggta gatgtggtgc tggaggaacc  1920
aagagttcta tatcctgatc tgaaggcagc caggagaaga ctgcctcttc tgcacagggc  1980
agagcttgag catagaacat caaagccctt ccccacactt cctccaacaa ggtcatacat  2040
acttcaacaa agacacacct cctaacggtg ccactccctg tggaccaacc atttaaacgc  2100
atgagtctat gagggtcaaa gctcttcaaa ccaccacact catgtacaca cacacacaca  2160
cacacacaca ctctcataca cacacacaca cacactcaca cacacacaca cacacacaca  2220
cacacacaca ccacacacac acacacacac agagttctat tttgcactgt ttcactgtca  2280
caaggttcta cttatctcag acacactgcc aggaattgtg tgggaagact ttcagtttct  2340
ttgggttcac atggacttag cagttcttgg tgatcctgaa agatttctgc agaaagaagc  2400
caaagtgttg agcccaaggc ctggccacac attagtcctg tctagatgaa caggggttta  2460
aaaataaggg ggcatcaagg tgaagccagc aggggctgac ttagagagga gacccaccca  2520
agccaactgc tcgaagtcaa aagcgatgaa tccccatatc cagctgtgcc cggtgctgtc  2580
ttgctacatc tttagtaaat gttcttttag ttgtatgcgt atgaatattt tgcttgcata  2640
tatttgtgta caccataggt gttcctaggg cctatggagg ccagaagagg gcatcagatc  2700
ctttggaact ggaattatag acacttgtta cccatagagt agattgtggg aaatgagcct  2760
ttagtcttcg agagcggcca gtgctcttaa ccttttgctg tcttccaggg tcttgagac   2820
tttattttct tggacatcag acaggatcc agggctttga gcttgttct tcagccagct    2880
ttcttttcat gtatattaaa ttttatgtta ttttgctttc ttttcccca agacagaatc   2940
acactctata tagctcaggc tgggtttgaa ttcagtttcc ctgtctcagt ctaccggta   3000
atatgattac agatgtgagt ctgactttgg tatcaaagtc cccagcccct ctggatatgt  3060
gttttaagga tatcagatat atccttgatt tgctttgaat tttcttttta gttacaacat  3120
aattagttcc gtgtcacctg aatatgtgta tgtcacctac atagtcttcc ttcttctctt  3180
cttccctctc ccaccttccc aggtacctgt ctgtcttcat atccttgtgc tgagagtctt  3240
gttgagggag atgatgaccg agacagagcc actggggaag ggagatgggc tagtgcaggt  3300
cttcagagag gagctcgtga atattgtagc cctttagtc cctggcatgt cctcttgtat   3360
agccaccgcc atgctggtgg ctggcagaag tgaataagtt gtcagctgt tgacaggcct   3420
gccctccaga cccagtctga tcccaagaaa gggcatctgt gtctgtctct gaggccgtaa  3480
gtgctgcctg gttgtctcca gcttgacttg acactccctc cttaataaga gtaccacaga  3540
acagggtctg cagagtccct gggccaggtc cctgtgctgt cctggaatgc caggcgtgaa  3600
tttcctgtga agtaggactt tgctcgccaa gctcccacgg cttgcccttc agatagccag  3660
aattatctgg taccctgcat tgccgttcaa tacgcagagt atcactggaa gcgcgcgcgc  3720
```

```
gcacacacac acacacacac acacacacac acacacacac acacgcccac tccatcttta   3780
aaccccaccc cccagcaacg gcggtgtaaa cactctccat caggaagctg aaacgcagtt   3840
gccctctgct ggggagatga aggcagcttg ctggggcga ggaccgtgct agcaaccttc    3900
cctggtgcac acgggctctg gtgcatgacg ggaacgaaaa cgcggaacta aagtcagtcc   3960
tgcttttttt tttttttttt tttttttttt tttttttttt tttttttttt ggcgttggtg   4020
gtggactgag tgacaatcag tgaaatcact taggttgttt ttctcttctt cgttgggttt   4080
gatagacggt gggagagggt cagaggagaa gggagggat ggggagagag ggaggaggga    4140
ggggcgggag gcgggggcg aggaaaacgt gctaacttct ccaatcctac aagacaaagg    4200
tttggagaaa gccgcactga gtgacccagc agaaggaatc caggaatgtc cgctggaatc   4260
tgactgttga ttccagcgcc atgcagagaa tctaggctgg taggaacatt ctttgtccta   4320
tccgacataa taactccaac caacacggaa agaaaggct atacaagtga agaaatggca    4380
ttttcacttt catgactata caatcacttc caggtagtaa cacgtgtcta gcacagcggt   4440
tctcaacctg ggggtcacga tcccccactt ttctgcatat cagacatttt tacgttgtta   4500
ttcataacag tagcaaaatt gcagctatga agtaacaatg aaatgcattt atggtgcgtg   4560
tgtgtgtgtg tgggggggta tcaccttaac atttactgta agaaggttga gaatactgct   4620
ccagcagcta gtgtgttgga cttaggttct gggtatatta ttagcaatag ccaaccagaa   4680
tccccaccca ccacagcatt gaggcccat gcagggcttg ctgggagagg cactgataag     4740
acttctttat gtatttattt agagacgaat actcattagg taggccaagc tagcgtcaaa   4800
ctcatggcaa ttctcctcct ccagtttcct aagtactgga ctcaggagtg tgttgccatc   4860
atatacagta aggattatt gactgaagaa aatctcaagt ggctttggtt aatccctact    4920
acgccagagg ctgaggcagg aggcgcgcaa ggtcaaggct gcctgggct acatatagag    4980
tgagctcaat tttgacactt ggtgcggtgt tagtagtaat agtaaagatg aaggtgtggc   5040
tcaggtgggg ccggtgattg gacacacttg gggtctcctg gtccatctgc agctgtgcaa   5100
caggaagagc ggagaatgag aggaaagaga gaaaagacag aatgagagag agggaggaag   5160
agagaaaaag gaaagagag aggaaaggaa aaggaaaat gaggaaagcg agaaagaaga     5220
aatgaggaa aggaaaggga gaaagaaatg agagagaaa aagaaaagac agaatgcgag     5280
agagggagga agagagaaaa aggaaaagag agagaaagg aaaaaggaaa atgaggaaag    5340
cgagaaagaa gaaatgagaa agaggaaagg gagaaagaaa tgagagagag aaaagaaaag   5400
acagaatgcg agagagggag gaagagagaa aaggaaaaag agagaggaag ggaaaagga    5460
aaatgaggaa agcgagaaag aaggaaatgag aaaggaaaga aatgagagag              5520
agaaaagaaa acagaatg cgagagaggg aggaagagag aaaaaggaaa agagaggaaga    5580
agggaaaaag gaaaatgagg aaagcgagaa agaaatg agaaagagga aagggagaaa      5640
gaaatgagag agagaaaaga aaagacagaa tgcgagagag gaggaagag agaaaaagga   5700
aagagaggag aagggaatgag cgagataaaa gacagaattt gagagaggga ggaagaaata   5760
ggaaaagaga ggaaaggatg gagaaaagag agaaagaaag agagtgaaa gagagaaagg    5820
agaaatgaaa tgagagagag agagagacac aaagagccag agagagaaga aaaaagggga   5880
aagagaaaga gaaagaggaa ggctcctctt ggacacatct tcctttatct ttccctgggg   5940
accgccaaag cctggtggca tactgtatact tctgtacact gttcattcaa acaggctct    6000
gtcttaaaga tggtctgagc ggtcagaaaa gggtattgtt aacttgtttg caaaactgcc   6060
tcaggagagt gctgagtgcg tgaaagttgc tgcccgttaa ggagaagtct ctactacttg   6120
tgatctcacc atcgaaaatt tctttaattg tctcctggtg ttctgggttt tgcagttttg   6180
tttctaagga tacattcttg ggtgatgtca caaagtcccc aaagacacgg tggagctgtg   6240
ttagatgggg aaagacagtc tgctgaggat ttatctggaa ctgtcagaag gaaagaaggg   6300
taaatgggc acttgggaaa gtggcctcta gtttgacttc tggcttagca aaggttgtgg    6360
ggagataagg catacacagt agttagcagg aggcaacagg gtcctgggag gacgcgaggc   6420
agaaggagag gctgggctga cagcatgcaa tcattgcata gtctccaaag gagattgcaa   6480
catggctgag ttttcagagg tcctacagag cccgtggtag agattctgtg ggttctgaga   6540
caacttgact ttagccagat ggtatttgag taatctggga gagagaaaac agctacagca   6600
aacagggcca catttagtga cgaaactctc actttgactg ttgagtcatt tgcagtgggc   6660
cctgaggtca ggctggccct cagctcaaaa acaagcgagg aactgaagca attactcaga   6720
taatccacag ccacagccac tggaaagggc cacatcccca gagacagcac agcagggtg    6780
ggggtggggc tatgagaaag ttagtgattg tagcagttat ctagaatgtg cggagcagag   6840
gaggttacac aaaaacctag aatgtcattc aatgtgggaa accgagaggc tcccaagccc   6900
taaaaggaac agtttgcttt cagccaaaat ggaaataaaa tttggggctt aaatctggca   6960
aatgattcag accttctgtg taggtgtctt taaatgcaca gcagattgat tttcatgttg   7020
gagtttattt gaactaaaag acagaaatgg tgaaaagcac acctgaagaa attgagatgc   7080
tatgaataaa atcatttact tacagctatc acttaattag tacctcccttc caccttgctg   7140
atttattggg ctagtcaagg aagaaaagat cttccctcct ccttctctcc tcctccccct   7200
cctctcctcc tccctcccc tccttgacct tcctctcctc ctttttccctc ctccccctct   7260
tcttctcttc acccctcct ccctcccct cctctgtact cctccccttt cctcccaatc    7320
tctttttttct cccccttctt ctcctttctcc cccctcctct tccctcctct tcctcccctcc  7380
ctccctcctc ctcctcatcc tcctcttcct cttcatcctc ttctccttcc tccctctcct   7440
cctcctcctt ttccagccct acctaccttc ccttttattc tcattttatct aaagtagctt   7500
tgaacagcac tactcggttt agttgtgtat aaaaggaaaa tgcaggtcca agcagcttgg   7560
ggaagattgc tttttgctct ctggaggcag atgatgacag ttcaagatca ttcctttgc    7620
tccatgtcac aggaaggggg acatgccgaa tctaccagtt tgcagccacc tacacaggat   7680
ccaccttcac ttctaaggaa atgtttggga agctaccta caaccactc tggcatctca     7740
tgggctagag gactcttaaa tggcactctt atttgtttaa taaaggaggt tgtgacgtgt    7800
agttttaaat cccttccaca caacaattgc tactctctga ccaaaaagaa agggagacag   7860
gatacggcta ggtgtctagt agactttacc actttgaaaa gccttaatat aaatcaggta   7920
gatacatctt tttaacttat tcttgtaaag acaaaaacaa aactttattt ttatttgtgt    7980
gtatgcttgt gtgtgtgtgc ctgtgtgtat accacatgtc gctggtgccg gagaacacca   8040
gaagaggga cctgatctcc tggagctaga gctatccatg gttctgagct gcctgatgtg    8100
ggtgctgga acagaactct ggtcttctgc aagagcaaca agcctcctct taactacgaa    8160
tctcctcccc atccccccaa atacatttaa ttattcatttt tagcagcttt attcgtaac    8220
tactatcac agcataaac aaggatttta tatatattac atgcaatcga ggataagagt    8280
tgaggggaga tgcgtgtgct ccttctgggt gtctgtgctt ttgaagaatg taagcagtgc    8340
acaagggacc gaggcgtgcc tgtctgccag gagctgtctt cttcccttgg actctgagct    8400
```

```
gagtgcagtg ctccgaagaa gtaaaagacg acctcatgaa gcaatgtctt caacccaaac   8520
atgctgtcca gacaaagtcc agcttcatta gtgctctgag gagagactta ctgagcctca   8580
ggaaagcccc cctcagcatg gcgaaagtcc actttgattg aagtgactcg aaagccatgg   8640
cagtgcggcg gcggccgcgt ggagcttgtg ctcgagtcgg aagcggcatc tttgtcaggc   8700
ggctgtgatt agcacgggga ggcaggactg gagtgaagga agagttgggg gcggggctta   8760
gcgctctggt ctcctaagct gtagtcagcg cctcaagatt tgtaacctgc cttctgcctt   8820
cccagccagg cagtcaagtg gctccaagct gaagactgca aagtgccct aacctttttgg   8880
ttatagcgag gctgaagaca ccgtgctctt tcatgaaagc cggatgtctg aaatccgatt   8940
tgataaatat ggataaaacg tataacgctc gatcaatcga atcgaaggag ctcacgattg   9000
gcaccacggc tttggggaca acagagtact gactcgttgg gaggacttgg atacttcccc   9060
tcctcttcca tctcttcccc tttcctcact tcctcctcct tccttctcca tttttctccct  9120
cttcactgtt tcttactatt tttacaaaag atttttattta tttatttatt tatttattta   9180
tttatttatt tatttattta tttatttaat gtatgcgagt acactgtagc tgtcttcaga   9240
cacaccagaa gagggcgtca agttccatta gagatggtgt cgagccacca tgtggttgct   9300
ggggcctctg gaaggaccgc cagtgctctt aaccctgag ccatttctcc agtacccttc   9360
tcaccgtttc tcttcaatct tcttcctctt ccttctccac tttccttgtc ttcttggttt   9420
cattatcttt ctcccttttct tcctcttctc ccttcttcc tcctcactg tagttttcct   9480
tccctactct tttcctgcct ccctcctcct ccctcctcat tccccctcct ctttcctcct   9540
tctccctcct cctccttcct tctccctctc ccctctcccc tctcccttct cccttctccc   9600
cctcctcttc ctctttctcc ttctccaccc ctcctgtcac agtatcaatg caagggtgt   9660
tctagaatgg aggagtgtcc cctaggcact aacgaaagcc agttaggatg ctctgagacg   9720
ggtacaattc aggagggcc gtgggatgg aaggttgtc ctgcgattca ttctggagca   9780
accccccaggc agaatcatga ggttggttcc ggattcgcag ggcacaattc agaagaggaa   9840
ggtttcagga aggacgagtt tgtctgagat aggagttaca tctgatgtct tggcagcaga   9900
gccactgtac aagcgtgctt tattaaccac gtgggattaa atcttctttt aaatttattt   9960
tcaactctta aggaaacgtg aacttttcaca ttcaaattta gacttgcagc tcttatggag  10020
aaaaaaaggg gatcttaaga atattaagca taggcggctg gagagatggc tcagcggtta  10080
agagcactct ctgctctccc agaggtcctg agttcaattc ctagcaacca cataatagtt  10140
aacaacagtc tttaatgaat tctaatgccc tcttctggtg tgtctgaaga cagttacagt  10200
gtactcatat aaataaaata aagaaattta aaaaatgaa tattaggcat agattcctgg  10260
atcctaagaa agccatcaga gctgagcca tgtgtgggat cctgcttggt gctggaggg  10320
cagagttcat gccccgggg tttttactta ttatcacatt ttcatcgttg ttttgaaaca  10380
gggtcttgtg tggtccaggc tggccttgaa ctcatctttc agcctctacc tcacaggttc  10440
tgggattact tggttcctaa aagtatctcc gtcaagctcc ctggtgttat ggctgtgcca  10500
accaggaggg tctatacact cgctcaggta gagggagaag atccgaatct ctgacaggga  10560
ctgctgcctc tcggggcaaa tggagtgaag gacagcggca gaaggattta ggaaagatgg  10620
acgggagagt ggaaatgctg cagaagcag aaaacaaagc aggaagcctg ctgtccagtg  10680
gggctcaaga gcggagggat gcgaggggc tgcgcaggaa catttagcgt ctgcgtctat  10740
gggggtaggg gcggggtgcc agcacctagt cacctgaagg ggaaatgctt gcccagggag  10800
caggtctcag tagctgacct agagaaagga gcggccccta cagaggagac acgggtcact  10860
gtttgttaaa gtgaaggaga aataaatatt ctttcaaaga atcttaggtg agcccagttc  10920
atctgcgctg tggaggcctg gggaacagtt aaaaagaccc tgacacacac ccaaggcaaa  10980
caagcaacac acggcttcctt ccgtaagggt ccatgattct ctgaagaatc agccccgaaa  11040
tcagccccgg aatcaggtag tccgtaaaca caatgagtgt tttactctgc agaagtccag  11100
cctgctggcg tctcccatta ccaaaataga gggatagtca cgtgagctca ccggctcgat  11160
ttaaggcacg tggttttcca gggtagatga gctttggctt ctggaaccat tatggggcac  11220
gaaggatgga gccaggattt ttttttttt tttttttttc tattagcaat tgatttgctt  11280
gggcttggct ggacttgccc agttcttagg cccagtcttc ttaactgccg atctgaagtc  11340
tgtcatggag tcagcctagc cttctcactt cccttcagct cgaataggaa gaggaggtgc  11400
acaccagatg gtctgagagc agggataaat ggtgtgcctt tgtctttcag tatttcgtta  11460
ttttaagtag gaagatgctt ttctgtatta cattgcttgt gaaaccgaaa gttgattcgg  11520
ggcacaggac aatggatttg gtgttttgca aggactgttt cagaagagag aggagtcgaa  11580
gggtggttag agtgaggagt ggggtgggac gggatggggg aagagaagga agggccagac  11640
aggctaggta gggctgagag gaggcggtgg gaacttcttg agttagcgca gcagtaaact  11700
tggatgtgcg tgtatctttg tgatatatga cccggagccg tgtagctggc tccgatagta  11760
ctgctaatgt cagtgtcggg ggggggggt cccatactgt tccacagggg ctgcacattc  11820
ccatcgagag caggagggct cctctctcca tacatcctcg ccagcattcc ttgttgtttc  11880
tgtgatgaca gggggtggga tgaaatctct ctgttggttt gagagaccgt gaagaagctc  11940
aaccccagga catttttgcag tcttggaagg cagtgcctcc atgtggagcc gtggagccca  12000
tctctgagtc caggtcactc ttgcagttcg cactcagctc ttcagatgca ggagagacgt  12060
tggtgggaaa gcaagattgt ttgcttgttg agatagacac attctccaca caaaggctca  12120
cgtgggcaa aggctgattg acgtacagcg ttcaggaacg cctgtggtag agctatgatt  12180
agctgtctcc atctatgaag cagacaaaga gttataaaaa aaatcaatgt tttcaaattg  12240
tcaaactttt aacccgacag caagcgctct gtccctggcc taatccctag ccctggtttc  12300
ttgagatggg gtcttttgtg cactagactg gcctagaact cacgatctta gtgttccagc  12360
ctcccagctg ctgggatgag ccgctataac cagtctgcct gccttcctaa attttaagtg  12420
atgggaagtg ggggagaata cagttaaaag tatgcagatc tgagagcagg aacctggcaa  12480
agccaagggg ccggagttac aggcggctaa catgggtgct gggaactgac ccagtccttt  12540
gagaggagca gtgtgtactc ttgaccaaac aggtccgtct ctccagtccc cgtagtatta  12600
aaaataggta ctacgggcat ggtggtgcac acctttaatc ccagcactag ggaggcagag  12660
gcaggtggat ttctgagttt gaggccagcc tggtctacaa aatgagttcc aggacagcca  12720
cggctataca gagaaaccct gtcttgaaaa caaacaacaa acaaaatagg tactacaaag  12780
cgatgtaatt gtgctcaaac atgcaaaccg aggggactga atgcataaga aagagaaaga  12840
cggccacact ggttctatct gggtgacagg aaatcagtat ttttatttt cacattcatt  12900
ttttgttgt tgttgttgac acagtgattt ttctatcaaa aacattattt cttttatagt  12960
tcccctgagg agctgttttt aaagccgtgc tttgaaaaac cattgaagga gcagaggcag  13020
ggagactcct gtgtggcagt cggtgaagca ggccctctgc aggcaggctg gccctggact  13080
tgggagtctc tttccctccc tcctgtgctc aaatagcaaa tgtcaggctt caatgtagct  13140
agaaggttct agaatgatta agtttccaag gctgaagagc ttcccgtgtt gcctttcact  13200
```

```
tccctggaga ggtcgttgtg tgttccggag tctgcaaggt gcctttggtg atgcgggtgg  13260
ttcatctcgg gagattccgc ctggaggacc caagttcaag ccctgcctga gctacagagt  13320
gactttcagg tcttctgcgc aattcagtga gacccagtct acaaataaaa agtaaaaaga  13380
aggctgtgga tggaactcgg tggtagagtt ctgggtttac tccctagagg aggggagaag  13440
gaggagggaag gaggaggaag aggaagaaag aagaagagaa aagaagagga gaaggaaggg  13500
agggaagggg ctgacaagaa gagagaagag ggagggaggg gagggaaagg aaggggaaag  13560
gaagggaggg aaggggctga caagaagaga aagagggag ggaggggagg gaaaggaaggg  13620
ggaaagaaga gaagggtaag aagaaactgt tccaatggtc tgggccacag agtgatggcc  13680
ttttgtggtg atcagctgta atccttgatt tgacacaaac tagaatctgg gaagcgagtt  13740
tctgtgaagg agcattcaca ctggctggcc tgtgggcgtg catgtgggag actgtcataa  13800
ttaggttcat taatacagga agtcccagcc cactacaaat ggcttcgttc catacccaag  13860
agatgctaac tgtagacggt tggagaaagc aagcaagctg tggataccc acgctctttc  13920
acctcggctc ctgggggtg ggtgcactgt gtctcttggt attttaaagt cctgccttga  13980
cgtccctgct gtgacagact gtaactgaa ttgtagcttg tagtccttta gttttctacg  14040
ttggttttc tcaggatatt ttatcgcagt aacagaaaca agaccaggac acttgatctc  14100
ctctgatcaa cactgaagag ttacaaaaca ggctgaggaa acaaactttc ttctccctct  14160
ccccccttctg tccctcccct tccttctcgc tccctccctt gccccctctc tccctgtctc  14220
tgtctgtgtc tctgtctctg tctctctctc tgtctctctg cctccctcc cctccctcc  14280
ctctgtctct gtctctgtct ctgtctctgt ctctgtctct gtctctgtcc ctttctcctc  14340
tatctcctaa atggctggag gccatgctag ctcaatgttg aactttgaac acgtatttag  14400
gaaatctttg ttcttaacag ttctgaagtg ctgaagtggt ggtttagtct ctcggcctga  14460
caagctcact tcctctcact ctgtcttaat gaccaaatct gccatttccc taaaacagca  14520
caggctccag ctccaggttg ctccggagcg gag                              14553

SEQ ID NO: 58        moltype = DNA  length = 4001
FEATURE              Location/Qualifiers
source               1..4001
                     mol_type = genomic DNA
                     organism = Cricetulus griseus
SEQUENCE: 58
ccaagatgcc catcaactga ttaatagatg ataaaattat tgtacatttc agtgtaatat    60
tattcagttt ttaagaaaaa tgaaattatg taataagcat gtaaatggat atatcttgaa   120
acaaccattc cccattatat tacctaaaca ttgaaagtcc aaaatcatat gatctttta    180
gtggatctac taatcttttg ctatatgtat tttattgaac tacccatgga tgtgagataa   240
ttggtaacaa cagcacatgg gatggagatt ag agagaattga   agagaatgca            300
ttttttagga gataatggag gagcaataga aaggattaaa tgaggttact gatgaaagtg   360
atggttagag aaggcaatat gaggagggat aactagcact tagggccttt tgaaaaagac   420
atagagaaaa tactattgta gaaacttcct ataattggtg tatagttata tacaccaaag   480
agctcagatg gagttaccct ataatgaaaa tattaactac tttttatcac tgtgataaaa   540
catcctgaac agagcaacat agattgggaa gcatttactt tggcttacag ttctaacggg   600
ataaaaattc atgatgaaag aatgaatatg tcagcaaaca gcagtagcaa tggcctgaga   660
agcaggtgag agctcacatc ttgaagtgta agaatgtagc agagagaaca aactgcaaat   720
gaccagaaaa tgcttttgga tcagagccca taccccctcg actgacttct ccagaaattc   780
tgaacaaata aaaactcccca aacagagcca taactgaagg tccagtgtct gagactacta   840
gggtatttc ttattcaaac cactacaatg gggtggggg agcaatcctc caagtaggca   900
ctacacacag acaaataaaa actctagtaa ctggaatgga ttgacttatt tgaattactt   960
gccagttgga ctacatagag cacaattatt gtatttaaat tacccttta gatcttacaa  1020
aacttgacag taagatcata ttgctaaaga aaccacatat ttgaatcagg gaacatggtg  1080
atatctagtt gttcttcaac tggaaactta tgctttctg cccagcattc atgttgctgg  1140
aaagagcaat gtacactacc agtgtagaaa ttaaatcatc aatcttatca agatgtggat  1200
cctataagtt acaataaaaa ttagcctgat aagtatcacc caccagaaga atattcacat  1260
aaatgctatg ggagcaacaa gctatttct aaattagctt taatcctatt ctacaagaga  1320
gaatccatat ctagaatagt tatagggatc aagaacccat ggcttgattg gtcataggcc  1380
caatgggaga tcctaatatt attgttctac aaaatgaaaa taactcctaa tgacttgttg  1440
ctgcagtaat aagttagtat gttgctcaac tctcacaaga gaagttttgt cttacaataa  1500
atggcaatta aagcagcccc acaagattta tatcataccg atctcctcat ggcctatgca  1560
tctagaagct aggaaacaaa gaggaccct agagagacat acatggtccc cctggagaag  1620
gggaaggggg caagacctcc aaagctaatt gggagcatgg gggaggggag agggagttag  1680
aagaaagaga aggggataaa aggagggaga ggaggacaag agagaagg aagatctagt  1740
caagaagaaga tagaggagag caagaaaaga gataccatag tagagggagc cttgtatgtt  1800
taaatagaaa actggcacta gggaattgtc caaagatcca caaggtccaa ctaataatct  1860
aagcaatagt cgagaggcta ccttaaaagc ctttctctga taatgagatt gatgactacc  1920
ttatatacca tccatagagcc ttcatccagt agctgatgga agcagaagca gacatctaca  1980
gctaaacact gagctagttg cagacaggga ggagtgatga gcaaagtcaa gaccaggctg  2040
gagaaacaca cagaaacagc agacctgaaa aaaatgttgc acatggaccc cagactgata  2100
gctgggagtc cagcatagga cttttctaga aaccctgaat gaggatatca gtttggaggt  2160
ctggttaatc tatggggaca ctggtagtgg atcaatattc atcctagtt catgactgga  2220
atttgggtac ccattccaca tggaggaatt ctctgtcagc ctagacacat gggggaggtt  2280
ctaggtcctg ctccaaataa tgtgttagac tttgaagaac tccttgaga agactcaccc  2340
tccctgggga gcagaagggg gatgggatga gggttggtga gggacaggag aggagggag  2400
ggtgagggaa ctgggattga caagtaaatg atgcttgttt ctaatttaaa tgaataaagg  2460
aaaagtaaaa gaagaaaaga aaacaggcca aaagattata aaagacagag gtggtgggtg  2520
actataaaga aacactatta tctaataaaa aacatgtcag aagcacacat gaactcatag  2580
tgttttagaa agtatgtata ataactacat aatctcaagc taagaaaaaaa atatcatctt  2640
tcagtgatga aggtgatttt atttctccca gaattaaagc caaagaccta atgaaagtaa  2700
ttatcttcaa aaggttgaaa atacatactt tgcaatacac agatctgcct agaaatctca  2760
tgttcacaat acacatgatg ctcaattgaa ttccattcaa tgttacagtt tagataaaca  2820
gtttgtagat aaactcacaa tgtatcattt cttttatttt tttgaccaaa cagcttctca  2880
tctgttattc agaataattc ctcgatggca ggatatccat cccaattggg ggaaggggag  2940
```

```
aatttgaaga aaacctagac cacatacata tttgccattg ggaaacaaag tctaaaatga    3000
tgttgttcac atcttctcta ctagtcctct ccccgtccca aagaaccttg gtatatgtgc    3060
ctcatttttac agagagagga aagcaggaac tgagcatccc ttacttgcca tcctcaaccc   3120
aaaatttgca tcattgctca gctctgccct tctcatatga cagttacaag tcaaggcttc    3180
caaagtccct ctgtcatgtt tggtgtcaat agtttataca gatgacttca tgtcttcata    3240
tctaatgtct tatatagatt aatattaaac aatgttattt ctctaaccac attttaaatt    3300
aatttaaaaa tccattaatt gtgtctataa aatgcagaca gagtgctgag acacaatata    3360
agcctgatga tctgaatttg aaactcacac ccaccacatg gagaatcaac ttccaaaaat    3420
tttcctatta cttccacact tacaccattg tacaaacaca ataataatga acaaaatgaa    3480
atgaaataaa aaattaagtc tctgtaggta atgctactgt gcagcaaaag taaaaatggc    3540
agcttaagct tgcttttatgg ttacacttta ccatcttcca ttaattataa ggacttcaat    3600
catggcagaa ctatgctgtt attgtctcag tgtaacctaa ccaggtgttc cagatgttct    3660
taatgtggac acctaaaacta tttgatattt gggttaagat ctttccctct ttcagaagaa    3720
acctcaggac agagggaatc ttgtcttttta attttgagtc tgtagacttt ttccatttca    3780
aatatacatg aaacaagtga tgaagaaaat taatcaaaag gtgggaattg caatgatatt    3840
aggttcaata ttaagcttca atattatcat ggaatcgcct gttatacact gagtgtttgg    3900
caataaggga tttttagaag aaggagtttt tattctcaac aggttcctta agtttagctc    3960
aaataaatct aagcaatcca ctctagaatt aaatagtttc                          4001

SEQ ID NO: 59        moltype = DNA   length = 14931
FEATURE              Location/Qualifiers
source               1..14931
                     mol_type = genomic DNA
                     organism = Cricetulus griseus
SEQUENCE: 59
catgtacact tatgcaagta tgatatggcc caacacagta ttttacacca atttttatct     60
ataaaatata catgtacatc aaaatatatt attaataata acatcattat tctttctttc    120
caagtaataa acacatacac tgaaattttg gttcttgtgg ataatttaa tgaaacagga     180
aatgcaaatt tatcttagca tgtttacttc acttctttg catagataac cagtaatcac    240
attgatggat catgtagtga aatgtatttt taggtatata aggaattttg gcttcgtttt    300
gtgcttgttg acactgaatt ctattcctaa caacagtgtg taaggattct gtctgatttc    360
ttttaccagt atttgtccat ttgcattttt tttattattc atggctgctg ttctagaaag    420
tggaaggtag tgtgtcaagt ctgtttaaca tgtttccctg atgatcagtg tcttaacacc    480
tctctgagta catgttggcc aatgtcgttt ctagacccat ctattcttgc ttgacttatc    540
ctggtacatg cctgccaaga aatttctcct catcctttct gtctcttcac tgatttactt    600
gatgtgtgga tttcacattg atcatatgga aatagaagat acaattttct ttattcacag    660
tttgaaagac tttcaatctc atagatcatc attattttt gctactgttc cctatgctat    720
ggtgaaattt ccatttgaat aattgcttaa acaattaaca agaaagaatc tattttttact   780
tgcaataact tccattcag aacattact acactgttac tatatccaaa aactagtttt      840
atatatcatg tgagaaatga ctaattcata atttggccat gacatttttt tcagaaacag    900
aaaaagtgac caatacatac acaatgctat aaatattaag acttcagcaa attaaatatt    960
tattcatgat atcacataaa attcatttat tatgttttat ttaaatgtgt ttttaaaaca   1020
gtggtatcac taaatattaa gttagatgtg tttatgtgct taaagtttt atattttaga   1080
atgttataag ttgtatatag tcaaatatgt aataaattt attttttagg tcttctcat    1140
taaggtattt taattttggg tccctttcc agagtgactc tagctcatga tgagttgaca   1200
taaaaactaa acagtacaaa atgtacattg cattcagtat tgcacttgat cttgtgcactg 1260
aagtttgagt cagttcatac atttagtact tgggaagtac attaagctaa ctttcattgc   1320
tctggcaaaa tgctcgataa gataagagtc tattgtggaa agccatggca gcaggaaagt   1380
aagactgctg atgatgttta atccatagtc aagacgcaga aggagatgaa tgctggtatc   1440
caacatttt tgctgttcat ttctctaga acccagtcc ataaagatgt atgacttgca     1500
ttcaaaatgc gtcccttca gttgttcaac ttttctgtaa atatcctttc aggcatgtct   1560
agaagattgt ttcgcaaata cttctcaatc cattcaagtt gatagtgcag attaatcact   1620
gcagaataaa agcctgtaac ttggctcacg tgccaaggaa tatgcacact cctgacacat   1680
caataagtaa atcaaagtgt agcttttgcc tttaacattg ccagactatt gtaatgttct   1740
gcacgttctt cctccatcac tttttattct aatggtgttt ccttgacatt gaatcacgct   1800
gtggaagctg cttagaatta acattgaaat ctactgatat atttatgatg cagcaattta   1860
gatttactat tttacttaga atttttata attgagagaa tataatattt tcacagttat   1920
ctatctgctg taaatagagg attttaaaaa aaatctctat aacttttttt tacaacacac   1980
agtaaaatta agttaaaatt taataaagtc actatgttga tttcaaagtg tgctacgccc   2040
acggtggtca cgcaggtgta gcagaagatg ccactaaggt gggctaaggc cgatgggttg   2100
gggtctgcgc tccctggaga tgagcccag gcggttccct ggcaatcagc tgcgatcatg    2160
atgcccgatg agccannnnn nnnnnnnnnn nnnnnnnnnn nnnnnnnnnn nnnnnnnnn     2220
nnnnnnnnnn nnnnnnnnnc tgggtgactt tatggaaaga atttgataga tttcatgatg   2280
tagaagaatt ttattaggct tatttacag gagactaaga cccgggaacc taaagatatc   2340
tgggtcctga gaatcaggaa atgggtagag acgtggttga tggtatgaga cagatttag    2400
agaactctta gatcatgggc aatgaccgca atctgatgct tagaatagat catctataaa   2460
caattatgct gttcttttc tttctgttgt atgatctgat gatgtagccc ccttgccaag    2520
ttccctgatc cccccttgcca agtccctga ttgtaacagt atataagcat tgctggagag   2580
catattcaac tacattgagt gtgtctgtct gtcatttcct cgccgattcc tgatttctcc   2640
ttgagccttt tcccttgttc tccctcggtc ggtggtctcc acgagaggcg gtccgtggca   2700
aaagtgtata aatgttctaa aacatttgaa ctctaaaaca tgcaaaatga aaaattaaaa   2760
taaataaaca tgaaaattaa aatatattag ctgctaaaag ttaaacaata ctatataata   2820
ttttgttatt agaattcaaa atcacattag ttggatttaa tttgaacatt gcattctttc   2880
aataaatt tcaataaaaa aagtttcccc atgatagtaa aaaataataa catatgatc      2940
tatctattta tttaactaca catatatagc atttgtttca actaaaataa atgaatgagc   3000
aaagcaccta agtaattggt gtctattata tttatgaagc caatagtttc aaataaatta   3060
tcatgcataa ggaggtattg caaatgttaa acctttttttg aaacagatat tcccagttac   3120
agaaattata atttctaatc tttcctataa gtagaatgat gataattaat ataggccatt   3180
tgtaaataat gttcagatta aaatattctc tatttcacta gagaagaatg atattaaatg   3240
```

```
tattatattt tatttcccat tttgtttgca ccactattct atatccctca gcagtttaaa   3300
tttgtttcac catatgtgtg tgtgtttgta tcttaaatat ggcactaaaa ttagaataat   3360
ttaatataaa tctttaggag aaaagatatt gaattatttt atgttgatag gaaaatatct   3420
tttaattgtc caagaatact ttttcttcta ttttaggact gatcagaccc aggactaata   3480
ttttatatgt actaattcta tgtaccaaaa tatgttatta tctcatgaat tctgtctcaa   3540
tattgaggta ataaaaatag tccatcatga actttaaaat taaaataatg attaattaat   3600
ttttattcat atttttgttg tatgaatggt tatacatcac atgtgtgcct ggtgactgtg   3660
aatgtcagga gaaggtatga aagccactgg aattggaata agagataata tttgagatgt   3720
tatgtgggtg ctgagaatta gacgcaagcc atcttcaaga atagccagca tactatacca   3780
ctgagtaatc cattcatccc tcaataatta tctttgtaga cagtaaatat atttctaaac   3840
tataaatgac cagaaaaatt aatgtattat taatgaagac attcatctca tgtgacacac   3900
ttcacctgtc taaatcagta acactctctc cactaattaa gattttctaa gtgcatgaca   3960
cttactattt ctaaagctgt ccaatggggg ccagtcccca gtcagcaccc agtagagata   4020
tccatgaatg catttatatc ttaggaaaaa ttcttatcta tgtagtattt agaacatttt   4080
catgtgaggg gataaacaag gaagcacaga tgctttctga tagaaacttt ctctttaatt   4140
catctagaaa aaaaaaacct ctcaggaaaa tctctcttgc tctcctccca atgctctatt   4200
cagcatcttc tccctactta attctagatc ttttttctcta tgcctccttg ctgctgccct   4260
gctggctctg ctctatgcct ccccatgtca cttttctttg ctatctcacc gttaccttct   4320
ctgcctcact ctctgccttc ttctctgctt ctcacatggc caggctctgg acaattatag   4380
ttatatgtta cattctcata acacatgata tgtcacatag tttctctcag gctagggata   4440
tcacaatgac tggccaatga gcaagtggcc ttgcatgtag ctctaagttg gtgatggttc   4500
ccagacagta agtagccatt tggttgaaat ttgaggttgg gtagtacatg aagactgaat   4560
tttcttcaaa ctctggcctt gaaatagtaa aacaacacct atgaaaatga cgacctgtat   4620
ttgtctttag aggcaaccac atattgtctg cagggcctgc tttgaatttg ctctgaagtt   4680
agcttgtttg tgtaaaagga agaatcctat atcagcctga gaaatgtaaa atatcctagc   4740
atttcaagtc atcaaaatta tatggagagt ataaatcatc cttctgacta ttcatagtca   4800
tatttgtgtc caccaagtat aaaacacact accaaagggc tgtggaaaaa atcgccataa   4860
ctgttcttat tagggaggca tagcagtggt acctgaggaa gttacagcaa caaccagtca   4920
tccagtcaat aaccccatgg ctttgccact tggaggtacc caataatgtt tggctttgcc   4980
gagtaggact ccaacaaatt cagagggtca attttttaagt gctggttgtc actgctgaac   5040
agtcccattg ccctctgcat aattccacaa tggaaagctt tttacactga ttgccaatca   5100
ttaaacagcc tactcagcat aaacaggtat gatattattc tgcattttgt tacattacta   5160
gatgaattcc tatttcttcc tacaatagtg gaactgaaaa aagatacaca atcatactac   5220
ccctctacta atcttatgac ttatatcatt tcaattttca gaccataatg caaactattg   5280
accaaaacat gtgaagatga aaaatagaaa tgtagaataa tattacatat aaaaagaaaa   5340
ggcggactta ttttgtttta tttcttagca tgcatagcaa tacatgattt gaggtttata   5400
taataaaggg acaataaatc ttcaagaaac ttacccctac tgaattaaaa tattaaagaa   5460
ggtcacacat ttactcaaat atattagact actgggcaaa tagacatgaa aagtagagtt   5520
aatattgagg taggccttct gtgaaatgtc taaggaaatt atgtttcata cagtgtgtaa   5580
ccaagtggga atcatatcag aaagcagtca aaagcttata ttacaagtaa cagatgcttg   5640
gttatatgac ctcccagagc ttgactgtct atacacaaaa agtggtgtta ataaaactgt   5700
aatttgggct atgtttttt aaatggcttc accaacatga aaggaaggga atgagcatgt   5760
catggatgct tagagattat gcttccagca agaagaattg agctttggct cttattacag   5820
aaacatgaca aggtgtgagt tttatttatt agaaattata taatatttta agctggggac   5880
taaaaatttt attgaaacaa acaggcaagg gataggcatg tactagaagc aaaaatagga   5940
tgtcaatgct gtaatgttat ttttttggacc aaaaatagta ttcctataga aatgacaatg   6000
atcttaggtt attattcttc ataaagatga caagttcaca agatatccta gttcattaaa   6060
atcgttttag tcatttaata gagtgctgtg atagattaca caaaggaaag cacttacgat   6120
gagaaataat gatatccaca attatttttct taattcttag aaacattcta ttgttatatc   6180
tcaatctcag aagccactta ttgctttatt attgaaacat atgaaattgt aagttatata   6240
ttgtctatgg tgcatttca aagaacatgt gacgtacagt gtagcacaga taaagaacat   6300
aactgcagct gaatcagtaa ctaaacttac atacattaaa tctgccatgt tggcaacagt   6360
gtgtgcacta ccaaaggatg tactaatgct cacgacactc ccctatgtca cccttttgttc   6420
atcattacat cataggtcta ttttgtttgc ttttgaaatc tagaccaagt cttttgtgtc   6480
tttccaagca cagagctcat taatttacct catagacttg ttaaacttct tctggttcat   6540
caattgaata gaaatactca ctactaatta tgtgagaccc tgccagtacc atagcacatg   6600
gataatttttt acataaaaca tgcatacaag taagattatt cagactgaac atgaattta   6660
gagaaatcag gaaggagtat atgggagtgg ttggagtgag actagagaaa tgtaattaaa   6720
ctataatctc aatacaaaga tctactaagc aaaaaacatg aaacattgtc attcaagtga   6780
aacatcagtc ttcaaattgg aaagatattt ttactaggaa aatgtctggt agatggttat   6840
tatctagaaa acacaaaaat tagaaaacgg taaactttaa taaaaagaat aatacaatga   6900
gactacatga aaagttctta actaatgaaa caaatatctt gaactttttt cttaaaagt   6960
ttaatatcaa taaccatcat ggaaattcaa attaaaacta tttacatatt acccctgaaa   7020
taataactaa tacccaataa aaataatata aacaaaaaat ggcaatgcat gccatcatga   7080
atttgggaga gagaatgttc attgcagttc tgaatggata ctggtgccac acggtgaaa   7140
atctctgtat aggtccttcc aaaagctgaa aatagacata tcacaagacc tgccacacat   7200
ttttcaagca aatccccaaa ggactctacc tgactgcaga gacactttct cataaaatat   7260
tattgttgat ctattcataa tatctggaaa atagaaacag ccaagatgcc catcaactga   7320
ttaatagatg ataaaaattat tgtacatttc agtgtaatat tattcagttt ttaagaaaaa   7380
tgaaattatg taataagcat gtaaatggat atatcttgaa acaaccattc cccattatat   7440
tacctaaaca ttgaaagtcc aaaatcatat gatcttttta gtggatctac taatctttg   7500
ctatatgtat tttattgaac tacccatgga gtgtgagtaa ttggtaacaa cagcacatg   7560
gagagcatgg gatcattcaa ggaagattag agagaatgca ttttttagga gataatggag   7620
gagcaataga aaggattaaa tgaggttact gatgaaagtg atggttagga aaggcaatat   7680
gaggagggat aactagcact tagggccttt tgaaaaagac atagagaaaa tactattgta   7740
gaaacttcct ataattggtg tatagttata tacaccaaag agctcagatg gagttaccct   7800
ataatgaaa tattaactac ttttttatcac tgtgataaaa catcctgaac agagcaacat   7860
agattgggaa gcatttactt tggcttacag ttctaacggg ataaaaattc atgatgaaag   7920
aatgaatatg tcagcaaaca gcagtagcaa tggcctgaga agcaggtgag agctcacatc   7980
```

```
ttgaagtgta agaatgtagc agagagaaca aactgcaaat gaccagaaaa tgcttttgga    8040
tcagagccca taccctctg actgacttct ccagaaattc tgaacaaata aaactcccca    8100
aacagagcca taactgaagg tccagtgtct gagactacta ggggtatttc ttattcaaac    8160
cactacaatg gggtgggggg agcaatcctc caagtaggca ctacacacag acaaataaaa    8220
actctagtaa ctggaatgga ttgacttatt gaattactt gccagtgacg ctacatagag    8280
cacaattatt gtatttaaat tacccttat gatcttacaa aacttgacag taagatcata    8340
ttgctaaaga aaccacatat ttgaatcagg gaacatggtg atatctagtt gttcttcaac    8400
tggaaacttc atgctttctg cccagcattc atgttgctgg aaagagcaat gtacactacc    8460
agtgtagaaa ttaaatcatc aatcttatca agatgtggat cctataagtt acaataaaaa    8520
ttagcctgat aagatatccc caccagaaga atattccacat aaatgctatg ggagcaacaa    8580
gctattttct aaattagctt taatcctatt ctacaagaga gaatccatat ctagaatagt    8640
tataggggatc aagaacccat ggcttgattg gtcataggcc caatgggaga tcctaatatt    8700
attgttctac aaaatgaaaa taactcctaa tgacttgttg ctgcagtaat aagttagtat    8760
gttgctcaac tctcacaaga gaagttttgt cttacaataa atggcaatta aagcagcccc    8820
acaagattta tatcataccg atctcctcat ggcctatgca tctagaagct aggaaacaaa    8880
gaggaccta agagagacat acatggtccc cctggagaag gggaagggg caagacctcc    8940
aaagctaatt gggagcatgg gggaggggag agggagttag aagaaagaga aggggataaa    9000
aggagggaga ggaggacaag agagagaagg aagatctagt caagagaaga tagaggagga    9060
caagaaaaga gataccatag tagagggagc cttgtatgtt taaatagaaa actggcacta    9120
gggaattgtc caaagatcca caaggtccaa ctaataatct aagcaatagt cgagaggcta    9180
ccttaaagc ctttctctga taatgagatt gatgactacc ttatatacca tcctagagcc    9240
ttcatccagt agctgatgga agcagaagca gacatctcaa gctaaacact gagctagttg    9300
cagacaggga ggagtgatga gcaaagtcaa gaccaggctg gagaaacaca cagaaacagc    9360
agacctgaaa aaatgttgc acatggaccc cagactgata gctgggagtc cagcatagga    9420
ctttctctaga aacctgaat gaggatatca gtttggaggt ctggttaatc tatgggagaca    9480
ctggtagtgg atcaatattt atcccctagtt catgactgga atttgggtac ccattccaca    9540
tggaggaatt ctctgtcagc ctagacacat ggggggaggt ctaggtcctg ctccaaataa    9600
tgtgttagac tttgaagaac tcccttgaga agactcaccc tccctgggga gcagaaaggg    9660
gatgggatga gggttggtga gggacaggag aggagggag ggtgagggaa ctgggattga    9720
caagtaaatg atgcttgttt ctaatttaaa tgaataaagg aaaagtaaaa gagaaaagaa    9780
aaacaggcca aaagattata aaagacagag gtggtgggtg actataaaga aacactatta    9840
tctaaataaa aatatgtcag aagcacacat gaacttatag tgtttatgaa agtatgtata    9900
ataactacat aatctcaagc caagaaaaaa atatcatctt tcagtgatga aggtgatttt    9960
atttctccca gaattaaagc caaagaccta atgaaagtaa ttatcttcaa aaggttgaaa   10020
atacatactt tgcaatacac agatctgcct agaaatctca tgttcacaat acacatgatg   10080
ctcaattgaa ttccattcaa tgttacagtt tagataaaca gtttgtagat aaactcacaa   10140
tgtatcattt ctttttattt tttgaccaaa cagcttctca tctgttattc agaataattc   10200
ctcgatggca ggatatccat ccccaattggg ggaagggag aatttgaaga aaacctagac   10260
cacatacata tttgccattg ggaaacaaag tctaaaatga tgttgttcac atcttctcta   10320
ctagtcctct cccgtccca aagaaccttg tgtatatgtgc ctcattttac agagagagga   10380
aagcaggaac tgagcatccc ttacttgcca tcctcaaccc aaaatttgca tcattgctca   10440
gctctgccct tctcatatga cagttacaag tcaaggcttc caaagtccct ctgtcatgtt   10500
tggtgtcaat agtttataca gatgacttca tgtcttcata tctaatgtct tatatagatt   10560
aatattaaac aatgttattt ctctaaccac attttaaatt aatttaaaaa tccattaatt   10620
gtgtctataa aatgcagaca gagtgctgag acacaatata agcctgatga tctgaatttg   10680
aaactcacac ccaccacatg gagaatcaac ttccaaaaat tttcctatta cttccacact   10740
tacaccattg tacaaacaca ataataatga acaaaatgaa atgaaataaa aaattaagtc   10800
tctgtaggta atgctactgt gcagcaaaag taaaaatggc agcttaagct tgctttatgg   10860
ttacactta ccatcttcca ttaattataa ggacttcaat catggcagaa ctatgctgtt   10920
attgtctcag tgtaacctaa ccaggtgttc cagatgttct taatgtggac acctaaacta   10980
tttgatattt gggttaagat cttttccctct ttcagaagaa acctcaggac agagggaatc   11040
ttgtcttttta attttgagtc tgtagacttt ttccatttca aatatacatg aaacaagtga   11100
tgaagaaaat taatcaaaag gtgggaattg caatgatatt aggttcaata ttaagcttca   11160
atattatcat ggaatcgcct gttatacact gagtgtttgg caataaggga ttttttagaag   11220
aaggagtttt tattctcaac aggttcctta agtttagctc aaataaaatct aagcaatcca   11280
ctctagaatt aaaatgttc ctaagggcac agctatgaat agagctcaat ttacatataa   11340
aattttgttc accatttatg tcattccagt tttcattagt acaaggaaaa tacaaaaatt   11400
ttagatgtca atatcaagtg aatagttcat ctccttttt aatatatatc acctaaatca   11460
ccattttctc agaaaaatct ggcctgaagt tctgtctgga acttcaacat gaaaaatatg   11520
cacagcttgc tattataaat cctagttgat ttttaagatt catgtctggt gtctgactca   11580
gagggccag aggctagaca aatatttttt gaatcttcat tgtgaagatt tttaatgatt   11640
attttaatat aaataacaaa gatgatggat aatgtaactt tgtacagttc atagacgctg   11700
aactactttg tgcttaaaat gttagttccc tatcataaat gataggtgat aagtgtatgt   11760
ttaatacttt ccctctgagc tatattcatg tactagagaa ttattttaaa catgaaagaa   11820
ctgtgtttat agtctcagct cctgagaact ggtccaacct taggcaggtg aatgccagga   11880
gcaacgtttt tcttctacag aggatgcttt gctgccaagc aacctggttg tgtgaaatg   11940
ttccttttttt aatcaagttt aaagggtctt catcatgctg ttgctccaca tattttcagg   12000
ttagagcttg gtccttggag tattatcttt taccagaaaa ttcatagtat tctttcaata   12060
actaacaact aaacttttcg ataaaaaaga attggaattt caatttttaaa gcctgagtaa   12120
aattcttgtg aatcaggata tttattttta agtcttatct tttaaaaagt tattttattt   12180
tttaaaaaat tataatatac tttcataatt tccctcctc acttttcttt acaaacactt   12240
ctatagatca ccatgtgttt ttttttttac atttatggcc tctttctgtt cattgttatt   12300
acatacaaat agtcttgcct atagaagaac accacaattg gttacctgat aacaaattat   12360
caaccccttaa aacctacaaa ctattgatat tactgaaaag actatactta tagatgtaaa   12420
gatatatgtg tgtgcacata tatagataca catatatgta ggattttaa ttttagattt   12480
tagacatcaa aattatttat atgactgaga aactagacac tataaatgag cattcagtat   12540
tcaacaccgt gatttagat attgtcacaa tgacagaaaa ttttcttata gaaaatttta   12600
agttttgtga ttgctctgtg cacttagtga agtctcacag aaaaagaatc atagtatttt   12660
tagtttataa taaaaagtac atataattaa aatggttggc acaaaacaac atttgagcat   12720
```

```
tttteetatt tactateaag tagtateatt ttgaaataat aatttgaeta gtttcaaaaa    12780
tgaaaacaaa atttaaacta aatgcctaat ctagcctgat aacatttta tgaatgaaat    12840
tattcaatag tgttatcaat taggggccca aaactttcc taaaataaaa ctttaattt     12900
ttttccatt ttatttaaat tagaaacaaa attgtttac atgtaaatca gagtttcctc     12960
accctcccct tctccctgtc cctcactaac accctacttg tcccatacca tttctgctcc   13020
ccagggaggg tgaggccttc catggggaaa cttcagagtc tgtctatcct ttcggatagg   13080
gcctaggccc tcacccattt gtctaggcta aggctacaa agtttactcc tatgctagtg    13140
ataagtactg atctactaca agagacacca tagatttcct aggcttcctc actgacaccc   13200
atgttcatgg ggtctggaac aatcatatgc tagtttccta ggtatcagtc tggggaccat   13260
gagctccccc ttgttcaggt caactgttc tgtgggttc accaccctgg tcttgactgc     13320
tttgctcatc actcctccct ttctgtaact gggttccagt acaattccgt gtttagctgt   13380
gggtgtctac ttctactttc atcagcttct gggatggagc ctctaggata gcatacaatt   13440
agtcatcatc tcattatcag ggaagggcat ttaaagtagc ctctccattg ttgcttggat   13500
tgttagttgg tgtcatcttt gtagatctct ggacatttcc ctagtgccag atatctcttt   13560
aaacctacaa gactacctct attatggtat ctcttttctt gctctcgtct attcttccag   13620
acaaaatctt cctgctccct tatattttcc tctccctcc tcttctcccc ttctcattct    13680
cctagatcca tcttcccttc ccccatgctc ccaagagaga tgttgctcag gagatcttgt   13740
tccttaaccc ttttcttggg gatctgtctc tcttagggt gtccttgttt cctagcttct    13800
ctggaagtgt ggattgtaag ctggtaatca tttgctccat gtctaaaatc catatatgag   13860
tgatgtttgt ctttttgtga ctgggttacc tcactcaaaa tggtttcttc catatgtctg   13920
tggatttcaa tagcacaaac aacatacagt atcttgggc aacactaacc aaacaagtga    13980
aagaccagta tagcaagaac tttgagttta aagaaagaaa ttaaagaaga taccagaaaa   14040
tggaaagatc tcccatgctc tttgataggc agaatcaaca tagtaaaaat ggcaatcttg   14100
ccaaaatcca tctacagact caatgcaatc cccattaaat accagcacac ttcttcacag   14160
acctgaaaga ataatactta actttatatg gagaaacaaa agacccagga taggccaaac   14220
aaccctgtac aatgaaggca cttccagagg catcccatc cctgacttca agctctatta    14280
tagagtaata atcctgaaaa cagcttggta atgcacaaa aatagacagg tagaccaatg    14340
gaattgagtt gaaaaccctg atattaaccc acatatctat gaacacctga ctttgacaaa   14400
gaagctaagg ttatacaatg taagaaagaa agcatcttca acaaatcgtg ctggcataac   14460
tggatgctgg catgtagaag gtcagcagta gatccatgtc taatgccatg cacaaaactt   14520
aagtccaaat ggatcaaaaa cctcaacata atccagcca cactgaacct catagaagag    14580
aaagtgggaa gtatccttga ataaattggt acaggagacc acatcttgaa cttaacacca   14640
gtagcacaga caatcagatc aataatcaat aaatgggacc tcctgaaact gagaagcttc   14700
tgtaaggcaa tggataagtc aacaggacaa aatggcagcc cacggaatgg gaaaagatat   14760
tcaccaatcc tatatctgac agagggctgc tctctatttg caaagaacac aataagctag   14820
ttttaaaac accaattaat ccgattataa agttgggtag agaactaaat aaagaattgt    14880
taacagagca atctaacttg gcagaaagac acataagaaa gtgctcacca t             14931
```

What is claimed is:

1. A eukaryotic cell from a eukaryotic cell line, wherein the eukaryotic cell comprises a polynucleotide comprising in order (i) a promoter, (ii) an intron, (iii) a first internal ribosome entry site, (iv) a first AAV Cap gene, (v) a second internal ribosome entry site, (vi) a second AAV Cap gene, and (vii) a polyadenylation site, wherein (i) to (vii) are operably linked.

2. The eukaryotic cell according to claim 1, wherein the polynucleotide is integrated into a cell genome.

3. The eukaryotic cell according to claim 2, wherein the eukaryotic cell is a CHO cell or a BHK cell.

4. The eukaryotic cell according to claim 2, wherein the eukaryotic cell is a HEK 293 cell or a human amniotic cell.

5. The eukaryotic cell according to claim 1, further comprising an operator.

6. The eukaryotic cell according to claim 5, wherein the promoter is a CMV promoter and the operator is a Tet operator.

7. The eukaryotic cell according to claim 1, further comprising:
   a polynucleotide encoding AAV Rep;
   a polynucleotide encoding Ad E1A;
   a polynucleotide encoding Ad E1B;
   a polynucleotide encoding Ad E2A or E2A orf;
   a polynucleotide encoding Ad E4 or E4 orf 6;
   a polynucleotide encoding VA RNA; and
   a polynucleotide encoding AAV ITRs and a protein of interest.

8. A method of producing adeno-associated virus (AAV) Cap protein in cell culture, wherein the method comprises the steps of:

providing the cell culture that comprises eukaryotic cells, wherein a eukaryotic cell of the cell culture comprises a polynucleotide comprising in order (i) a promoter, (ii) an intron, (iii) a first internal ribosome entry site, (iv) a first AAV Cap gene, (v) a second internal ribosome entry site, (vi) a second AAV Cap gene, and (vii) a polyadenylation site, wherein (i) to (vii) are operably linked; and culturing the eukaryotic cells in a culture medium to allow the eukaryotic cells to produce AAV VP1, VP2 and VP3 protein.

9. The method according to claim 8, wherein the polynucleotide is integrated into a cell genome.

10. The method according to claim 9, wherein the eukaryotic cell is a CHO cell or a BHK cell.

11. The method according to claim 9, wherein the eukaryotic cell is a HEK 293 cell or a human amniotic cell.

12. The method according to claim 8, wherein the eukaryotic cell further comprises an operator.

13. The method according to claim 12, wherein the promoter is a CMV promoter and the operator is a Tet operator.

14. The method according to claim 8, wherein the eukaryotic cell further comprises:
   a polynucleotide encoding AAV Rep;
   a polynucleotide encoding Ad E1A;
   a polynucleotide encoding Ad E1B;
   a polynucleotide encoding Ad E2A or E2A orf;
   a polynucleotide encoding E4 or E4 orf 6;
   a polynucleotide encoding VA RNA; and
   a polynucleotide encoding AAV ITRs and a protein of interest, wherein the eukaryotic cell can produce recombinant AAV.

15. The method according to claim 8, wherein the eukaryotic cells in the cell culture can express VP1, VP2 and VP3 proteins in a ratio of 1:2:9.3 of VP1 to VP2 to VP3.

* * * * *